US011254930B2

(12) United States Patent
Baltes

(10) Patent No.: US 11,254,930 B2
(45) Date of Patent: *Feb. 22, 2022

(54) METHODS FOR TARGETED INSERTION OF DNA IN GENES

(71) Applicant: BLUEALLELE CORPORATION, Oakdale, MN (US)

(72) Inventor: Nicholas J. Baltes, Oakdale, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/366,290

(22) Filed: Jul. 2, 2021

(65) Prior Publication Data

US 2021/0332347 A1 Oct. 28, 2021

Related U.S. Application Data

(63) Continuation of application No. 16/800,444, filed on Feb. 25, 2020, now Pat. No. 11,091,756, which is a continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
*C12N 15/10* (2006.01)
*C12N 15/90* (2006.01)

(52) U.S. Cl.
CPC ......... *C12N 15/102* (2013.01); *C12N 15/907* (2013.01); *C12N 2310/20* (2017.05); *C12N 2800/80* (2013.01)

(58) Field of Classification Search
CPC .................................................. C12N 15/102
See application file for complete search history.

(56) References Cited

U.S. PATENT DOCUMENTS

| | | | |
|---|---|---|---|
| 6,228,639 B1 | 5/2001 | Gaitanaris | |
| 6,740,503 B1 | 5/2004 | Harrington et al. | |
| 7,005,299 B1 | 2/2006 | Smith et al. | |
| 9,255,250 B2 | 2/2016 | Gregory et al. | |
| 9,677,070 B2 | 6/2017 | Allison et al. | |
| 9,765,404 B2 | 9/2017 | Sastry-Dent et al. | |
| 10,240,115 B2 | 3/2019 | Tang | |
| 2004/0106566 A1 | 6/2004 | Lin et al. | |
| 2005/0064474 A1 | 3/2005 | Urnov | |
| 2005/0208489 A1 | 9/2005 | Carroll | |
| 2013/0280222 A1 | 10/2013 | Kay et al. | |
| 2014/0130205 A1 | 5/2014 | Bhyri | |
| 2016/0040155 A1 | 2/2016 | Maizels et al. | |
| 2016/0102322 A1 | 4/2016 | Ravinder et al. | |
| 2016/0281111 A1 | 9/2016 | Cotta-Ramusino et al. | |
| 2017/0073664 A1 | 3/2017 | Mccafferty et al. | |
| 2018/0023075 A1 | 1/2018 | Liang et al. | |
| 2018/0110877 A1 | 4/2018 | Wilson et al. | |
| 2018/0112213 A1 | 4/2018 | Welstead et al. | |
| 2018/0119123 A1 | 5/2018 | Gori et al. | |
| 2018/0273932 A1 | 9/2018 | Bothmer et al. | |
| 2018/0296603 A1 | 10/2018 | Gori et al. | |
| 2018/0362590 A1 | 12/2018 | Monds et al. | |
| 2019/0032089 A1 | 1/2019 | Townes et al. | |
| 2019/0032092 A1 | 1/2019 | Gong et al. | |
| 2019/0032156 A1 | 1/2019 | Gong et al. | |
| 2019/0093114 A1 | 3/2019 | Bower et al. | |
| 2019/0134221 A1 | 5/2019 | Bumcrot et al. | |
| 2019/0136210 A1 | 5/2019 | Cotta-Ramusino et al. | |
| 2019/0276850 A1 | 9/2019 | Brinkmann et al. | |
| 2019/0330603 A1 | 10/2019 | Ahlfors et al. | |
| 2019/0390189 A1 | 12/2019 | Lee et al. | |
| 2020/0040362 A1 | 2/2020 | Carlo et al. | |
| 2020/0231974 A1* | 7/2020 | Jarvis | C12P 19/34 |

FOREIGN PATENT DOCUMENTS

| | | |
|---|---|---|
| BR | 102014027 448 A2 | 9/2015 |
| CA | 2906747 A1 | 9/2014 |
| EP | 2893025 B1 | 7/2015 |
| EP | 3114227 A1 | 1/2017 |
| EP | 3122880 A2 | 2/2017 |
| EP | 3344771 A1 | 7/2018 |
| EP | 3375877 A1 | 9/2018 |
| EP | 3426784 A1 | 1/2019 |
| EP | 3556858 A2 | 10/2019 |
| EP | 3592140 A1 | 1/2020 |
| ES | 2653212 T3 | 2/2018 |
| ES | 2699848 T3 | 2/2019 |
| ES | 2730378 T3 | 11/2019 |
| WO | 2013075008 A1 | 5/2013 |
| WO | 2013169802 A1 | 11/2013 |

(Continued)

OTHER PUBLICATIONS

Pluta et al. (Acta Biochimica Polonica. Nov. 23, 2009. 54(4): 531-595) (Year: 2009).*
Kurosaki et al. (Journal of Human Genetics (2011) 56, 727-733). (Year: 2011).*
BLUEALLELE, LLC in connection with PCT/US2019/058857 filed Oct. 30, 2019, "The International Search Report and the Written Opinion of the International Searching Authority, or the Declaration", 19 pages, dated Jun. 23, 2020.
Robert, Francois, "Bidirectional terminators: an underestimated aspect of gene regulation", Curr Genet, vol. 64, pp. 389-391, 2018.
Ouyang et al., "CRISPR/Cas9-Targeted Deletion of Polyglutamine in Spinocerebellar Ataxia Type 3-Derived Induced Pluripotent Stem Cells", vol. 27, No. 11, pp. 756-770, 2018.
BLUEALLELE, LLC in connection with PCTUS2019/056083 filed Oct. 14, 2019, "The International Search Report and the Written Opinion of the International Searching Authority, or the Declaration", 21 pages, dated Dec. 19, 2019.

(Continued)

*Primary Examiner* — Scott Long

(74) *Attorney, Agent, or Firm* — Arrigo, Lee, Guttman & Mouta-Bellum LLP

(57) ABSTRACT

Methods and compositions for modifying the coding sequence of endogenous genes using rare-cutting endonucleases and transposases. The methods and compositions described herein can be used to modify the coding sequence of endogenous genes.

20 Claims, 8 Drawing Sheets

Specification includes a Sequence Listing.

(56) References Cited

FOREIGN PATENT DOCUMENTS

| | | | |
|---|---|---|---|
| WO | 2015017866 A1 | 2/2015 |
| WO | 2015089351 A1 | 6/2015 |
| WO | 2015153780 A1 | 10/2015 |
| WO | 2015173436 A1 | 11/2015 |
| WO | 2016073990 A2 | 5/2016 |
| WO | 2016109840 A2 | 7/2016 |
| WO | 2016161380 A1 | 10/2016 |
| WO | 2016172727 A1 | 10/2016 |
| WO | 2016182959 A8 | 11/2016 |
| WO | 2017048995 A1 | 3/2017 |
| WO | 2017155408 A1 | 9/2017 |
| WO | 2018009534 A1 | 1/2018 |
| WO | 2018009562 A1 | 1/2018 |
| WO | 2018195555 A1 | 10/2018 |
| WO | 2018197020 A1 | 11/2018 |
| WO | 2019005851 A1 | 1/2019 |
| WO | 2019092505 A1 | 5/2019 |
| WO | 2019113149 A1 | 6/2019 |
| WO | 2019118875 A1 | 6/2019 |
| WO | 2019157326 A1 | 8/2019 |
| WO | 2019157326 A2 | 9/2019 |
| WO | 2019183123 A1 | 9/2019 |
| WO | 2019210216 A2 | 10/2019 |
| WO | 020082042 A2 | 4/2020 |
| WO | 2020082041 A1 | 4/2020 |
| WO | 2020082046 A2 | 4/2020 |
| WO | 2020082047 A1 | 4/2020 |

OTHER PUBLICATIONS

Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.
Gilles et al., "Efficient CRISPR-mediated gene targeting and transgene replacement in the beetle Tribolium castaneum". The Company of Biologists, vol. 142, pp. 2832-2839, Jun. 29, 2015.
Hahm et al., "Construction of retroviral vectors with enhanced efficiency oftransgene expression", Journal of Virological Methods, vol. 121, pp. 127-136, May 27, 2004.
Hildinger et al., "Design of 5' Untranslated Sequences in Retroviral Vectors Developed for Medical Use", Journal of Virology, vol. 73, No. 5, pp. 4083-4089, May 1999.
Intellia Therapeutics, "Q3 2018 Earnings and Corporate Development", Powerpoint, 23 pages, presented Oct. 31, 2018.
Ruan et al., "Highly efficient CRISPR/Cas9-mediated transgene knockin at the H11 locus in pigs", Scientific Reports, 10 pages, Sep. 18, 2015.
Suzuki et al., "In vivo genome editing via CRISPR/Cas9 mediated homology-independent targeted integration", Nature, vol. 540, 24 pages, Dec. 1, 2016.
Uno et al., "CRISPR/Cas9-induced transgene insertion and telomere-associated truncation of a single human chromosome for chromosome engineering in CHO and A9 cells", Scientific Reports, 10 pages, Oct. 6, 2017.
Yao et al., "Homology-mediated end joining-based targeted integration using CRISPR/Cas9", Cell Research, vol. 27, pp. 801-814, Apr. 6, 2017.
Sheng et al Canadian Journal of Microbiology, 445-454 (Year: 2014).
Ryu et al Plant Molecular Biology 54: 489-502 (Year: 2004).
Senis et al Nucleic acid Res. , 45(1), e3 (Year: 2016).
Kaiser Science, 317, 580 (Year: 2007).
Frank et al N. Engl. J Med. Jul. 9;361 (2): 161-9 (Year: 2009).
Edelstein Journal Gene Med., 597-602 (Year: 2004).
High Nature, 435, 577-579 (Year: 2005).
Ramirez Nature Methods, 5(5): 374-375 (Year: 2008).
Li Nature, Jul. 14,, 475, 7355, 217-221 (Year: 2011).
Christian Genetics, 757-761 (Year: 2010).
Hauschild PNAS, 108( 29), 12013-12017 (Year: 2011).
Hsu et al Nat Biotechnology. Sep;31 (9):827-32 (Year: 2013).
Lee et al., (Drug Discovery Today: Disease Models, vol. 20, 13-20 (Year: 2016).
Kosicki et al Nature Biotechnology, 36, 765-771 (Year: 2018).
Robert et al Curr Genetics, 64(2):389-391 (Year: 2018).
Cox et al , Nature Medicine 21 (2), 121-13 (Year: 2015).
Kuscu et al Nature biotechnology, 32(7), 677 (Year: 2014).
Kleinstiver Nature, 523, 481-485 (Year: 2015).

* cited by examiner pBA1012-D1 (SEQ ID NO: 10); pBA1135 (SEQ ID NO:17)

METHODS FOR TARGETED INSERTION OF DNA IN GENES

REFERENCE TO RELATED APPLICATIONS

This application is a continuation of previously filed and co-pending application U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 14, 2019 is named 2019-10-14_BALTES_P12987US03_SEQUENCE_LISTING_BA2018-4WO.txt and is 517,077 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
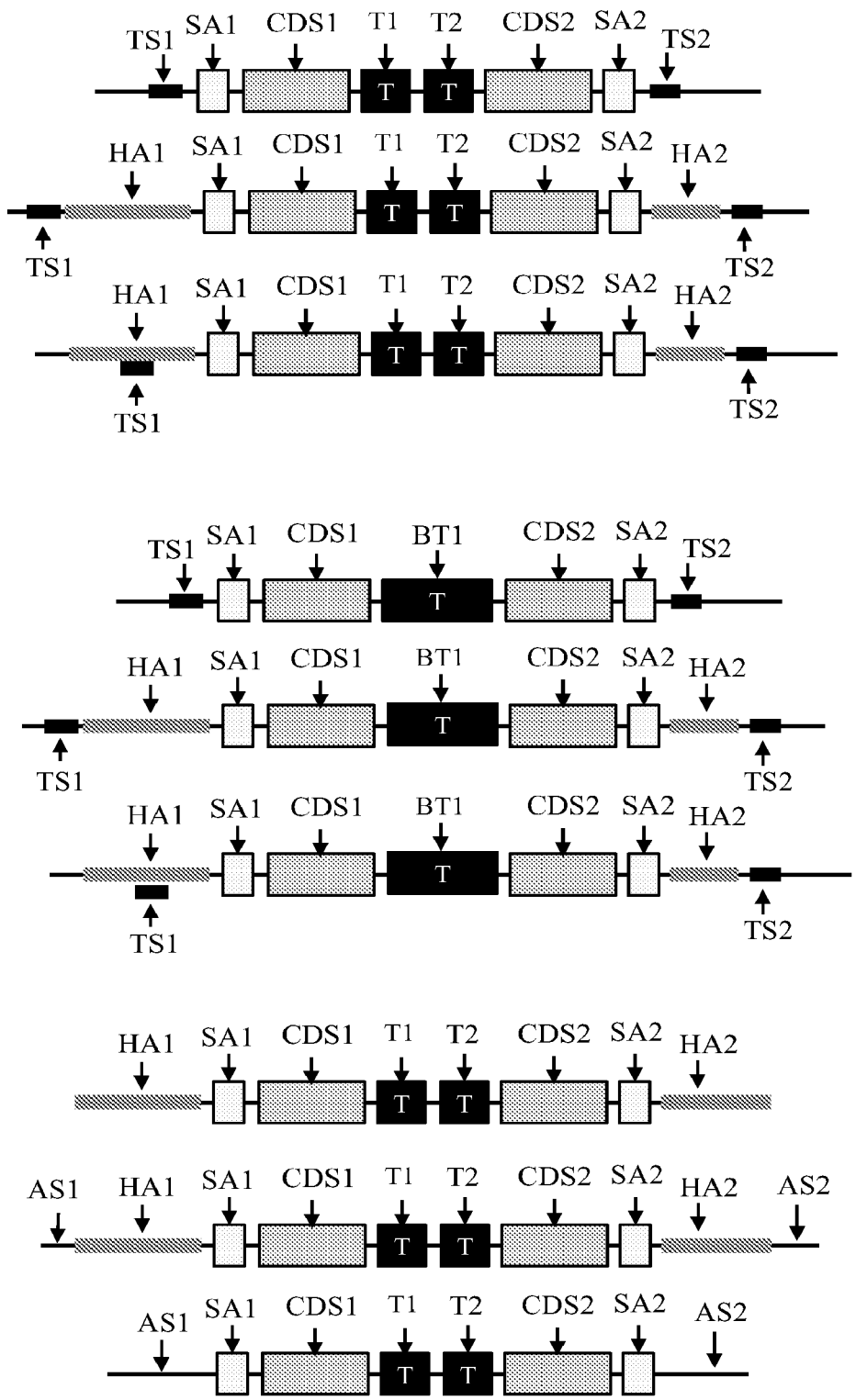
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HA1 homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector is can include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO:41, and the right end can comprise the sequence shown in SEQ ID NO:13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

As used herein, the terms "nucleic acid" and "polynucleotide," can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" can be used interchangeably to refer to amino acid residues covalently linked together. The term also applies to proteins in which one or more amino acids are chemical analogues or modified derivatives of corresponding naturally occurring amino acids.

The terms "operatively linked" or "operably linked" are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron's 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequence. For example, the product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]-[partial coding sequence 1]-[terminator 1] and a second nucleic acid having the elements [splice acceptor 2]-[partial coding sequence 2]-[terminator 2] can be placed in tail-to-tail orientation resulting in [splice acceptor 1]-[partial coding sequence 1]-[terminator 1]-[terminator 2 RC]-[partial coding sequence 2 RC]-[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC1, GAL1, GALT, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG_008198.2 and corresponding SEQ ID NO:42. The exon and intron boundaries can be defined with the sequence provided in SEQ ID NO:42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alpha1A protein. A representative sequence of the CACNA1A gene can be found with NCBI Reference Sequence: NG_011569.1 and corresponding SEQ ID NO:43. The exon and intron boundaries can be defined with the sequence provided in SEQ ID NO:43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
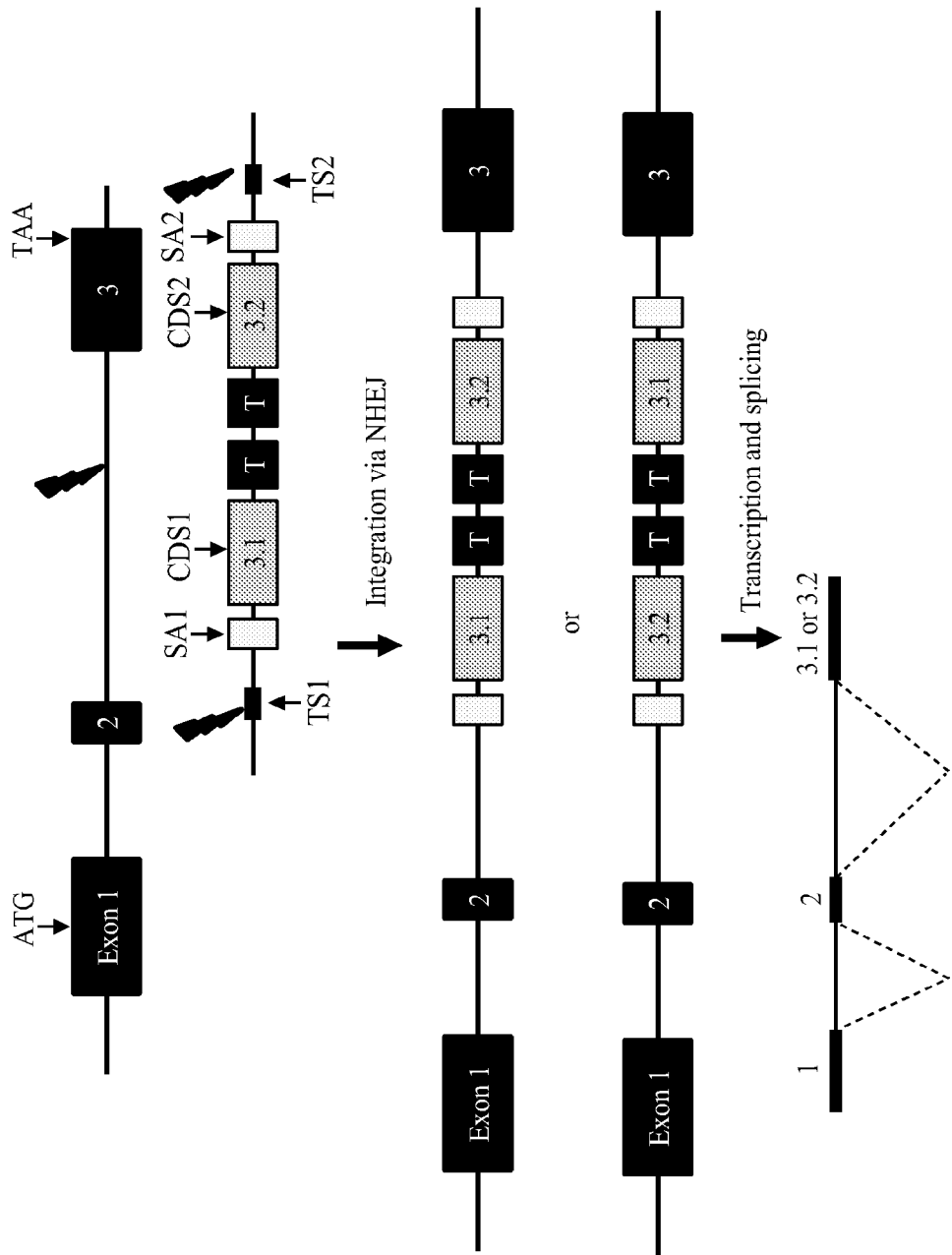
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
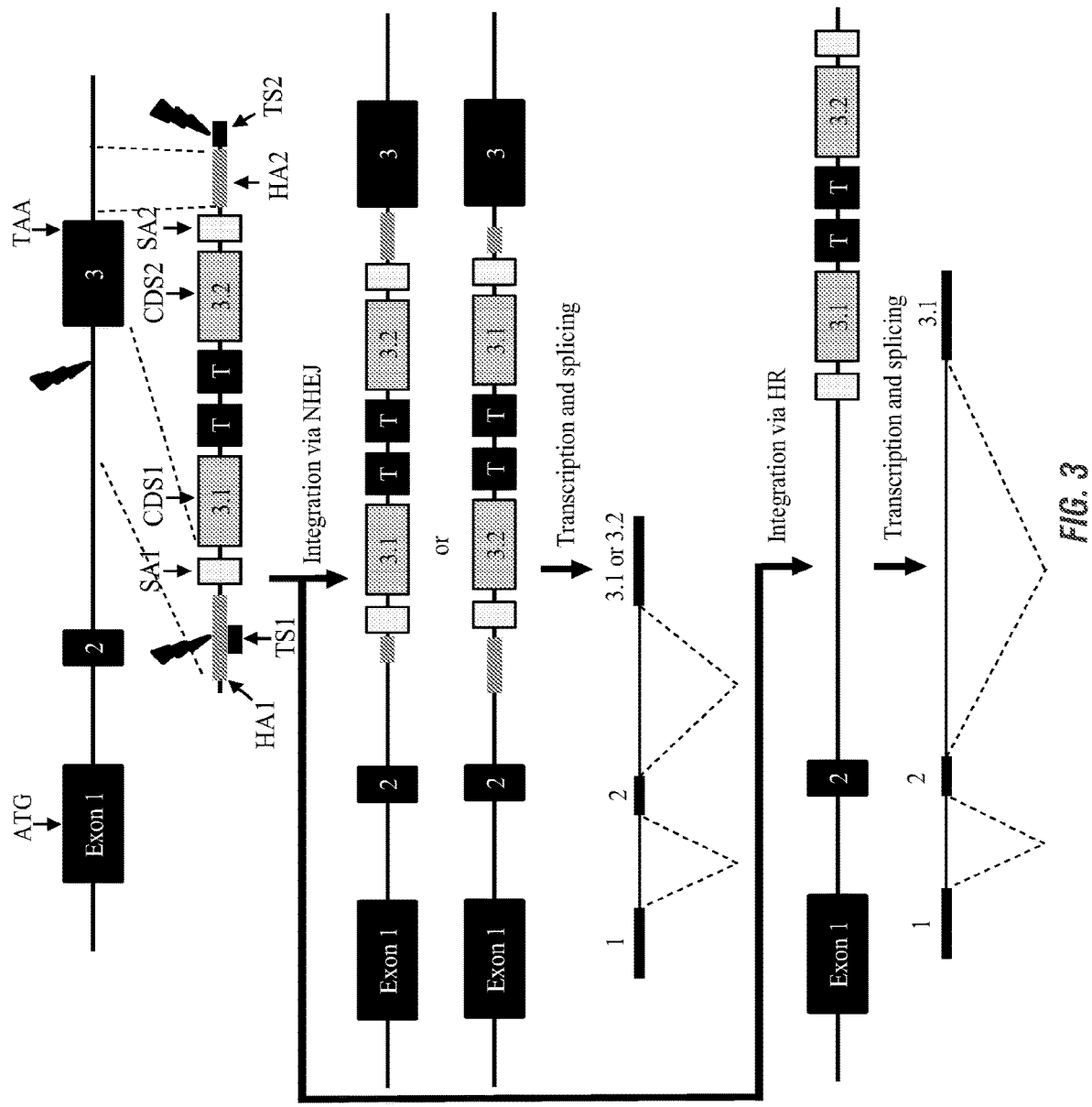
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., *Science* 10.1126/science.aax9181, 2019; Klompe et al., *Nature*, 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO:30) or *Anabaena cylindrica* (SEQ ID NO:31). In one embodiment, the transgenes described herein comprising a left (SEQ ID NO:32) and right transposon end (SEQ ID NO:33) can be delivered to cells along with ShCas12k, tnsB, tnsC, TniQ and a gRNA (SEQ ID NO:14). Alternatively, the CRISPR transposase can include the Cas6 protein, along with helper proteins including Cas7, Cas8 and TniQ. In one embodiment, the transgenes described herein comprising a left (SEQ ID NO:41) and right transposon end (SEQ ID NO:13) can be delivered to eukaryotic cells along with Cas6 (SEQ ID NO:37), Cas7 (SEQ ID NO:37), Cas8 (SEQ ID NO:37), TniQ (SEQ ID NO:37), TnsA (SEQ ID NO:37), TnsB (SEQ ID NO:37), TnsC (SEQ ID NO:37) and a gRNA (SEQ ID NO:12). The proteins can be administered to cells directly as purified protein or encoded on RNA or DNA. If encoded on RNA or DNA, the sequence can be codon optimized for expression in eukaryotic cells. The gRNA (SEQ ID NO:12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]-[partial coding sequence 1]-[terminator 1]-[terminator 2 RC]-[partial coding sequence 2 RC]-[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[rare-cutting endonuclease cleavage site 1]. In another embodiment, the combination can be, from 5' to 3', [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]-[splice acceptor 1]-[partial coding sequence 1]-[terminator 1]-[terminator 2 RC]-[partial coding sequence 2 RC]-[splice acceptor 2 RC]-[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: *achondroplasia*, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *Porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7 kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), *Herpes simplex*, pox virus, hybrid adenoviral vector, epstein-bar virus, lentivirus, or *Herpes simplex* virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, *algae*, animals, *fungi* and protists. The eukaryotic organisms can also include plant cells, *algae* cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J.

Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, *tomato*, alfalfa), fruit crops (e.g., *tomato*, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc.), flowering plants (e.g., *Petunia*, rose, *Chrysanthemum*), conifers and *pine* trees (e.g., *pine* fir, spruce); *poplar* trees (e.g. *P. tremula* x *P. alba*); fiber crops (cotton, jute, *flax, bamboo*) plants used in phytoremediation (e.g., heavy metal accumulating plants); oil crops (e.g., sunflower, rape seed) and plants used for experimental purposes (e.g., *Arabidopsis*). The methods disclosed herein can be used within the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary *algae* species include microalgae, diatoms, *Botryococcus braunii, Chlorella, Dunaliella tertiolecta, Gracileria, Pleurochrysis carterae, Sorgassum* and *Ulva*.

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpfl). The CRISPR system can include variants which display broad PAM capability (Hu et al., *Nature* 556, 57-63, 2018; Nishimasu et al., *Science DOI:* 10.1126, 2018) or higher on-target binding or cleavage activity (Kleinstiver et al., *Nature* 529:490-495, 2016). The gene editing reagent can be in the format of a nuclease (Mali et al., *Science* 339:823-826, 2013; Christian et al., *Genetics* 186:757-761, 2010), nickase (Cong et al., *Science* 339:819-823, 2013; Wu et al., *Biochemical and Biophysical Research Communications* 1:261-266, 2014), CRISPR-FokI dimers (Tsai et al., *Nature Biotechnology* 32:569-576, 2014), or paired CRISPR nickases (Ran et al., *Cell* 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1: Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO:17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO:18. The individual elements within pBA1135 are shown in SEQ ID NOS:44-51. SEQ ID NO:44 comprises the left homology arm, nuclease target site, and splice acceptor. SEQ ID NO:45 comprises the partial coding sequence (exon 10 and 11) of a non-pathogenic ATXN3 gene. SEQ ID NO:46 comprises the SV40 p(A) terminator sequence. SEQ ID NO:47 comprises the BGH terminator in reverse complement. SEQ ID NO:48 comprises the reverse complement, codon adjusted partial coding sequence (exon 10 and 11) of a non-pathogenic ATXN3 gene. SEQ ID NO:49 comprises the sequence for the splice acceptor. SEQ ID NO:50 comprises the sequence for the right homology arm. SEQ ID NO:51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO:19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO:20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
|---|---|---|
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
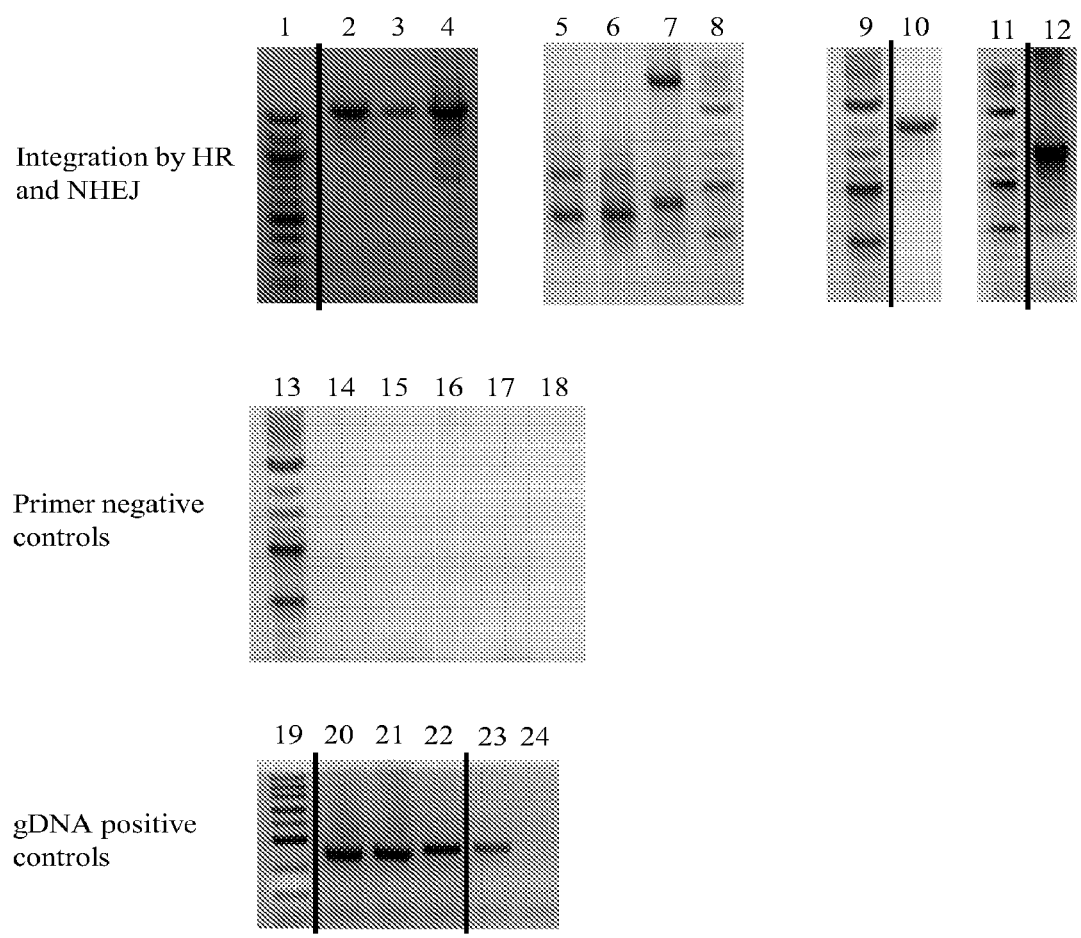
FIG. 8 are images of gels detecting integration of transgenes into the ATXN3 gene. 1, 100 bp ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1 kb ladder with darker bands running at 500 bp, 1,000 bp and 3,000 bp; 9, 1 kb ladder with darker bands running at 500 bp, 1,000 bp and 3,000 bp; 10, pBA1135 inverted 5' junction; 11, 1 kb ladder with darker bands running at 500 bp, 1,000 bp and 3,000 bp; 12, pBA1136 inverted 5' junction; 13, 1 kb ladder with darker bands running at 500 bp, 1,000 bp and 3,000 bp; 14; primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate size bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2: Targeted Integration of DNA in the CACNA1A Gene

Figure 4:
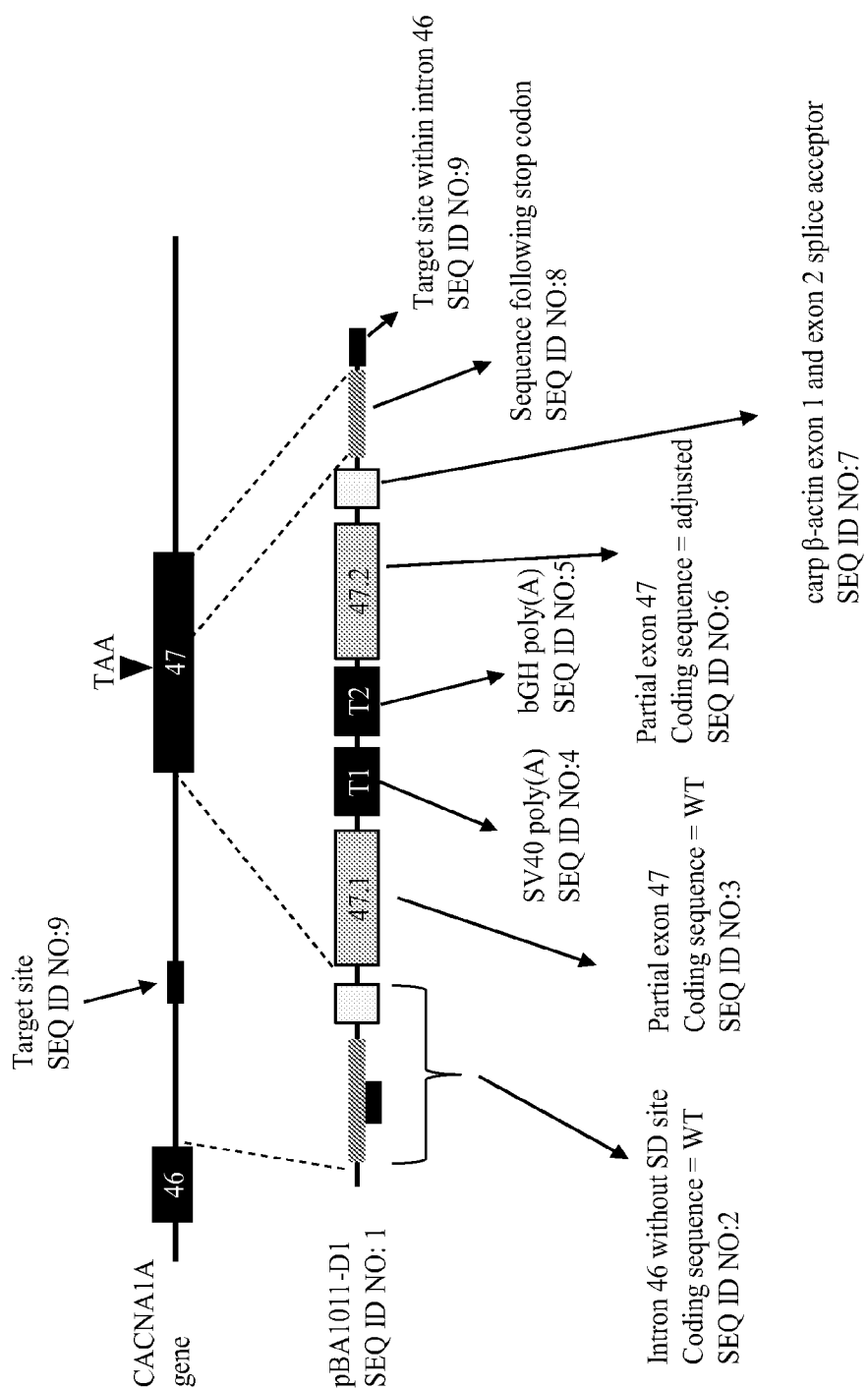
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO:9) and a splice acceptor sequence. The first homology arm is followed by a first coding sequence comprising the CACNA1A exon 47 and a non-expanded CAG repeat sequence (SEQ ID NO:3). Following the first coding sequence is a SV40 poly(A) termination sequence (SEQ ID NO:4). In a tail-to-tail orientation, a second set of functional elements is present. The beginning of the second set of elements comprises a target site for the nuclease (SEQ ID NO:9) followed by a second homology arm. The second homology arm harbors 446 bp which is homologous to sequence immediately following the stop coding (SEQ ID NO:8). This sequence was determined to be free of consensus branch or splice acceptor sequences via in silico analysis. Following the second homology arm is a second splice acceptor from carp beta-actin intron 1 (SEQ ID NO:7). Following the splice acceptor is a codon optimized version of the CACNA1A exon 47 (SEQ ID NO:6) and a bGH poly(A) terminator (SEQ ID NO:5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO:9.

Figure 5:
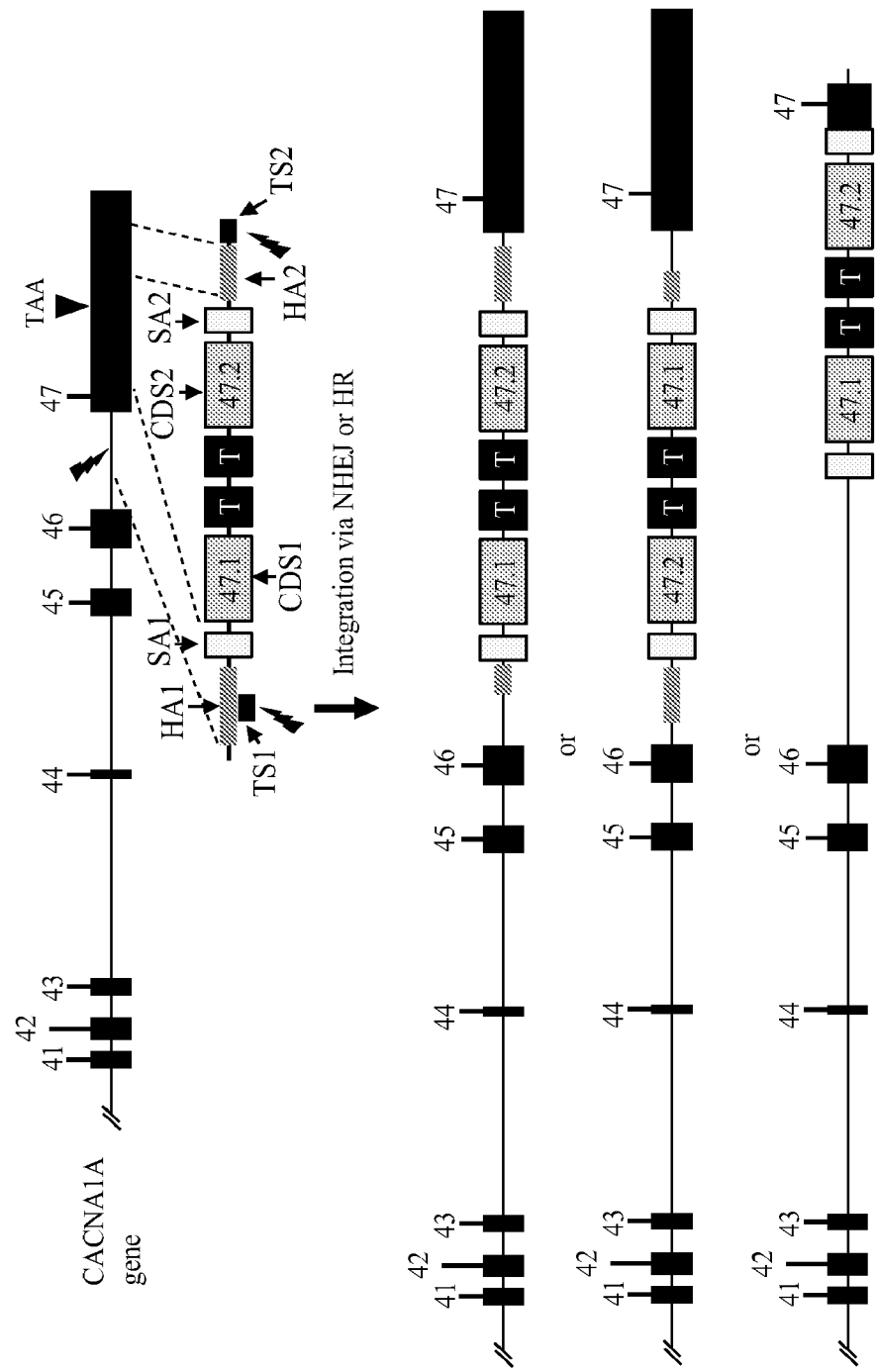
FIG. 5 is an illustration of the integration outcomes for the pB1011-D1 transgene within the CACNA1A gene.
Figure 6:
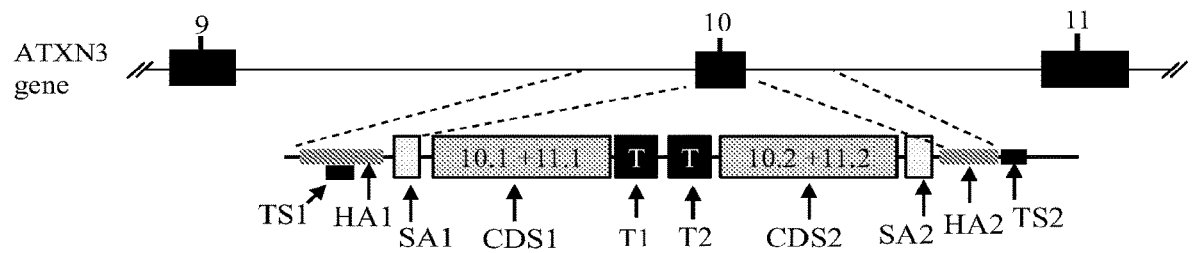
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3: Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO:10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO:11.

Figure 7:
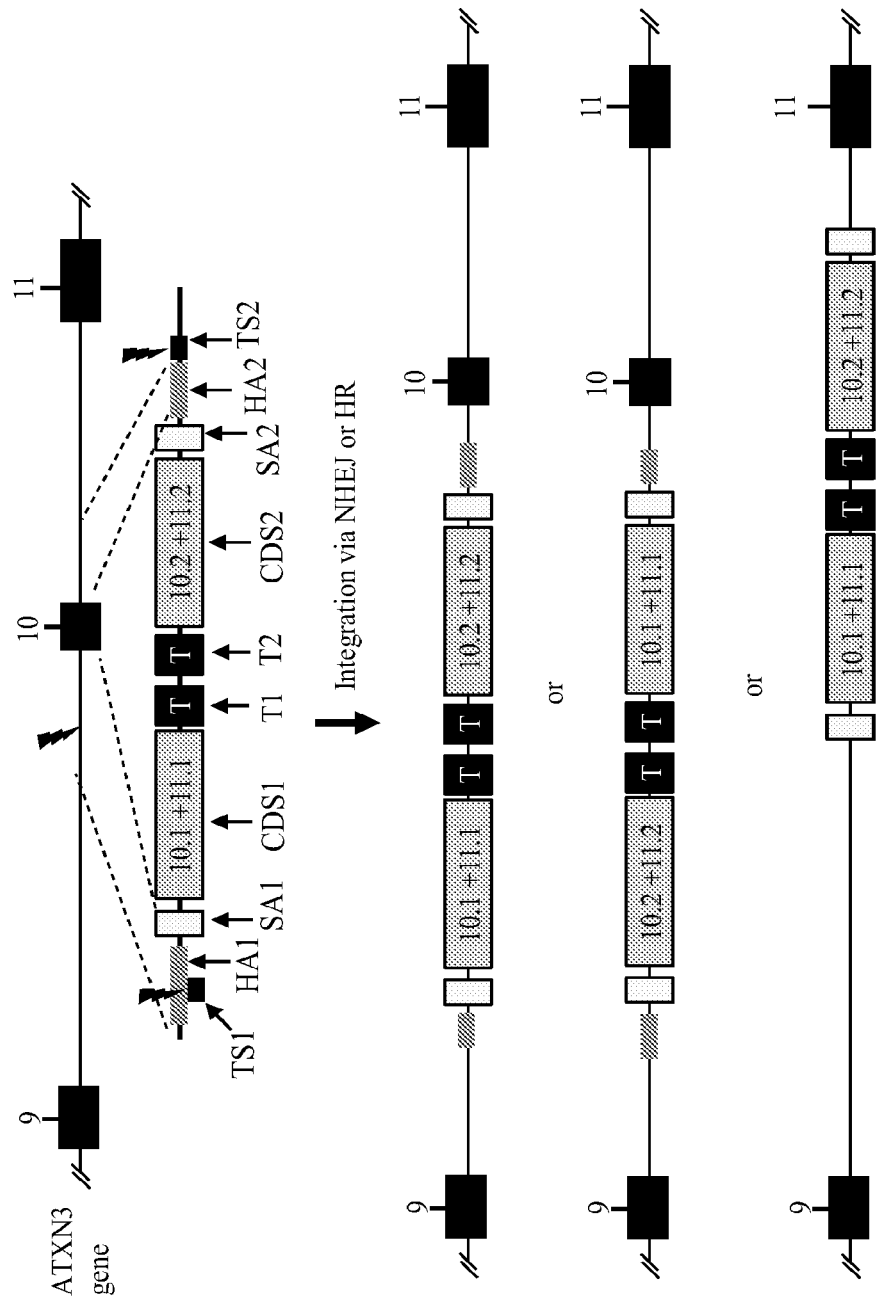
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4: Targeted Integration of DNA in the ATXN3 Gene Using Cas12k Transposases An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA targeted sequence CCGCCCGACCTTTCACTTTC (SEQ ID NO:15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5: Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA is designed to target sequence CCCGGATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant nucleic acid comprising a transgene, the transgene comprising in 5' to 3' orientation:
   a first splice acceptor, a first coding sequence, a first terminator, a second terminator reverse complement, a second coding sequence reverse complement, and a second splice acceptor reverse complement,
   wherein the first coding sequence encodes an amino acid sequence, and the second coding sequence encodes the same amino acid sequence as the first coding sequence.

2. The recombinant nucleic acid of claim 1, wherein the first coding sequence and second coding sequence comprise different polynucleotide sequences, but each encodes the same amino acid sequence.

3. A recombinant non-viral vector comprising the recombinant nucleic acid of claim 1.

4. A recombinant viral vector comprising the recombinant nucleic acid of claim 1.

5. The viral vector of claim 4, wherein the viral vector is selected from the group consisting of an adenovirus vector, an adeno-associated virus vector, and a lentivirus vector.

6. The recombinant nucleic acid of claim 1, wherein the first coding sequence and second coding sequence each encode a peptide produced by exon 10 of a non-pathogenic ATXN3 gene.

7. The recombinant nucleic acid of claim 1, wherein the first coding sequence and second coding sequence each encode a peptide produced by exon 47 of a non-pathogenic CACNA1A gene.

8. The recombinant nucleic acid of claim 1, wherein the first coding sequence and second coding sequence each encode a peptide produced by a gene selected from Factor V, Factor VII, Factor XIII, Factor IX, Factor X, Factor XI, Factor XII, Factor XIII, an LDL Receptor, and TTR.

9. The recombinant nucleic acid of claim 1, wherein the recombinant nucleic acid is equal to or less than 4.7 kb.

10. A cell comprising a transgene, wherein the transgene is integrated into an endogenous gene, said transgene comprising in 5' to 3' orientation:
   a first splice acceptor, a first coding sequence, a first terminator, a second terminator reverse complement, a second coding sequence reverse complement, and a second splice acceptor reverse complement,
   wherein the first coding sequence encodes an amino acid sequence heterologous to the cell, and the second coding sequence encodes the same heterologous amino acid sequence.

11. The cell of claim 10, wherein the first coding sequence or second coding sequence of the transgene is operably linked to a promoter of the endogenous gene.

12. The cell of claim 11, wherein the first coding sequence and second coding sequence of the transgene comprise different polynucleotide sequences, but each encodes the same heterologous amino acid sequence.

13. The cell of claim 11, wherein the first coding sequence and second coding sequence each encode a peptide selected from Factor V, Factor VII, Factor XIII, Factor IX, Factor X, Factor XI, Factor XII, Factor XIII, an LDL Receptor, and TTR.

14. The cell of claim 11, wherein the first coding sequence and second coding sequence each encode a peptide produced by exon 10 of a non-pathogenic ATXN3 gene.

15. The cell of claim 11, wherein the first coding sequence and second coding sequence each encode a peptide produced by exon 47 of a non-pathogenic CACNA1A gene.

16. A recombinant nucleic acid comprising a transgene, the transgene comprising in 5' to 3' orientation:
   a first splice acceptor, a first coding sequence, a first terminator, a second terminator reverse complement, a second coding sequence reverse complement, and a second splice acceptor reverse complement,
   wherein the first coding sequence encodes an amino acid sequence, and the second coding sequence encodes the same amino acid sequence as the first coding sequence, and
   wherein the recombinant nucleic acid is linear or circular.

17. The recombinant nucleic acid of claim 16, wherein the nucleic acid is in a circular conformation.

18. The recombinant nucleic acid of claim 16, wherein the first coding sequence and second coding sequence comprise different polynucleotide sequences, but each encodes the same amino acid sequence.

19. A viral vector comprising the recombinant nucleic acid of claim 16.

20. The viral vector of claim 19, wherein the viral vector is selected from the group consisting of an adenovirus vector, an adeno-associated virus vector, and a lentivirus vector.

* * * * *

SEQUENCE LISTING

```
<160> NUMBER OF SEQ ID NOS: 51

<210> SEQ ID NO 1
<211> LENGTH: 3527
<212> TYPE: DNA
<213> ORGANISM: Artificial Sequence
<220> FEATURE:
```

<223> OTHER INFORMATION: Construct

<400> SEQUENCE: 1

| | | | | | |
|---|---|---|---|---|---|
| gtgcggctgc | aagtgacccc | aggctgggct | cggccgggag | gcggggagga | gagaagggga | 60 |
| taccccatcc | aacagccact | ctaggcaaag | gtccccggat | cccggctgtg | accacctccc | 120 |
| atcctgcccc | caagccaccg | gggtgcccgg | cggcggagc | ggacacggat | ccccaccaca | 180 |
| ccagctgcct | atgctgtccc | cccagccccc | ttgcccaccc | gccgcccct | ccccgccgcc | 240 |
| cgcagctgct | tgctcctcgg | ttgtggatca | tatttgagtt | ctgggccgtg | ccgcccgacc | 300 |
| tttcactttc | ctttaacccg | gcttctgttt | ttgtttcaat | tatgatttct | gtcctctgga | 360 |
| cgcctgtgag | taattttga | aacttctgct | atttttaacc | ccgaaactta | caaaactcca | 420 |
| tttctcattt | ctcttttcac | tttgttgtgt | tggttttcga | ctcctcccct | ccctgtctca | 480 |
| ctccccctcc | tccctcct | cctccctgtg | gctgttgctt | ttttccattc | aatgtcctgt | 540 |
| gtcccccctc | tcctcctcct | cctcctcctc | cccctcccc | tcctccctct | cctcccggcc | 600 |
| cctctcccctt | cgctccctc | tcttcctccc | aatcccgtgt | ctcctttgat | tttgttgtat | 660 |
| cttttttttt | gatttccttt | gtttcaattt | tcgtgtaggg | cagtagttcc | gtaagtggaa | 720 |
| gcccagcccc | ctcaacatct | ggtaccagca | ctccgcggcg | gggccgccgc | cagctccccc | 780 |
| agacccctc | caccccccgg | ccacacgtgt | cctattcccc | tgtgatccgt | aaggccggcg | 840 |
| gctcggggcc | cccgcagcag | cagcagcagc | agcagcagca | gcagcagcag | caggcggtgg | 900 |
| ccaggccggg | ccgggcggcc | accagcggcc | ctcggaggta | cccaggcccc | acggccgagc | 960 |
| ctctggccga | gatcggccg | cccacggggg | gccacagcag | cggccgctcg | cccaggatgg | 1020 |
| agaggcgggt | cccaggcccg | gccggagcg | agtcccccag | ggcctgtcga | cacggcgggg | 1080 |
| cccggtggcc | ggcatctggc | ccgcacgtgt | ccgaggggcc | cccgggtccc | cggcaccatg | 1140 |
| gctactaccg | gggctccgac | tacgacgagg | ccgatggccc | gggcagcggg | ggcggcgagg | 1200 |
| aggccatggc | cggggcctac | gacgcgccac | ccccgtacg | acacgcgtcc | tcgggcgcca | 1260 |
| ccgggcgctc | gcccaggact | ccccgggcct | cgggcccggc | ctgcgcctcg | ccttctcggc | 1320 |
| acggccggcg | actccccaac | ggctactacc | cggcgcacgg | actggccagg | ccccgcgggc | 1380 |
| cgggctccag | gaagggcctg | cacgaaccct | acagcgagag | tgacgatgat | tggtgctaaa | 1440 |
| acttgtttat | tgcagcttat | aatggttaca | aataaagcaa | tagcatcaca | aatttcacaa | 1500 |
| ataaagcatt | tttttcactg | cattctagtt | gtggtttgtc | caaactcatc | aatgtatctt | 1560 |
| atcatgtctg | gatctcccca | gcatgcctgc | tattctcttc | ccaatcctcc | cccttgctgt | 1620 |
| cctgccccac | cccaccccc | agaatagaat | gacacctact | cagacaatgc | gatgcaatt | 1680 |
| cctcattta | ttaggaaagg | acagtgggag | tggcaccttc | cagggtcaag | gaaggcacgg | 1740 |
| gggaggggca | aacaacagat | ggctggcaac | tagaaggcac | agtcagcacc | agtcgtcgtc | 1800 |
| ggattcgctg | tagggttcat | ggagacccct | ccgagaccca | ggtcctcttg | gccgggccaa | 1860 |
| gccgtgtgca | gggtaatatc | cattgggag | cctccggcca | tgccgagaag | gtgaagcgca | 1920 |
| cgctggtcct | gacgcccggg | gggtgcgagg | agacctccct | gtcgcccgg | aagacgcatg | 1980 |
| cctaacggga | ggcggagcat | cataagcacc | agccatcgct | tcctcgccac | caccactgcc | 2040 |
| gggcccgtca | gcttcgtcat | agtcagaacc | ccgataatat | ccgtgatggc | gaggccctgg | 2100 |
| aggtccttcg | ctaacgtgtg | gcccagaagc | aggccaccgc | gcacctccat | ggcgacatgc | 2160 |
| tctaggactc | tcgcttcttg | caggtccagg | aacccgccgc | tccattgcg | ggcttcgccc | 2220 |
| actactgtgt | ccacctgtcg | gagggcggtc | tccggcaagg | ggttcagcgg | ttgggcctgg | 2280 |

```
atagcgccgc ggaccggagg tagcagcccg accgggtcgt gctaccgctt gctgttgctg    2340
ttgttgctgt tgctgctgtt gttgttgggg tggcccgcta cctcccgctt ttctaataac    2400
tggtgaataa ctcacatgtg ggcgcggagt ggatggtgtc tgagggagtt gccttctccc    2460
tcggcggggt gtagacgtac cagatgttga aggcgccggg ctcccgctta ctgaactact    2520
gtaaatgaat gagaaaaccg gtttagaaag tgcacagctg tcaggaagt caacacttca     2580 gtgagcatgt gaccatgtgg agtcagcttc ctgtttcgtg ctgcaatcgc ccgggcgagg    2640
tggcgcccgc ccggcccccc acgcaccccca cgcacacacc ccacccgagg agccgcgcag   2700
aggccgcggg ggcccagcac agagggcccg ggagagggcc agccgggaga ccccagactc    2760
tggagaggcc agggctgggc cacaagggtg tcccgcagag accctcggcc aaaagagacc    2820
ctcctgggca gccacggcgc ccccaacca gccccgatcc ccccacccac gacagggct      2880 ctcgggtggg aggcagggag cagacaaacc acacagccaa gggatttgaa ttaactcagc    2940
cattttggga gaactttggg gaacatgaaa aaaaaaaaaa aaaaaaaaaa aaaaaacatt    3000
tttaaaagaa aaaacgggga gaaaaaaata gcttctattg atgagtttta tcatctcaat    3060
tgaatctttc ctttccctga tgaagacagc tggtggccga gtgcggcaaa gaagccagaa    3120
ggaaccagaa tcccagtgcc ctacacccac caccagacac actcacaccc acacgttc     3180 tcagacacac acaagagtgc ttgccggtta taccaaaccc tactattact gcctgcagaa    3240
atcaatttaa aaaataata ataacaataa acaattttaa aaaggacaaa aaaattaatg     3300
attgagaaaa gaggcatttt tttctgacat ttggtcctgc ttgaaacaac aaaagaagaa    3360
gaaaaaccca ccatcaccac cgattccttt gcttcttttt tccttttttc ctaccttgtt    3420
tgaaaaccgt gggcttggga ctgtgaatta ttgcatgaca ttcaaaaaga aaaaaaaat    3480 aaaaaaagt tgaatcaaat ttctgtcctc tggacgcctg tgagtaa                   3527
```

<210> SEQ ID NO 2  
<211> LENGTH: 703  
<212> TYPE: DNA  
<213> ORGANISM: Artificial Sequence  
<220> FEATURE:  
<223> OTHER INFORMATION: Construct

<400> SEQUENCE: 2

```
gtgcggctgc aagtgacccc aggctgggct cggccgggag gcggggagga gagaagggga    60
taccccatcc aacagccact ctaggcaaag gtccccggat cccggctgtg accacctccc    120
atcctgccct caagccaccg gggtgccggg cggccggagc ggacacggat ccccaccaca    180
ccagctgcct atgctgtccc cccagccccc ttgcccaccc gccgcccct ccccgccgcc     240 cgcagctgct tgctcctcgg ttgtggatca tatttgagtt ctgggccgtg ccgcccgacc    300
tttcactttc cttaaccccg gcttctgttt ttgtttcaat tatgatttct gtcctctgga    360
cgcctgtgag taattttga acttctgct atttttaacc ccgaaactta caaaactcca     420
tttctcattt ctcttttcac tttgttgtgt tggttttcga ctcctcccct ccctgtctca    480 ctcccccctcc tccctccct cctccctgtg gctgttgctt ttttccattc aatgtcctgt    540
gtcccccctc tcctcctcct cctcctcctc ccctccccc tcctccctct cctcccggcc    600 cctctcccctt cgctcccctc tcttcctccc aatcccgtgt ctcctttgat tttgttgtat    660
cttttttttt gatttccttt gtttcaattt tcgtgtaggg cag                      703
```

<210> SEQ ID NO 3

<211> LENGTH: 736
<212> TYPE: DNA
<213> ORGANISM: Artificial Sequence
<220> FEATURE:
<223> OTHER INFORMATION: Construct

<400> SEQUENCE: 3

```
tagttccgta agtggaagcc cagcccctc  aacatctggt accagcactc cgcggcgggg      60
ccgccgccag ctccccccaga cccctccac  ccccggcca cacgtgtcct attccctgt      120
gatccgtaag gccggcggct cggggcccc   gcagcagcag cagcagcagc agcagcagca    180
gcagcagcag gcggtggcca ggccgggccg  ggcggccacc agcggccctc ggaggtaccc    240
aggccccacg gccgagcctc tggccggaga  tcggccgccc acgggggcc  acagcagcgg    300
ccgctcgccc aggatggaga ggcgggtccc  aggcccggcc cggagcgagt ccccccaggg   360
ctgtcgacac ggcggggccc ggtggccggc  atctggcccg cacgtgtccg aggggccccc    420
gggtccccgg caccatggct actaccgggg  ctccgactac gacgaggccg atggcccggg    480
cagcggggc  ggcgaggagg ccatggccgg  ggcctacgac gcgccacccc ccgtacgaca    540
cgcgtcctcg ggcgccaccg ggcgctcgcc  caggactccc cgggcctcgg gcccggcctg    600
cgcctcgcct tctcggcacg gccggcgact  ccccaacggc tactacccgg cgcacggact    660
ggccaggccc cgcgggccgg gctccaggaa  gggcctgcac gaaccctaca gcgagagtga    720
cgatgattgg tgctaa                                                     736
```

<210> SEQ ID NO 4
<211> LENGTH: 135
<212> TYPE: DNA
<213> ORGANISM: Artificial Sequence
<220> FEATURE:
<223> OTHER INFORMATION: Construct

<400> SEQUENCE: 4

```
aacttgttta ttgcagctta taatggttac aaataaagca atagcatcac aaatttcaca     60
aataaagcat ttttttcact gcattctagt tgtggtttgt ccaaactcat caatgtatct    120
tatcatgtct ggatc                                                     135
```

<210> SEQ ID NO 5
<211> LENGTH: 208
<212> TYPE: DNA
<213> ORGANISM: Artificial Sequence
<220> FEATURE:
<223> OTHER INFORMATION: Construct

<400> SEQUENCE: 5

```
tccccagcat gcctgctatt ctcttcccaa tcctcccct  tgctgtcctg ccccacccca     60
cccccagaa  tagaatgaca cctactcaga caatgcgatg caatttcctc attttattag    120
gaaaggacag tgggagtggc accttccagg gtcaaggaag gcacggggga ggggcaaaca    180
acagatggct ggcaactaga aggcacag                                        208
```

<210> SEQ ID NO 6
<211> LENGTH: 736
<212> TYPE: DNA
<213> ORGANISM: Artificial Sequence
<220> FEATURE:
<223> OTHER INFORMATION: Construct

<400> SEQUENCE: 6

```
tcagcaccag tcgtcgtcgg attcgctgta gggttcatgg agacccttcc gagacccagg     60
```

```
tcctcttggc cgggccaagc cgtgtgcagg gtaatatcca ttggggagcc tccggccatg    120
ccgagaaggt gaagcgcacg ctggtcctga cgcccggggg gtgcgaggag acctccctgt    180
cgccccggaa gacgcatgcc taacgggagg cggagcatca taagcaccag ccatcgcttc    240
ctcgccacca ccactgccgg gcccgtcagc ttcgtcatag tcagaacccc gataatatcc    300
gtgatggcga ggccctggag gtccttcgct aacgtgtggc ccagaagcag gccaccgcgc    360
acctccatgg cgacatgctc taggactctc gcttcttgca ggtccaggaa cccgccgctc    420
cattcgcggg cttcgcccac tactgtgtcc acctgtcgga gggcggtctc cggcaagggg    480
ttcagcggtt gggcctggat agcgccgcgg accggaggta gcagcccgac cgggtcgtgc    540
taccgcttgc tgttgctgtt gttgctgttg ctgctgttgt tgttggggtg gcccgctacc    600
tcccgctttt ctaataactg gtaataact cacatgtggg cgcggagtgg atggtgtctg    660
agggagttgc cttctccctc ggcggggtgt agacgtacca gatgttgaag gcgccgggct    720
cccgcttact gaacta                                                   736

<210> SEQ ID NO 7
<211> LENGTH: 110
<212> TYPE: DNA
<213> ORGANISM: Artificial Sequence
<220> FEATURE:
<223> OTHER INFORMATION: Construct

<400> SEQUENCE: 7
ctgtaaatga atgagaaaac cggtttagaa agtgcacagc tgtcagggaa gtcaacactt     60
cagtgagcat gtgaccatgt ggagtcagct tcctgtttcg tgctgcaatc                110

<210> SEQ ID NO 8
<211> LENGTH: 446
<212> TYPE: DNA
<213> ORGANISM: Artificial Sequence
<220> FEATURE:
<223> OTHER INFORMATION: Construct

<400> SEQUENCE: 8
gcccgggcga ggtggcgccc gcccggcccc ccacgcaccc cacgcacaca ccccacccga     60
ggagccgcgc agaggccgcg ggggcccagc acagagggcc cgggagaggg ccagccggga    120
gaccccagac tctggagagg ccagggctgg gccacaaggg tgtcccgcag agaccctcgg    180
ccaaaagaga ccctcctggg cagccacggc gccccccaac cagccccgat ccccccaccc    240
acgacagggg ctctcgggtg ggaggcaggg agcagacaaa ccacacagcc aagggatttg    300
aattaactca gccattttg gagaactttg gggaacatga aaaaaaaaa aaaaaaaaa      360 aaaaaaaca ttttaaaag aaaaaacggg gagaaaaaaa tagcttctat tgatgagttt    420
tatcatctca attgaatctt cctttt                                       446

<210> SEQ ID NO 9
<211> LENGTH: 24
<212> TYPE: DNA
<213> ORGANISM: Artificial Sequence
<220> FEATURE:
<223> OTHER INFORMATION: Target site

<400> SEQUENCE: 9
tttctgtcct ctggacgcct gtga                                          24

<210> SEQ ID NO 10
```

<211> LENGTH: 2288
<212> TYPE: DNA
<213> ORGANISM: Artificial Sequence
<220> FEATURE:
<223> OTHER INFORMATION: Construct

<400> SEQUENCE: 10

| | | | | | |
|---|---|---|---|---|---|
| atttcattta | tcaggtgttc | agtgaatgct | tactatgtaa | cagcacagtt | atcagcactg | 60 |
| gggaaataga | tgagtaagat | aagatttgca | ctttcattag | cttacatgcc | ataaagaggg | 120 |
| aaataaagag | aacaccagat | gatgataagt | ttatgctgag | aattaaaatg | aagtgatgaa | 180 |
| ataatgggaa | tgtcaggtgg | ctactttggg | tgggatggtc | aggaaaggca | tctctgggga | 240 |
| gataaatttt | aagctcagac | ctgagtgaaa | agaatgagcc | agccatggaa | acattatgtt | 300 |
| aactcacatg | gtagtttgaa | atgctttatc | tgatcaaagg | tacttatttt | tggtgacttt | 360 |
| caacaatatt | aagggtctat | aaaccaacac | tcatttgcat | aagaataact | accagtgaat | 420 |
| cttttttgtat | gataggtttt | ttgtttgttg | ttttttttgag | acagagtctc | gctctgtcgc | 480 |
| ccaggctgga | gtgcagtggc | gcgatcttgg | ctcactgcaa | cctctacctc | cccggttcaa | 540 |
| gtgattctcc | tgcctcagcc | tcccaaagta | gctgggatta | caggtgcctg | ccaccacgcc | 600 |
| tggctaattt | ttgtattttt | agtagagatg | gggtttcacc | gtgttgtcca | ggctcgtgtc | 660 |
| aaacttctga | cctcaagcca | tccacccgcc | tcggcctccc | aaagtgctgg | gattacaggt | 720 |
| gtgagccacc | actcctggcc | atgataggtt | attttgtgat | gaaataccct | acctcttaat | 780 |
| ttgtctgata | aatttaaatt | ttatgtctag | atttcctaag | atcagcactt | ccatatttta | 840 |
| aagtaatctg | tatcagacta | actgctcttg | cattcttta | ataccagtga | ctactttgat | 900 |
| tcgtgaaaca | atgtattttc | cttatgaata | gtttttctca | tggtgtattt | attcttttaa | 960 |
| gttttgttttt | taaatatac | ttcacttttg | aatgtttcag | acagcagcaa | aagcagcaac | 1020 |
| agcagcagca | gcagcagcag | caggggggacc | tatcaggaca | gagttcacat | ccatgtgaaa | 1080 |
| ggccagccac | cagttcagga | gcactggga | gtgatctagg | tgatgctatg | agtgaagaag | 1140 |
| acatgcttca | ggcagctgtg | accatgtctt | tagaaactgt | cagaaatgat | ttgaaaacag | 1200 |
| aaggaaaaaa | ataaaacttg | tttattgcag | cttataatgg | ttacaaataa | agcaatagca | 1260 |
| tcacaaattt | cacaaataaa | gcatttttt | cactgcattc | tagttgtggt | ttgtccaaac | 1320 |
| tcatcaatgt | atcttatcat | gtctggatct | ccccagcatg | cctgctattc | tcttcccaat | 1380 |
| cctccccctt | gctgtcctgc | cccaccccac | ccccagaat | agaatgacac | ctactcagac | 1440 |
| aatgcgatgc | aatttcctca | ttttattagg | aaaggacagt | gggagtggca | ccttccaggg | 1500 |
| tcaaggaagg | cacgggggag | gggcaaacaa | cagatggctg | gcaactagaa | ggcacagcta | 1560 |
| cttcttgccc | tcggtcttca | ggtcgttgcg | cacggtctcc | aggctcatgg | tcacggcggc | 1620 |
| ctgcagcatg | tcctcctcgc | tcatggcgtc | gcccaggtcg | ctgcccaggg | cgccgctgct | 1680 |
| ggtggcgggg | cgctcgcagg | ggtggctgct | ctggccgctc | aggtcgccct | gctgctgctg | 1740 |
| ctgctgctgc | tgctgctgct | tctgctgctg | tctgtaaatg | aatgagaaaa | ccggtttaga | 1800 |
| aagtgcacag | ctgtcaggga | agtcaacact | tcagtgagca | tgtgaccatg | tggagtcagc | 1860 |
| ttcctgtttc | gtgctgcaat | cgtaaggcct | gctcaccatt | catcatgttc | gctaccttca | 1920 |
| cactttatct | gacatacgag | ctccatgtga | tttttgcttt | acattattct | tcattccctc | 1980 |
| tttaatcata | ttaagaatct | taagtaaatt | tgtaatctac | taaatttccc | tggattaagg | 2040 |
| agcagttacc | aaaagaaaaa | aaaaaaaaaa | agctagatgt | ggtggctcac | atctgtaatc | 2100 |
| ccagcacttt | gggaaaccaa | ggcaggagag | gattgctaga | acatttaatg | aatactttaa | 2160 |

```
cataataatt taaacttcac agtaatttgt acagtctcca aaaattcctt agacatcatg    2220
gatatttttc ttttttgag atggagtctt gctctgtcac tttgagacag agtctcgctc    2280
tgtcgccc                                                            2288

<210> SEQ ID NO 11
<211> LENGTH: 24
<212> TYPE: DNA
<213> ORGANISM: Artificial Sequence
<220> FEATURE:
<223> OTHER INFORMATION: Target site

<400> SEQUENCE: 11
tttgagacag agtctcgctc tgtc                                            24

<210> SEQ ID NO 12
<211> LENGTH: 60
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (9)..(40)
<223> OTHER INFORMATION: n is a, c, g, or t

<400> SEQUENCE: 12
ctgataacnn nnnnnnnnnn nnnnnnnnnn nnnnnnnnnn gtgaactgcc gagtaggtag     60

<210> SEQ ID NO 13
<211> LENGTH: 47
<212> TYPE: DNA
<213> ORGANISM: Vibrio cholerae

<400> SEQUENCE: 13
aattatcaat ttatgggtgt aattatcatt ttatggttgt atcaaca                   47

<210> SEQ ID NO 14
<211> LENGTH: 258
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (236)..(258)
<223> OTHER INFORMATION: n is a, c, g, or t

<400> SEQUENCE: 14
tattaatagc gccgcaattc atgctgcttg cagcctctga attttgttaa atgagggtta     60
gtttgactgt ataatacag tcttgctttc tgaccctggt agctgctcac cctgatgctg    120
ctgtcaatag acaggatagg tgcgctccca gcaataaggg cgcggatgta ctgctgtagt    180
ggctactgaa tcaccccga tcaaggggga accctccaaa aggtgggttg aaagtnnnnn    240
nnnnnnnnnn nnnnnnnn                                                  258

<210> SEQ ID NO 15
<211> LENGTH: 20
<212> TYPE: DNA
<213> ORGANISM: Artificial Sequence
<220> FEATURE:
<223> OTHER INFORMATION: Target site

<400> SEQUENCE: 15
```
ccgcccgacc tttcactttc                                                    20

<210> SEQ ID NO 16
<211> LENGTH: 20
<212> TYPE: DNA
<213> ORGANISM: Artificial Sequence
<220> FEATURE:
<223> OTHER INFORMATION: Target site

<400> SEQUENCE: 16
cccggatccc ggctgtgacc                                                    20

<210> SEQ ID NO 17
<211> LENGTH: 2391
<212> TYPE: DNA
<213> ORGANISM: Artificial Sequence
<220> FEATURE:
<223> OTHER INFORMATION: Construct

<400> SEQUENCE: 17
atttcattta tcaggtgttc agtgaatgct tactatgtaa cagcacagtt atcagcactg        60
gggaaataga tgagtaagat aagatttgca ctttcattag cttacatgcc ataaagaggg       120
aaataaagag aacaccagat gatgataagt ttatgctgag aattaaaatg aagtgatgaa       180
ataatgggaa tgtcaggtgg ctactttttgg tgggatggtc aggaaaggca tctctgggga      240
gataaatttt aagctcagac ctgagtgaaa agaatgagcc agccatggaa acattatgtt       300
aactcacatg gtagtttgaa atgctttatc tgatcaaagg tacttatttt tggtgacttt       360
caacaatatt aagggtctat aaaccaacac tcatttgcat aagaataact accagtgaat       420
cttttttgtat gataggtttt ttgtttgttg tttttttgag acagagtctc gctctgtcgc      480
ccaggctgga gtgcagtggc gcgatcttgg ctcactgcaa cctctacctc cccggttcaa       540
gtgattctcc tgcctcagcc tcccaaagta gctgggatta caggtgcctg ccaccacgcc       600
tggctaattt ttgtattttt agtagagatg gggtttcacc gtgttgtcca ggctcgtgtc       660
aaacttctga cctcaagcca tccacccgcc tcggcctccc aaagtgctgg gattacaggt       720
gtgagccacc actcctggcc atgataggtt atttttgtgat gaaaatacct acctcttaat      780
ttgtctgata aatttaaatt ttatgtctag atttcctaag atcagcactt ccatatttta       840
aagtaatctg tatcagacta actgctcttg cattcttttta ataccagtga ctactttgat     900
tcgtgaaaca atgtatttc cttatgaata gttttttctca tggtgtattt attcttttaa      960
gttttgttttt ttaaatatac ttcacttttg aatgtttcag acagcagcaa aagcagcaac    1020
agcagcagca gcagcagcag caggggggacc tatcaggaca gagttcacat ccatgtgaaa   1080
ggccagccac cagttcagga gcacttggga gtgatctagg tgatgctatg agtgaagaag    1140
acatgcttca ggcagctgtg accatgtctt tagaaactgt cagaaatgat ttgaaaacag    1200
aaggaaaaaa ataaaacttg tttattgcag cttataatgg ttacaaataa agcaatagca    1260
tcacaaattt cacaaataaa gcatttttttt cactgcattc tagttgtggt ttgtccaaac    1320
tcatcaatgt atcttatcat gtctggatct ccccagcatg cctgctattc tcttcccaat    1380
cctcccccctt gctgtcctgc cccacccac ccccagaat agaatgacac ctactcagac     1440
aatgcgatgc aatttcctca ttttattagg aaaggacagt gggagtggca ccttccaggg    1500
tcaaggaagg cacggggggag gggcaaacaa cagatggctg caactagaa ggcacagcta     1560
cttcttgccc tcggtcttca ggtcgttgcg cacggtctcc aggctcatgg tcacggcggc    1620
ctgcagcatg tcctcctcgc tcatggcgtc gcccaggtcg ctgcccaggg cgccgctgct    1680

-continued

```
ggtggcgggg cgctcgcagg ggtggctgct ctggccgctc aggtcgccct gctgctgctg    1740
ctgctgctgc tgctgctgct tctgctgctg tctgtaaatg aatgagaaaa ccggtttaga    1800
aagtgcacag ctgtcaggga agtcaacact tcagtgagca tgtgaccatg tggagtcagc    1860
ttcctgtttc gtgctgcaat cgtaaggcct gctcaccatt catcatgttc gctaccttca    1920
cactttatct gacatacgag ctccatgtga tttttgcttt acattattct tcattccctc    1980
tttaatcata ttaagaatct taagtaaatt tgtaatctac taaatttccc tggattaagg    2040
agcagttacc aaaagaaaaa aaaaaaaaaa agctagatgt ggtggctcac atctgtaatc    2100
ccagcacttt gggaaaccaa ggcaggagag gattgctaga acatttaatg aatactttaa    2160
cataataatt taaacttcac agtaatttgt acagtctcca aaaattcctt agacatcatg    2220
gatatttttc tttttttgag atggagtctt gctcttttaa gctcagacct gagtgaaaag    2280
aatttgagac agagtctcgc tctgtcgcct ttcctaagat cagcacttcc atatttggtg    2340
actttcaaca atattaaggg tctataaacc aacactcatt tgcataagaa t             2391
```

<210> SEQ ID NO 18
<211> LENGTH: 20
<212> TYPE: DNA
<213> ORGANISM: Artificial Sequence
<220> FEATURE:
<223> OTHER INFORMATION: Target site

<400> SEQUENCE: 18

```
aatatggaag tgctgatctt                                                  20
```

<210> SEQ ID NO 19
<211> LENGTH: 1205
<212> TYPE: DNA
<213> ORGANISM: Artificial Sequence
<220> FEATURE:
<223> OTHER INFORMATION: Construct

<400> SEQUENCE: 19

```
tttaagctca gacctgagtg aaaagaattt gagacagagt ctcgctctgt cgcctttcct      60
aagatcagca cttccatatt ttaaagtaat ctgtatcaga ctaactgctc ttgcattctt     120
ttaataccag tgactacttt gattcgtgaa acaatgtatt ttccttatga atagtttttc     180
tcatggtgta tttattcttt taagtttgt ttttaaata tacttcactt ttgaatgttt      240
cagacagcag caaaagcagc aacagcagca gcagcagcag cagcagggg acctatcagg     300 acagagttca catccatgtg aaaggccagc caccagttca ggagcacttg ggagtgatct     360
aggtgatgct atgagtgaag aagacatgct tcaggcagct gtgaccatgt ctttagaaac     420
tgtcagaaat gatttgaaaa cagaaggaaa aaaataaaac ttgtttattg cagcttataa     480
tggttacaaa taaagcaata gcatcacaaa tttcacaaat aaagcatttt tttcactgca     540
ttctagttgt ggtttgtcca aactcatcaa tgtatcttat catgtctgga tctccccagc     600
atgcctgcta ttctcttccc aatcctcccc cttgctgtcc tgccccaccc cacccccag     660 aatagaatga cacctactca gacaatgcga tgcaatttcc tcattttatt aggaaaggac    720
agtgggagtg gcaccttcca gggtcaagga aggcacgggg gaggggcaaa caacagatgg    780
ctggcaacta gaaggcacag ctacttcttg ccctcggtct tcaggtcgtt gcgcacggtc    840
tccaggctca tggtcacggc ggcctgcagc atgtcctcct cgtcatggc gtcgcccagg    900 tcgctgccca gggcgccgct gctggtggcg ggcgctcgc aggggtggct gctctggccg    960
```

```
ctcaggtcgc cctgctgctg ctgctgctgc tgctgctgct gcttctgctg ctgtctgtaa    1020
atgaatgaga aaaccggttt agaaagtgca cagctgtcag ggaagtcaac acttcagtga    1080
gcatgtgacc atgtggagtc agcttcctgt ttcgtgctgc aatctttaag ctcagacctg    1140
agtgaaaaga atttgagaca gagtctcgct ctgtcgcctt tcctaagatc agcacttcca    1200
tattt                                                                 1205
```

<210> SEQ ID NO 20
<211> LENGTH: 1723
<212> TYPE: DNA
<213> ORGANISM: Artificial Sequence
<220> FEATURE:
<223> OTHER INFORMATION: Construct

<400> SEQUENCE: 20

```
atttcattta tcaggtgttc agtgaatgct tactatgtaa cagcacagtt atcagcactg      60
gggaaataga tgagtaagat aagatttgca ctttcattag cttacatgcc ataagagggg     120
aaataaagag aacaccagat gatgataagt ttatgctgag aattaaaatg aagtgatgaa     180
ataatgggaa tgtcaggtgg ctacttttgg tgggatggtc aggaaaggca tctctgggga     240
gataaatttt aagctcagac ctgagtgaaa agaatgagcc agccatggaa acattatgtt     300
aactcacatg gtagtttgaa atgctttatc tgatcaaagg tacttatttt tggtgacttt     360
caacaatatt aagggtctat aaaccaacac tcatttgcat aagaataact accagtgaat     420 cttttttgtat gataggtttt ttgtttgttg tttttttgag acagagtctc gctctgtcgc     480
ccaggctgga gtgcagtggc gcgatcttgg ctcactgcaa cctctacctc cccggttcaa     540
gtgattctcc tgcctcagcc tcccaaagta gctgggatta caggtgcctg ccaccacgcc     600
tggctaattt ttgtattttt agtagagatg gggtttcacc gtgttgtcca ggctcgtgtc     660
aaacttctga cctcaagcca tccacccgcc tcggcctccc aaagtgctgg gattacaggt     720
gtgagccacc actcctggcc atgataggtt attttgtgat gaaatacct acctcttaat      780 ttgtctgata aatttaaatt ttatgtctag aaatcctaag atcagcactt ccatatttta     840
aagtaatctg tatcagacta actgctcttg cattcttta ataccagtga ctactttgat      900
tcgtgaaaca atgtattttc cttatgaata gttttttctca tggtgtattt attcttttaa    960 gttttgttt ttaaatatac ttcacttttg aatgttcag acagcagcaa aagcagcaac      1020
agcagcagca gcagcagcag caggggggacc tatcaggaca gagttcacat ccatgtgaaa   1080
ggccagccac cagttcagga gcacttggga gtgatctagg tgatgctatg agtgaagaag    1140
acatgcttca ggcagctgtg accatgtctt tagaaactgt cagaaatgat ttgaaaacag    1200
aaggaaaaaa ataaaacttg tttattgcag cttataatgg ttacaaataa agcaatagca    1260
tcacaaattt cacaaataaa gcatttttt cactgcattc tagttgtggt ttgtccaaac     1320
tcatcaatgt atcttatcat gtctggatcg taaggcctgc tcaccattca tcatgttcgc    1380
taccttcaca ctttatctga catacgagct ccatgtgatt tttgctttac attattcttc    1440
attccctctt taatcatatt aagaatctta agtaaatttg taatctacta aatttccctg    1500
gattaaggag cagttaccaa aagaaaaaaa aaaaaaaaag ctagatgtgg tggctcacat    1560
ctgtaatccc agcactttgg gaaaccaagg caggagagga ttgctagaac atttaatgaa    1620
tactttaaca taataattta aacttcacag taatttgtac agtctccaaa aattccttag    1680
acatcatgga tattttctt tttttgagat ggagtcttgc tct                       1723
```

```
<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
caaaggtgcc cttgaggtt                                                  19

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aggagaagtc tgccgttact                                                 20

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ggacaaacca caactagaat gc                                              22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
taggaaagga cagtgggagt                                                 20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
ccattatgtc tcagttgttc agtg                                            24

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ccagaccatc tcagacacc                                                  19

<210> SEQ ID NO 27
<211> LENGTH: 18
<212> TYPE: DNA
<213> ORGANISM: Artificial Sequence
<220> FEATURE:
<223> OTHER INFORMATION: Primer
```

-continued

```
<400> SEQUENCE: 27
ggctgggctt ccacttac                                                   18

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gtggtttgtc caaactcatc aa                                              22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
agtaactctg cacttcccat tg                                              22

<210> SEQ ID NO 30
<211> LENGTH: 639
<212> TYPE: PRT
<213> ORGANISM: Scytonema hoffmanni

<400> SEQUENCE: 30
```

Met Ser Gln Ile Thr Ile Gln Ala Arg Leu Ile Ser Phe Glu Ser Asn
1               5                   10                  15

Arg Gln Gln Leu Trp Lys Leu Met Ala Asp Leu Asn Thr Pro Leu Ile
            20                  25                  30

Asn Glu Leu Leu Cys Gln Leu Gly Gln His Pro Asp Phe Glu Lys Trp
        35                  40                  45

Gln Gln Lys Gly Lys Leu Pro Ser Thr Val Val Ser Gln Leu Cys Gln
    50                  55                  60

Pro Leu Lys Thr Asp Pro Arg Phe Ala Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Gln Leu Asp Gly Lys Thr Arg Trp Leu
            100                 105                 110

Glu Met Leu Asn Ser Asp Ala Glu Leu Val Glu Leu Ser Gly Asp Thr
        115                 120                 125

Leu Glu Ala Ile Arg Val Lys Ala Ala Glu Ile Leu Ala Ile Ala Met
    130                 135                 140

Pro Ala Ser Glu Ser Asp Ser Ala Ser Pro Lys Gly Lys Gly Lys
145                 150                 155                 160

Lys Glu Lys Lys Pro Ser Ser Ser Pro Lys Arg Ser Leu Ser Lys
            165                 170                 175

Thr Leu Phe Asp Ala Tyr Gln Glu Thr Glu Asp Ile Lys Ser Arg Ser
        180                 185                 190

Ala Ile Ser Tyr Leu Leu Lys Asn Gly Cys Lys Leu Thr Asp Lys Glu
    195                 200                 205

Glu Asp Ser Glu Lys Phe Ala Lys Arg Arg Gln Val Glu Ile Gln
    210                 215                 220

Ile Gln Arg Leu Thr Glu Lys Leu Ile Ser Arg Met Pro Lys Gly Arg

-continued

```
            225                 230                 235                 240

Asp Leu Thr Asn Ala Lys Trp Leu Glu Thr Leu Leu Thr Ala Thr Thr
                        245                 250                 255

Thr Val Ala Glu Asp Asn Ala Gln Ala Lys Arg Trp Gln Asp Ile Leu
                        260                 265                 270

Leu Thr Arg Ser Ser Ser Leu Pro Phe Pro Leu Val Phe Glu Thr Asn
                        275                 280                 285

Glu Asp Met Val Trp Ser Lys Asn Gln Lys Gly Arg Leu Cys Val His
                        290                 295                 300

Phe Asn Gly Leu Ser Asp Leu Ile Phe Glu Val Tyr Cys Gly Asn Arg
        305                 310                 315                 320

Gln Leu His Trp Phe Gln Arg Phe Leu Glu Asp Gln Gln Thr Lys Arg
                        325                 330                 335

Lys Ser Lys Asn Gln His Ser Ser Gly Leu Phe Thr Leu Arg Asn Gly
                        340                 345                 350

His Leu Val Trp Leu Glu Gly Glu Lys Gly Glu Pro Trp Asn Leu
                        355                 360                 365

His His Leu Thr Leu Tyr Cys Cys Val Asp Asn Arg Leu Trp Thr Glu
                        370                 375                 380

Glu Gly Thr Glu Ile Val Arg Gln Glu Lys Ala Asp Glu Ile Thr Lys
        385                 390                 395                 400

Phe Ile Thr Asn Met Lys Lys Lys Ser Asp Leu Ser Asp Thr Gln Gln
                        405                 410                 415

Ala Leu Ile Gln Arg Lys Gln Ser Thr Leu Thr Arg Ile Asn Asn Ser
                        420                 425                 430

Phe Glu Arg Pro Ser Gln Pro Leu Tyr Gln Gly Gln Ser His Ile Leu
                        435                 440                 445

Val Gly Val Ser Leu Gly Leu Glu Lys Pro Ala Thr Val Ala Val Val
                        450                 455                 460

Asp Ala Ile Ala Asn Lys Val Leu Ala Tyr Arg Ser Ile Lys Gln Leu
        465                 470                 475                 480

Leu Gly Asp Asn Tyr Glu Leu Leu Asn Arg Gln Arg Gln Gln Gln
                        485                 490                 495

Tyr Leu Ser His Glu Arg His Lys Ala Gln Lys Asn Phe Ser Pro Asn
                        500                 505                 510

Gln Phe Gly Ala Ser Glu Leu Gly Gln His Ile Asp Arg Leu Leu Ala
                        515                 520                 525

Lys Ala Ile Val Ala Leu Ala Arg Thr Tyr Lys Ala Gly Ser Ile Val
                        530                 535                 540

Leu Pro Lys Leu Gly Asp Met Arg Glu Val Val Gln Ser Glu Ile Gln
        545                 550                 555                 560

Ala Ile Ala Glu Gln Lys Phe Pro Gly Tyr Ile Glu Gly Gln Gln Lys
                        565                 570                 575

Tyr Ala Lys Gln Tyr Arg Val Asn Val His Arg Trp Ser Tyr Gly Arg
                        580                 585                 590

Leu Ile Gln Ser Ile Gln Ser Lys Ala Ala Gln Thr Gly Ile Val Ile
                        595                 600                 605

Glu Glu Gly Lys Gln Pro Ile Arg Gly Ser Pro His Asp Lys Ala Lys
        610                 615                 620

Glu Leu Ala Leu Ser Ala Tyr Asn Leu Arg Leu Thr Arg Arg Ser
                        625                 630                 635

<210> SEQ ID NO 31
```

-continued

```
<211> LENGTH: 642
<212> TYPE: PRT
<213> ORGANISM: Anabaena cylindrica

<400> SEQUENCE: 31

Met Ser Val Ile Thr Ile Gln Cys Arg Leu Val Ala Glu Glu Asp Ser
1               5                   10                  15

Leu Arg Gln Leu Trp Glu Leu Met Ser Glu Lys Asn Thr Pro Phe Ile
            20                  25                  30

Asn Glu Ile Leu Leu Gln Ile Gly Lys His Pro Glu Phe Glu Thr Trp
        35                  40                  45

Leu Glu Lys Gly Arg Ile Pro Ala Glu Leu Leu Lys Thr Leu Gly Asn
    50                  55                  60

Ser Leu Lys Thr Gln Glu Pro Phe Thr Gly Gln Pro Gly Arg Phe Tyr
65                  70                  75                  80

Thr Ser Ala Ile Thr Leu Val Asp Tyr Leu Tyr Lys Ser Trp Phe Ala
                85                  90                  95

Leu Gln Lys Arg Arg Lys Gln Gln Ile Glu Gly Lys Gln Arg Trp Leu
            100                 105                 110

Lys Met Leu Lys Ser Asp Gln Glu Leu Glu Gln Glu Ser Gln Ser Ser
        115                 120                 125

Leu Glu Val Ile Arg Asn Lys Ala Thr Glu Leu Phe Ser Lys Phe Thr
    130                 135                 140

Pro Gln Ser Asp Ser Glu Ala Leu Arg Arg Asn Gln Asn Asp Lys Gln
145                 150                 155                 160

Lys Lys Val Lys Lys Thr Lys Lys Ser Thr Lys Pro Lys Thr Ser Ser
                165                 170                 175

Ile Phe Lys Ile Phe Leu Ser Thr Tyr Glu Ala Glu Glu Pro Leu
            180                 185                 190

Thr Arg Cys Ala Leu Ala Tyr Leu Leu Lys Asn Asn Cys Gln Ile Ser
        195                 200                 205

Glu Leu Asp Glu Asn Pro Glu Glu Phe Thr Arg Asn Lys Arg Arg Lys
    210                 215                 220

Glu Ile Glu Ile Glu Arg Leu Lys Asp Gln Leu Gln Ser Arg Ile Pro
225                 230                 235                 240

Lys Gly Arg Asp Leu Thr Gly Glu Glu Trp Leu Glu Thr Leu Glu Ile
                245                 250                 255

Ala Thr Phe Asn Val Pro Gln Asn Glu Asn Glu Ala Lys Ala Trp Gln
            260                 265                 270

Ala Ala Leu Leu Arg Lys Thr Ala Asn Val Pro Phe Pro Val Ala Tyr
        275                 280                 285

Glu Ser Asn Glu Asp Met Thr Trp Leu Lys Asn Asp Lys Asn Arg Leu
    290                 295                 300

Phe Val Arg Phe Asn Gly Leu Gly Lys Leu Thr Phe Glu Ile Tyr Cys
305                 310                 315                 320

Asp Lys Arg His Leu His Tyr Phe Gln Arg Phe Leu Glu Asp Gln Glu
                325                 330                 335

Ile Leu Arg Asn Ser Lys Arg Gln His Ser Ser Leu Phe Thr Leu
            340                 345                 350

Arg Ser Gly Arg Ile Ala Trp Leu Pro Gly Glu Lys Gly Glu His
        355                 360                 365

Trp Lys Val Asn Gln Leu Asn Phe Tyr Cys Ser Leu Asp Thr Arg Met
    370                 375                 380

Leu Thr Thr Glu Gly Thr Gln Gln Val Val Glu Glu Lys Val Thr Ala
```

Ile Thr Glu Ile Leu Asn Lys Thr Lys Gln Lys Asp Asp Leu Asn Asp
385                 390                 395                 400

Lys Gln Gln Ala Phe Ile Thr Arg Gln Gln Ser Thr Leu Ala Arg Ile
            405                 410                 415

Asn Asn Pro Phe Pro Arg Pro Ser Lys Pro Asn Tyr Gln Gly Lys Ser
                420                 425                 430

Ser Ile Leu Ile Gly Val Ser Phe Gly Leu Glu Lys Pro Val Thr Val
    435                 440                 445

Ala Val Asp Val Val Lys Asn Lys Val Ile Ala Tyr Arg Ser Val
450                 455                 460

Lys Gln Leu Leu Gly Glu Asn Tyr Asn Leu Leu Asn Arg Gln Arg Gln
465                 470                 475                 480

Gln Gln Gln Arg Leu Ser His Glu Arg His Lys Ala Gln Lys Gln Asn
            485                 490                 495

Ala Pro Asn Ser Phe Gly Glu Ser Glu Leu Gly Gln Tyr Val Asp Arg
                500                 505                 510

Leu Leu Ala Asp Ala Ile Ile Ala Ile Ala Lys Lys Tyr Gln Ala Gly
    515                 520                 525

Ser Ile Val Leu Pro Lys Leu Arg Asp Met Arg Glu Gln Ile Ser Ser
530                 535                 540

Glu Ile Gln Ser Arg Ala Glu Asn Gln Cys Pro Gly Tyr Lys Glu Gly
545                 550                 555                 560

Gln Gln Lys Tyr Ala Lys Glu Tyr Arg Ile Asn Val His Arg Trp Ser
            565                 570                 575

Tyr Gly Arg Leu Ile Glu Ser Ile Lys Ser Gln Ala Ala Gln Ala Gly
                580                 585                 590

Ile Ala Ile Glu Thr Gly Lys Gln Ser Ile Arg Gly Ser Pro Gln Glu
    595                 600                 605

Lys Ala Arg Asp Leu Ala Val Phe Thr Tyr Gln Glu Arg Gln Ala Ala
625                 630                 635                 640

Leu Ile

<210> SEQ ID NO 32
<211> LENGTH: 208
<212> TYPE: DNA
<213> ORGANISM: Artificial Sequence
<220> FEATURE:
<223> OTHER INFORMATION: Transposon left end

<400> SEQUENCE: 32
tacagtgaca aattatctgt cgtcggtgac agattaatgt cattgtgact atttaattgt     60
cgtcgtgacc catcagcgtt gcttaattaa ttgatgacaa attaaatgtc atcaatataa    120
tatgctctgc aattattata caaagcaatt aaaacaagcg gataaaagga cttgctttca    180 acccaccct aagtttaata gttactga                                        208

<210> SEQ ID NO 33
<211> LENGTH: 219
<212> TYPE: DNA
<213> ORGANISM: Artificial Sequence
<220> FEATURE:
<223> OTHER INFORMATION: Transposon right end

<400> SEQUENCE: 33
cgacagtcaa tttgtcatta tgaaaataca caaaagcttt ttcctatctt gcaaagcgac     60

-continued

```
agctaatttg tcacaatcac ggacaacgac atctattttg tcactgcaaa gaggttatgc      120
taaaactgcc aaagcgctat aatctatact gtataaggat tttactgatg acaataattt      180
gtcacaacga catataatta gtcactgtac acgtagaga                             219
```

<210> SEQ ID NO 34
<211> LENGTH: 394
<212> TYPE: PRT
<213> ORGANISM: Vibrio cholerae

<400> SEQUENCE: 34

```
Met Phe Leu Gln Arg Pro Lys Pro Tyr Ser Asp Glu Ser Leu Glu Ser
1               5                   10                  15

Phe Phe Ile Arg Val Ala Asn Lys Asn Gly Tyr Gly Asp Val His Arg
            20                  25                  30

Phe Leu Glu Ala Thr Lys Arg Phe Leu Gln Asp Ile Asp His Asn Gly
        35                  40                  45

Tyr Gln Thr Phe Pro Thr Asp Ile Thr Arg Ile Asn Pro Tyr Ser Ala
    50                  55                  60

Lys Asn Ser Ser Ser Ala Arg Thr Ala Ser Phe Leu Lys Leu Ala Gln
65                  70                  75                  80

Leu Thr Phe Asn Glu Pro Pro Glu Leu Leu Gly Leu Ala Ile Asn Arg
                85                  90                  95

Thr Asn Met Lys Tyr Ser Pro Ser Thr Ser Ala Val Val Arg Gly Ala
            100                 105                 110

Glu Val Phe Pro Arg Ser Leu Leu Arg Thr His Ser Ile Pro Cys Cys
        115                 120                 125

Pro Leu Cys Leu Arg Glu Asn Gly Tyr Ala Ser Tyr Leu Trp His Phe
    130                 135                 140

Gln Gly Tyr Glu Tyr Cys His Ser His Asn Val Pro Leu Ile Thr Thr
145                 150                 155                 160

Cys Ser Cys Gly Lys Glu Phe Asp Tyr Arg Val Ser Gly Leu Lys Gly
                165                 170                 175

Ile Cys Cys Lys Cys Lys Glu Pro Ile Thr Leu Thr Ser Arg Glu Asn
            180                 185                 190

Gly His Glu Ala Ala Cys Thr Val Ser Asn Trp Leu Ala Gly His Glu
        195                 200                 205

Ser Lys Pro Leu Pro Asn Leu Pro Lys Ser Tyr Arg Trp Gly Leu Val
    210                 215                 220

His Trp Trp Met Gly Ile Lys Asp Ser Glu Phe Asp His Phe Ser Phe
225                 230                 235                 240

Val Gln Phe Phe Ser Asn Trp Pro Arg Ser Phe His Ser Ile Ile Glu
                245                 250                 255

Asp Glu Val Glu Phe Asn Leu Glu His Ala Val Val Ser Thr Ser Glu
            260                 265                 270

Leu Arg Leu Lys Asp Leu Leu Gly Arg Leu Phe Phe Gly Ser Ile Arg
        275                 280                 285

Leu Pro Glu Arg Asn Leu Gln His Asn Ile Ile Leu Gly Glu Leu Leu
    290                 295                 300

Cys Tyr Leu Glu Asn Arg Leu Trp Gln Asp Lys Gly Leu Ile Ala Asn
305                 310                 315                 320

Leu Lys Met Asn Ala Leu Glu Ala Thr Val Met Leu Asn Cys Ser Leu
                325                 330                 335

Asp Gln Ile Ala Ser Met Val Glu Gln Arg Ile Leu Lys Pro Asn Arg
            340                 345                 350
```

Lys Ser Lys Pro Asn Ser Pro Leu Asp Val Thr Asp Tyr Leu Phe His
        355                 360                 365

Phe Gly Asp Ile Phe Cys Leu Trp Leu Ala Glu Phe Gln Ser Asp Glu
        370                 375                 380

Phe Asn Arg Ser Phe Tyr Val Ser Arg Trp
385                 390

<210> SEQ ID NO 35
<211> LENGTH: 640
<212> TYPE: PRT
<213> ORGANISM: Vibrio cholerae

<400> SEQUENCE: 35

Met Gln Thr Leu Lys Glu Leu Ile Ala Ser Asn Pro Asp Asp Leu Thr
1               5                   10                  15

Thr Glu Leu Lys Arg Ala Phe Arg Pro Leu Thr Pro His Ile Ala Ile
            20                  25                  30

Asp Gly Asn Glu Leu Asp Ala Leu Thr Ile Leu Val Asn Leu Thr Asp
        35                  40                  45

Lys Thr Asp Asp Gln Lys Asp Leu Leu Asp Arg Ala Lys Cys Lys Gln
    50                  55                  60

Lys Leu Arg Asp Glu Lys Trp Trp Ala Ser Cys Ile Asn Cys Val Asn
65                  70                  75                  80

Tyr Arg Gln Ser His Asn Pro Lys Phe Pro Asp Ile Arg Ser Glu Gly
                85                  90                  95

Val Ile Arg Thr Gln Ala Leu Gly Glu Leu Pro Ser Phe Leu Leu Ser
            100                 105                 110

Ser Ser Lys Ile Pro Pro Tyr His Trp Ser Tyr Ser His Asp Ser Lys
        115                 120                 125

Tyr Val Asn Lys Ser Ala Phe Leu Thr Asn Glu Phe Cys Trp Asp Gly
    130                 135                 140

Glu Ile Ser Cys Leu Gly Glu Leu Leu Lys Asp Ala Asp His Pro Leu
145                 150                 155                 160

Trp Asn Thr Leu Lys Lys Leu Gly Cys Ser Gln Lys Thr Cys Lys Ala
                165                 170                 175

Met Ala Lys Gln Leu Ala Asp Ile Thr Leu Thr Thr Ile Asn Val Thr
            180                 185                 190

Leu Ala Pro Asn Tyr Leu Thr Gln Ile Ser Leu Pro Asp Ser Asp Thr
        195                 200                 205

Ser Tyr Ile Ser Leu Ser Pro Val Ala Ser Leu Ser Met Gln Ser His
    210                 215                 220

Phe His Gln Arg Leu Gln Asp Glu Asn Arg His Ser Ala Ile Thr Arg
225                 230                 235                 240

Phe Ser Arg Thr Thr Asn Met Gly Val Thr Ala Met Thr Cys Gly Gly
                245                 250                 255

Ala Phe Arg Met Leu Lys Ser Gly Ala Lys Phe Ser Ser Pro Pro His
            260                 265                 270

His Arg Leu Asn Ser Lys Arg Ser Trp Leu Thr Ser Glu His Val Gln
        275                 280                 285

Ser Leu Lys Gln Tyr Gln Arg Leu Asn Lys Ser Leu Ile Pro Glu Asn
    290                 295                 300

Ser Arg Ile Ala Leu Arg Arg Lys Tyr Lys Ile Glu Leu Gln Asn Met
305                 310                 315                 320

Val Arg Ser Trp Phe Ala Met Gln Asp His Thr Leu Asp Ser Asn Ile

```
                    325                 330                 335

Leu Ile Gln His Leu Asn His Asp Leu Ser Tyr Leu Gly Ala Thr Lys
                340                 345                 350

Arg Phe Ala Tyr Asp Pro Ala Met Thr Lys Leu Phe Thr Glu Leu Leu
            355                 360                 365

Lys Arg Glu Leu Ser Asn Ser Ile Asn Asn Gly Glu Gln His Thr Asn
        370                 375                 380

Gly Ser Phe Leu Val Leu Pro Asn Ile Arg Val Cys Gly Ala Thr Ala
385                 390                 395                 400

Leu Ser Ser Pro Val Thr Val Gly Ile Pro Ser Leu Thr Ala Phe Phe
                405                 410                 415

Gly Phe Val His Ala Phe Glu Arg Asn Ile Asn Arg Thr Thr Ser Ser
            420                 425                 430

Phe Arg Val Glu Ser Phe Ala Ile Cys Val His Gln Leu His Val Glu
        435                 440                 445

Lys Arg Gly Leu Thr Ala Glu Phe Val Glu Lys Gly Asp Gly Thr Ile
    450                 455                 460

Ser Ala Pro Ala Thr Arg Asp Asp Trp Gln Cys Asp Val Val Phe Ser
465                 470                 475                 480

Leu Ile Leu Asn Thr Asn Phe Ala Gln His Ile Asp Gln Asp Thr Leu
                485                 490                 495

Val Thr Ser Leu Pro Lys Arg Leu Ala Arg Gly Ser Ala Lys Ile Ala
            500                 505                 510

Ile Asp Asp Phe Lys His Ile Asn Ser Phe Ser Thr Leu Glu Thr Ala
        515                 520                 525

Ile Glu Ser Leu Pro Ile Glu Ala Gly Arg Trp Leu Ser Leu Tyr Ala
    530                 535                 540

Gln Ser Asn Asn Asn Leu Ser Asp Leu Leu Ala Ala Met Thr Glu Asp
545                 550                 555                 560

His Gln Leu Met Ala Ser Cys Val Gly Tyr His Leu Leu Glu Glu Pro
                565                 570                 575

Lys Asp Lys Pro Asn Ser Leu Arg Gly Tyr Lys His Ala Ile Ala Glu
            580                 585                 590

Cys Ile Ile Gly Leu Ile Asn Ser Ile Thr Phe Ser Ser Glu Thr Asp
        595                 600                 605

Pro Asn Thr Ile Phe Trp Ser Leu Lys Asn Tyr Gln Asn Tyr Leu Val
    610                 615                 620

Val Gln Pro Arg Ser Ile Asn Asp Glu Thr Thr Asp Lys Ser Ser Leu
625                 630                 635                 640

<210> SEQ ID NO 36
<211> LENGTH: 352
<212> TYPE: PRT
<213> ORGANISM: Vibrio cholerae

<400> SEQUENCE: 36

Met Lys Leu Pro Thr Asn Leu Ala Tyr Glu Arg Ser Ile Asp Pro Ser
1               5                   10                  15

Asp Val Cys Phe Phe Val Val Trp Pro Asp Asp Arg Lys Thr Pro Leu
            20                  25                  30

Thr Tyr Asn Ser Arg Thr Leu Leu Gly Gln Met Glu Ala Ala Ser Leu
        35                  40                  45

Ala Tyr Asp Val Ser Gly Gln Pro Ile Lys Ser Ala Thr Ala Glu Ala
    50                  55                  60
```

-continued

```
Leu Ala Gln Gly Asn Pro His Gln Val Asp Phe Cys His Val Pro Tyr
 65                  70                  75                  80

Gly Ala Ser His Ile Glu Cys Ser Phe Ser Val Ser Phe Ser Ser Glu
                 85                  90                  95

Leu Arg Gln Pro Tyr Lys Cys Asn Ser Ser Lys Val Lys Gln Thr Leu
            100                 105                 110

Val Gln Leu Val Glu Leu Tyr Glu Thr Lys Ile Gly Trp Thr Glu Leu
        115                 120                 125

Ala Thr Arg Tyr Leu Met Asn Ile Cys Asn Gly Lys Trp Leu Trp Lys
    130                 135                 140

Asn Thr Arg Lys Ala Tyr Cys Trp Asn Ile Val Leu Thr Pro Trp Pro
145                 150                 155                 160

Trp Asn Gly Glu Lys Val Gly Phe Glu Asp Ile Arg Thr Asn Tyr Thr
                165                 170                 175

Ser Arg Gln Asp Phe Lys Asn Asn Lys Asn Trp Ser Ala Ile Val Glu
            180                 185                 190

Met Ile Lys Thr Ala Phe Ser Ser Thr Asp Gly Leu Ala Ile Phe Glu
        195                 200                 205

Val Arg Ala Thr Leu His Leu Pro Thr Asn Ala Met Val Arg Pro Ser
    210                 215                 220

Gln Val Phe Thr Glu Lys Glu Ser Gly Ser Lys Ser Lys Ser Lys Thr
225                 230                 235                 240

Gln Asn Ser Arg Val Phe Gln Ser Thr Thr Ile Asp Gly Glu Arg Ser
                245                 250                 255

Pro Ile Leu Gly Ala Phe Lys Thr Gly Ala Ala Ile Ala Thr Ile Asp
            260                 265                 270

Asp Trp Tyr Pro Glu Ala Thr Glu Pro Leu Arg Val Gly Arg Phe Gly
        275                 280                 285

Val His Arg Glu Asp Val Thr Cys Tyr Arg His Pro Ser Thr Gly Lys
    290                 295                 300

Asp Phe Phe Ser Ile Leu Gln Gln Ala Glu His Tyr Ile Glu Val Leu
305                 310                 315                 320

Ser Ala Asn Lys Thr Pro Ala Gln Glu Thr Ile Asn Asp Met His Phe
                325                 330                 335

Leu Met Ala Asn Leu Ile Lys Gly Gly Met Phe Gln His Lys Gly Asp
            340                 345                 350

<210> SEQ ID NO 37
<211> LENGTH: 199
<212> TYPE: PRT
<213> ORGANISM: Vibrio cholerae

<400> SEQUENCE: 37

Met Lys Trp Tyr Tyr Lys Thr Ile Thr Phe Leu Pro Glu Leu Cys Asn
 1               5                  10                  15

Asn Glu Ser Leu Ala Ala Lys Cys Leu Arg Val Leu His Gly Phe Asn
                 20                  25                  30

Tyr Gln Tyr Glu Thr Arg Asn Ile Gly Val Ser Phe Pro Leu Trp Cys
             35                  40                  45

Asp Ala Thr Val Gly Lys Lys Ile Ser Phe Val Ser Lys Asn Lys Ile
         50                  55                  60

Glu Leu Asp Leu Leu Lys Gln His Tyr Phe Val Gln Met Glu Gln
 65                  70                  75                  80

Leu Gln Tyr Phe His Ile Ser Asn Thr Val Leu Val Pro Glu Asp Cys
                 85                  90                  95
```

```
Thr Tyr Val Ser Phe Arg Arg Cys Gln Ser Ile Asp Lys Leu Thr Ala
                100                 105                 110

Ala Gly Leu Ala Arg Lys Ile Arg Arg Leu Glu Lys Arg Ala Leu Ser
            115                 120                 125

Arg Gly Glu Gln Phe Asp Pro Ser Ser Phe Ala Gln Lys Glu His Thr
        130                 135                 140

Ala Ile Ala His Tyr His Ser Leu Gly Glu Ser Ser Lys Gln Thr Asn
145                 150                 155                 160

Arg Asn Phe Arg Leu Asn Ile Arg Met Leu Ser Glu Gln Pro Arg Glu
                165                 170                 175

Gly Asn Ser Ile Phe Ser Ser Tyr Gly Leu Ser Asn Ser Glu Asn Ser
            180                 185                 190

Phe Gln Pro Val Pro Leu Ile
        195
```

<210> SEQ ID NO 38
<211> LENGTH: 230
<212> TYPE: PRT
<213> ORGANISM: Vibrio cholerae

<400> SEQUENCE: 38

```
Met Ala Thr Ser Leu Pro Thr Pro Ser Ala Ile Thr Thr Ser Ala Leu
1               5                   10                  15

Glu Tyr Ala Phe His Thr Pro Ala Arg Asn Leu Thr Lys Ser Arg Gly
                20                  25                  30

Lys Asn Ile His Arg Tyr Val Ser Val Lys Met Ser Lys Arg Ile Thr
            35                  40                  45

Val Glu Ser Thr Leu Glu Cys Asp Ala Cys Tyr His Phe Asp Phe Glu
        50                  55                  60

Pro Ser Ile Val Arg Phe Cys Ala Gln Pro Ile Arg Phe Leu Tyr Tyr
65                  70                  75                  80

Leu Asn Gly Gln Ser His Ser Tyr Val Pro Asp Phe Leu Val Gln Phe
                85                  90                  95

Asp Thr Asn Glu Phe Val Leu Tyr Glu Val Lys Ser Ala Tyr Ala Lys
                100                 105                 110

Asn Lys Pro Asp Phe Asp Val Glu Trp Glu Ala Lys Val Lys Ala Ala
            115                 120                 125

Thr Glu Leu Gly Leu Glu Leu Val Glu Glu Ser Asp Ile Arg
        130                 135                 140

Asp Thr Val Val Leu Asn Asn Leu Lys Arg Met His Arg Tyr Ala Ser
145                 150                 155                 160

Lys Asp Glu Leu Asn Asn Val His Asn Ser Leu Leu Lys Ile Ile Lys
                165                 170                 175

Tyr Asn Gly Ala Gln Ser Ala Arg Cys Leu Gly Gln Leu Gly Leu
            180                 185                 190

Lys Gly Arg Thr Val Leu Pro Ile Leu Cys Asp Leu Leu Ser Arg Cys
        195                 200                 205

Leu Leu Asp Thr Arg Leu Asp Lys Pro Leu Ser Leu Glu Ser Arg Phe
210                 215                 220

Glu Leu Ala Ser Tyr Gly
225             230
```

<210> SEQ ID NO 39
<211> LENGTH: 603
<212> TYPE: PRT

-continued

<213> ORGANISM: Vibrio cholerae

<400> SEQUENCE: 39

```
Met Ala Lys Lys Gly Phe Ser Ser Phe His Arg Lys Ala Val Ser Ser
1               5                   10                  15

Gln Asp Thr Leu Glu Ser Ile Glu Leu Val Ser Ser Ala Asn Cys Leu
            20                  25                  30

Glu Ser Val Thr Tyr Gln Asp Ile Ser Ala Phe Pro Glu Thr Ile Ala
        35                  40                  45

Val Glu Ile Asn Phe Arg Leu Ser Ile Leu Arg Phe Leu Ala Arg Lys
    50                  55                  60

Cys Glu Thr Ile Val Ala Lys Ser Ile Glu Pro His Arg Val Glu Leu
65                  70                  75                  80

Gln Gln Asn Tyr Ser Arg Lys Ile Pro Ser Ala Ile Thr Ile Tyr Arg
                85                  90                  95

Trp Trp Leu Ala Phe Arg Lys Ser Asp Tyr Asn Pro Ile Ser Leu Ala
            100                 105                 110

Pro Asn Ile Lys Asp Arg Gly Asn Arg Glu Thr Lys Val Ser Thr Val
        115                 120                 125

Val Asp Ser Ile Met Glu Gln Ala Val Glu Arg Val Ile Ser Gly Arg
    130                 135                 140

Lys Val Asn Val Ser Ser Ala Tyr Lys Arg Val Arg Arg Lys Val Arg
145                 150                 155                 160

Gln Tyr Asn Leu Thr His Gly Thr Lys Tyr Thr Tyr Pro Lys Tyr Glu
                165                 170                 175

Ser Val Arg Lys Arg Val Lys Lys Lys Thr Pro Phe Glu Leu Leu Ala
            180                 185                 190

Ala Gly Lys Gly Glu Arg Val Ala Lys Arg Glu Phe Arg Arg Met Gly
        195                 200                 205

Lys Lys Ile Leu Thr Ser Ser Val Leu Glu Arg Val Glu Ile Asp His
    210                 215                 220

Thr Val Val Asp Leu Phe Ala Val His Glu Glu Tyr Arg Ile Pro Leu
225                 230                 235                 240

Gly Arg Pro Trp Leu Thr Gln Leu Val Asp Cys Tyr Ser Lys Ala Val
                245                 250                 255

Ile Gly Phe Tyr Leu Gly Phe Glu Pro Pro Ser Tyr Val Ser Val Ser
            260                 265                 270

Leu Ala Leu Lys Asn Ala Ile Gln Arg Lys Asp Asp Leu Ile Ser Ser
        275                 280                 285

Tyr Glu Ser Ile Glu Asn Glu Trp Leu Cys Tyr Gly Ile Pro Asp Leu
    290                 295                 300

Leu Val Thr Asp Asn Gly Lys Glu Phe Leu Ser Lys Ala Phe Asp Gln
305                 310                 315                 320

Ala Cys Glu Ser Leu Leu Ile Asn Val His Gln Asn Lys Val Glu Thr
                325                 330                 335

Pro Asp Asn Lys Pro His Val Glu Arg Asn Tyr Gly Thr Ile Asn Thr
            340                 345                 350

Ser Leu Leu Asp Asp Leu Pro Gly Lys Ser Phe Ser Gln Tyr Leu Gln
        355                 360                 365

Arg Glu Gly Tyr Asp Ser Val Gly Glu Ala Thr Leu Thr Leu Asn Glu
    370                 375                 380

Ile Arg Glu Ile Tyr Leu Ile Trp Leu Val Asp Ile Tyr His Lys Lys
385                 390                 395                 400
```

```
Pro Asn Gln Arg Gly Thr Asn Cys Pro Asn Val Ala Trp Lys Lys Gly
            405                 410                 415

Cys Gln Glu Trp Glu Pro Glu Glu Phe Ser Gly Ser Lys Asp Glu Leu
        420                 425                 430

Asp Phe Lys Phe Ala Ile Val Asp Tyr Lys Gln Leu Thr Lys Val Gly
        435                 440                 445

Ile Thr Val Tyr Lys Glu Leu Ser Tyr Ser Asn Asp Arg Leu Ala Glu
    450                 455                 460

Tyr Arg Gly Lys Lys Gly Asn His Lys Val Gln Phe Lys Tyr Asn Pro
465                 470                 475                 480

Glu Cys Met Ala Val Ile Trp Val Leu Asp Glu Asp Met Asn Glu Tyr
                485                 490                 495

Phe Thr Val Asn Ala Ile Asp Tyr Glu Tyr Ala Ser Arg Val Ser Leu
            500                 505                 510

Trp Gln His Lys Tyr Asn Met Lys Tyr Gln Ala Glu Leu Asn Ser Ala
        515                 520                 525

Glu Tyr Asp Glu Asp Lys Glu Ile Asp Ala Glu Ile Lys Ile Glu Glu
    530                 535                 540

Ile Ala Asp Arg Ser Ile Val Lys Thr Asn Lys Ile Arg Ala Arg Arg
545                 550                 555                 560

Arg Gly Ala Arg His Gln Glu Asn Ser Ala Arg Ala Lys Ser Ile Ser
                565                 570                 575

Asn Ala Asn Pro Ala Ser Ile Gln Lys His Glu Asp Glu Ile Val Ser
            580                 585                 590

Ala Asp Asn Asp Asp Trp Asp Ile Asp Tyr Val
            595                 600

<210> SEQ ID NO 40
<211> LENGTH: 330
<212> TYPE: PRT
<213> ORGANISM: Vibrio cholerae

<400> SEQUENCE: 40

Met Ser Glu Thr Arg Glu Ala Arg Ile Ser Arg Ala Lys Arg Ala Phe
1               5                   10                  15

Val Ser Thr Pro Ser Val Arg Lys Ile Leu Ser Tyr Met Asp Arg Cys
            20                  25                  30

Arg Asp Leu Ser Asp Leu Glu Ser Glu Pro Thr Cys Met Met Val Tyr
        35                  40                  45

Gly Ala Ser Gly Val Gly Lys Thr Thr Val Ile Lys Lys Tyr Leu Asn
    50                  55                  60

Gln Asn Arg Arg Glu Ser Glu Ala Gly Gly Asp Ile Ile Pro Val Leu
65                  70                  75                  80

His Ile Glu Leu Pro Asp Asn Ala Lys Pro Val Asp Ala Ala Arg Glu
                85                  90                  95

Leu Leu Val Glu Met Gly Asp Pro Leu Ala Leu Tyr Glu Thr Asp Leu
            100                 105                 110

Ala Arg Leu Thr Lys Arg Leu Thr Glu Leu Ile Pro Ala Val Gly Val
        115                 120                 125

Lys Leu Ile Ile Ile Asp Glu Phe Gln His Leu Val Glu Glu Arg Ser
    130                 135                 140

Asn Arg Val Leu Thr Gln Val Gly Asn Trp Leu Lys Met Ile Leu Asn
145                 150                 155                 160

Lys Thr Lys Cys Pro Ile Val Ile Phe Gly Met Pro Tyr Ser Lys Val
                165                 170                 175
```

```
Val Leu Gln Ala Asn Ser Gln Leu His Gly Arg Phe Ser Ile Gln Val
            180                 185                 190

Glu Leu Arg Pro Phe Ser Tyr Gln Gly Gly Arg Gly Val Phe Lys Thr
        195                 200                 205

Phe Leu Glu Tyr Leu Asp Lys Ala Leu Pro Phe Glu Lys Gln Ala Gly
    210                 215                 220

Leu Ala Asn Glu Ser Leu Gln Lys Lys Leu Tyr Ala Phe Ser Gln Gly
225                 230                 235                 240

Asn Met Arg Ser Leu Arg Asn Leu Ile Tyr Gln Ala Ser Ile Glu Ala
                245                 250                 255

Ile Asp Asn Gln His Glu Thr Ile Thr Glu Glu Asp Phe Val Phe Ala
            260                 265                 270

Ser Lys Leu Thr Ser Gly Asp Lys Pro Asn Ser Trp Lys Asn Pro Phe
        275                 280                 285

Glu Glu Gly Val Glu Val Thr Glu Asp Met Leu Arg Pro Pro Pro Lys
    290                 295                 300

Asp Ile Gly Trp Glu Asp Tyr Leu Arg His Ser Thr Pro Arg Val Ser
305                 310                 315                 320

Lys Pro Gly Arg Asn Lys Asn Phe Phe Glu
                325                 330

<210> SEQ ID NO 41
<211> LENGTH: 105
<212> TYPE: DNA
<213> ORGANISM: Vibrio cholerae

<400> SEQUENCE: 41
tgttgatgca accataaagt gatatttaat aattatttat aatcagcaac ttaaccacaa    60
aacaaccata tattgatatc tcacaaaaca accataagtt gatat                   105

<210> SEQ ID NO 42
<211> LENGTH: 48031
<212> TYPE: DNA
<213> ORGANISM: Homo sapiens

<400> SEQUENCE: 42
gtgggggccg ttggctccag acaaataaac atggagtcca tcttccacga gaaagtgagt    60
gtccgcgttc ggtggggagc tgtctgccgc gcggtggcgg gcgtggagcg cggcatcacc   120
gcctctcgga gggctgggtg gggcccgagt cgcccccatg ccgatctcgc ccggcgaggg   180
gcgacgccgc agcctcccgc ctcctcggct cgaggagggg agcatcacct acgcccctac   240 ttccccgcg gccccgccc tgggagccgg gagggagtat gggcggggcc ggggcgtct    300 cgggacacgg gagtggggtg gcgcccagtg ggtttgcttc tgcctttctc cgtcactttc   360
catcgctttt cggaggattc cttcacccct ccccaatcct tccctctccc tagggtctag   420
ctagagtcat ctctgggaca cctccctcaa ccctcctac cctaatcctg cagaattaa    480 cttttcctcc tccggactgc tcaattctat attggagtct ccctacacg tagatctttg   540 gggtcttgtt cgtgtctttc ccctgcacta ggtccgcgag cctccgagg gaggagacct   600 tggctcgccc actgtagggc ctgacattta ggaagtgaag taggaaaccc ggcgtgcccc   660
taaacaggga agtcgtcaca agagtttta ttacgggatg tttgggtttg gtttcttttg   720
gtactcccat ctttccggag caggcggcca gctttgtttt taggtattag gagtggactg   780
ggatgatttt gttgtagtct gcctagcctg ctgtcccttt aactcttccg tgaccatgca   840
```

```
cttgaagata ctgtttgtga tatgtaaaga aactcctcgt ttctctcata ctattatcca    900
gccatttgtg tgtgagtgaa gccttcccca ggacagcttt ggcacatggt atcatgtttc    960
ataatagttt cgtgtttgga aagagttgct ggtaaggctg ttatttaata ggaggagcaa   1020 agggttttttg ttttattaaa tacttataaa tgatcattta tcccagacat ttaaaattca   1080
cacacacaca acaaataaag caaagacaaa agaatacatt taccaaatgt aaatctgtag   1140 cataaattt ttttaattt tattttaaag atggggtctc attctgtcac ccaggcaggt    1200
gtgcaatgga gagatcatgg ctcactgcag ccttgatctc ctaggcacaa gcgatcctcc   1260
cgcctctgcc tccagagtag ctgggactac aggtgcatat cgccaggcc aggtaatgtt    1320 tttgggagag acgggtctc gctgtgttgc ccaggctggt ctcgaactcc tggactcagg    1380
tgattctccc acctcggcct ctcgaagtgc tgtgattaca ggcgtgagcc actgtgcctg   1440
gaacaaattg ttaagtacaa tgcttttcat tgtagaaaac atctcggaaa cttttgaaat   1500
aggctgatgt tcagtggggg aggaaggact cagtcgtata gttgtcacta atttttgac    1560 ttgattgaca tgactcgtaa atcatagaca atagagattt ggttgcttgg ctgagtagag   1620
tgcgtgaaaa atacacacgt acttttttt ttttttttt gagatggagt ttggctcttg    1680
tcacccaggc tggagtgcaa tggcgccatc atggctcact gcaacctccg cctcccgtt    1740 caagcgattc tcctgcctca gtctccccag tagctgagat tacaggcgcc cgccaccacg   1800
cccagctaat ttttgtattt ttagtagaga cagggtttca ccatgttggc caggctggtc    1860
tccaactcct gacaggtggt ccgccgcct cggcctccca aagtgctggg attacaggcg   1920
tgagccaccg caccgggcca tatttttgtt attaattttc aaaggctttg gtgtgggacc   1980
acatttcaac atggaaggcc ttaaacatgt tccacactac ttcctgagaa ttagacaaga   2040
tttttaacaa tattgttacc tagttgggac acatttgtac tgacccatgg gatgaaaaaa   2100
agctgagtgc tagcctagtg aaaatctact tacccgaaag aaatccctct tagtctgggt   2160
gcagtggctc acaccagtgc tttgggaggc ccagacgggc ggatcatgag gtcagtagtt   2220
tgagaccagc ctggccaaca tggtgaaacc ccgtctctac taaaaataca aaaaattagc   2280
caggtgtggt ggcaggcgcc tgtaatccca ggtactctgg aggctgaggc aggagaattg   2340
cttgaacccg agaggcagag gttgcagtga gccgagaccg tgccactgca cttcagcctg   2400
ggcaacagag cgagactccg tctcaaaaaa aagaaaagga aaaagagtc cctcttaatt   2460 atcagcatgt gtataggcct acagatactt caggaatacc tttaccatta tcatcaactt   2520
gtatctacat agcatgtgaa gattcaacaa tttagttttt tgggcgtcct caagagtacg   2580
cacctataac catatggccc aattgttaat ctcctataca gtccattctg ggaatgtttg   2640
ggcttactgt gccatttttc cgttcactgc cttcccctct gcaatatacc tttaacccctt   2700 gctaggtcct gggtttggag agccagagaa ccaactttgg ccctaaagaa gctgtgtagg   2760
tagcaatatc tgcctacgaa gggccttgca accatttcct cttggaacct tggtttcctc   2820
tttctgagta gtcactttga gtacccttta ttaagttaga atgtaaaaac agtttctcac   2880
tgatatatct gcagtgcctg agagagggcc tggcacagag taagtactca ataaatattt   2940
gaatggggcc gggcgtggtg agacctgtct ctacaagaat gaacaaaatt agctgggcgt   3000
gttagcacat gcctgtagac ttgggaggct gaggtgggag gattgcatga gtctgggagg   3060
tcgaggctgt agtgagccat gatcgcacca ctgcactcca gcctagggga cagagcaaga   3120
tcctgtctca aaagaaaaaa atgtatatat ttgaatggat aaagagatgg ctttgagttt   3180
ctgagatata tatggtgctg tttatctaaa gtaaacaagt tttctgtaaa tattttaagg   3240
```

```
ctttgcaggc cagctgtagt ctctgtcaca cattcttatt tgtgcatgtt tttcccaacc    3300
atgtaaaaat gtaaagtgca ttcttagcta ctggggcagg ttgaatttgg cccatgggct    3360
agagtttgcc aaccoctaac ttaaacctttt gtactaactt tatgaccact actggatttt    3420
tgttgttgtt tgttttagtt ctggtgcctg cttttgttttt ttttttttttt ttaatcctct    3480 tgctgatgtt tcttggtgca gttactgtgc catttgtatt ggtgctttta atgtaatgca    3540
aactggtaat aatatctaaa cttgctgggg ttgtacataa aattattgaa aagattgaaa    3600
agatgctgag cattgactct gtggcattca ttatgccctt tgtgattgc tggattttag    3660 ccatctttag gacatttgag ctttaggaga agccaaattc tgtataaatg acttgaagtg    3720
ctaatagcac aggttttgaa acctctgcct gggtttgagt ctcagctctg cctttactta    3780
cctgtgtgat cctgagcaag ttacttagta tccctgtcct ctagtttcct cctctgtagt    3840
gtggggataa taacatagac ataacctgag agttagagtg tagagaaggc tccctggcag    3900 ataagtgctgt agaagtactg gccattgcca ttactcaggt gcttgtgttt gctgaacctc    3960
atagtaaggg ctcggagagc actaagagga ggtgagaaat gctgctagat tgacagcttg    4020
tccccagata gcccattccc gagagcacct taggtttata cctgatttgt gttgtagtta    4080
gtagtgtctc tggtaatttg aactagtttc aggttggtct tgaaaacctg gggaggttgg    4140
gggtaaatga tttggtagca gttctctttt gtgattttat acattatctt tgtagaactg    4200
cagtttgcta attctctgag cccaacacaa tgaagtctgg gcctaaaatc atagaatttc    4260 ttttatttttt tttttgttt ttaatttatt tattccctcc ctccctcctt tcttcctttc    4320 ttcctttct ttctttcttt ccttccttcc ttccttcttt cttttctttc tttcttttct    4380
ttctttggag tctcactctg tcaccaggct ggagtgcagt ggcacgaact ttcttcagag    4440
tctcactttg tcaccaggct ggagtgcagt ggcgcgaact cagctcactg caacctccgt    4500
ctcctgagtt caagagattc tcctgcctca gcctcccgag tagctgggac tataggcatg    4560
tgccaccatg cccagctaat tttcttattt ttagtagaga cgaggtttca ccatgttggc    4620
caggatggtc ttgatctctt gacctcgtga tccacctgcc tcagcctccc aaagtgcggg    4680
gattacaggc gtgagctacc acgcccagcc tatttttat tttttgaggc agagtctcac    4740
tctgtcaccc aggctggagt gcagtggtgc aatctcagct cactgcaacc tccgcctcct    4800
gggttcaggt gattctcctg ccttagcctc ctgagcacct gggactacag gcgcctgcca    4860
ccacacctgg ctaattctta tattttagt agaggcgggg tttcaccatg ttggccaggc    4920
tggtctcgaa ctcctgatct caagtgatca acctgccttg gcctcccaaa gtgctggaat    4980
tacagccatg agccaccatg cccagccaaa tcatgagatt tcaataccgc tgaactttga    5040
ttatggcaaa gtgaacttct gctttgatta aagcttgatg agagaggtgg ctggggatag    5100
tttgagataa gggcaaggca ggaaaatgca taatcttacg tgggctcatt gtcattgtac    5160
aattcttttg gtccatgtgg aatttgatcc gtcctatgac ttaagttatg tttatttttg    5220
tttttatttt tatttatttt gtgtctttt gagagacatg atgttgctct gtcacctggg    5280
ccagaataca gtggcacaat cttagctccg tgtagccttg aactcctggg ctcaagtgat    5340
cctcccacct cagcccctca aacagttgag attatagtat gaaccactgt gcctagcctt    5400
aagtgatttt taaatttgta ctgaacagtt tgtcctttcc ttccattaaa tcatattaga    5460
agtacagaac ttgatatttc ctgtagcaat acagttttttc tttgatgaag tttgatttca    5520
agtacttatt tttcataatt taaagctatt ttttatagag agaattttaa tcaaatattt    5580
```

```
ggatgtcact attgctatat atggtattaa gtatggtgac catagtttgt aaactccaaa    5640
ctgacagcaa gacaggaaat ttgtgttagc aaaggctttt ttcttactgt ttgaatttt     5700 taaaaattag atacaataca gagaggagca cacaaatcat taagagtaca gctcagcgaa    5760 tttcacaca gtgaacatgt gtaaacagca agtaacaaaa gatttacctg catcctataa    5820
cctcccatta ttcccttttc taggtactgt ctctccactg cattcccacc aaatataacc    5880
actatgctga attctgacat cataaatgag ttttgcctga ttttgagctt ttgtgactgg    5940
aagtgtacag tgtatatacc ctttcgattc tgtcctcttt agtttaccat tgtttgagaa    6000
atttatccat actgttccag aattaactac tgttaattat tgttaattaa ctactgttgt    6060
agttaattca tcctcattgt tatctagtat tcttttgtga gtaaacacaa tttccattct    6120
actgtgatcc cagctatcca tttgggtcgt ttccagtttg gggtccatta caaatagtaa    6180
tgctatctgt aatgctattt tgtattacta caaatagtaa tgctatttgt ggcacaaaaa    6240
tactgctttt gtgaacattc ttatacatgt cttttgatga atgtatgttt gcattgctgt    6300
tgtttacatt atgtacctag taatggaatt gctagatcat aggagatgta tatattaagc    6360
tttagtggat gcattacata attattagtt attattggtt ataccaattt atcctctcat    6420
cagtagtata caacagtttc tgtatctcta atctccaaca ttttagccat tttagagttt    6480
gtgtactaac acattgtggt tttaatttac atttccctga tgactaataa agttgagtac    6540
ctcttttgtg ttctttatag ccatttgact gtcttgtgaa gtgcttgttt gtcttgccta    6600 ttttctttt ctttctttct ttttcttcct tccttccttt ctttctttct tctttctttc     6660
cttccttctt ttcttttcttt ctgtctttct ttcttgtctt tcttgtcttt ctgtctttct    6720
tggtcttgcc ctgtcaccca tgctggagtg cagtggtgca gtctcagctt actgtagcct    6780
cgactttttt ggggctcaag ttatcctcct ttctcagcct cccaagaagc tggactacaa    6840
gcacgcacca ccatgctcag ttaatttttt attttttgta gaaatggggt ttcaccatgt    6900
tgtccaggct ggtctcaaac ttctgggctc aagtaatcct cctgccttgg cctcccaaaa    6960
tgctgggatt acaggcatga gccaccgcag ccagccttgg ctatttttca aaaggatata    7020
agtagaacat ctgtatatcc cttcaatttg catattattc agtaagagtt gcactctggt    7080
agtagaaata tataaggagg agaaagaagt ggaaacaaaa agtctattct catgagaaga    7140
cttgggggat agtgttctct ctagctccaa gctacttatt ccttacgaaa agttgaagat    7200
aaacttatct cagactgagg ctgtctcaat gttgtcttcc tattccatta tacacatata    7260
acccatattt ttttcaccag ctgaatttg ctccctagaaa attgattcat caggaaaaat     7320
atccgtcttg caaggtggtt ctctttagag tctgctgtgt gacatagctc aggacaaatt    7380
gtgtgatgtc agataggttg ggttaaggaa tagaccttat tggggaaaga gagaacttgg    7440
agggccaagg ttagcaggag aaggaaatgt tctctcatct gccgtcaatt cagggagggg    7500
caaacctggt gtctgtgttc acagggaggg atccatccat ctgtgattct cccttcttat    7560
caggtagcat gggaaagcta cactgttgcg gggaggaggg tcacacgcag gctacttagt    7620
accaggcacc ctggacttgg attcaggttg ccagttgtgt gagaaactgc ccagcacctg    7680
aaggccctga acccatgaga agttgtacct acctcccatg aggaggaatc ctgtcatccc    7740
atgggagctg agcttgggtg cagtccctct tgctggcttg tccaggagtg agctccaggg    7800
ttgtttggga cagttctgct cattgcttta cactgtgtat acattatctg tagagttcca    7860
tgaagagaac ttcagcactg taactgcaag ttttaacatg gaacagaatt tttctcacct    7920
gtattaattc ttaagatttg aagttctatc aacaagcatt tagattgtgt ggagattttt    7980
```

```
ttatttttat tttggagac agagtcttgc tctgttaccc agactggagt ggcagtggca    8040
tggtcttggc tcactgcagg ctctacttcc tgggttcaag cgattctcat gcctcagtgt    8100
cctgattagc taggactaca ggtacacacc accatgctgg ctaattttg tattttagt     8160 agagacgagg tttcaccgta ttggtcaggc tggtctcgaa ctcccagcct caagcagtcc    8220
acccacctcg gcctcccaaa ctgctgggat tacaggtgtg agccaccatg cttgactgac    8280
atcatcatgt taaaagaata aatgttctag ggagctgggc acagtgtcat gtttctgtag    8340
ttctagctgc tcgggaggct gaggcaggaa gatcccttga gccctggagt tcaagtccag    8400
cctgggcaac atagtgagat ctcttttttt aaataaataa ataactgttc tagggactaa    8460
aatttccttt caccattagt aatttactgt agaatctcca agaatgaact tattttaggt    8520
actgaaaatg agggagacta aatgttttat acagtagttt ttagtaaaat atgagatttg    8580
atgcatttga tagatgatgt ttgtttaaaa taattcttaa attttgatc atgtaattat     8640 agtttcatta atggtagatt tgtaaaataa atgttaccaa atgaaaatgc atgtacctat    8700
gttaattatc cttatctaaa gctgaaagtt cagttcaact atgttaaaac atagtagggg    8760
cctggcaggt ggctcttgc ctgtaatccc agaacttagg gaggccaagg tgggcagatc     8820
acgaggtcag gagatcgaga ccatcctggc taacattgtg aaaccgtatc gctactaaaa    8880
atacaaaaaa ttagccgggc atggcggtgg gcacctgtag tcgcagctac ttggtaggct    8940
gaggcaggag aatggcgtga actcaggagg cagagcttac agtgagccga gatcatgcca    9000
ctgcactcca ggctgggtga cagagcaaga ctccatctca aaaaaaaaaa aaaagttggc    9060
caggtgtggc ggctcacacc tgtaatccca gcacttttgg aggccgaggc aggcggatca    9120
caagatcagg agtttgagac cagcctggct aacagagtga aaccctgtat atactaaaaa    9180
tacaaaaatt agccaggcat ggtggtgcat gcctgtagtc ccagctactt gagaggctga    9240
ggcaggagaa tcacttgaac ccgggaggcg gaggttgtgg taagctgaga ttgctccact    9300
gcactccagc ctgacaaca gagcaagact ctgtctcaaa aaaaaaaaa attaatgatt      9360 aaattattta ggggagccgg gcgcagtggc tcacgcctgt aatcccagca ctttgggagg    9420
ccaaggcggg cggatcacga ggtcaggaga tcaagaccat cctggctaac acaggatgaa    9480
accccgtctc tactaaaaat acaaaaattt agccgggcgt ggtggcgggt gcctgtagta    9540
ccagctactc gggaggctga ggcaggagaa tggcatgaac ccgggtggcg gagcttgcag    9600
tgagccaaga tagcgccact gcactccggc ctgggtgaaa gagtgagact ccgtctcaaa    9660 aaaaaaaaa aattatttag gggaagatac tatacaattc tgtttaacaa gtcacatttt     9720
aattttttct tttggaaata ttagcaagaa ggctcacttt gtgctcaaca ttgcctgaat    9780
aacttattgc aaggagaata ttttagcccct gtggaattat cctcaattgc acatcagctg   9840
gatgaggagg agaggatgag aatggcagaa ggaggagtta ctagtgaaga ttatcgcacg    9900
tttttacagg tactgatttt aaactcacta agtcacattt cttttttttt tttttttttg    9960
agacggagtc tcgccctgtt gcccatgctg gagtgcaatg gcgcgatctc ggctcactgc   10020
aacctctgcc tcccgggttc aagcgattct cctgcctcag cctcccaagt agctgggatt   10080
acaggcacac ggcactatgc ccggctaatt ttttgtatct ttgttagaga tggggtttca   10140
ccatgttggt caggttggtc tcaaactcct gaccttatga tccacctgtc ttggcctccc   10200
aaagtgctgg gattataggt gtgagccacc acacccggct tacatttctt ttaaaaatgt   10260
ggataccatt tagaaaagga tgggccattc ttcctatagg gatctgactg gtgaattata   10320
```

```
actgtgctgt taactttgga aatgggaatg cacaagatat tgttttaaat atgcacgcta   10380
atgacagttt gtatccttct ttccccaccc ccacccttgc ttcaactacc tgtcaaaatt   10440
aacagcagcc ttctggaaat atggatgaca gtggtttttt ctctattcag gtaagtagtc   10500
acaagcatgt actatgtgtt gcttacatcc caggcaccgt ttcacagcct ttcaatagtc   10560
actgtaacaa ggcgaccttc ggaagttctt ctgtctacag agtatagatt atactctaga   10620
gtactagatt ttttttttct tgagacagag tctcgttctg tcacctaggc tggagtgcag   10680
tggcgtgatc ttggctcact gtagcctctg cctcccgggt tcaagcgatc ctcctgcctc   10740
agcctcccaa gtagctggga ttacaggcac ccgccaccac accagttaat atttgtattt   10800
ttagtagaga tagtggggtt tcaccgtgtt ggccagtctg gtctccaact cctgacctca   10860
gcctcccaaa gtgctgggat tacaggtgtg agccactgca cctggccaac tagagtacta   10920
gatttttata tagataaaca tgaaaggatt gtagaatctt catattagag tggggcattt   10980
aaaaattcct tcttgagaaa gattaatttg catctggatg ctaataataa ccttaattct   11040
ggccgggcgc ggtggctcac acctgtaatc ccagcacttt ggggaggccg aggtgggcgg   11100
atcacgaggt caggagattg agaccatcct ggctaacatg gtgaaacccc gtctctacta   11160
aaaatacaaa aattagctgg acgtggtgac acgtgcctgt aatcccagct actcggggagg   11220 ctgaggcagg agaatcgctt gaaccaggga gtcgtaggtt gcagtgagcc aagatcgcgc   11280
cactgcactc tagcctggtg acagagcgag actccatctc aaagaaaaaa agaaatcctt   11340
aattctaata agtcacaatg tctcaaactt accatctgtt gggtaaattt gagaaaatgc   11400
aataccttgc taccatcctt ttaaatcagc ctaccagact ggatttcctt attatggttt   11460
gtggcttttg atttttttt tttaatgtat agctctcttt gaattctttg gtggttatat   11520
atatatgtac tcgcaagatt cttttatctg tgggtctttc attcttttc taacactgtg   11580 agttgtatcc agagtacttt cggaacctct cctgagcgac ctatctctgc agatatcttt   11640
gtttatgttt cccttgtact gccctcctgg actcttcctc atccaccagc atttccatct   11700
agtgctttac cgtgccactg ctaacaggta atggctactg cagggctgaa atcagaggcc   11760
agagtaggcc cagcacttgg cgtttcctat ttgtgccttg ctgctcttgg tgcctgttca   11820
tgtgtgccca ctaccttgca ctcaatttct gtctttgctg gtacctggct cacttgcttc   11880
tttgttggct accttggagg gcagatagtg aattttcaga aatttccctt tttttgtcag   11940
acagattgaa ataaacaggt ttgcattttg ttttttctac aagcggcaag cccatgaccc   12000
tagaagtctg acatctatgg aaccttcagt ttaaatgccc agggagaact tattttggta   12060
gatatgattt ctgacattgc aggtagcaag ttgaatataa ttttttctaaa gtagcaccca   12120 cagcagccaa attatcagat gtatatagta gactagtttt aagaaaagca cttatgggta   12180
gaatatacat ctggattttt gaggcagttt tatttaggaa ttgtgtggtt ttctggaaca   12240
tctcagagac ctggtatgaa aagcactctt ctaatatata tgtgttttt tttatggatt   12300 tagtgatata tctatacaca cacactttttt aaaacctata gccggctggg cgtggtggct   12360
catgcctgta atcccagtac tttgggaggc ccaggcgggt ggatcacaag gtcaggagat   12420
tgagaccagc ctggccaaca aggtgaaacc ctgtctctac taaaaataca aaaatagctg   12480
ggtgtggtgg cgtgtgcttg taatcccagc tactcgggag cctcaggagg agaatcgctt   12540
gaacctggga ggcggaggtt gcagcgagcc gagatcgtgc cactatactc cagcctgggc   12600
gacagagcaa gactctgtca caaaaaaaaa aaaaaaaacc tatagccttc tagagaaatt   12660
tatatatgaa gtacacaact aacatagcta cacttcctaa atttggaatg gagtggttta   12720
```

```
gcttatgaaa agttgctatt tttcttaaca ggttataagc aatgccttga aagtttgggg    12780
tttagaacta atcctgttca acagtccaga gtatcagagg ctcaggatcg atcctatgta    12840
agattctgtt ttgcatttca tacatttctt ttcccaaatt tgatttttaa agttgtaatt    12900
tcttaaagaa gagaaataca ttttgaatac ttttgttttg atgttccctg tttcattcac    12960
tcagactttc ctatttcacc tttgtgatgt ccatgagcat ctgccctgta gccttcctgg    13020
caccccagtg tctgtggcag cacagagctg accccataag tggtgcatga ggccatcttg    13080
tggcacagca tcactaagct gctgcagaga cgttcatatg gttgtgtgat cttttaaaaa    13140
catcagtgac acttaactat aaatataatc ttaaattatc acaaatttta tataatattt    13200
gccagtagac aacataaata tgaattcaat atttcaagtt aatattgtct gttttctttt    13260
ttagaaatga aagatcattt atatgcaatt ataaggaaca ctggtttaca gttagaaaat    13320
taggaaaaca ggtaacattt cttacccttc cttgtctttt tttcttatat tgtacccat     13380 ttaaaactaa aatgtgggcc aggtgtggtg gctcatgcca acagtttggg aggctgaggt    13440 gggggggatca cttgaagcca ggagtttgag accagcctgg gcaacaaagg gaggtcctgt    13500
ctcttaaaaa aaaataaaa ataaaaataa aaataaataa aaaaaaaaac aaagagccag     13560
gcatggtggc tcacatctgt aattccagct tacttggaag gctgagtcag aaggatcact    13620
tgagctcagg agtttgaggc tgcagtgaac tatgattttg tcactgtacc ccagcctggg    13680
tgacagagta agactgttct ataaaacata aaaataaaaa aatatattt aaaaattaaa     13740 aaaaaaaag gattgctgac tttaaaatta ggaaactgac cagtaatgtg tgtgtgtgta    13800
gcatggttta tccttcttga tagatagaaa ttgtcatttt aaaagataat atcagttttc    13860
cttataaatt tatttgtgac aagtatatgc aatttaacta tatcataaga aaaattctat    13920
attaaagata atacaaatgt ggttacttt aagtgggttt ttatgtgatg actatgttct     13980
gtcagttaat tattacatttt atagatttgt atttagcata gtgctgtcac aaagcctgaa    14040
atagtgtcaa gcatgaataa agcattcaat tatgtttgct ttagtgtaag attattcatt    14100
atgattccaa aagccatgta atacgtacgt ctacagaaaa tcacttctat ttttttaaata    14160 aaacatgaaa tatgtcttga gcaagctatt ttaagaaaca atcatttaac gtccttgtta    14220
ttagaatttt gaatctttga aagagggtta ttgaaaacca gctaggacag taaaaagaa     14280 taaactagtg atacatgcag caatatggat gaatctcaaa ataattatgc tgaaagaata    14340
acccacaaac aaaatactac ctgctgtatg gtatcattta ttaaaagtct agaaagtgc     14400 agattcatct gtagtgatgg aaagcagatt gaccagcgt tgcctgggga cgagaaggct    14460
atggaggagt gagaggggag ggttacagag aggcacggga acatggcaa tgaggaatgt    14520 gttcactatc ttggttgtag taatggtttc atgggagtac agtatacaaa tgtgaaaaca    14580
tttcagaggc cagatgcagt ggctcatgcc tgtaatccca gcacttttgg aggccaaggc    14640
aggaggattg cttgagctca aggagttcag gaccagcctg gcaatggca caagacccca    14700 tctctaaaaa aaaatgaaa gaaaaaaaa ttggctaggc gtggtgatgc atggccgtag     14760
tcccaggtgc tagggaggct gaggagggag cacagaggtc aagcctgcag tgaatcatga    14820
tcgtgctact gcactccagc ttgggtgaca gaaggagatc ctgtctcaaa aaaaagttt    14880 caaattatac actttaaata tgtgcagttt attatatgtc acttataccc caataaatct    14940 gttttttta aaatgtaaat acaagccaaa aaaggtataa gtcaagaaaa tatattgaat     15000
taaatctgta agagataatt caaaaacaaa aaccctattg ttatcttta agtcacccaa     15060
```

```
atcaaatttg ggaaaagtca cctacttagc ttcatcctaa gttggttctt tctttctttc    15120
tttccttctt ttgagacgga ttcttgctct atcgcccagg ctggattgca gtggcgggat    15180
cttggctccc tgcaacctcc gccacctggg ttcaagcaat tctcttgtct cagcctccca    15240
aatagctgtg tctacagcca cgcaccacca cacccagcta attttgtat ttttagtaga    15300
gacggggttt cgccatgttg gtcaggctgg tcttgaactc ctgacctcag gtgatccgtc    15360
cgtctctgcc tctcaaagtg ctggggttac aggcgtgagc caccatgccg agccctaagt    15420
tggttctttc ttaaagttct tcctgaggag ccaagagcaa gttaaggaga tgtaacctag    15480
aagcttacag tggaggctag ctgggtgcag tggttcacgc ctgtaatccc agcactttag    15540
gaggctgagg cagggagatc actgaggcca ggagcttgag agcagcttgg cccaacacag    15600
tgacaccttg tctctacaaa aaaaaaaaaa aaaaaggca gcttacagca gtagaggctg    15660
atgcgagtgg gaatcacctc taggtaaaaa ccagtgtagc gtactgctga gattatttaa    15720
cctctgggtt ttatttatgt gtttttaaaa attatgatcc agtattttt acttttttt    15780
gtataaagta agcactgaat ttttaaggtt gtattaattt gcaaataaat gtctatctta    15840
ttattttgag agatttaaaa aattttagtt cttcaaaatt gcattttcac attttgaatt    15900
acgttatctt tgacaaatac agaagatgtc aaattttggt ttattttctt tggttctaat    15960
ttatatttt gtttaaaact atattttca ctatagactc tttctgtctc tcgaggtccc    16020
tgtataatga aaaagaaggc tggaaaagt attaacattg tcaaaatcca ggaaaagtag    16080
ttggtcatga tattgatcgt taactttaga aacttttgt atcttgtggg ttaaattagg    16140
attactatgt ggtagtgata aatgatgtta attagggccg agtgcagtgg ctaacacctg    16200
taattccagc atgtagggag gctgaggtgg gaggatgtct tgaatccagg agtttgagac    16260
cagcctgtac aacatagtgt aagacccctt ctccacacaa aaaaattaga aaatttgtca    16320
agcatcttgg tgcacacctg tagtcccagc tgcttgggag gatgaagcga gagaatcact    16380
taagcccagg tgttcgaggc tgcagtgagc tatgattgca ccactgcact ccagactaga    16440
tgaccatctc ttttaaaaaa atgtgtttat atgttatatg tgatagtgct ttttaaaaac    16500
attttaaat tatagagaca gggtctcact atgttcagc ccaggctggt ctcaaattcc    16560
tgggctcaag caatcctccc accttagcta acctcccaaa gtgctcggat tataggcatg    16620
agctgcatgc ccagctaatt tagtgatttt taaaaactga ctggtaatt ataaattctc    16680
ttcctggaac ttctgactt tcacaattg gaatcttttg acaaaatta tcagtaatgg    16740
gaaaactttg tgtagttgtc atttttcctc ccatcagtgt gatagatatg attggagtta    16800
tgttggactg atattttgaa aaaagattta attatagcta ttaataaga catttaaact    16860
actgactatg catttttatt cttttgggag ggtttaatgt ttatagttta agcaaactg    16920
ttgttttaa aaagtatct aacagggccg ggcgcggtgg ctcacacctg taatcccagc    16980
actttgggag gccaggcgg gcggatcaca aggtcaagag atcaagacca tcctggctaa    17040
catggtgaaa ccctgtctct actaaaaata caaaaaata gctgggtgtg gcggcgtgcg    17100
cctgtagtcc cagctactcg ggaggctgag gcaggaggat ggcatgaacc cgggaggcgg    17160
agcttgcagt gagccgagat cgcgccactg cactccagcc tgggcgacag agcaatactc    17220
tgtctaaaaa aaaaaaaaa aaaaaaaaa gagtatttag cagaggccag gtgcagtggc    17280
tcatgttgt aatcccagaa ctttggggagg ctgaggcggg cggatcattt gaggtcagga    17340
gtttgagacc agcctggcca atgtggcaaa tgtgctgtct ctaactaaaa atacaaaaat    17400
tagctgggtg tggtggtgca gacctgtagt cccagctact tgggaggctg aggcaggaga    17460
```

| | |
|---|---|
| atcacttgaa cctgggaggc agaggttgca gtgatccgag atcatgccac tgcactccag | 17520 |
| cctgggttac agagtgagac tcttctcaaa aaaaaaaaaa agtatttaat agtgataaat | 17580 |
| ctgcagtatt ctcttgtagt ttttaagatc atattattca gtcaaagaaa agagctcaac | 17640 |
| ttgaaatatt tccagagttt aaacaatctt actaagcttt gatgggttgt atctattctt | 17700 |
| aacatgtgaa acttccttat tacctataat atacactaac ttaaatattg acaattttt | 17760 |
| tccagtggtt taacttgaat tctctcttga cgggtccaga attaatatca gatacatatc | 17820 |
| ttgcactttt cttggctcaa ttacaacagg aaggtaagta acggctgaac attttgtaat | 17880 |
| gttacctttc gaagtagtta ataaccagg cacattagat gacagtgtga taaaactgtt | 17940 |
| tttctggcag tggcagtgaa acaatcttta gttttgacgt ggtgataggc tgtgatttgg | 18000 |
| gtgacgctgt tcagttagag ttctcactga cacctggccc ttcctcttct gaggatgctg | 18060 |
| cttctttgc agcccttcta agtaatggct ttttctttta tacatcacat atcacacggc | 18120 |
| tgagaggagg gatagatgtt tttcttcttt gcctcttcta ggccactgtt cttccttata | 18180 |
| aactccagtt tctttgaaat acatgcccct aacggctggg cacggtggct cacgcctgta | 18240 |
| atcccagcac tttgggaggc tgaggcaggc ggatacgat gtcaggagat cgagaccatc | 18300 |
| ctggctaaca cggtgaaatc ctgtctctac taaaaataac aaaaaattag ccgggggtgtg | 18360 |
| gtggcggacg cctgtagtcc gagctactcg ggaggctgag gcaggagaat ggcgtgaacc | 18420 |
| caggaggcgg agcttgcagt gagctgagat cgcgccactg ccctccagcc tgggcgacag | 18480 |
| agcgagactc cgtctcaaaa aaaaaagaa aagaaaaaa aaagaaatac atgcccctag | 18540 |
| attaaactat cccttgtcct tttgcactca tccacaagtc tcttttcatc agtgatttta | 18600 |
| ggatctgact cgttgtcttt ttctctactt caactacttt tatcattctt aattatttct | 18660 |
| gtatcgtcaa tcaatccagt acctgcctct tagtttcaaa atcacttact cttgcttagc | 18720 |
| tattaccagt aatcataacc actgtcaaat ctcaattgca agcatattac tcttaacta | 18780 |
| ccacctccta tctttaaacc atgttttgtc tgtttttta ttccagccat tctttaaacc | 18840 |
| ctactgtggg gcccaagcat ttcctttata cgcattcttc ctttcttcta ctgcttattt | 18900 |
| tctgtaatcc gtcatcataa tcactccatt gcattcttca acgtgtttcc cctctctccc | 18960 |
| tccatcatac ttgaatgaca aaaatctcaa ccctggttaa accacatctt ggccttgtcc | 19020 |
| attcctgtac cagagtagct ggacgtggct aaaaaataac ataaacatg atgattggt | 19080 |
| ttacttttt cttaaatgat ctatccatcc attcacccat ccatctatca aagtgactag | 19140 |
| gcctatttct gaagcccagg ctggagtgca gcagcataat cacagctcat tgcagctcca | 19200 |
| aactcctggg ctcaagtgat tctcttgcct tagcctgttg agtagctggg actacaggct | 19260 |
| tgtgctacca cacctagcta aggttttact ttaaatttat tataatcaca aaattcagat | 19320 |
| gagcctttag tgctgtctga tatttctact atgttttctt agtgatgtac caccctccaa | 19380 |
| ggtgttata aaaaattatg taccactctc caagaagttt ataaaaaata atgtgccacc | 19440 |
| ctccaaggtg actaatttca cagcttatgt ctttaaacct ttaagcactt tcctctccct | 19500 |
| tacacacctt ccttgtggct ttccgttaca ttctgctgag aacatagaag caattaaaat | 19560 |
| tatgttcttt ctaccagcaa atttatcaat ttgcttatat cttcacctgt gctttgagcc | 19620 |
| tatttaaata gatgaatggt cccctacctc taaccaaaac cagtccctca cttgtgggct | 19680 |
| ggatcccagc tcttctcacc tactcaagat gttcctgctt tcatctctcc actctcttat | 19740 |
| ataatcagtt cccccccct ttttttgtaa tattcctata agcagtaaaa taagcttttt | 19800 |

| | |
|---|---|
| atttccattg attaaaaata aaaatcctct cttaattcca tgaaactcca gctgcctccc | 19860 |
| cattttatt ttttccttag gattgtctct agtgtgcctt ctccttttct tgaactctgc | 19920 |
| ctcctgggtt caagcgattc tcctgcctca acctcccgag tagctgggat tacaggcgtg | 19980 |
| caccaccatg accggctaat tttttttttt tttttttgag atggagtttc cctcttgttg | 20040 |
| ctccggctgg agtgcaatgg cgtgatctcg gctcaccgta acttctgcct cctgggttca | 20100 |
| agcgattttc ttgcctcagc ctcccgagta gctggattta caggcatgtg ccaccatgcc | 20160 |
| tggctaattt tgtattttag tagagatgga agggggtttct ccatgtttgt taggctggtc | 20220 |
| tccaactcct gacctcaggt gagccgccca cctcggcccc ctaaagtgct gggattacag | 20280 |
| gcatgagcca ctgcgcctgg ccccggctaa atttttttt tttttttttg tatttttagt | 20340 |
| agagacaggg tttcaccata ttggccaggt tggtctcgaa ttcctggcct cgagtgatcc | 20400 |
| acctgcctca gcctcccaaa gtgctgggat tacaggcgtg agtcaccttg cctagccatc | 20460 |
| ttttagtaat ggtatttgga gatcacaatt tgagtgctgg catgcttatt gctgctgggt | 20520 |
| ttgttatgta gttattgtga attcacattt aggaatatag ggttttttaat tctttgattt | 20580 |
| tagatacttg tatctttttt cttttatatt taaaaccttg gttcctgatg atatcccttc | 20640 |
| ttagaaaccc tgtctacctt tggccttcag cccaccatgc tgtggttttc ctaacttgct | 20700 |
| gcctgcactt ttcagattcc tttcatggat cttaaatatc atctgtaaat aagatctatg | 20760 |
| tgtcaataat taccaaactt ttatctttag tcttgacatc taccctgaac acctagcttt | 20820 |
| gactaactcc tagctttggc atctccactt ggaaatccaa aaagtgtttc aaactgaaca | 20880 |
| tgtctatgaa agacttattt ttttctctct atccatgcta tccatcaggt tttccatttc | 20940 |
| cataagggtg actcttgtac tctggttcct atatattata ccgacagagc agcccagagt | 21000 |
| gcttcttaac cagtgtaagg cctgttatgt cccacccctca ctctttgtcc ttcagtggct | 21060 |
| tcccagcaca cttagaataa aatctgaagt cttaggccgg gcttggtggc tcatgcctgc | 21120 |
| aatcccagca ctttgggagg atgagggggc agatcacttg aggtcaggag ttgatgagac | 21180 |
| cagcctggcc aacatggtga aaccctgtct ctaccaaaaa atacaaaaat taactgggtg | 21240 |
| tggtgttgtg cacctgtagt cccagctact cgggaggctg agataggaga atcacttgaa | 21300 |
| cccgggaggc agaggttaca gcgagccaag atcataccac tgcactccag cctgggtgac | 21360 |
| agaacgagac tctcaaaaaa aaattaaaaa aaaaaaatat gtgaagtctt gaataaaacc | 21420 |
| caagatcttt accatggccc ctgaacaggg cagagtatcc attcttcaga cactcttcat | 21480 |
| agaataccat ggtgagctgg catatttatt atacaataca gaaacaattt tactggcaga | 21540 |
| aaacacatta aaccgtctaa actctgaata cagttgtcct cataaaaaat gttcaacata | 21600 |
| ctattttgag gttttccatt aatagttctt ataatctttg tcccattatg tgttaatcca | 21660 |
| acaaaggata tccaataaca aacaccaaag tttaagaaaa atgtgctagg cgcggtggct | 21720 |
| cacacctgta atcccagcac tttgggaggc cgaggtgggc agatcacctg aggtcaggag | 21780 |
| ttcgagacca gcccagccaa catggtgaaa ccctgcctct cctaaaaata caaacattaa | 21840 |
| ctgggtgtgg tggtgggtgc ctgtaatccc agctactcag gaggctgagg caggagaatc | 21900 |
| gcttgaacct cctgggaggc agaggttgca gtgagctaat attgcaccac tgcactccag | 21960 |
| cctgggtgac agagtgagac tccatctcaa attaaaaaaa aaaaaaatt aatgatagag | 22020 |
| aaacttaaat cagttagatt gttttaggta tagcccatcc ttggttttg tgtgtagcat | 22080 |
| ctagcttggg gaaccctggg attttctggaa tcatatttag acacagtcac actagactaa | 22140 |
| tgtaattctt ttgggatgca aaccacacgt ttgacaccctt aaatagcttt taggtatttg | 22200 |

```
gcttcccagc ccctattttt agttacaagg ggtgtacatg tgtgggtcag ggtgggggta   22260
gctctttccg cagatgatta gttttagcca tgttactagt tattgcacac attatctgtg   22320
tcctcacagc agccctgtga gtaagtgtat tagggttctc tagagggaca gaactaataa   22380
ggtagatgta tatatgaagg gtaatgtatt aaggagtatc gactcgtatg atcacaaggt   22440
gaagtcccac aataggctct ctgcaggctg aggaaccagg aagccagtcc aagtcccaaa   22500
acctcaaaag tagggaagct gacagtgcag ccttcagtct gtggcaaaag gcctgagagc   22560
ccctggcaaa ccactggtgt aagttcaaga gtccaaaaga tgaagaactt ggagtctgat   22620
gtttgagggc aggaagcatc cagcatggga gaaagatgaa ggctcagcaa gtctagtact   22680
tccacactct tatttctgcc tgctttattc tagctgagct ggcagctgat tagatggtga   22740
ccacccagtt tgagggtggg tctacctctc ccagttcact ggcttaaatg ttaatctcct   22800
ttggcaacac cctcgcagac acacccagaa acaataattt gtagccttca atccaatcaa   22860
gttgataata ttaaccatca caggaaggta ctagtatcat atgtttaaca gtagaaacca   22920
agacaaatgc agctaggaag tgggagaact gggatcagat gcaggcagtc tgattctaaa   22980
tcagttgctg ttacccactc tgacaacagt aagtgagtag cctgctcagt caagtactat   23040
attagtaggg cccttttacag acatatttat ttctcacagt cactcaatga gacggctctt   23100
ccagtcttac aatggagaaa gtgaggctca gagactttaa gtaacttacc ttagacgact   23160
ttactagtaa gtataagaat cattatttgg actaaagtct ttctgaatcc tcagcttgta   23220 ttttttttcca gtgttctgtg ctgccttttt atctactagt gttttacatc aattttgaat   23280
ctctttacta actggttagg ttgattttg cctttttttt ttaggttatt ctatatttgt   23340
cgttaagggt gatctgccag attgcgaagc tgaccaactc ctgcagatga ttagggtcca   23400
acagatgcat cgaccaaaac ttattggaga agaattagca caactaaaag agcaaaggta   23460
aaaatgaggc ctgcagtatg gaatatatgg tagtatttca ttatgagaat taaattttca   23520
tgcttagatt gaatatgtgg tccttgtgtt gttggcgact ctattttgga ccttatattt   23580
tagtgaagtt tattagttta aacttgaatc aactctttga aatacttaaa tatattaact   23640
tagttagctg gtatggtata ttcctagcac ttcggggaggc tgaggcaggc tgattgcttc   23700
aacccaggag ttcgagacca gcctgggcaa catggcaaaa cctcatctct acaaatagta   23760
caaaaattag ccagatgtgg tggtgtatgc ctatagtccc agctacttgg gaggcagagg   23820
aagaaggatc acctgaaact ggggaggtag agactacagt gagccataat cacactaccg   23880
cactccagcc tggtcgagag agtcagaccc tgtctcaaaa aaaaaaaaa aaagaaacgg   23940 aaaaaaaaaa cttagttgga ttcaaattgc aacacaatca ttatattact agagcttatt   24000
tgccagaaaa catttaagt tttgacttac ttaaagcctt tacattacaa atgcctttat   24060
gttatgtcta aaatagaaga ttggttgcag ttattaccag tgcttttgtt ctttagagtc   24120
cataaaacag acctggaacg agtgttagaa gcaaatgatg gctcaggaat gttagacgaa   24180
gatgaggagg atttgcagag ggctctggca ctaagtcgcc aagaaattga catggaagat   24240
gaggaagcag atctccgcag ggctattcag ctaagtatgc aaggtaaaga cattctgatg   24300
tgtgttgtat tcattgctga agaattgatt ccaattattc ttagatttca tggaagttaa   24360
tgtactctta gaggtgtttt gacaattact gcagaagcaa tagctatata gtgggctttc   24420
cctttagatt tcttataatg gaaatcactt tttacaaccct atattttatt aggagtagtt   24480
atatttttac tcctggttat tttatttggt ttcaacactg tactaacaca atagtaaatt   24540
```

```
gtggttttaa tctttgtggg tatcagttga cccttatcca aatcagctgt tacataaata    24600
tgtgccatta gacactatgg aagggcctgg acagggaata taaactgatt ttacaaaaac    24660
ccaacattta ttggctatgc aacttaaacc gtaagcccac tttggtgggc ccagtttttt    24720
agtgatataa actatcaata gagaaaagcg aaaacatatc ccctagacaa tctaggcaaa    24780
gaaaaatgtt aagacatagc tcaaagtagc ttaattaaaa gtttgaagtg ggttttttgt    24840 tttattttt tctaactcat atgtatttgc ttctactttc taatgaaatt atttatcagt    24900
tgatttcctt agatatctaa ataaaattga aatttcatta atgggaagat tatttttatc    24960
ctgaactttt cttgcctcta tgcatgcctc tgagtactcc atatggtgtg caatcccatt    25020
tttgattaat agagtcctgc tggattagca gggacagaaa tcagctttag atttctttct    25080
tttttttttt tctttctttt tttttttttt ttttttgag tcagagtctc actgtcgccc    25140
agcctggagt gcagtgatct tggctcactg caacccctgc ctccgaggtt caagcgattc    25200
tcctgcctca gcctcctgag tagctgggac tacaggcgcc taccaccacg cccagctaat    25260
tttttgtact tttagtagag atagggtttt gcccttttgg ccaggctggt cttgaactcc    25320
tgacctcagg tgatccacct gccttggcct cccaaagtgc tgggattaca tgtgtgagcc    25380
accacgccca gccagaagag tagaatattc ttaaagagaa aacgttttaa aggcttactc    25440
aaatgagtat aaacaaacat attgttgctt gaattggtaa atacagtgat tggtttttgt    25500
tgtgttgtgt tttgttttca ggtagttcca gaaacatatc tcaagatatg acacagacat    25560
caggtacaaa tcttacttca gaagagcttc ggaagagacg agaagcctac tttgaaaagt    25620
aaagtagttg gtacaagtta aagtagcatg tttaatattt gctttggcta ttttgtctat    25680
ttgtaaatgg ttactgcctg aatcctgtga atatttgaat gtatttttta aaaatttaca    25740
gcaaatagga cgggcacggt ggcttacgcc tgtgatgcta gcagtttggg aggccaaggc    25800
gggcagattg cctgaggtca ggagttcgag accagcctgg gcaacacagt gaaaccccat    25860
ctctactaaa aatacaaaag aatcagctgg gcatggaagc gtgcgcctgt agtcccagct    25920
gcttgggagg ctgagccagg agaattgctt gaacccggga cgtggaggtt gcagtgagcc    25980
gagatcgcac cactgccctc cagactgggt gacagagtga gactccgtct ccaaaaatat    26040
atgtatatat atataaataa aaataaaaat ttacggcaaa taacatgaaa caaaaaaacc    26100
ttgccccaat actggataaa tttttttaaac tgagtgaagg aaaccttata aaatttcatt    26160
tattaaaaga aaaatgaaat taggacaaga caagaagaat gccaattgat cctttggatg    26220
tacttcttgc ttacctgatt aaccctgcaa aattcctcta ccaatcagta cgaaaaacag    26280
ctttggaggt atgggagcgc attcccaaat agacgtggta gttcatttag ctgctcatgg    26340
ccgcttcagg cagtcctgta agcctgttag catcagggga atggatgcaa accataaatc    26400
tggatcaact cctaaaacct taccttgtgc ccagccttgt aagtgcttgc taaataggaa    26460
ttccaccata tgaaaataca ttcttttcaa gtaactatca ttcagacttt tgtcccccac    26520
tttttttttt taaagaaaaa taaaaggctg ggcacggtgg cttacgtctg taatcccacc    26580
attttaggag gccaaggcag gtggatcacc tgaggtcagg aattcaagac cagcctgacc    26640
aacatggtga aacctcatct ctactaaaaa tacaaaaatt agccgggcat ggtggtgggt    26700
gcctgtaatc ccagctactt gggaggctca gacaggagaa tcgcttgaat ctgggaggca    26760
gaagttgcag tgagctgaga taacgccatt gcactccagc ctgggggaca agagcgagac    26820 tcgtctcaa aaaaaagag aaagaaaact tcatgttaaa gattacaaga taataatca    26880 gacccactga tcctaggtca gaaaacagag tcatagctca atctgactta ctatttgctg    26940
```

```
tatttcatcc attctgagat gcacatagtt tcacatttca atgtctctga aattgagaag    27000
catcttacag tcataattga cagtatatta gcagcaccta taaatattgg ctcattttac    27060
atttgatggt ataatgaaga aaatatttac cttttttttct gttttgtttt taagtcacaa    27120
ctcagaagta gatgaaggaa aattctgatc agctgacatc ctcttaatgt gagatatttc    27180
tagtctttat tcagtataga ttaatggcta attatatgtt aaatttcaaa gtagtgctta    27240
ttagtgcttt ttacttttaa gtttcaaaat taacttttt attataataa actccaaatt     27300
tatacaaaag tagaaaaact agcatactcc tgtttatgac ccagattcaa caaatactag    27360
cacacggcca atcttgcttt tttttttttt ttttttgag atggagtctt gctctgttgc     27420
ccaggctgga gtgcaatggc acaatttctg ctcactgcaa cctctgcctc ctgagttcaa    27480
gcgattctcc cacttcagcc tcccaagtag ctgggattac aggtacacac caccatgcct    27540
ggctaattct tgtatttta gtagacacgg gatttcacca tgtcgtccag gctggcctta     27600
aactcctgac ctcaagtgat ccacctgcct cggcctccca gagtgctggg attacaggca    27660
tgagccactg agcccggccc aatctcgttt tataatactc ccatctccca ttctttccac    27720
tgtcccacct gcaagtttgg attattttgt aacaaatctc aatcatcata ttattctata    27780
accattttaa tatgtgtctc taaaatatat tagctttatt tttaacatag ttaaatgcta    27840
ttgtcataaa ataataatca taataattaa ttgtaattct atatcatcaa ttatctagtt    27900
aatgtaaaaa ataaatctaa ggccaggcgc ggtggctcac acctgtaatc ccagcacttt    27960
gggaggctga ggtgggcaga tcacctgaga tcaggagttc aagaccagcc tgaccaacat    28020
ggagaaaccc catctctact aaaaatacaa aaaattagcc aggcgtggtg gcgcatgctt    28080
gtaatcccag ctacttgaga ggctgaggca ggagaatcac ttgaacccgg gaggcgaggt    28140
tgcggtgagc cgagatcgtg ccattgcact ctagcctggg caaaaagagt gaaactccat    28200
ctcaaataaa taaataaata aataataaaa aataacttaa atctacttaa ttagaaaaac    28260
taacattcta aaaattttat tttaagaaat atcaaaattg gctgggcacg gtggctcacg    28320
cctctaatcc ctgcactttg gaaggctgag gtgggcggat cacctgaggt caggagggtc    28380
aggagtacaa gaccagcctg gccaacatgg cgaaaccctg tctccactaa aaatacaaaa    28440
attagccagg catgatgatg ggcacctgta atcccagcta ctcaggaggc tgagacagaa    28500
gaatcgcttg aacccaggag gtagaggttg cagtgagctg agatcacccc actgcactcc    28560
agcctgggtg acagagtgaa actccgcctc aaaaaaaaaa aaaagagaaa agaaatatag    28620
aaattaaagc atacatggcc aggcgtagtg gctcatgtct gtaatcccag cactttggga    28680
ggctgaggca ggcagatcac ttgaggccat gagttcaaga ccaacctggc caacatggcg    28740
aaagcctgtc tctactaaaa atacaaaaaa attagttggg catggtggtg cacacctgta    28800
atcacagcta ctttggaggc tgaggcagga gaatcgtttg aacccagagg tggaggttgc    28860
agtgagccga gattgtgcca ctgcactcta tcctgggtga cagagcgaga tactgtctca    28920 aaagaaaaa aaaaaggctg gcgcggtag ttcatgcctg caatcccagc actttgggag     28980
gccgaggcag gcagattacg aagtcaggag atggagacca tcctggctaa tacagtgaaa    29040
ccccgtctct actaaaaaat acacaaaaat tagctgggtg tggtggcagg cacctgtagt    29100
cccagctact ctggaggctg aggcaggaga atggcatgaa cccgggaggt ggagcttgca    29160
gtgagcagag atcacaccac tgcactccag tctgggcgac agagcgaggc tctgtctcaa    29220
aaaaaaaaaa gaaagcatac tctcacctcc ttcagtgact gatgttagta ttttggcaca    29280
```

```
ttcttttttct gtgacatata cacacttacc ttgtaagtgt tgtactcatt tcctatgaca    29340
gtaaatagtc tttgtaacag gctgcatgat atttcataaa atgaatggat gtggcataat    29400
ttatatgtga gccttttgaa ttctgctatt ataattaata ttgcaatgaa caattcttat    29460
attgcctcta cacctcaaat gtcttatcat ttcttctagt ttttctgagg atgtcagatt    29520
attgggttaa aggatatgaa cattttttaag gccttggaac agatttctaa attgctttcc    29580
agaataattc ccatgtgata cttttcaccat gtttatttca gactttttttt tttttttttt    29640
tttgagacga aatctcactc tgtcacccag gctggagtgt agtggcatga tctcggctca    29700
ctgcaacctc cgcctcctga gtttaagcga ttattctgcc tcagcctccc aagtagctgc    29760
ggttacaggc aagtgcctcc atgcctggct aatttttgtg tcttttgtag acatggggtt    29820
tcaccatgtt gcccaggctg gtttcgaact cctgagctca ggcaatctgc ctacctcggc    29880
ctcccaaagt tctgggatta caggcgtgca ccaccgcgcc cagccatcag agtctttttt    29940
gtcaaaataa aatggtctaa agacatacat catagagaaa ctataataca aaatttacag    30000
gtatatctaa gaaaagaaaa gtatatttaa agcataaaaa taaactgctc ttttacttaa    30060
aatttttaa aaactggatt aaaaatatga aacttccaac aaattgagct ttttttttt    30120
ttttttcttt ttttgagacg aggtctcgct tttgtcaccc agtctggagt gcagtggcgc    30180
gatctcggct cactgcaacc tccacctccc tggttcaagc aattcccctg cctcagcctc    30240
ccaagtagct gggattacag gcgcatgcca ccacgtcggg ctaattttttt tgtattttta    30300
gtagagaggg ggtttcacca tgttggccag actggtctcg aactcctgat ctcaggcaat    30360
ctgccagcct gggtctccca acatgctggg attacaggca tgagccactg cactcggcct    30420
gaacttttta tagtagtaac gataattcag taatgtccaa taatgactaa gtaagttata    30480
acaagtacaa tgtcagcaat aactagtgct ttttagtaaa cagggtcagg caaccttgta    30540
cccttttaaa aatgttcgaa tatcgatata cctccttcct acttggtgga ggattgattg    30600
aggaggaaag tgtgcagtga tggttaccag cttcagcctc ttggcttgac tttgcaaata    30660
ctggtgagaa tttggaaaga gcttgagaat atcttacata gtcacatgtt gctgagaaga    30720
gttaagaact aacttcttga tgttcatttt taacaatggc ttgcattcaa accttgtag    30780
agctcattag taggagctaa gaagctaata tttgcctttc actaaaattc ctgattactt    30840
agcctaggta gttcgttgtc tctctaggtt ctgtcttttgg gagcttgggt ctaaggttat    30900
caagctaact cttttcttccc tctcaccctt cccaaattga ccctggtgct gatttgttat    30960
tcatacgatt ttctagttttt tctttttccct ttttgagtat ttgaagcttc atactgaata    31020
tagtaatcat agtattcatg cataaagaaa atcataaagt aattgcataa atgcataaag    31080
taatcatagt tttcatgcat taaaaaaact agttttggct gggcgctatg gctcacgctt    31140
gtaatcccag cactttcgga ggccaaggca ggcgaatcat ctgaggtcag gagttcgaga    31200
ctagcctggc caacatggcg aaaccctcttc tctactaaaa atacaaaaaa attagccgag    31260
tatggtggcg ggcgcctgta atcctagcta tttggcaggc tgaggcagga gaatcacttg    31320
aacctgggag gcagaggttg cagtgagccg aggttgtgcc attgcactac agcctaggcg    31380
acaagagcaa gactccatct caaaaaaaaa aaaaaaaaa aaaaaactcc ctattacaga    31440
ttcataattt atgagtcatt aaataatatt ttcaagccat gacattttttt ccagcagtag    31500
tctctaaatc tgttttacca tcataaaacc ccaagcaaaa ctctactaca tcagctgtgt    31560
cactgtaaaa cctgccttaa ctcacagaag catgaaatta agcaatgtgt gtgaaactat    31620
tttataaact gtaaagtatt ccatacatac atgttggcag ttattaatgt cttctctagg    31680
```

```
tgtggctttg aaatggatgc agatgctttc tgttacaaaa aacataagtt gcaaatgttc    31740
tataacaagg agagacacaa atatcttcat ggacatggat tgctatgagt gtttgattgc    31800
ctaatacttg agccaccact tcagtgatat ggtataattt atcaaacagt gttgagaaac    31860
agaaactact ggggatgttt aaagaggaa aatacttaat atagaaatta ggggtttaca    31920
taatcttaag aaaggatgaa ggtgcagctc ttagccaggc ctccacagta ccacaaacca    31980
acttgcagga agagctgtaa ccactgcccc agttgggaca atgggtaatg aggatattaa    32040
atttaagaac atactgctat agcaatgatc cttggcatag aaagctgcca ccacaattgc    32100
ctagagatgg gaacatgaag tctggccccc attgcaacag cagtgaagca gaattttggg    32160
actggcatct cccaaatggc tttgcttgcc accagagaac aaccaaagtg gagggagatg    32220
gctaggcctc atttctgcct atttattttt attttttgag acggagtctt gtctgtcgcc    32280
caggctggag tgcagtagtg tgatctcggc tcactgcagc ctccgcctcc cagcttcaaa    32340
caattctcct gcctcagcct cctgagtagc tgggattaca ggcacccgcc actgtgccca    32400
gccaattttc ttattttag tagaggtggg gttttgccac gttggccagg ctggtcttga    32460
actcctgacc tcaggtgatc tgcccgcctc agcctcccaa agtgttgtga ttacaggtat    32520
gagccaccat gcctggccca tttctccctt tttttttttt tttttttttt gaggtggagt    32580
ctcactctgt tgcccagact ggagtgcagt ggtgcaatct tggcgcattg caacctctgc    32640
ctcccagttt caagcaattc ttctgcttca gcctcctgag tagctgggac tacaggtgtg    32700
tagcaccaca cctggctaat ttttgttttt gttttgtttt ttttgagaca gagtctcact    32760
ctgtcaccca ggctggagtg tagtggcatg atctgggctc actacaacct ccgcctcccg    32820
ggttcaagca attctcctgc ctcagcctcc agagtagctg ggattacagg tgtgcgccaa    32880
cacacctggc taattttttt gtattttaa tagagatggg gtttcaccat gttggccagg    32940
ctggtctcga actcctgacc tcgtgatccg cccgcctcgg cctcccaaag tgctgggatt    33000
acaggcatga gccaccgtgc ccagacaagg tttgtatttt tagtagagac agttttgcca    33060
tgttggccag gctggtcttg aactcctcac ctcaggtgat ccgcctgcct ggcctccca    33120 aagtgctggg attacaggcg caagccactg tgcctgaccc gtttctgctt tttaaagctc    33180
atgtgagcac ttaatttgta accagaatcc tacttgtaaa ataatctaag acatgtagct    33240
tttagctttg taacctctat aatattgatg gcacagtggg agtggatgct gagtaccact    33300
tgaacatgtt ccacctcagt gtcttcacag ctggaaggtg tctacattgt ttcaaggtgg    33360
acaattgatt tacttctcat ttttcataaa ctaaaagtag aataaaggct attcctctaa    33420
aattgctatc tcacctgtca ctcccttgca ttctcacata ccttcttgag tggaggggca    33480
gagggcatgg agtgatagca gatgtgccag gaattctcca taactcagtc cgtccctctt    33540
gtgctatgtt gcagcatcag gatttgctaa tgggaggata ctgcccttac gtgcatcatt    33600
agccatgcac actaaggtct tacacctaca cacaggtcag tattctggct cagagaccaa    33660
cagggagaaa ttgcagttct cattagttga actttcttta ttgttcacag ttttaaaaca    33720
caaaattgag aggaactcta taaaaaatgt gccattctat taataattgt tgctggtaat    33780
ttaaaaatcc ttgttccttt tcaaattctt atatacccttt ttttttttaaa cacttgatct    33840 tagccaaaag accgagaagc aatcttttt tttttttttt tttttttaa cctatagctt    33900 ctcactgaga ttgtcagctg tttgtaagtt ttggttttttg gttttctgtg tttgtattta    33960
catatatgaa atacagattg agtatcccctt atccaaaatg cttaagactg gaagtgtttt    34020
```

```
agatttgggg ttttttagga tttgtgaata tttgcactat acttaccagt taagcattcc    34080
aaatccaaaa tttcaaatct gaagtgttcc actgagcacc tcttttgagt atcatgttgg    34140
tgctcaaaaa gtttctgatt ttggagcatt tggatttctg attctcggat ttaggatgct    34200
tgacctgtaa tttcagattt acataaaagc agaaatagta cacagagctc cttatatcct    34260
tcacccagat tccccaatta ttggcctttc tgaaccattt gggaataata tgcagatatg    34320
attttccatt atgtctcagt tgttcagtgt atattttcta agtacaagaa tatattccta    34380
catatttaca tgataaccgt catgtttaaa cattttaaaa tggggatttg tattacattg    34440
tttctctttt tgaaaaaatt acagaggagc ttaatgcaat cagtattact taaaatctga    34500
taatgtgtgt taaatagtag ttttcattta tttcatttat caggtgttca gtgaatgctt    34560
actatgtaac agcacagtta tcagcactgg ggaaatagat gagtaagata agatttgcac    34620
tttcattagc ttacatgcca taagagggga aataaagaga acaccagatg atgataagtt    34680
tatgctgaga attaaaatga agtgatgaaa taatgggaat gtcaggtggc tacttttggt    34740
gggatggtca ggaaaggcat ctctggggag ataaatttta agctcagacc tgagtgaaaa    34800
gaatgagcca gccatggaaa cattatgtta actcacatgg tagtttgaaa tgctttatct    34860
gatcaaaggt acttattttt ggtgactttc aacaatatta agggtctata aaccaacact    34920
catttgcata agaataacta ccagtgaatc ttttttgtatg ataggttttt tgtttgttgt    34980 tttttttgaga cagagtctcg ctctgtcgcc caggctggag tgcagtggcg cgatcttggc    35040
tcactgcaac ctctacctcc ccggttcaag tgattctcct gcctcagcct cccaaagtag    35100
ctgggattac aggtgcctgc caccacgcct ggctaatttt tgtatttttta gtagagatgg    35160 ggtttcaccg tgttgtccag gctcgtgtca aacttctgac ctcaagccat ccacccgcct    35220
cggcctccca aagtgctggg attacaggtg tgagccacca ctcctggcca tgataggtta    35280
ttttgtgatg aaaatacctg cctcttaatt tgtctgataa atttaaattt tatgtctaga    35340
tttcctaaga tcagcacttc catattttaa agtaatctgt atcagactaa ctgctcttgc    35400 attctttttaa taccagtgac tactttgatt cgtgaaacaa tgtattttcc ttatgaatag    35460
tttttctcat ggtgtattta ttcttttaag ttttgttttt taaatatact tcacttttga    35520
atgtttcaga cagcagcaaa agcagcaaca gcagcagcag cagcagcagc aggggggacct    35580 atcaggacag agttcacatc catgtgaaag gccagccacc agttcaggag cacttgggag    35640
tgatctaggt aaggcctgct caccattcat catgttcgct accttcacac tttatctgac    35700
atacgagctc catgtgattt ttgctttaca ttattcttca ttccctcttt aatcatatta    35760
agaatcttaa gtaaatttgt aatctactaa atttccctgg attaaggagc agttaccaaa    35820
agaaaaaaaa aaaaaaaagc tagatgtggt ggctcacatc tgtaatccca gcactttggg    35880
aaaccaaggc aggagaggat tgctagaaca tttaatgaat actttaacat aataatttaa    35940
acttcacagt aatttgtaca gtctccaaaa attccttaga catcatggat attttttcttt    36000 ttttgagatg gagtcttgct ctgtcaccca ggctggagtg cagtgtcgcg atctcggctc    36060
actgcaagct ctgcttcctg ggttcatggc attctcctgc ctcagcctcc tgagtagctg    36120
ggactacagg cgcccgccac atcgcctggc taatttttttg tatttttagt agagacaggg    36180
tttcaccatg ttagccagga tggtctcaat ctcctgacct catgatccgc ccgcctcggc    36240
ctcccaaagt gctgggatta caggcgtgag ccatcacgtc cggccagaaa tcatgaatat    36300
tagtaggtga aaaataaaca cattttacca cctggaaaat gaaaaatact tgagtataat    36360
ctaaataaca atgggaagtg cagagttact ttccaggtct cggtttaaat atgtcttaaa    36420
```

```
ctttggccaa ttagtagtag aagttgagag aaaaagtaac tatctgacaa agaaattata    36480
agcagaatat ataaagaact cttaaaactg aataatcaga aaacaactca ataaaaaggt    36540
gaaggatttg aaaagatatt tcaccaaata agacataggg atgacaaata agcacatgaa    36600
aagactctca gcatcactag tcacagggaa atgcacgata aaaccacagt gagacaccat    36660
ggcacccctg taggtatggc tttaatgaag aaataaaact gacaatacca agtgttggca    36720
aggatccaag cagctgagac tcatatactg ttaatgggaa tgtaaaagtg tacagctttg    36780
gaaaacagtt tggcattttt ttgataaatg tatacttagc catgtgatcc agcagtccca    36840
atcatgtata tataaccaaa agaaaagaaa acttaggttc acataaaaac ttatatcaaa    36900
tgcttatagc tgaccaggca tggtggccca tgcctataat cccagcactt tgggaggccg    36960
aggttggcag atacctgaag tcaagtgttc gagaccagcc tggccaacat ggcaaaaccc    37020
tgtctctact aaaatacaa aaattagcca ggcgtgatgg caggcacctg tagtccagct    37080
attcaggagg ctgaggcagg agaatcacgt gaacccggga ggcagaggtt gcagtgagcc    37140
gagatcgtgc cactatactc cagcctgggt gacagagcaa aactctgtct caaaaaaaaa    37200
aaaaaaaaaa agggctggac acggtggctt acgcctgtta tcccggcact ttgggaggcc    37260
aaggctgatg gatcacctga ggtcaggagt tcaagaccag cctggccaac atggtgaaac    37320
cccatctcta ctaaaaatac aaaaatttgc tgggcatggt ggtgggcacc tgtaatccca    37380
ggaggctgag gcaggagaat cacttgaacc cgggaggcgg agattgcagt gagccaagat    37440
tgtgccattg aactccagcc tgggtgacaa gaccaaaact ccttctcaaa aaaaaaaag    37500 attatagcat ctttattcat cattgcccaa aattacaaac tgcctaaatg tagaccttca    37560
tttagttaat gaatgcacaa actgtggtat atccaaacaa ttgaataaaa aaaggaatga    37620
actggtactt ttttctattc ctcctgttta agtacagcca aaacacctca acatttgtat    37680
aaaacatgag ctgggctggg tgcggtggct cacacgtgta atcccagcac tttgggaggc    37740
tgaggcgggt ggatcaccta aggttgggag ttcaagaccg gtctgaccaa catggagaaa    37800
ccctgtctca actaaaaata caagattagt cgggcatggt ggcgcatgcc tgtaatccca    37860
gcttcttggg aggctgaggc aggagaattg cttgatcccg ggaagcgaag gttgcagtaa    37920
gctgagattg caccattgca ctccagcctg gcaacaaga gcaaaactct gtctcaaaaa    37980
gaaaaaaaaa accattcagc tgaatctcaa aggcagagag aagacagact ggctagggac    38040
cttggaacca gaggagcagt gtggtgggga gtggactgga ttttctttt gcctcattta    38100 tcctggactt ggtgctggag aagctatggg ttcagaccaa gagaaaccc catgaaaagc    38160 ctgctctctc tagccaaaag aggcaaccta gcaagataaa aacctttaga taataagcac    38220
ttgactccag tcaaacaaaa cagaataaac tggccccatt caccctgtc agcaaaggcc    38280 aagtgggagc caagatatgt accccaacct ggaagtcata aggtacactt ctccccttc    38340 ccagccaagg tggtgttaga gaaggctgac tgggagctg ggattctcat tccctccagg    38400
aggtgataac actcctttca catggtgtca gtggtcacag ggaggctgaa cttccaccca    38460
gtaatacata ggcatctctc tggctcctat atgggtgatg ttggagaaga ggccgagtag    38520
agaatccaga ctgttgctga cacccagcag taacaaggac acctcacaa tgtccgtgga    38580 ggccatgtgg agatcagtaa caaggcactg ctctccctcc cagtcagaga gatgtcagtg    38640
gaggactagg gggctagaac tcccatgtgc gttcagcagt aatccccatg accgccactc    38700
cttgacatca caggccttga agaaacctgg actttcactc ccctctggtt gtagcgaggt    38760
```

```
ggcactccct tttccctgtt gccagtgctg tgtcagtgga ggcttgctaa attggaagat   38820
gtaaataaga ttcacattct cataacataa taccccaaat tttcaggatt taattgaaaa   38880
tcactaagct gggcatggtg gctcacacct gtaatcccag cactttggga ggccaaggtg   38940
ggccaaacac ttaaggtcag gaattcaaga ccagcctggc cagcatggtg aaaccctgtc   39000
tctactaaaa atacaaaaat tagctgggcg tggtggcaca tgcctgtaat cccagctact   39060
gggaaggcta aggcaggaaa atcactggaa cctgggagac ggaggttgca gtgatccaag   39120
atcgcactag tgtactgcag cctgggcaac agagcaagac tccatctaaa tttgtgtcag   39180
gattcccaga aggagatgag aaagggtggg gctgaaaaaa attgaggaag aagtcatggc   39240
tgaaaatttc ccaaatttgg caaagtcag aaacctacag attgaaaaag ctgaatgaag   39300
ctcaaatatg ataaactcaa agaagttcac acagagacac atcacagtca gatttctgaa   39360
cactgcagac aaaaaatgaa gatctcgaaa ttagcaagaa atgaccttac ctaagcaatt   39420
tgaatgacag cagatttccc atcagagatc ataaaggcca gaaggaaggg gtacatacaa   39480 catttttct agtgctgaaa gacaaaaact ctaggctggg cacggtggca cacctgta   39540 atcccagcac ttttggaggc tgaggcaggc agatcacctg aagtcaggag ttcgagacca   39600
gcctggccaa catggggaaa ccctgtctct actaaaaata caaaaattag ccaggtgtgg   39660
tggcacgcac ctataatcct agctacttgg gaggctgagg caggggaatc gcttgaacct   39720
gggaggcgac ggttgcagtg agccaaggtc gcgccactgc actccagcct gggcagttga   39780
gcgagactcc atctcaaaaa aaaaaaaatt atccaggctt ggtggtgggc gcctatagtc   39840
ccagctactt gggaggctga ggcaagagaa ttggttgaac ccaggaggtg gaggttgcag   39900
tgagccaagc tcatgccact gtactccagc ctgggtgaca gagcgagacc ttgtctcaaa   39960
aaaaaaaaaa aaaaaaaaaa acaagaaaaa aactctaaac ccagagttac atatccagtg   40020
aaatatcctt caggagtgaa gggaaaatta acgatttgtc ttcaggagac ctaccctaaa   40080
agaatggcta aaggaatttc tctaaacaga aaagaaatga taaagaagt aattttggaa   40140 catcaggaag gaagaaagaa caataaaaag agtaaaatat gggtaaacac aatagacttt   40200
cccctccttt tgaattttct aaattgtatg atggttgaag caagaattat agcactgatt   40260
tggttttcag tatatatatt ggaaatattt aaggcattat gttacagatg aaggagggtc   40320
aaaggatata aagggaggta acctttctat atttcttttg tactgatgca ggcactttgg   40380
aaaataattt cactatttgt ttaaaaactg aacatacct gaccatatga catagcatct   40440
atactcctgg gcatttatcc cagagaaaca gaaatttatt tattttttt ttagtattac   40500 actccgtaag tgctgtaata ctagcactta gggaggctga ggcaagcaga ttgcttgagc   40560
ccaggagttc aagaccagcc tgggcaatgc tgcacagtca aaagaaaa acaaacattt   40620 agaaaactat tttaaaagtc tttaattgct gaatgcctct ttggctaata tttggaagat   40680
cattattatt attttctttt ttaggcaga gtcttgctct gtcactgagg ctggagtgca   40740
gtggcgccat ctcggcttac tgcaacctct gcctcccggg ttcacgccat tctcctgcct   40800
cagcctcccg agtagctggg actacaggcg tgtgccacca tgcccggcta atttttgtg   40860 ttttagtag agatggggtt tcactatgtt agtcaggatg gtctccatct cctaacctcg   40920
tgatccgccc acctcggctt cccaaaatgc tgggattaca ggcgtgagcc actgtgccca   40980
gcctggaaga tcattattta gtcctacaac tgacacattg ttccactgac gcaattgccc   41040
aggctggtct tgaactcctg ggctcaagca atctgcctgc ctcggcctcc ctaagtgcta   41100
gtattacagg cttgagccac tgtgcccagc caaaaataga aatttatatt ctcacaaaaa   41160
```

```
catgtacatg aatgtttata gcagctttac ttgtcataat caaaaactgg aaacaaccaa    41220
aatgtcctac agtgaaacaa actgtagtac atccatagca tgtaatactc tactgtcagg    41280
attaaaaaga aacccactgt tggcacaggc agcaccgtgg ctggatctca ggggcattat    41340
gctgagtgca aaaaagcctc aaagggtctt acactgtatg attccacttg ttcaactaaa    41400
aatgacagct gtatagagat agagaacata ttagtggttt ccactagtta gagaaagtgg    41460
gtaaaagata ggtgggtggg aatataaatc gatagcaggg agatctttgt ggtattataa    41520
cacttctatg tcttgattgt agtggtggtg gttacatgaa tacacgtgtg ataaaatgcc    41580
atgtagaact acatataacg ttgtgccaat gtcaatatct aggttttagt ttgatcttta    41640
gttacataag atgtaactat tgggtgaaat tgggcaaaag agtacacgaa acctctctta    41700
aatatcttta caacttcctt tgaattgaca gttttcaaa atagaaagtt gggttttgt    41760 aaatacatga attgttgata tacacaacaa atctcaaatg cattatgcta cgtgaaagaa    41820
gccatattca aaaggctaca tacctactga tgccttttat atgacgtgca ggaaaagata    41880
aaactgtagg acagagaata tactggtggc tatctgggat taggaaatgg ggatcgacca    41940
caaaggggca gcatggggga attttctggg gcaatgaat ggttgtgtat cttgatggtg    42000
tatttgtcaa aatatataga actataaaag taaattttgc tttatatgta ttaaatcaaa    42060
aaaagaaact cgtgctcaaa tagaaataca ttttctgaga acttgccttt tgatgacttt    42120
gagaattttc tggaaatttt aaagaaatgt ggttttgttt cccaacaggt gatgctatga    42180
gtgaagaaga catgcttcag gcagctgtga ccatgtcttt agaaactgtc agaaatgatt    42240
tgaaaacaga aggaaaaaaa taatacccttt aaaaaataat ttagatattc atactttcca    42300
acattatcct gtgtgattac agcatagggt ccactttggt aatgtgtcaa agagatgagg    42360
aaataagact tttagcggtt tgcaaacaaa atgatgggaa agtggaacaa tgcgtcggtt    42420
gtaggactaa ataatgatct tccaaatatt agccaaagag gcattcagca attaaagaca    42480
tttaaaatag ttttctaaat gtttctttt ctttttgag tgtgcaatat gtaacatgtc    42540
taaagttagg gcattttct tggatctttt tgcagactag ctaattagct ctcgcctcag    42600 gcttttcca tatagtttgt tttcttttc tgtcttgtag gtaagttggc tcacatcatg    42660
taatagtggc tttcatttct tattaaccaa attaaccttt caggaaagta tctctacttt    42720
cctgatgttg ataatagtaa tggttctaga aggatgaaca gttctccctt caactgtata    42780
ccgtgtgctc cagtgttttc ttgtgttgtt ttctctgatc acaacttttc tgctacctgg    42840
ttttcattat tttcccacaa ttcttttgaa agatggtaat cttttctgag gtttagcgtt    42900
ttaagcccta cgatgggatc attatttcat gactggtgcg ttcctaaact ctgaaatcag    42960
ccttgcacaa gtacttgaga ataaatgagc attttttaaa atgtgtgagc atgtgctttc    43020
ccagatgctt tatgaatgtc ttttcactta tatcaaaacc ttacagcttt gttgcaaccc    43080
cttcttcctg cgccttattt tttcctttct tctccaattg agaaaactag gagaagcata    43140
gtatgcaggc aagtctcctt ctgttagaag actaaacata cgtacccacc atgaatgtat    43200
gatacatgaa atttggcctt caattttaat agcagtttta ttttattttt tctcctatga    43260
ctggagcttt gtgttctctt tacagttgag tcatggaatg taggtgtctg cttcacatct    43320
tttagtaggt atagcttgtc aaagatggtg atctggaaca tgaaaataat ttactaatga    43380
aaatatgttt aaatttatac tgtgatttga cacttgcatc atgtttagat agcttaagaa    43440
caatggaagt cacagtactt agtggatcta taaataagaa agtccatagt tttgataaat    43500
```

-continued

```
attctctttta attgagatgt acagagagtt tcttgctggg tcaataggat agtatcattt    43560
tggtgaaaac catgtctctg aaattgatgt tttagtttca gtgttccta  tccctcattc    43620
tccatctcct tttgaagctc ttttgaatgt tgaattgttc ataagctaaa atccaagaaa    43680
tttcagctga caacttcgaa aattataata tggtatattg ccctcctggt gtgtggctgc    43740
acacatttta tcagggaaag ttttttgatc taggatttat tgctaactaa ctgaaaagag    43800
aagaaaaaat atcttttatt tatgattata aaatagcttt ttcttcgata taacagattt    43860
tttaagtcat tattttgtgc caatcagttt tctgaagttt cccttacaca aaggatagc     43920
tttattttaa aatctaaagt ttcttttaat agttaaaaat gtttcagaag aattataaaa    43980
ctttaaaact gcaagggatg ttggagttta gtactactcc ctcaagattt aaaaagctaa    44040
atattttaag actgaacatt tatgttaatt attaccagtg tgtttgtcat attttccatg    44100
gatatttgtt cattaccttt ttccattgaa aagttacatt aaactttcta tacacttgaa    44160
ttgatgagct acctaatata aaatgagaa  aaccaatatg cattttaaag ttttaacttt    44220
agagtttata aagttcatat ataccctagt taaagcactt aagaaaatat ggcatgtttg    44280
actttttagtt cctagagagt ttttgttttt gttttgtttt tttttgaga  cggagtcttg    44340
ctatgtctcc caggctggag ggcagtggca tgatctcggc tcactacaac ttccacctcc    44400
cgggttcaag caattctcct gcctcagcct ccagagtagc tgggattaca ggcgcccacc    44460
accacacccg gcagatttttt gtattttgg  tagagacgcg gtttcatcat gtttggccag    44520
gctggtctcg aactcctgac ctcaggtgat ccgcctgcct tggcctccca agtgttggg     44580
attacaggca tgagccactg cgcctggcca gctagagagt ttttaaagca gagctgagca    44640
cacactggat gcgtttgaat gtgtttgtgt agtttgttgt gaaattgtta catttagcag    44700
gcagatccag aagcactagt gaactgtcat cttggtgggg ttggcttaaa tttaattgac    44760
tgtttagatt ccatttctta attgattggc cagtatgaaa agatgccagt gcaagtaacc    44820
atagtatcaa aaaagttaaa aattattcaa agctatagtt tatacatcag gtactgccat    44880
ttactgtaaa ccacctgcaa gaaagtcagg aacaactaaa ttcacaagaa ctgtcctgct    44940
aagaagtgta ttaaagattt ccattttgtt ttactaattg gaacatctt  aatgtttaat    45000
atttaaacta ttggtatcat ttttctaatg tataatttgt attactggga tcaagtatgt    45060
acagtggtga tgctagtaga agtttaagcc ttggaaatac cactttcata ttttcagatg    45120
tcatggattt aatgagtaat ttatgttttt aaaattcaga atagttaatc tctgatctaa    45180
aaccatcaat ctatgttttt tacggtaatc atgtaaatat ttcagtaata taaactgttt    45240
gaaaaggctg ctgcaggtaa actctatact aggatcttgg ccaaataatt tacaattcac    45300
agaatatttt atttaaggtg gtgctttttt ttttttgtcct taaaacttga ttttctcttaa   45360
ctttattcat gatgccaaag taaatgagga aaaaaactca aaaccagttg agtatcattg    45420
cagacaaaac taccagtagt ccatattgtt taatattaag ttgaataaaa taaatttttat   45480
ttcagtcaga gcctaaatca cattttgatt gtctgaattt ttgatactat ttttaaaatc    45540
atgctagtgg cggctgggcg tggtagctca cgcctgtaat cccagcattt tgggaggccg    45600
aagtgggtgg atcacgaggt cgggagttcg agaccagctt ggccaaaatg gtgaaacccc    45660
atctgtacta aaaactacaa aaattagctg gcgcggtgg  caggtgcctg taatcccagc    45720
tacctgggag tctgaggcag gagaattgct tgaaccctgg cgacagagga tgcagtgagc    45780
caagatggtg ccactgtact ccagactggg cgacagagtg agactctgtc tcaaaaaaaa    45840
aaaaaaaatc atgctagtgc caagagctac taaattctta aaaccggccc attggacctg    45900
```

```
tacagataaa aaatagattc agtgcataat caaaatatga taattttaaa atcttaagta    45960
gaaaataaa  tcttgatgtt ttaaattctt acgaggattc aatagttaat attgatgatc    46020
tcccggctgg gtgcagtggc tcacgcctgt aatcccagca gttctggagg ctgaggtggg    46080
cgaatcactt caggccagga gttcaagacc agtctgggca acatggtgaa acctcgtttc    46140
tactaaaaat acaaaaatta gccgggcgtg gttgcacaca cttgtaatcc cagctactca    46200
ggaggctaag aatcgcatga gcctaggagg cagaggttgc agagtgccaa gggctcacca    46260
ctgcattcca gcctgcccaa cagagtgaga cactgtttct gaaaaaaaa aatatatata     46320
tatatatata tatgtgtgta tatatatg  tatatatata tgacttccta ttaaaaactt     46380
tatcccagtc gggggcagtg gctcacgcct gtaatcccaa cactttggga ggctgaggca    46440
ggtggatcac ctgaagtccg gagtttgaga ccagcctggc caacatggtg aaaccccatc    46500
tctactaaaa atacaaaact taagccaggt atggtggcgg gcacctgtaa tcccagttac    46560
ttgggaggct gaggcaggag aatcgtttaa acccaggagg tggaggttgc agtgagctga    46620
gatcgtgcca ttgcactcta gcctgggcaa caagagtaaa actccatctt aaaggtttgt    46680
ttgttttttt ttaatccgga aacgaagagg cgttgggccg ctattttctt tttctttctt    46740
tctttctttc tttttttttt tttctgagac ggagtctagc tctgctgccc aggctggagt    46800
acaatgacac gatgttggct cactgcaacc tccacctcct gggttcaagc gattctcctg    46860
cctcagcctc ccaagtacct gggattacag gcacctgcca ctacacctgg cgaatatttg    46920
ttttttttag tagagacggg cttttaccat gttaggctgg tctcaaactc ctgacctcag    46980
gtgatctgcc tgccttggcc tcccaaagtg ctgggattac aggtgcaggc caccacaccc    47040
ggccttgggc cactgttttc aaagtgaatt gtttgttgta tcgagtcctt aagtatggat    47100
atatatgtga ccctaattaa gaactaccag attggatcaa ctaatcatgt cagcaatgta    47160
aataacttta ttttcatat  tcaaaataaa actttctttt tatttctggc ccctttataa    47220
ccagcatctt tttgctttaa aaaatgacct ggctttgtat ttttttagtc ttaaacataa    47280
taaaatatt  tttgttctaa tttgctttca tgagtgaaga ttattgacat cgttggtaaa    47340
ttctagaatt ttgattttgt ttttaatttt gaagaaaatc tttgctatta ttattttttc   47400
caagtggtct ggcattttaa gaattagtgc taataacgta acttctaaat ttgtcgtaat    47460
tggcatgttt aatagcatat caaaaaacat tttaagcctg tggattcata gacaaagcaa    47520
tgagaaacat tagtaaaata taaatggata ttcctgatgc atttaggaag ctctcaattg    47580
tctcttgcat agttcaagga atgttttctg aattttttta atgctttttt ttttttgaa    47640
agaggaaaac atacattttt aaatgtgatt atctaatttt tacaacactg gctattagg     47700
aataacttt  taaaaattac tgttctgtat aaatatttga aattcaagta cagaaaatat    47760
ctgaaacaaa aagcattgtt gtttggccat gatacaagtg cactgtggca gtgccgcttg    47820
ctcaggaccc agcctgcag  ccttctgtg  tgtgctccct cgttaagttc atttgctgtt    47880
attacacaca caggccttcc tgtctggtcg ttagaaaagc cgggcttcca aagcactgtt    47940
gaacacagga ttctgttgtt agtgtggatg ttcaatgagt tgtattttaa atatcaaaga    48000
ttattaaata aagataatgt ttgcttttct a                                   48031
```

<210> SEQ ID NO 43
<211> LENGTH: 300019
<212> TYPE: DNA
<213> ORGANISM: Homo sapiens

<400> SEQUENCE: 43

```
gatgtcccga gctgctatcc ccggctcggc ccgggcagcc gccttctgag ccccgaccc       60
gaggcgccga gccgccgccg cccgatgggc tgggccgtgg agcgtctccg cagtcgtagc      120
tccagccgcc gcgctcccag ccccggcagc ctcagcatca gcggcggcgg cggcggcggc      180
ggcgtcttcc gcatcgttcg ccgcagcgta acccggagcc ctttgctctt tgcagaatgg      240
cccgcttcgg agacgagatg ccggcccgct acggggagg aggctccggg gcagccgccg       300
gggtggtcgt gggcagcgga ggcgggcgag gagccggggg cagccggcag ggcgggcagc      360
ccggggcgca aaggatgtac aagcagtcaa tggcgcagag agcgcggacc atggcactct      420
acaaccccat ccccgtccga cagaactgcc tcacggttaa ccggtctctc ttcctcttca      480
gcgaagacaa cgtggtgaga aaatacgcca aaaagatcac cgaatggcca tatccttttg      540
cccgaacccc agcagcagct gcgcctcccc ctcctccctc cgcctcccct cttccaggct      600
gggagagaga cccgggggtt gatgggaggt ggggaggagg ggggtcttcc agggctggg       660
agaggggca ccgggaggag tgtgaaagaa tctctccacc ccgagctggg ttgagctacc       720
ctggaggctt gggaatgggt ttgtgggggg ctgggggggtg ggcagcggag agtggatcct     780
tcccaaggac cgactctaga atgagatctg gggcctgggg tcgtgcagga gccttggtgg      840
gggctttcga gccaagtccg gagggtttgg agttctacgg agtgagcttg gagcgggctc      900
gggcctgggc gcttctggcc agggcagggg aactatgggg gccttggttg ggttttcttg      960
gccgtcgctc actggagtcc acgcagggga agctggacag cctctccact actgctttcc     1020
ccaaggtggg gggccgccgc acttttaggg cagggcgctt gggggctccc agggctaaga     1080
gcaagaggga gtccatgtgg ccttcacact gagaagccag cactggccga agtgagtacc     1140
ccagggtggg ccgctgttcc tatctggaga ggatagtgat gggctggggg gcgcttatgt     1200
ttccctcatg tgtgcaggtc ccattgcctt taaccgctga ttggggaacc tcatcatctt     1260
tgggggtgtc gagaaagaga tcccacttgc tttatctggg cccctggcct gggaagacct     1320
gatctggaca ctttcagtaa gaaagacagg gcaacagcaa atgaggtggt gggtccattt     1380
tagagcacca tgtccagctt ttcctacccc gagtagccga gagggaacac caggagaatc     1440
agcacccatg tggacatctt aggtaggtaa atgccttta aattttttt tttttaatca       1500
aagatccaga ggaaaaaggt gaagcccaca ttttcttctg tggagatgct atcaaaatgc     1560
agatcttctg tgtttctta atccctgcc tgcttgaaat aaaccttgag gagggcttaa        1620
catctatcga gatgtaggca ggcaagggtg ggtaattagt cgggcttct agcagttatc      1680
taagcatgac ccagattcca ggagggggga cacccctgc tgcccaggct ggctggccac      1740
tgtgccatgc ccagatgtgc cgcttctccg cacagttcca accagctgcc ctctgtgtaa     1800
aaatgaacgg gctggatggg tccctggggc tcagcgatga gtcccctatc cctttttgtat    1860
gtggttttgc agttatagac taaacgggc tgggccctgt gtggtctccg ggggttgctg      1920
tttgaggagc atgcgggtg gtagagggac tcacttcagg ggggttcaaa atcgagcctg      1980
gcgcttggat cctgggtgct gggattgcaa cagagggcac tgaggttttg gagtgtgtga     2040
gtggtctact ttgagggtgg ggaaaattaa gaagttcagc agaggtgctt ttgagggggag    2100
catacctcta actacgatgc catctccgtt ggtgcccaaa gcaggtgcca ggtctttgct     2160
tcctaagttt cagactctta aagaggctgg ttcttaaggt tagcaattcc tcaccatccc     2220
aggcccattg aagtgctcag gggtggcttg attactctgc ctatcaacag agtgaggagt     2280
gggagtgcct tgcaggagga cagggtattc atgggtgcac acccagttag ctccaggagt     2340
```

```
gagagggctt tgctcggctg acaggtttcc tcattgaaaa tggctttaga tcgccttctg    2400
gagcctggat ttggagactt ctaagaggaa aggaaggagg tggggagccc ttctgctgtg    2460
tccttagctt acctctgtcc agcctgaatc ctgcagattg gagggctgtt gggggagagg    2520
gggattgcag tggcccctcg aaggggga tcgtgggaga gggaggcagg tgaattgcga     2580
gtgttgcttg ccacttcatc tattctctgg ccagctcgcc cggggctttc ttgctcttat    2640
gatgagtttg tgcattatgc tctctgcaga ctgttttgt tctctttgac ccagggtaac    2700
aaacacatta tacagcccta ctctggaagg gaaaactccc cacctcacaa tctgtcatcg    2760
agctgggtca tccaggactg agctttctct gtcctggatg gagcggaggg cggtggcggg    2820
gtgggtggga gggttggaga tgagagggga tggacagaga cctggggagg gaggtagtga    2880
ataaaagaat tcaggccagt gtaaagagaa agacacgtgg aatgtcagag tcacgatacc    2940
agggcagaac attctacttt ttaatctaaa tatttctgcc attaaaaaaa aatgtttcag    3000
catatcctga gagtgaaaaa aaagtgtgt aggtacttaa ataaagtcta atatatgtac     3060
aggcaagtac atatattcag atgcatagat ttttacaaaa tgaacacacc cacgtatcca    3120
gcacccaggt cccgatcagt gccctggaag tccccctccc cataccgcct cctagttgct    3180
cccccaacaa gggtaccgct cacctgactt ctaaggttca ttttgcctct tttaaacatg    3240
taaatggagt cacacagtac gttcttttgc cactggcttc ttttgctcac atctgtgtat    3300
gtgactctac tacaatctat ccattctact gttgatgggc atttgtgtca tttctgtttg    3360
tgccactggg aacattcttg tgtcttctat tattttttc ccacagttct cttagatagg     3420
agtggaatcg cccctgctac ttttgatgc atgtgttgtg ggatgtgtat ttggaaatgg     3480
tgttgactaa gggttgcagg tcgatatgga aagcaggttc ctccctgtct tgtttaagag    3540
aagtgagtga atgatccatg aacttgtcgg tatgctcaca gggcctaaga gtgctacttc    3600
caaatgtaaa ttctggcatg gtacactggt gaaggatgca gtcttgcttt ctccacactc    3660
ggggcaattt gtcactatga tttcttcctc tttcatccct cagtgggtca aacttgaagc    3720
catcaatgac aattaagaat cctcatttat ttcattttt cccctcttcc taagtgagga    3780
aacccaaatg gaagtctttg atgttcaaat ttacattgcc gtgttttct catgccaggc    3840 agcaagccgt cttgaccaca caccttggtt tcatgttttc attgactgga attgtgattc    3900
aaatagggcc atgagggtct ctgatgattg ccgaagagct cagatctgtc agctcaaaaa    3960
ggagcatctg tcagccttcc tagagttccc tcccccactta atgccactca ctccttctac    4020
caagtgccaa ggtgaatgtc atcttccag ccctccctgt gccaccaggt ctcccactga     4080
acatgatgta gaaactcagg ccatcggagg aacactggaa gcaggtcagt gtattatcac    4140
gcacagttgc ctgaattaca cgtagaattc cagcttttca tccggtttgc agaaatctta    4200
acaagacacc taaagtcaca ttgacatcag gtgacatcac tttgacatct gtggacattg    4260
gctgattggc actcctctca tttttttttt tttttttttt tttaagaaaa gctctctaaa    4320
gagaaacttt ctgcatgaga agcgctggga gacatgggag caggttatca gactcttggc    4380
ctgtcctgag agatagaatg ttctagaagg tactgccgta gagggcagga tggtgtcact    4440
tacgtgatcc ttgtactaga ccggcttggc tggtatttcc agaggagcaa aattctgcga    4500
agtaaaattt agcacggctt ttccaatggg agtattttca aaagggtgc aatttcttat     4560 ccacaattcc ccaatccaaa aagctccaaa accaaagaga cgagctcata tagaggtaaa    4620
acctaacctg aactgacttc agtttgaagt cttaatttac agttttcatt cattctactt    4680
```

-continued

| | | | | | |
|---|---|---|---|---|---|
| ggtgtgcatt | tgagtatgtt | ttgcagcaga | aatgttagat | gtgcttgatg | atgaggtgct | 4740 |
| gcttcagctc | ctgactgtta | ggtctgcatt | gtagtcctgt | caaactttca | ggtgtatgga | 4800 |
| agttgtcttg | ttaacaggat | ggttctggtc | cagcaggatt | tgggtggggt | ctgggattct | 4860 |
| gcttttctag | ctagcttcta | gggattcccc | atgtggtaag | ttcatgggct | agggttggag | 4920 |
| tatccaggtt | agatcataga | gacatcttgt | tatcattttt | cttttcctta | aaaatcaggt | 4980 |
| ttatagggc | cggtctggt | ggttcacgcc | tataatccca | gcactttggg | aggctgaggc | 5040 |
| cggtggatca | tgaggtcagg | agttcgagac | cagcctggcc | aacatggtga | aaccccgtct | 5100 |
| ctactaaaaa | tacaaaaatt | agccaggcgt | ggtattgtgc | gtctataatc | ccagctactc | 5160 |
| gggaggctgg | caggagaatc | atttgaacct | gggaggcaga | ggttgcagtg | agccgagatt | 5220 |
| gcaccactgt | acttttttt | gagactctgt | ctcaaaaaaa | aaatagattt | attgatgtat | 5280 |
| aatttatttg | tagcaaaatt | cacccttttg | acatactggt | ctgcaagctt | tgacaaatgg | 5340 |
| atgtagttgt | ggccaccacc | caaatcaaga | tatgggacag | tttcatcaac | cctaaaatac | 5400 |
| ccccacagtg | cccctcttga | gtcagcaccc | cacttctcca | gccccttcaa | ccactgatct | 5460 |
| gttctccatc | cctacagctt | tgccttttgc | cgaaggtcat | ataaatgtaa | tttcacagta | 5520 |
| tatagccttt | tgaatgtgga | ttcttttact | cagactttga | gattcattca | tgctgttgcc | 5580 |
| tgtgacagta | gcgccttcct | ttttggtgtt | gagcaggatt | ccatgatatg | gatggaccag | 5640 |
| agtttgcttc | ccagccgaag | gacattggga | tgcttccagt | ttcaatgatt | atgaatagag | 5700 |
| ctgctataaa | cattggctta | tgggttttag | tgggaacatt | tcatttcata | catttcattt | 5760 |
| ctcttgggta | aattaaccca | ggagtgagat | tgctgagttg | tgtggtaggt | gtatgtttaa | 5820 |
| ttttataaga | ggctctcaaa | ctgttttcct | aagtggttgt | accatttac | attcccatct | 5880 |
| ttgcaatgcg | tctaaaagcc | ctgagttctg | aattccaaag | cacgtctggc | ctcgatggct | 5940 |
| taggattaag | gatgtggatc | tatggaaagg | agtggaagta | atagtgttaa | atcccggtca | 6000 |
| gagaaataag | aaagattaag | gatgtcattc | aaagctatgt | gcctgcacta | gagagagaga | 6060 |
| aagaaggggt | tctcttgggt | ggggttccac | ccctccctgg | tagttctacc | attccccagg | 6120 |
| aaaaagtcaa | gctctgaggc | tgtgagaccc | atgatcttta | ccctgttctt | caccactgca | 6180 |
| accccagtgt | gtgggacaaa | gcaggcgtcc | tataaacgtt | tgctgagcaa | atgagaaaag | 6240 |
| gtacctgtct | tcacccatta | actaaattgt | ataacatcta | tctgatctac | ccttgtgcca | 6300 |
| acgtttagg | attttgatgg | gttttagttg | caggggttg | agagactgtc | catgagatta | 6360 |
| tcagaccaat | gaaagtttct | gaaatgttag | tgcttgagta | gattggatgc | agcggcccct | 6420 |
| tgagaatgaa | gtctttcttc | agggacttgg | agtgggaggc | atctgttggg | tgcgtagggc | 6480 |
| ttatgcttcc | ccctccctgt | ttcccccca | gtagcaagca | cacatataca | ctttctcagc | 6540 |
| aataaaaagc | accgccggga | aggtggactc | catccagaaa | tgatcagagc | ctaagagccg | 6600 |
| tgcagtaacg | catttccgag | aatgccagct | cagctcctga | gaaagggcc | ggatgggatg | 6660 |
| gtgcctgctc | tgaaagaggg | cagagaggag | agggaaaaca | ctccggactc | tgggtcagac | 6720 |
| tggcccaggt | tcacattatt | caccagccat | gttatcttgg | gcaccagagc | ctatttcttg | 6780 |
| acatgcatga | tgaggatatt | ccttctagta | gcatctccct | tggagggctc | tcaggagatt | 6840 |
| aaatggggtc | gtgcgtgaaa | atggccagc | acagtctcca | gcacagagaa | aaaccccaaa | 6900 |
| acgccagagc | cgtaatacta | tggagtcatt | taggttccag | tgttcttttt | ttggaaaccg | 6960 |
| gccagaaaag | aggctttctg | ggtgggaatg | ggagcgaagt | gccccccccc | accccccct | 7020 |
| gcgactggtc | agtgtggatt | gattaacctg | atcgtggcgc | tctttaaagc | cacctttgga | 7080 |

```
cattttgcat tctccgttct ctctggaagc tttcagggga aaaaaaattc gtggccactt    7140
gacccatttt tctattccct tgagtctaag gtaaaaatta attctctttc ctcctttggt    7200
ccctccctct ctctgtgggt gacaaggtga gggagtttta aagtatataa ttagcttccc    7260
tcttccccttt ttgcactccc tgtctcttcc ttttggggccg gtcgagagtg cagcccagga   7320
tggccacccc aggtgtccac tgcaaactcc acagaaaaac tttgctcaac ttttggttta    7380
gaatttaggt acccccctcc ccttccaaac tttggtcttc tttctcctca ctccctaaaa    7440
aaataggaaa aacaaggaac attcctggcg agggaaccat gagtgggcac agcaacttag    7500
gtttcaaaaa ccactgggcc tcagttctta tctgagtagg gtgacccttc agccaggggt    7560
gcctgggact atcctgggtt tagcatctct ggaaactcac agtcctgggc aaactgggac    7620
gctggtcacc ctaatggtga gttcttaaca cctgagagag aagaatggtg caagagatgg    7680
tgccgttgac caagaaaggg ggagagtcag ttacttattc cctctgaaaa gccaagactt    7740
tttattggaa tgaatgcagc ttttagaagc cgtctttaag gcagctaata caagagagat    7800
tccagctatg aagggaaatg cctgagttaa gtccggatca agttttgaca tctcgcttcg    7860
gtcagacacg gctttatctg ccgttcagac tgggagcagc cgtgagtctt ccttaaaggt    7920
gcctgttgct caggcggcac ctgcagttag aaattagcag cctcccaccc ccagcccccca   7980
aataacagga ttcaagagtc ccctctctga agccatgagg gaaacccaac ttagtcaccc    8040
acttgccagt aaataatatt catgctgtta agttctgttc tcattttagg cctatgtgta    8100
aaaaatatat gtaattttaa actgattttt aaagtatttt catacgaaca gcatttgcag    8160
gagggcgaag tctggatgtt acctttttgt aaaagtggat ggatttgtct tcaatgagac    8220
tctggggcag acttaaaaact tggcccgcag tggtgttaca tggattctga tcttccagag    8280
tctgtcacgt tcttttatct ccatgatctt tattatcttc tttattgaga atgatgggca    8340
tggtgtgtgt gggtgggagg gctatgctga ccatcactgc agtgaaatgt gttcgtggca    8400
tgttgtggcg tctgcatagg aatgtgtctg tttgattaac agcacaagca gtggaggctg    8460
taaggaggaa aagaggaggg aaggtgatat tggatggagg ggagacatat agagcttggg    8520
aacagtccac cctggctgca aatctcagct ccagctcaca gttgtggagc ctcagtcttc    8580
tcctctgtaa aacggggaca gtagtcctat gtccgaggaa ttgtaagaag gttaaaagat    8640
actgtaccca gaaagcacat ggcatatata atcatcctgt gaagtagcca actcaatgaa    8700
ttttatttta tttatttga gtcagagtct cactctgtca cccaggctgg agtgcagtgg    8760
catgatcatg gctcactata gcctcgacct cctaggctca agcgatcctc ctgccttagc    8820
ctcccgagaa gctgggacta taggcatgca ccaccgtacc cagctttaac aacataaatt    8880
tatatatata tatatatata tatatatata tatatatata tatatatata tatatatatt    8940
tttttttttt tttttttttt tttttttttt ttgagatgga gtttcattct tgttgcccag    9000
gctggagtgc aatggcgcga tctccggctca ctgcaacctc cgcctcccgg gttcaagcag    9060
gacgatgggc atttgggatg tttctagttt ggggtggggg attgtttgtt tgtttgctgt    9120
tatgaacaat gctgctgtaa ggaatcaata attttgaatg aatgaattcg aggtgttaat    9180
tttagtctgt gtacttggaa atctagcttc acctagaatc agctgagatt catcagcatt    9240
tatggcagga gctaagacat ttcacagctt actcatcatt ttctctaaga ggctgggtca    9300
accggttagc tcttggtcct gcttgtattc tgagagtcag aacctgtggt ttagacactg    9360
gcaattgata tggttgtaga gaagcagcat ggttgagttg agagcatgga ttctggagct    9420
```

```
aggtggctgg ggttcaaatc ccagctctac tagtcactgg ctgcgtgatc ttgggcaagt     9480
cacttaagtg ttctgtgctt cagtttccca gtctgtccca gtggtgattc taatagctcc     9540
atggggatcc taatagctcc tatctgggag gattaaatga gttaatacat ctgatgttta     9600
gagtggtgcc tgacacttag gaagcactat atgtgtttat acatggaaga gtggatagat     9660
ggatggactt atgtgggtgg ccatatttgg gcttctctga tccactgctg agaatagtgt     9720
gtggcacaca gtaggtgctg cataagtgtt aatattctgc tctttcttgc caagtctctc     9780
aactcccttg atctctgtta ttttggcgt ctgtgttgtt aacccattct tctgaatgat      9840
cagctgaatc actgttgctc caatatataa gccaaggaga acacaatcac aaggtctcat     9900
tgattgtcca tactagaatt ccatgattcc taggcccaag taggattttc cccacgtctc     9960
agcaatcctt cttccatgtt tctaatcttt ttctctcatt tgttatgccc cattgccaga    10020
ctctccaatc tccccacagc ttccccttcc tctaactata ctgtctctag tcttaccttc    10080
tccctaaggg caccgtcttt gaagacatca aatacttcag agcaccaaat ataggttagc    10140
ttctctgagg gccttacaag gacatggagt gtttgggtct tacacaaatt ggaatggtca    10200
gaaatgttta gagacttgag ttgtctttga aagagttgtc agaatgcaaa tttttgactt    10260
gtggcctgtt tctgatcaca acgcagtctt ttaagttatg gatcatagct ggatgtttgt    10320
ggtttagagg ggatggaggc atcctctgca gttagtgttg gatgtctggg tggatggatg    10380
gatgatggga tggatggatg gatggatgga tggatggttg aacagatgca tggatgagtg    10440
gatggatgga tggatgggat gaaggaagga aggaaggatg ggtgattgga gggtaggtgg    10500
gtggataagt agattggtag atgactcgat gggtgggtgg acaaatggat gggtgaatgg    10560
atgactggat ggatgactgg atggattggt gtatgagtga atatatggct ggatgaataa    10620
ataggcagat gactagactg gattgagggg taaaaatatg gatgactgga tggtggatg     10680 agtggatgat agatggttga atgggtgggt ggatgggtgg atgttggata agggtgta    10740 tggtagggta gctgtctatg tgtgggtctc cctgatattt ggtgttctgt ttgacttggg    10800
aatgaccaag tctctccgct taccacctta tttgtacctt ttccagtatc aagtgaattt    10860
tgcacacttt tgtaaaaatc aataagattg tatgtttagg actttgggag gccgaggcag    10920
gcagatcaca aggtcaggag atagagacca tcctggctaa cagggtgaag ccccatctct    10980
actaaaaata caaaaaatta gccaggcgtg gtggcgggca cctgtagtcc cagctacctg    11040
ggaggctgag gcaggagaat ggcatgaacc cgggaggtgg agcttgcagt gagccaagat    11100
catgccactg cactccagct tgggcgacag aacgagactc catctcaaaa taataaaata    11160
aataaatatt atatgcttag gttttaccta tgtaattaga aagctccttg agggtagggg    11220
acagtgattt gccttcctca catccccca aagttcctgc actatatcat gcataagtat    11280
ttaattgagt aatggtgagg aaagtaaaca gtgttattga acaaagatta ttaaaattct    11340
ggaaacacct ggttttgttt cagcactggg actgaaagtg gaattccttg gattttgctc    11400
cattggtgga taggatagca tgtggtggtg gactggtaga ctctttctct tccaagcaga    11460
ttgggtaaat gccccagatt cttacccact agtcagagat tacagattac tgattgatat    11520 ggttttctc tgtgtcccca cccaaatctc atctcaaatt gtaataccca catgtcatgg    11580
gagggacctg gtgaaggtga ctggatcatg ggggtgattt ccccatgct gttcttgtga     11640 tagtgagttc tcatgagatc tgatggtttt aaacttgtgt gggcctcttt cctctctctc    11700
ctctcctgct gccatgtaag acgtgccttg ctttcccttt gccttctgcc atgatttgta    11760
agtttcctga ggcgtcccca gccatgcaga actgtgagtc aattgaacct cttttcttta    11820
```

```
taaattactt ttatagcagt gtgaaaacgg actaacacac tgatgtagca aggtccttta    11880
aggccccatg tgatctggtc cctgttttgt ctttgatctc atctctttca ttgtctacct    11940
tcctttcatt gtctattctg tctcagccct gctgaccatt ttactcacac ccatgtcatt    12000
tgcattacat gacattcctt ctgttcagca taagctattt cctctgcctg catcactgtt    12060
tctccaggtc tccccatggc taactccttc tcttcattta ggtctcagcc caaaagttac    12120
ctcctccaag aggcctatcc ttttcattta ctgaacatct catgtacaaa aagaatata     12180 aaatatatgt atactctctc atccacaaaa aaatctctga agacatttta atgtatttca    12240
tcccatacct ttttatgcat gtaaactttt aggaacacat ttccatgcca ctaggtatcc    12300
ttgaaaaaat aagggccacc atgtatagtt gcacaggttg tgcactgcac aaagatagca    12360
tgtcacatat cttaagtatc atggagcttg tatgtctact atttcagtac cccagctgat    12420
aaaagcttaa gtatcttgtt ctagcaagat gaagctatta tgacaatttt tgacagagaa    12480
aggggtgttt tgtttaagtt cacaatcaga gaaatgggtg tcttgtttaa tttcacaacc    12540
agagaaaggg gtgtcttgtt taaattcata cagtggtgct gtatgggttg gtggcaaccc    12600
cagaaaagac tgttgttaat atctgataat gttccactttt atacgtgtat tatattcatg    12660
taacaatctc tggctgtttg ttttgccatt ataaataaca gtgcagtaaa catctttgtg    12720
tgtgaatctc tgtccaaggt tctgatagtt ttctgaatga aattcctgtc tatatatggc    12780
actccaagcc cataattgaa actctgctgt taccactttc tttgaatctg tagaaggaat    12840
tttgagaaca ggtgactggt atattcagga tgttgatgac aaggaacaga gaaagaacag    12900
ttaaatggtt tggaattttt cctgggctgc atgtaaagca gtgcttttga actgggagca    12960
atttttcccc caaggggact tttggcaatg tctggagacg ttttttggttg tcacgaatgt    13020 aggggagggg ggcaagatgc tactggcatc tggctggtag aaaccaggga tgcagttcag    13080
catcttaaaa tgcacaggac agcctttctc agtaaagaat tatccagctc caaatgtcag    13140
taataccaag gttgagaaat cttgatgtaa tcgatgtcat gggtttcttc aagaggagtg    13200
ggtggattta gggttttttgg gtgacttaaa tttaatttac agtttgtctt cctagctggg    13260
tgtctaagcc agctttctgt gaactttaga tcccacacaa gaagcaacag gcttgctacc    13320
gacagattcg ttgatgtaaa tatagatgag tgtatagaag gaaatctcac ccagagctgg    13380
aaaatgttgg aatgaaaact gcggcggcct ccccttctct ctccttcccc ttctgttgcc    13440
ctgtttgaaa atcgtgcctt actttctttg gtctcctggc atggtgaatg ctgctggtat    13500
ggactgtgtt tctatatccc cttgatcccc acacccttag gaacgtacag gagagagacc    13560
ctggagcata tcagcttaga gatggagggg aatgggaagg agtgcgttca ttcattcata    13620
aatgttgact gagcacctac tgtatgctag gtgaatggga ggacgtgagg gcagggaggt    13680
gacaaggttg gcttattctg ggctttgtga actatggtga ggattttgtt ttttttccaaa    13740 ggaaatggaa taaccactcc ttttttcccc ccgatatacc taaactttt gattttcata    13800 acaaaaatgg gcttcctttt gtatatttgt tttgagacca gccgtttttc caccaacact    13860
gatcacactg cagtgagcat cctggtagag aagtctttgc acacttctgt cactgtttcc    13920
ctaggacaga ttcctggaaa tggtatggca aggttgtatg tcaggctttt gggccaggtt    13980
gcaagaaaca ggaagtctgt gccctttcaa attccaaggt cccctttccc tgacgacgtg    14040
gcccaatcag gcttgccctc ccttgatttt acatcttcac caatcagata agtgaaagtg    14100
aaatcctgtt gtggtatcct gtgcatttct ttggtgactt aagacataga gcattttcca    14160
```

```
gatctctgtg ggctgtttgg atatcctttc ctctgttttc tcaggcacat tctttaccga    14220
tgtctttgag ggattgagca agtttctgtt gaaattgagg catgtcatgg ctctgtgtgg    14280
ggcttgaggc agtccagtgt agtggaggga gggaggctgt ggagcctggc tgcctaggtt    14340
caaataccaa ctctgcttat ttccattcat atcattttag gcaaatcact tagcccctg     14400 ggcctgcctt tcctcatcag taaaagtggt ataacattag tgcctgcatt gtggggtggt    14460
tgtgaggaaa gcagcactca aaacagtacc tgacacacag tgggtgccaa ataagagtct    14520
gatgtattag tgttataggt atcggcctcc tccctcccca gtgcaatagt gtgtgtgcgc    14580
ctctgtgtac ctctgttggt gctgacaagc cctttttaaa atttagaggt gaggtctcac    14640
tctgtcccct aggctggagc acagtggtgc aatcatggct cactgcagcc tcaaccgcct    14700
gggctcaagc aatcctccca gcttagcctc ctgagtagtt gggactatcg gtgtgcacca    14760
ccacacctgg cccttagaca gccccttat ttcaaagcga aatggcagcc acaagattta     14820
gtgcaagctc tccaagcttt aggaccagct gcaactcctc taactgacca aacaggatcc    14880
cccatgtccc caaccccaa aacctgatga aaagcaaaca gaccattttc cacattcatg     14940
acggaaaggc ccttttcttg gctcctgccc ttgctcatgt caggatttca ctccatccct    15000
gataaagagg aagcaccatg tcccaggagg acatggaaac tctctgcttt gtggtgaata    15060
gttacagtaa cagtagctcc tctctgtggg gagcttatga gcccctaagc tttatagaac    15120
tgccctggca gtttatgaga acttcatccc agccccaga gctcatggca cttattttg      15180 cccccagttt gcagatgtgc acactgagac tcagagagct aacactgctt gccaaggtca    15240
cacatctagc aaatggagaa actttatgag acaggtgaag gcacagcaag gataaaaacc    15300
cagagggaaa aatactcaag ttttctccgg gaaaccattt gcattccaga gaggttggtg    15360
tgcgagtggg caagagatgt cgcgggacga tggttaaggg acagagtctg agctcaacta    15420
ggactaggtt tcttccttc cttccttcct tcctttcttc cttccttctt cctttccttt     15480
gtctttctct ccctcccttc cttcttcctt tccttccttt cctttctctt tccctcccctc   15540 cctcccttcc ttcttccttc cttactccttt tccttccttc ctcctttcct tccttcctt   15600 tctctttccc tccttccctc cctccttct tccttccttt cttcttcc ttccttttc       15660 ctttctcttt cctttctttc ctttccttcc ttcctctctt cttccttctt tctttctttt   15720
cttttctctt tcttcttc tttctttctt tcttctttc tttctttcct ttctttctct     15780
ctctctctct ttctttcctt ctttctcctt ccttccttcc ttcttttctt ttcttttcct   15840
ttcttttctt ttgttttttg agatggagtc tcgctctgtt gcccaggctg gagtgcaatg    15900
gcacaatctc agctcactgc aacctctgcc tcccggttca gcaatttc ctgccttggc      15960 ctcccaagtg gctgggacta caggcacgcg ccaccacacc cagctaattt ttgcatttt     16020 agtagagatg gagtttcacc atgttggcca agctggtctc gacctcttga cctcgtgatc    16080
ctcctgcctc agcctcccaa agtgctggca ttacaggcgt gagctaccac gcctgggcta    16140
ggactaggtt tctatcggtg gtgtggcttt tgggaagcta cctaatctta accactctgt    16200
ttcgtcatct ataagataag cagtgtagca ttttcttgca ggaatgttgc aaggattaag    16260
tggatggtga ctgtaaaaca tcatgcgtgg cacatagtaa attctcagca ggtagtcatt    16320
gctggtcatt tacttttctc taatgaccag caagctctta atttcctcct tggcatgggc    16380
actgggacgt agatggacaa aacacagaga gaaataaaca cacgacaaa atccccgcc      16440 ctggtgtggc tgatattctg ggtggggaga gagagggagt ccaaggacca gataaacagg    16500
taaaggatag tttgagtgtg gtaagtacta aggctcaaaa ataaagatct cccaggtgat    16560
```

```
cttagctgca tttggaggtg acaggagata caactgagaa actgagatag gaggaaaccc    16620
aaggggagat gtgggcttga tttagggtga tctgaggagt aggagaagtc aggggctggt    16680
gtggggaggc tctgatggtt ctctctgggg agtgaagcag ggattcgttg gggagaccca    16740
aggggacagg tgaaggcccc tgaacaggtg gccagtgctg agaaaggaaa ggtggaggac    16800
ccaagtgagt tcctaatttc ttcattgctc ccctaaggtg tttgtctcac ccttggccat    16860
agtcttggat cacttacaga tgcagaccag gctgggctca atggcttgtg cctgtaatcc    16920
cagcactttg agaggctgaa cccaggagtt tgagagcagg ctgggcaaca tggtgaaacc    16980
ccgtctctac aaaaaaatac aaaaattggc cgagggtgtt ggcacatgcc tgtagtccca    17040
gctacttggg aggctgaggt aggaggatct cttgagcccg ggagacctat gctgccaaat    17100
aaggtaggca gtagccacac atggctattg caatttttaga aattaattac aggccacatg    17160
tggtggctca cacctgtaat cccaacactt tgggaggccg aggcgggcag atcatgaggt    17220
caggagatcg agatcatcct ggccaacatg gtgaaacccc atctctacta aaatacaaa    17280 aattagctgg gcatggtggt gcacacccgc agtcccagct actcgggaga ctgaggcagg    17340
agaattgctt gaacccagga ggcagaggct gcagtgagct gagattgcac cactgcactc    17400
cagcctgggc aacagagaga gactccgtct caaaaaaaaa aaaaaaaaaa aaaaaagaa    17460 aagaaaagaa attaattaca ataaaaacag tccctgagtt tcactggcca catttgaagt    17520
gcccgatgac cctgtgtggc ttagtgacca ctgtgctgaa tagtgcagat ctagagcatc    17580
ctactggaca tgttgccagg gtccctgaac caacagaatt agcatctcct gggagcttgt    17640
tggaaatgca gaatctcatc ccctacccca gacctgctca atcccaatct gctcttcagt    17700
gagattcctc aggtgatctt gactgcacct tctaatcact tggaagcttt aaaaatgctg    17760
aggctgggca cggtggctca cgtgtgtaat cccagcactt taagaggcca aggcgggtgg    17820
atcacctgag gtcagaagtt tgagaccagc ctggccaaca tggtgaaact ccatctctac    17880
taaaaattac aaaaattacc caggtgtggt ggcacacacc tgtagtccca gctacttggg    17940
aggctgaggc aggagaactg cttgaacctg ggaggtggag gttgcagtaa gctgagatgg    18000
cactgctgca ctccagcctg ggtgacagag tgggactctg tctcaaaaaa aaaaaaaaaa    18060
aaaaaaaaaa gaaagaaaaa aggaaaatgc tgatgcccca agctccaccc ccacagatgc    18120
tggagagatt tgtccagggc ttcccctgga gtggggaatg tttgaaaact ccccaagggt    18180
ttctaaagtt cagccagagt tagcagaaag cccattaggt ggctaagcag gtagactgaa    18240
gttggagctg tgtgaccttg ggcaagccac ttaccctctc tgaaccacaa gctcccttct    18300
ctctaaaact agagacctgc tggcacctcc ctcccagggc tgtgagaagt aaatgatggg    18360
atgattcaaa gtgctgagta gggtcagatg cagtggctca cacctataat cctagcactt    18420
tgggacgctg aaatgggagg attgcttgaa gccaggagtt tgagaccagc ctgggcaaca    18480
tttaaacatt acccaggtgt agtggtgcat gcctgtagtc ctagctgctt gggaggccga    18540
ggtgggggga tcccttgagc ccaggagttc aaggctgcag tgaacaatga tggtgccact    18600
gcactccagc ctgggggaca agagtgagac cctatttcta aaaagaaag aaacccaaaa    18660 tgctgagcga gtgccttgga ttgatagtaa gcagtgcctg tgtaataagc atgaattta    18720 aaaaatgagg tcagcagcct tagagctaat ggttaatggg tttgggtgtg ggatttttt    18780 ttttttaatt tttaaaacat tgagataaaa ttcccataac ataaaattga ccattaacca    18840
ttttaaagtg tacagtttgg tggcatttaa tacactcagt gttgtgcaac catcacctct    18900
```

```
ctgtagttca aagaccccaa aaaggagacc ccgtactcac tgagcgctca ctccctgtct    18960
ctccccgctc ccccagcccc tggcaactac taatcttctg tctgtataga ttgacctatt    19020
ctgattttgg gggttttttga actcgccttc cctggctgac aacctctcgc catccaggtg    19080
agactgtgtg aaagcccagc tccctgcatt tctgggtctt cctctcccca ctgggggctg    19140 ccccccacctg tttcccctc tgggcaccct ggttctactc atcagcctgg cttaatccca    19200
gcagcaggtc catgttctgc tctcctgtgg ctgccacaaa tgagaggttt catctcagct    19260
gggtttctcc tagttaaata tttaataaat aagacctaca acttgtgatg ctgggagtgt    19320
ttgatagtga aattaatgat ggggagagag tggcaggcgg cccacaggtc catgctggag    19380
ctgggatgag gcgccctggg caggcgtccg tgccactgat gcttgggaac cacggtgggc    19440
catgccatcc catttccccc agccagggcc tctttttttag cactgtgtcc agcacagggt    19500
agccacctga taaataagtg ttaaaagaaa gagaggctgc gtgtgtaggg aagaaggaag    19560
agacagagga gacaaagagg agacacagag agagagagag agatgagaga gaaagaaaag    19620
tggaaggtga gaaagagaca gagatggaag gggagagaag gacctggatg gaggaagtgc    19680
aaggaaggca atggtgaggg aaaagagaga gagacaaaga tggaagggat gaaggagagg    19740
gagagatatg gaggtagaga aagagagaca gaaagagagg agagaatatt gcttcttgta    19800
tcttcccctt ctcctgttat ccttgaccat cttattattt ttttcttttt tctgtctctc    19860
cagttctcat ttccttaccc tcgccgtctt gccaactcgt catctctttt catttcctgt    19920
gtctatgtta tcttttaatt ttctgtctgg gtattttccc cttttctctt tctcagcata    19980
aactgttggt tggtgtatgt gtcttctttc ttttttagtc tttaactgac gtgtgtgtgt    20040
atgtgtgtgt gtgagagaga gagagacaga cagacagaga gagagagaga gagacagaac    20100
aaacctagag agcagtgtag gaacatagat gaacatttta aagaccaaac catgaagcgt    20160
acacccattt tacccaggtc aagagccaca gggccaccat cagattctcc ctcatgctca    20220
tcctcaatca cagccactcc ttccctcctg gaggaaccac tattggagat tgtatgggaa    20280
ccattcgctt gctttcttgt gtggttgtac cacctaagta cgcatcctga agcaatatag    20340
tcagatatta tgtggttttg agttttatat gaataaaatc atgtgagagg agttgttttg    20400
tattttgctt cattggtttg cagttacctt tgtgagattt catcctcatt gtggtcactg    20460
cagctccttc atgatcttgt ttattcattg atgatgagca tgtgactttg ttctcttttg    20520
ggcactggca taagcagctt tgttggttgt ttatggattc tgctgctcgc ttgcaggggt    20580
ctctctggag cacatcgctc tgtgtgaaat tgttggatac taagatttgt acattttcac    20640
cttgactaaa cactgccaaa caattttcca aagtgcttgt gctaatttac actcctgccg    20700
gtggtgggtg agcattcaag atgcttcaca accttgccaa cacttggtat tgtcaggttt    20760
ttaagttata gcctttctca tggtgatttc tcattgtgat tttagtttgc atccccgat     20820 tgcaaattag agtgaacata gtttaaaata tttattgact attcaagctt gcttttttgt    20880
gaagtgcctc tacatgctct gtccattttt gattaggtca cttttaaaaa aaaaatattg    20940
atttgtgggt gatccttaca tagcctggaa actgattctt catcattata tgttgtgcaa    21000
tattttctct tggcttggct tttgatcttt tttataatgt cttttgatca ccaacagttc    21060
ttaattttga tgtggttgat tttagaaatc ttttccttta tagtttgtgg gctttgtatc    21120
ttatttaaga aaatcatttc tacccctgagg ccatggatat attttatgtt atttctgaaa    21180
gttttacagt tgtgttcact gtatgtcttt aatcagcttg ggattgattt ttatatgtgg    21240
tggtaggtag gggtccaatt tcctttttat tccataagaa ttgtcccagc atcatttatt    21300
```

```
aaaaagccca ttcttgcccc aatgatctgc aagacaacct cttgactgtt taacttttac   21360
cttctttcat ctggtctgtt tttatactca acctttgaag ccacaaatat ttattgagtg   21420
ccaactgtgt gccaggcact gagttacagt gacggatatg acagatgcaa tcatggcttt   21480
catggagttt acagtctggc aaggatgaca tgtaaatagt tattactact tataatttaa   21540
aatgttatag gccttgcaaa aagggacaag tctggcttgc tctaaaagaa acatgtgaaa   21600
caacatcttc cagggaagtg ctgataaact gagtctttag tgggcctctg ctattgtagg   21660
ggtgggaatg gtggaaaaga tgttttggcc acagggaaca gcatgtgcaa aggtcctgtg   21720
gaaggtgctt aggagtttga tatttatcct aaaggcactg tcaggctact gaagcagtaa   21780
tacaatgatt ttatgtctgt gaatagttcc actggttgct gcatggagaa tgtattggaa   21840
tacagcaaga ataaaaagcc atgagaccaa ttaggaaatg atttcactca ttcagggaag   21900
tgtgccttgg gctggcatgg tggctgtgga gatggaaatc attgatcaga ttaaaagaaa   21960
ttttgagctg gcatgatttt tccctctct ccctctctc tatctctgtt tcttttctgg   22020
ttgtgttttc tgggtgagaa aagcagtttg tgatcctgcc aagggtatgt gctctggagg   22080
atgtatttgc cacagatggt ctttggaatt ctggccaaga gagtcactgg acagcccctg   22140
gcccccaggg tttctggagc caattcaaca atgactgttt attaacaaca gcaaggatga   22200
gttgctagcc tttccttcag agcacctttt aactgttacc ttactttgtt acccaaaccg   22260
acactatgga attggtgggg gagaagtgga agggttttta tctccatttt ttatagaacg   22320
ggggaagtta attggcactc ttgaaatcat acaaaagatg ttggtttcag gattggtttc   22380
tggactttca gcccaatccc aattactcaa gctcacacac ccaatcccca aacatactct   22440
tttgcaaata atttccctac tgaggtgctc ctggccaatt taaaaggtcc ccatttcctt   22500
gcctataaaa tgggaattaa agtaaaaata tctacctgtt gacttgctgt gaggtcagtg   22560
ggcctgacac atggtgtgga ctcattatat ttacctatgt gaatccctta gttcccttta   22620
cttggaagag gtggaaaact caaaggggct taaacaagaa gtggggattg tattggctca   22680
tgagactgaa gagtctcagg agtgtccagc ttcaggcttg tttggatcta gggatcagat   22740
aacaccatta ggcctctgtt tctgtttctt ggctctactt tttgcagctg gctccattat   22800
ccatgactta gctgcacttc cagccctcca gtctgcccaa gaccatattc agagagagat   22860
tcttctctct ttttcagcta tcttcccgga attttcagca aatgctttct tgcttttgat   22920
tggctgttgc tgaggtcgtg tgctcatgcc agaaccaatc actgtgggga aatgggaggt   22980
ggagaacggg gtgctctgat tggcttaggc ttgggtcaca tgactttatg gagttgggt   23040 ggagccaact tctccaagtg gggaagagca gtcttcttaa aggtgtatta ggatatgctt   23100
gctgctgtaa caagcaaccc ccaagtctgc agtagcttaa ggcaatacga atgtacttct   23160
cactcaccct aaatccaatc agataatcag caagtggcat tccatgtggt gatttcagga   23220
cccggctctt tccatctgtg gctccaccat cccctaagat cagaaagtcc ttcacttccg   23280
gcctgtagga aaagagtatg aaggctcaca caggaagttt tgggaggcca catatagaag   23340
tagtgaacct tacttctgcc tgcattctgt ggactggaat ttcatcccat ggtgtatgag   23400
agagggtccc agtaggaaac ggaagacaca gaccaagaat caaattaaga gatagcttaa   23460
gaatcaaatt aagagatagc ttacaaaggt gtgggcccct actgaaatag agaaggagga   23520
agagaggaag gaggcagaga cagagagaga ctgagactca caaagacaca cacacacaca   23580
cacacacaca cacacacaca cacacacaca caagttgaga gaaagaaggg gggagagaaa   23640
```

```
gagagagagg gagcatttcc taacaggaag ctggcagaat aaatgtcccc cattgtccaa    23700
agccagaggg ctgggagccc agtgagccca tccacacagg tcagccccccc atgtgacagt    23760 cctagaaggg taaagaagga aggagagtgg atttggggta atggaagaca gccaataccc    23820
atggtccatc tgactgcagg gggaactgag aaattcagtc catggagaag aaggtttagt    23880
ggacacgtca ctttgtcttt ttcacaaagt gaaactaggt tctcaggtgg aaaaaagaaa    23940
aagaaggttt gccttgctgc tattcttttt tttttttgta gacggagtct cactctgtca    24000
cccaagcggg agtgcagtgg cacgatctcg gctcactgga agctctgcct cctgggttca    24060
cgccattctc ctgcctcagc ctcccgagta gctgggacta caggcaccca ccaccacgcc    24120
cggctagttt ttttgtattt tagtagagac ggggtttcac tgctagccag gatggtctcg    24180
atctcctgac ctcgtgatcc gcccgcctca gcctcccaaa atgctgggat tacagacgtg    24240
agccaccgca cccggcctcc ttactgctat tcttattatt ggtggtagca gtggtggtga    24300
tggttattgg ttcttagttc cctctacatg ccagtatctg ctctcttctt ttttctccc    24360 ttacttcttt ccttgttctg caaattcttt ccctttaagt gaaaatcttt ccgtgttctc    24420
caagggagat aaattctatg ccaagcttga gtgtggggtc ctctgcttgg atagctgtct    24480
tctccaggag atgaggtaga actgagatag tgggggtctc tgcaggcagt ctgtgcccct    24540
ggcaagcccc tcaccttaac ctgaggctgg gtggggaaag atgccttgat ggagtcagaa    24600
cagaaagcaa gtgatcgctg cctgaaccaa gcagtcactt tcctggaggt gaaacctaga    24660
aacggtccct caggctgggt ccagggaggt ggacttgggt cccaggggca ggaagcaacc    24720
tgcccctcac ctgctcctac ctctttgtag cctatcttgg caaccagaag taggtataca    24780
agtgacgttg aagctgggca tgttaacaat ggtgtgagcc cgcctgactc caatctggtc    24840
cagctgtact ggccgtgcat cctcatctcc agccccagg gtcagcccag cggctgtaac    24900
aatggtctgt cccctccccg ccccacccac ttctttgaac tcctccaagg atctgtgatg    24960
atagggctgt cactgtctta gcttccacca ttcaagctta accggccttc ttcccctcca    25020
tggagaacgg aagagcaacc cctcattgcc tctggcagct gaccagcagg tccctgcctt    25080
ctgcccactc ccaggtctag gacaatgagg tgagaggtag acaggaccaa gttccccagt    25140
gctgtcttct aggtccacct atcatgagag ccgtgattcc tagttttat caccctctcc    25200 ccaactttgc cagctctcca cttctggcag tggtggctgc ccatgacttc accttcccgt    25260
gcctcagttt cctcatctgt aaaataagga cagccatggt aatgagagtt ctggtcaata    25320
tgccaggcac ctcgcttgca tcaatttagc tcatcctttc agtgccctga ggggtgggta    25380
ctgttatcat cccgtgtaac aaaaagagaa aaccgaaaca gagagagaga ctcactatct    25440
gaggtcttgc acccctcaag caacaaaagt gggatttcag cctaggctat ctagattcgg    25500
agtccacggt ctcaatgaat aataacaaca ataataatat tgtcctaatc tgatgagttt    25560
ttgatcagat tcaatacaag agcataggca gaaaagctta gcccagtgcc cagcacatgg    25620
taagaactca gcatgttatt tataatagta ataaccatt ttatgttatg taattatata    25680
ttcatagata aatatagttg actcttgaac aacataggg ttgggcaat gacctcctgt    25740 gcagtcaaaa atgtgtgtgt aactttttt ctctattttt tagaaatttt aaaattagag    25800
acaaggtctc gcttttgttg ctcaggttga tctcgaactc ctgggctcaa gtgatcctcc    25860
tgcctcagcc tctcaaagtg ctaggattac aggtgtgagc cccgcaccc agcctgtgta    25920 taacttctga ctcccccaaa gcttaactac taacagtcta ttcttgacca gaagccttac    25980
cagtaacata aacagtcgat gaagacagat tttatatgtt atatgcatta tatactgtat    26040
```

```
tcttacaata aagtaagcta gggaggagaa agtattattt taagaaaatc ataaggaaga  26100
gaaaatatat ttactattca ttaattggaa agggatcatt ataaaggtct tcatcctcat  26160
tgtcttcaca ttaagtaggc tgaagaagag gaggagttgg tcttgttgtc tcagggggtgg  26220 cagaggtgga ggtggaaggg gaggccagaa agacaagcac gcttggtgta actgttattg  26280
gaaacaaatc tacataagtg gacccataaa attcaaacct gagttgttca ggggtcaact  26340
atatatgcta caaatacgta atatgctaat atagttgtat gttattgtta tagtacgggg  26400
atcagaaaat gttttctgca aaggattagc tagaaaatgt ctagtaaata ctgtctcttt  26460
gggaccactc tactctgcca ttatagcaaa ggcagctaca ggcaatacgt aaatgaatgg  26520
gcatggccat ttgccaataa aactttgttt acacaaacaa gccatgggcc agagtttgtc  26580
aacggctggt atagtatatg ttattatata ttagctttac tttttctgtt gctttgttta  26640
tgttcttctt tgcccttcct ttcttaaagg ccagcctttc tttctctctg ttggtctgtc  26700
ttttaggaca gcatggcagg ccactgggac atgggctctc ctgactccag gcttgtttgt  26760
ctgataagac atgaagagtg aaggtggcag gactctgagc tcaggcctgt cctcctcctc  26820
ttccctctct tcgttttttc tttcctcttt cctctttttct tcccaagctc cagaagttgc  26880
cattttcctt tcccattgct gatttttctct gccttgggag aaagcccgag aagatcactt  26940
ggaaaagccc acgagcatct ctggcctcac tcacccagct cctgccattg tctttactct  27000
tcctcagaca caccaggcac agtcctacct cagggccttt gcactggctg tttcctctgt  27060
ctgcattgtt cttctctcag gtgacctcat ggcttctccc tcctctcctt caggacttca  27120
ctcaaaggcc accttctcag catttgcctc ccgcccttct gccttatttt cccctttgga  27180
acttttcacc ttcttactta ctcatctgtc tgctatctgt caccctacat cactatgatc  27240
tccacaaggg aaggtgattt tattcgtttt ttgttctgtt ttgttgaaga tgaggttttg  27300
ctcttgttac ccaggctgga gtgtggtggc acgatctggg ctcactgcaa cctccacctc  27360
ccggattcaa gtgagtctcc tgcctcagcc tcctgagtag ctgggattac aggcacccac  27420
caccatgcct ggctaatttt tgtattttta gtacagatgg ggtttcacca tgttggccag  27480
gctgatctca aactcctgac ctcaggtgat ccacccacct cagccttcca aagtgctggg  27540
attactgtga gccaccacac ctgatctttt ggttttaccc accaatgtgg actagaacag  27600
cctagatcag caggtggcat gcagtaagca gttgataaat atgtgttgga tgagtgagca  27660
ctgtggcttc tgtcattctg ttgctcaata gcattcatct ggaaataacc acagtttgtt  27720
tatccattta cctgttgatt ggcatttctg ttgattctcg tttgggccat tatgaacaaa  27780
gctgctgtga aatacttata cctttgccca attcttcact tggtgaaccc ttataaatcc  27840
tttaggccag gtgtggtagc tcacgcttgt aaccccagca ctttgggaag ccgaggtagg  27900
aggatcgctg gaggccagga gttcaaaacc agcctgggta acatagcaag acccgtctct  27960
acaaaaaaat aaaaaattgg ctggacgtgg caatgcatgc ctgtagttcc agctacttag  28020
gaggctgagg tgggaagagt gcctgagccc aggagttcaa gaccgcagtg agtgatcgcg  28080
tcctgcactc caggctgggc gatagagtga gaccctgtct gtaaaaatga cagcaacaac  28140
aacaataata aaaccttttag gtttcctctt aaaaggaaca tccttagagc ttttcctgac  28200
ccagcaactc accccaagtc tgaattagac ttcaccccat ttctttcata acatttatca  28260
caatgacatg tttattttgt gggggcgggt ggcattctgg ccagaactgt cgacttccag  28320
agtgaaaata cggaagaacc aaataaaaca caacacacac atttgcacag cagctcgagg  28380
```

```
gaggtgctta gttctttgag tttccaagaa cagagagacg aagatttgtc tggggaggaa    28440
aaatcaggga ctgcttcttg gaggaggtgg actgttgctg ccccatccac ccacacattt    28500
gcagatgtgg tgatgagaag atgactgtca cgaggtctct gagcccaggg ggcccatggt    28560
tgagtgcaaa gatagtgggg ttgacaaata atcgtcgtat aacaaaagaa aagccaccac    28620
agttgcataa tggaaaggcg gcttctatag aacattcaga tcatagttga aggcatgtca    28680
cactgtgtta ctcagaggcc actgtcagag ccaaaagtga gagtggatga gagtttgggc    28740
aggaaacaac tgaaccagat acagcatcac ctccatgagg gctcagcttt atctattttg    28800
tcttctgttg catccccagc ccttagaaca ctgcctggtc catctttgct gtgtgaataa    28860
taataaggaa cgatcgctgt gttgagtttg ggctgtgaat tcagacagtt tgctgctgca    28920
tacctgatta tgagtctcag ttttcctcct ccataaaatg ggcaaaacag tccttgcctc    28980
atggggctgt gcatttgttt agcaaacact gaaggagtat acatggtggc caaggcactc    29040
ttcaagacac aggaagcaga caaaagtccc tgccctctgg gagcttacat gctcatgggg    29100
agagatgtat gataagaaac aaaaatagta ggtaagttgc atagtacttt agaagattat    29160
aagggtaatg ggaagagaac agcagagaaa gggctgggga ggcagttgct gtattagata    29220
gagctttatc gaggcgatgg cattggagcc aagacttgag gaagctgtga ggatgtctag    29280
agaaagaagg aacagctggt gcaaaggccc tgaggtaggg gtatatgtga catgtgtgac    29340
agtgaggagg cagatgtggc tgaagccagt gagcaagaga gagggaaggt gcaaggataa    29400
ggacagagag gtgacgggac aggttttgga gggccttatg ggctgcgggg aggactttgg    29460
cttttgctct gagggagctg ggagccacgg agggcttttg agcagaggag ggacgtgacc    29520
tgactcagat attcataggc tcctctggct gctgtgaaaa gaacagactt gaaggttgg    29580 gggcaggcag ggcagaagct ggggaattag gaaggaggtg acagtgttgg tcctggcagg    29640
taatagtggg ggtggaacca ggttgttgtc tgtggagata ataatgagtg ctggattct    29700 ggttataatt tttaagtttt tttattgtga taaaatgaat tttttttattg tgataaaatg    29760 aaatttacca ctttgaggtg tgcaattcca cagcacttac tacagtcacc ctgttatgca    29820
acagtcacct ctatttaatc tcagaacatt tcatccccc taaaggaaac cctgcaccca    29880
ttagtagtta cttccagttt ctccctccc ccagcttctg gaaactacta attctggata    29940
taagttgaaa gttgaccagt aggatttcta ggcagacagg tggtgagggc tcaatgcatt    30000
catgcacaga aagtactcag gtggcatatc ataggtgctc aaaactgaaa tggtgatgat    30060
gagttggcaa tgatggtgag tccttccaga atccctgctc tagtgctaaa ctgacctacc    30120
tggctgtgta gaattctcac ctgctggccg ggagggtggc agaaccagga tcccttctta    30180
cttccagtct ggcttgggtt agggataggg gaggaatgat cagaagaacc aagctagcac    30240
catctgttct ggaacatcat ccaactcttg tccagatttc ccagaactga gcaggaaaat    30300
gtccagggag gaacagtgca gctgatggaa gtcctggtaa gccctggccc cagcttcctg    30360
agctgctgtt gcaccaacta gcatttgttg gaccttcagt ctgagccaag atggcagctt    30420
cagaggaaga acaagaagtg tacaagtttc tttcatggtt gtgtccccgc ctccttatat    30480
agcctcatat aaacccctgc actatcccgt tactgtttgc ctctccctga aaagagtgta    30540 aaactcccc acttttttccc tacttttcac aatgtgtttt ggtttctaaa gatgaaactc    30600
ctttaattat gttctggttg taattttctg gctccttta tttctccctt acttgatgta    30660 ttatttttccc ttgttccttc tgcccctgc ctccattgat gtttctcttc actgctatct    30720
agatttaatt ctcaactcct gccaagttca gggtgatagt gcaaaaagac atggaccatt    30780
```

```
tagtcttgaa ttcaggtccc acttctgaca ccttcaaagc tgctttactt tgggcaagtc    30840
atatgatctt cctgagggg tatcctttac cttgttcagc taacatttct tgtttttctc    30900
tgggcacaga gtagagtgtc attttcccca cctccctgaa gttaggtatg gctgtgtgat    30960
ttggtttcat caatgaaatg tgaggggaag tgacgtgagt ccttccggac agaagcctta    31020
agggtgagca tgggattcac catgtttcct ttttcctgcc tccactgtca tggatgcaca    31080
aagatggacc ctctctcaaa gtaagtgctg gagagaggat gacatagatc agtccccatc    31140
ccacttcata gcatgagtag aaaaatagac ctggggtgtg ttcaaccact gagatctggg    31200
gattgtttgt tactgcagca ggacatagac taggctgact gtatacctca ttatctgcat    31260
tttggggctg atatctaatc acagtgtctc caggaagatt atgttgatgt atgttttagg    31320
gatggatatt catattttcc tataagggct caataggttt ggaaatgtca catgcatgta    31380
aacttctgat taacaaatat ttcttgcttt ccaatttctt cctatagtgc ttctaatttt    31440
cctgtttttc aatcttgaat aaaatgtgag aagtgtttga cttctccttc gaggagatta    31500
atggtttcta aagcctgggg cattgattta gtcattctca acctccttgt ttctatgacc    31560
tttttttctc cttctctggt cacttagtgt ctgctaaggg gtgaaggaat gtctgtttta    31620
actcattgca ttttttttt ttttgagacg gagtctccct ctgttgccca ggctggagtg    31680
cagtggtgtg atgttggctc actgcaacct ctgcctcctg ggttcaagtg attctcctgc    31740
ctcagcatcc caagtagctg ggactacagg tgtctgccac cactcccggc taattttttgt    31800 attttttagta gagacggggt ttcaccatat tggccaggct ggtctcgaac tcctgacctt    31860
gtgatccgcc cgccttggcc tcccaaagtg ctgggattac aggcgtaagc caccacacct    31920
ggcaaactct ttgcattttt aactcttgac atcttcatct tcttttttccc acctcccctt    31980 tgcctgttcc tcccctgctc accccaccag ggagtttata atcaggttct agaacctgca    32040
atgtttttct gttgttgtct tccatcttcc ttgagtctta tgggaatcgg ccatagtcgc    32100
aaattaacaa atagctctga agcgcctcaa gcttggaggc atttccttt gctcacctaa    32160 gcaagatcct ggagctgttg caaatatcct gccccctact gtaaatctgt cttcatggtt    32220
gtaagagatt cagtcggggt cagtgaagac ccgagcagga gatcttggcc gaggctcctt    32280
gatgttctgt ctgcgctggg tgttgtcata ttgattaagc tcctgggact gctgccagca    32340
gcctctagga ttaaatcaat agagtttgca aaagtaaaag cttcttttgg agacacagaa    32400
tatgtgggtt tattttttaa tgataaagct tcaaggagaa tcttcatgga tggcagaacc    32460
agtgatggaa aaggcgaggc agacccaaat atttggggaa gtgcagtggg gagcaagtga    32520
gggaggtttc attgggaggc cggggctttc cagaaaatct gtttaactgg agttgctaat    32580
gcaacagctc agagttagaa gtgaaggtgg aagatgcaag aaggactgcc gctgagatgt    32640
aaagagaaat gaaggagagg tggatccatt tgctcattca ataaacattt tgggaggcag    32700 ggggtgggg gggagcctgc catgtgcctg gaactgggat gtacatggtg gggacatgac    32760
agtgggcagg acagatgtgg ttcctcctgg ccctcctgga acttgtaaca ggaaaagaag    32820
gcataaaata aggaataggc aaatacagac ataattacta attgtggtaa gtgtttggga    32880 gaaaccagc agggtcctgt gtttgttccc tagggctgcc aggacaaatt gccatgaact    32940
atatggctta aaacaacata aatatattgt cacccagttc tgaaggctgg aagaccaaaa    33000
tcaaggcatc agcagtgctg agctcccttg gacggtctcta gagaagaatg cttccttgat    33060
tcttccagtt tctggtagtt gttagcatac attggcttga ttggcttgtg gctgcatcac    33120
```

```
tgcagtctct gcctctgtct tcacatggcc ttctccttca tgtcagtgtc ttctcttcct    33180
cttctctctc tctcttttt tttttttgt cagggcctca ctctgtcacc ctgtacaaga      33240
gtacagcagt gcaattatag ctcactgcaa ctgctgcttc ccagcatcaa acaatcctcc    33300
cacctcagcc tcctgagcag ctgggactta caggcgtgca ccaccatact cagctaattt    33360
ttaaattttt gatagagatg ggatctcact atattgccca gactggtctt gaacttctgg    33420
gctcaagtga tcctccctcc tcagcctccc gaagtgctgg gattacaggt gtgagccact    33480
gcacctggcc tcttctgtct cttataagga tctttgtcga tggattttga gcccgtcaga    33540
taatccagga caatctcatc ttgagatctc taatttaatt atacttgcag aggccgtttt    33600
actaaataag gtcatggcca gaggctccag aggctaaagc atgggtatga ttgcaccact    33660
gcactttagg ctgggtgaca gagcaaggcc ccatctctga aaaataaaat aaaataagta    33720
acctactaca ggccctttgc gtagaggata attagaagta caggggtacc acgtaagtga    33780
agacctgaag gttgttaagc acagagcaga gtgtgaacag aatgagacag agggaggaag    33840
agaatcccag gcagagggaa cagcatgtgc aaaggccctg gggaaggaac aagttcatca    33900
tgttaaaaat gagccagtgt agctagagtc tgatgagcaa agggactcac aggtgggaag    33960
acacccaaga agttggcaga gacaggtcac acaagacctt ctaggtcaag ttccggaggt    34020
gaactttatt ctacatgcaa tgagaagtcc tcagagaagc ttaagtggga tgggacagaa    34080
ctgctttact ttaaatatat atacatatat acaaacatat aatattacat atataaagca    34140
tatatatgta tacatatata catatctatc tacctgtcta tatattttt agctgggcat     34200 ggtggctcac acctgtgatc ctagcacttt gggaggctga ggtgggagga tcacttgagc    34260
ccaggagttc aagaccagcc tgggcaacat agggagaccc catcactaca aataaaaata    34320
aaaattaaaa attagctggg tgtgatagtg tgcacctgta gtcccagcta cccgggaggc    34380
tgaggtagga ggattgctgg agccccaaag gttgaggctc cagtaagccg tgattgtgcc    34440
cctgcactct agcttgagca acagagtgag atcctgtctc aataaaataa ttttgtatt     34500 gaggtgaaat tcatgcaaca taagttaacc attttaaaat gagcaattca gtggcattca    34560
gcgcattcac aatattgtac aacctccacc tcttcctagt gctgaaatat tttcatcacc    34620
acccctccag aaaaccctgt atccatgagg cagttgctcc tcatcctccc ctcccggtat    34680 cccccaacc cccaccactc ctggtaacta caaatttgtt ttctgtttct atggatttac     34740
ctatactggc tctttcatat aaatgaattc aggcactgtg tgacctttcg tgtctggctt    34800
ctttcactta gcataatgcc ctggcttctc tctggagaat gaaatggata gaccactttg    34860
gagtctactg agattataga tatttctgtg ggaagggaca gtggcttgac cttgggtggt    34920
gctgaagagg caatgctgag caggaggatt caaagtctaa tttcggaagt agaattggtg    34980
gggtctgatg atacatcagc tgtagggga ggaagatgta ggaactggga aggtctctta    35040
gggtaacctt acctgattga gctccttact aggcagctgg tggtacaatt cataacaaag    35100
gttaatagag aaagagacat gggattaggg agggaatgga agagtttggg ccttggacac    35160
tgtagtggtt tgaatcctgt ccaccaaaaa ttcagatgca tttggaactt cagaacctga    35220
gacctcattt gaaagtagga tctttgcaga tgtcattgag tcaggattg agatgaggtc     35280 atcctggatt acagtggact cgagattcca tggtaagtgc ttttatatga aaggtacag    35340 gggagaaagt catgtggcaa tagaagcaga gaatggagtg ctgcagccac aagccaaaag    35400
acatgtagag gcaccaaaag cgggaagagg caaggaagga tcctccccta gagcctttga    35460
agggaaaccc cctaatttca gaaccttgcc tccaggatga cgagagaata aatttctgtt    35520
```

```
gttttaagcc acccaatctg tggcaatttg tcatgactgc cctaggagac taatatagac   35580
actcctatga gatgctctaa gaagacacag agtggtatag ctattgctaa gaccacacac   35640
tgtagcaggg aggaaatcaa atggagaaat gccccaactc cccctcctct ctgatctctt   35700
gctggtgcct cccgttggcc aagccaaccc agaaggcaga agatgtggtg gagggcagcg   35760
ttgcagggct tggatgatgc agtcacagaa gtcagccctg cctctaccag gatgccaaac   35820
agggcaatga gtggatattt tagggagaaa gggcaacaag agaatggcaa aatacatcga   35880
aatgcatgca agctctagaa agaggataga gatagataaa gggtgattac ctaggattaa   35940
gccccaggga agaccaacat ttagagattg gatagaaaaa gaggagcaaa aagggaagat   36000
tgagaagtag agaccaggag gataggagga aaactagaac aacattaaga agggcatggt   36060
caagtaatct gggcacagaa aaatggccct gggatttggc agcctggggg tctttggtga   36120
tcctctttgg aagagttttg gttgagtgat gggggctaga aaccagcctg gggagggtag   36180
gagaagaatg tgcagtgagg aagtggcagg aacacgtgaa ggcaactctt catgaagggg   36240
agtagagaaa ttggttggtg gctgaaggaa aattttcagt caagggtgga ggttttaatg   36300
atggaagaat attgatttct gtaaattggg tcattcccat ccattatacc aatatgcacg   36360
ggtgtcttct ctgatatagg atgctgggat tctcaaatgc ccatttgagt ttagcatcat   36420
gaatttaatg tcaccagccc agatagttga tctcattcag gaatgctcca ctgcccaggt   36480
atggggaagg caactagttg agttcatgca gggatggatt ttttccagga gagaaacagg   36540
aggcaagaaa gtgcgatata atcaacctat gtaaggttga caaggcagga gagggtcctg   36600
agaaatggcg gggtcagtgg gttgcagggc tcgatgggat ggacgttggt ttgcatttaa   36660
gggagttagt gagctgggag gtggttaaag aggaggtggt tcagccgggc gcggtggccc   36720
acacctgtaa tcgcagcact ttggggagcc gaggcgggcg gatcacaagg tcaggcgatc   36780
gagaccatcc tggctaacac ggtgaaaccc tgtctctact aaaaatacaa aaaaaaaaa    36840 aaaaattagc caggcgtggt ggcgggcgcc tgtagtccca gctactcagg agcctgaggc   36900
aggagaatgg cgtgaacccg ggaggcggag ctgctgtact ccagcctggg cgacagggcg   36960
agactccgtc tcaaaaaaaa aaaaaaaaa aaaaaaaaaa gaggtggttc aagacaagga    37020
tgctggaaac aggtgttttg gaggtggctg gtgtagcttc tgagcatgca tagctggagt   37080
ggcttggagg agacattggt tattgatgaa gaggtaggga catcctccag tgatcaagga   37140
agcaggggac cagcatggac aatggtctct ccacagggaa attggaggtc atcaaatgtt   37200
aacaggttcc gtcggagtct tagctcccag cttctgtttt cctgtggatc tcaggatctt   37260
ggctgctggt gctacctctg actttggact tcccattgag cccagcagca ctgggaggga   37320
ccttcatggc attggctggt ttaaggaaga cttccttggc tttgctgact ttcttggggg   37380
ccttcttggc tacacctgct tttgagggag ccctcctcac ctcacctgac ttcttggggg   37440 cacctttttcc accttatctg agttgggaag gtctttcttt gattctcttg ctttcttggg   37500
gcccttctca ctggtttttc tgggggccat gatggtggac atattccaga gctgagcttt   37560
ccttttgttc ttaggaacta atttgaggct gccagtggcc ccaccttggt cttagagttg   37620
atggtctgca gggaatttcc aggttaaagg tttttttattt gtttgtttaa ttttgagaca   37680
gagtcttgct ctgtcaccca ggttggagtg cagcggcacg atcttggctc actgcagcct   37740
ccgcctcctg ggttcaaaca gttttcctgc ctcagcctcc taagtagctg ggattacaag   37800
cacgcaccac catgcccagc taactttgt atttttagtg agacagggt ttcaccatgt     37860
```

```
tgaccaagct ggtctcaaac tcctgatctg aagtgatccg gccaccttgg cctcccaaag    37920
tgctgggatt acaggtgtga gccactgcgc ctgacctcca ggtttaagtt taaaccatga    37980
agtagatgga ctgtgtagag agagaccagg gaaatggagg attttactga ccactgaaca    38040
gggatgtcac tattgccaga gaggaaaagg attccccctt ggtagagtga acatataagg    38100
gaaagtggtt gaaaattgaa tcaggagaca gagacctcac accactcaga ggtccctaga    38160
gaactttact gacctagaaa aaagataaa caggggagaag gtcttcagtt cttgtttgga    38220
atctgacact gaagcatcct cactcctcac tctcttcccg accccgagag tctgaaattg    38280
attaatactt tttgtttaaa acttggcttg ttgttttgtt ttttcttttct gttttcatca    38340 agggatcttt attttacttt tgtgtatttg tgtgttttcc atgagtcatg ttaattcttc    38400 catgttttaaa cttttggcc cagaggaatt tatacattta aattatggat ttaatttcag    38460
aaggtacata cacacacaca cacacacact cactcatctc acttttttaaa aactgtaaaa    38520 tatagccctg taaatatcca gaaaatatct aatgtgggcc gggtatggtg gctcatgcct    38580
gtaatctcag cactttggga ggccgaggtg ggtggatcac ctgaggtcag gagttcgaga    38640
ctagcctggc caacgtggtg aaaccctatc ctcactaaaa ataaaaaaat tagctgggca    38700
tggtggcagg tgcctgtaat cccagctact cgggaggatg agacaggaga atcacttgaa    38760
cccaggaggc agaggctgca gtgagccgag atcaccccac tgcgcccag cctgggcgac    38820 agactgagac tctgtctcac aaaaaaaaaa aaagaaaaga aaagtcagt gtgcatcccc    38880 tctgacatcc agcaacttca catcttggaa tttatgctgc aggaaaatta tcacaagtgc    38940
acaaggatgt atggtgagat agttattatt atcattttaa aagatagggt ctcactgtgt    39000
cacccaggct ggagtgcagt gaagtgatca cagctcactg cagccttgac cttctgggct    39060
cgagtgatcc tcgtgcctca gcctcccag tagctgggat tacaggtgtg agccaccatg    39120
cctggcatcc cccttttttt aaaaaaggt tttaattatg aaaagaatat gggcttgttg    39180
ttttgtgtgg ttttttaaaa gcttaaaaaa tgtgtagtgt gtcatttaga aggtgaaaag    39240
cccttacccc atcccacctc ccagagataa cctctgctag caatttcgtg tttgtctttc    39300 aaatttttc ccacacacat tctttgtact ggctgcttcc cctcctgggt tactcttctc    39360
ccagacagaa acagggctca ttcccttgcc tcctccagct tttattaaaa cattaacttc    39420
cctgtagctg gatgcagtgg ctcacgcctg taatcccagt gttttgggag gtggggaggc    39480
aggaggatag cttgagccca ggagtttgag actagcctgg gcaacatagc gagacccatc    39540
tctacaaata aataaataaa taaataaata aataaataaa taatgaaaat ttaaaagaga    39600
gagggaagga ctcttgaaaa ccgtccatat catgcttctc taaatggttg agggctcaga    39660
ggaaaaaaaa tcagcaattt cacatcacgg aatttattct gcagaaaaat tctcacaagt    39720
gcacaaggat gcgtggtcag atgatgatga tgatgattat tattattatt attgaagaaa    39780
gtagcagcag cagcagcagt attttaaaag acagagtctc ggatgggcat ggtggctcac    39840
gcctgtaatc ccagcacttt gggaggttga ggtgggcaga tcacttgagg tcaggagttc    39900
gagaccagtc tggccaacat ggtgaaaccc caactctact aaaaatgcaa aaattagcca    39960
ggtatggtgg tgggtgcctg cagtcccagc taccagggag gctgaggcac gagaatagct    40020
tgaacccagg aaatggaggc tgcagtgagc caagatcgtg ccactgcact ccatgcactc    40080
cagcctgggt gctgacccag gttaggtgca agactccgtc ttaaaaaaaa agaaaaggaa    40140 aaaaaaaaa aaaggacaga gcctcactgt gtcgcccagg gtaaagtgca atgagtaaag    40200
gcccatgatg ggaaccctga ggagagagtc aaggggaaag aaaaaaaaaa aagcaaaacc    40260
```

```
aaaatggaat ttaaaaaaaa tcaggtgcaa tttgcataac agaaaattaa ccattttaaa    40320
gtgaacggct ctgtggcatt tactgcactc caactgttat gtaactacca cctctgtcta    40380
gctccagaac attttcacca ccctaaagg agaccttgta cccattaagc agtctctctc     40440
cttctcccct ccccaccacc ttcctccagc ctctggcaac cacccatctg cattctgtct    40500
ctatggattt acctattcta ggtagtcaac aggatgagat atcccaaaag tccatccatg    40560
gatgaacaga taaaccaagt gtgatatgcc ttcctcagat attagtctgc cttaaaaagg    40620
aatgaaatac taatctttgc tacaacatag atgaacctca aaaatatgat gtggctggac    40680
acagtggctt acacctgtaa tcccagaact ttgggaggct gaggtgggcg gatcgcttga    40740
gcccaggtgt tcaagaccac cctgggtaac atagcaaaac tccatctcta caaaacaatt    40800
tacaaaaaac tagccaggtg tggtgacatg tgcctgtagt cccagctatt caggagactg    40860
aggcgagagg atcgattgag cccaggaggc cgaggctgca gtgagccatg atcataccac    40920
tgcactccag cctaggcaac agagtgagac cctatctcaa aaacaaaac aaaacaaaac    40980 aaaaaagttg atgctgagtg aaagaagcca gacacaaaag gcaacatcgt gtttaattcc    41040
atttacatga aatgtccaat gaagattttt tttggcaaca tttatttga gtataatatt     41100 cagtgagtgg accacacata tgcatgcact gcagtatgtt cttggaaaca tttcagattt    41160
gagaggtctg ttcagctatg atgacggtag gtattgtccc ttccctccct ccttgaagaa    41220
aaggaactaa ggctggacgc ggtggctcat gcctgtaatc ccagtacttt gggaggctga    41280
ggtgggcaga tcacttgagg tcaggagttc aagactagcc tggccaacat ggtgaaacca    41340
tgtctctact aaaaaataca aaaaattagc caggtatggt gctgcacgcc tgtagtccca    41400
gctactcggg aggctgaggc aggagaattg ctcgcaccca ggaggtggag gctgcagtca    41460
accgagattg caccattgca ctccagcctg ggtggcagag caagactctg tctcaaaaag    41520
aaaagagaag agaagagaaa agaaaagaaa ccaaaagaaa aggaaagaaa agaaaaggaa    41580
ccaagaccta gaagggcaaa ataggaaaa gttggccggg cgcagtggct cacgcctgta    41640
atcccagcac tttgggaggc caaggtgggc agatcacaag gtcaggagat cgagaccacc    41700
ctggctaaca cggtgaaacc ccgtctctac taaaaatact aaaaattagc cgggcgcggt    41760
ggcaggcgcc tgtaatccca gctactcggg aggctgaggc aggagaatgg cgtgaacctg    41820
ggaggcggag cttgcagtga ccgagatag caccactgca gtctggcctg ggcgaaagag     41880
caagactcgg tctctaaaaa aaaaaaaaa aaaaaaattg gaaaagttat ttactattag     41940
cagcaattgt cataaagtaa tgaacattta ttgcatgatt acaatgagat aaattgtatc    42000
ctgtttttat aagcatatta agttttcttt tttaaaaaaa tgtatgtatt tatttatttt    42060
aagagatagg gtcttgctct gttgcccaga ctggagtgcc atggtatgat catagctcaa    42120
tgcagcctca aattcccagg ttcaagcaat cttcttgcct cagtctctcg agtagctagg    42180
actacaggca tgtgccaaca tgcctggcta gttttcttat ttttaaatgt attttttgtag    42240 agacaggatc ttgctgtgtc gcccaggctg tcctcaaact cctggcctca gcgatcctc    42300 tgccttggcc tcccaaaggg ctgagatgat aggcatctac ctctgcattt ggcccacatt    42360
aaattttcta gtcatcatgg gaaccaaaat aaacaatata aaacactcac attccttgag    42420
cacttactat atgcagggcc ctgtaataga ttattgtgtg tatcagctca ttccattctc    42480
acacaaccta tgaggttgat gctatttttct acctttata tatgaggaaa ctgaggctca    42540
gagaaggaaa ctgccttgcc caaggtcaag gccacgtctg atccccaaat cctttcaact    42600
```

```
cctctgcact actatttttt agtgcagata ttgccagttt tctaagcaga agcatgattt    42660
agcagccctg agtagacttc tcatttcaga accaaagtgt tggacattgt tggataatat    42720
gaaaaacaaa tgacacacaa acctatttga tactgttttt aattttctct tcatttgatt    42780
ttcctgatga catgattaat cttttttgcc tctaccctgt atgtgaaatg taggtctttg    42840
cagatgtctc agagagtgtt aatagttgct gctggttttg ttttctctcc ccggggattc    42900
ccatccctgg gtgcaagtga aattaaactt gtgcctcttt gccgctggcc gtggtgctga    42960
aaacatcccg ggcagcgcta gggttgccct tgttagcatg ccatccctgc taagagtctt    43020
aggctgatca gcgagtggag agatcttttc caggcttcat tttggttaga actgtgtgtt    43080
gaagatttta aagcccatgt ctgggaactg gagactgttt ggattgtttg aagttgaaat    43140
agtcatgaat aattcctact tgagatgggc ttatgagggc gtggactagc atgcaatggt    43200
tggcctttac taaactgtgg ccattggttg ggacttgggt gaggtgtaac ccatttggtc    43260
taatccatat ggttagggcc ccaagtgcac ctgcattcta tttttttttt ttttttaaata    43320 aaggcaaacc catctatctt ctaaccagga tagctcctga gtggtctttg gggaccacca    43380
gcttaaaagc atagactgtg ggctgggcac agtggctcat acctgtaatc ccagcacttt    43440
gaaaggccaa ggtgagagga tcgcttgagc ccaggagttc aagaccagcc taggcaacat    43500
ggtgagaccc tcatctctac aaaaatgtta aaagttagcc aggtgtgttg gcatgcacct    43560
atagtcccag ctactcagga ggctgaagtg ggtggatcgc ttgagcctgg gaggtcaagg    43620
ctacagtgag ctgtgatcgt gccactgtat tcaccctggg caacagagc aagaccctaa    43680 ctcaaacaaa caaacaaaaa aaggcataga ctgtggagtt gggcagacct gggtgtgagc    43740
cccagctctg ccagtacctc ctatgtgacc ttgaaaattt gtttaatctc tctgagcctg    43800
gattttcttg tgtggaaaat gaggcttacc acagaaccca ccttgtagaa atgttgcaag    43860
gaattaactg aaacaaagtg cttaccacgg tatctgccca agaagcagt tggaaacaag    43920 gcagctgtaa ttatggtcgc tgtgcttgtt aatggcccca taatagttga tcatattgca    43980
gagtgaaatt ggggtatgtg tttaatggac caaggaatat gtcttaaacc catatatcta    44040
gggttctggt accctctact cttttttcctg gtgattgtga tgagcatgga acttacatga    44100
aaatgaggtc tgtttggctt cttcacacaa gctcaatgac ctggctaact gctacaagta    44160
tctgtttcct tagaacccac ccatcagcag tccccatagt ggagacaagg tcacaaagag    44220
ttgacaaacc tgatttgatt tccgcaccaa ccacaggagg cttgaaatga gatgagggtg    44280
aagggcacca cagagggatg caaggattac ttggacactg caaggtcttg ctaagggatg    44340
ggaaccatca gccacgccca ctttgagaat tttccttcat gttctgaatc tgaagagcaa    44400
ggtcctgttc tcagatgcaa gccctccttc ttccctacgc agagtcaaac ttggtctttt    44460
ccagggtcac atacagcctc tctctggggc ctctgcaggt cctgatcaat ttcattgtgt    44520
atagagctct gtgtctcctc acctgcctgc agggctgtct gctatcctga cttccgagag    44580
ccatttcgga agccagcttt tcctcccatc agggatgctt ctcttctttc agccccgcc    44640 ccgctttggc ctcctaggat ggctgatttt tctggatccc gctgacacag gtgctttctc    44700
tccgagccaa tcagggagca gaaaggctca gctcagctaa cagaggcatt gctcaccgca    44760
gctgtgagtt agaactcagg ctttctaaat cgggaggatc aggcatgact tgaggttggg    44820
ctgagaaagc ctcgcctgcc ccccagctcg actacccagt gaaacctttg gcttctgcct    44880
cgggcgaggc atctcttacc atgccaagaa ctcagcagcc catctttctt tcatctgggc    44940
accaagtaca tcattgcata tttcaggggg tttcattgtg tccttaacat gctcatggag    45000
```

```
acttggcttg agatgaagtc ggggtttcta ggcagcagga cccatgtccc cttccttcat    45060
ttcctccacc ggtgattttt gttttgtttt gttttgtttt gttttgtttt gttttgtttt    45120
tgagacggag tctcgttctg ttgtccaggc tggagtgcag tggcgttatc tcggctcact    45180
gcaaactctg cttcccgggt tcaggtgatt ctcctgcctc agcctcccaa gtagctgaga    45240
ttacaggcgt ctgccactat gcccagctaa ttttttgtatt tttagtagag acggggtttc    45300
accatgttgg ccaggctggt ctcgaactcc tgacctctgg tgatccaccc gcctcggcct    45360
cccaaagtgc tgggattaca ggtgtgagcc accgcaccag gcccttccac tggtgttttt    45420
tgagcatcta ctatatagag aatgctctcc tgggcacaga ggatgaagca gtgaacaaag    45480
tagacaaaaa atccccacgt gcatagagtg tgcagtctcg tgggagagac agggaacaag    45540
ataaagaagg aaaaaaatag cagatgcttg actggggacg gggactaaag aaagaaaaaa    45600
ataagcaggc taaggggggtt gatggatgtg acctttgagt aaaggcctaa aggaagtgag    45660
ggagggagtc atgtggatgt ctggggaaag actattccag gagaatgaac agcaggtaca    45720
aaggcccctg ggtacaaatg tgcctgggga gtttgggaa taaaagggag gccggcgttg    45780
ctgtagctga gtgactaagg gagagaatag aggagatgag gggagggagg taatgggagc    45840
aggtcatgca ccttgctggt gctggaagga cttttgttttt gcttttgagt gagatgggat    45900
ccatgggaag gctttgaata cttccacatg cattaggctg aaattttctt ttctgctttt    45960
gtcgcattcc aacattgctt ttatttcatc aaaatcttcg gtttcttctc aggctcttta    46020
cccaagtggg agcagaaggc tggtacccag ggctgttcag ttctcccct ggggtcagaa    46080 cgtggaggag aaagcttgga ggagaaacag gaaccccccac ctctttctgg atgactcaaa    46140
accgcaatta cctgagctcc tcctcctatc cctgaaatag aggcacttag cacttcctaa    46200
acttcccggt gcacacaaat cccctggcga tcttttttaaa tgcaggttct gactcagcag    46260
gtggatgcaa ggtctaaggc tgcattccta accggtgctg gttctgggac cacactttga    46320
gtagcaaggg tctgaggtca ttgttgcaga tgtccatctg gggcatgtct gtggacactt    46380 gcggggtgc gggtgagcag agggagggggg gatgatgttg gaaaagcagt gtgagtatct    46440
gtgtttgata agaagtaaga aaatgaagca aggtgggaga gtagaacctc tttattttttg    46500 cctacgtgct aaggttttat tgccataccc agagagccct gggtctgaaa tccaggcaac    46560
actggccagt tgaaaccctg atattgcagc ccataaaagt gctgcatgct gcatggtgga    46620
cttctgggac tcttcctgga accttcagtg ccagagccgg tccaaaggaa gtcacatccc    46680
tgccattgag gggcaggaga ccagggaacc ggaggagtgg gatggcagaa gcgcgtgtaa    46740
ggaggctgag ttggcaggga gagaaagcga agtcagcttc aaatcatagc gagaggagac    46800
cagggaaggg cttggcgttg ctgctctgtg tacaaatatt gtctcttatt ttccaggctg    46860
cagggtgagg cagagtggag tatttgtgca acacagccca gctttgttct ctgggctcct    46920
aatgcctgtc agctcagagg cagaaagcca atcagagatg atcgtcggca aggccggctt    46980
ttgttggctc cccaaattgc cctgagtctc ggattttgct tttcagagtg tgctttcagc    47040
tggaggcaaa ggctgaagct ggtgacaaaa ggaagcctgg ttttcctggc tttccgagac    47100
ttttactgag ggggtttcta tttcagactc cgttttccca cctggaaagc aggttccact    47160
ctccctccgg cctggaaggg atggttttat ggtgcttcca aaatgccaaa cctaactcca    47220
gggcagaaga ggagactgaa accaattaat tttccaaagg ttagagctac gaggagggga    47280
gaggtttagc atggtcaagt tccccaagac atactaattg atctctctac agaatgcggg    47340
```

```
atttcagtgc ccccagggga cactcagcaa tgtttagaga ccacttgagg ttgtcatcac    47400
tggacaggag gggctgctac tggcatctag cacacacagg ccagggatac tgttgaacat    47460
gctgcagtgc ccagacagcc ccaccaagga gaatgatcca cccctaaacc tagtgctgag    47520
gttgggaaat cctgctccgg agtaaccaac accctatggc ttttcactc aagcagccgc     47580 ttctccagcg cttacacctc ctcagagatt gccagatcca tatgcagagc ctgttggcgt    47640
gggacacttc tgaggggtgt ggcagggaga cagcggacat tcccatttac cagctgatca    47700
gcaggttagg agctaatatg aaatgaacaa gatagaccct ccccacctgc cctgcagatc    47760
ctctggtggg acactaggga gggaggcctc ctaaacccaa atgacagttc ccaggatgca    47820
gggaggagtt tacctatgca aactggagag aatgcaaatg gggcatctag agatacttac    47880
tggacgaccc ctcccctgcc tcgggtcttg aagaacaga ttctcagagg tctgccctga     47940
tcactgtaat tttttttta ttgaggtaaa attaatataa cacaattaac cattttaaag    48000
tgacatttag ggctgggcac agtggctcat gcctgtaatc cccgcacttt gggaggctga    48060
ggaagaaagg tcgcccagga gttcaagacc accctgggca acaaagtaag actctgtctc    48120
ttacaaaaaa aaaattaggc acacatggtg ttgtgcacct gtagtcccag ctactcagga    48180
ggctgaggca ggaggatcgt ttgagcctag gaattcaagg ctgcggtgag ctatgatcat    48240
gccactgcac tccagcctgg gtgacagagc aaaattgtgt ttctttaaaa aaataaaagt    48300
aaaaataaat aagaaaagaa aggagagggg aggggagagg cgtttagtac actcacaatg    48360
ttgtgtaact gtcaccttca tctagttcta aaacattaag cagccactcc catttccctt    48420
gccattcccc aggaacaaca aatctgctgt ctgtctctgg atttgcctgt tcgggatatt    48480
tcatatacat ggaatcatac aatatggggt attttatgtc tgcttctttc gcttggcata    48540
atgttttcaa ggttcattcc tgttctatca tgtatcagta cttcattcct ttttttttt    48600 tttttttgaa acggagtttt gcttttgttg cccaggctgg agtgcaatgg cacaatcttg    48660
gctcactgca acctccgcct cccgggttca agcaatcctc ctgcctcagc ctcctgagta    48720
gctgggatta caggcatgcg ccaccacacc cagctaattt tgtactttt ttagtagaga    48780 tggggtttct ccatgttggt catgctggtc ttgaactccc aacctcaggt gatctgcctg    48840
cctcggcctt ccaaagtgct gggattacag gcgtgagcca ctgcacccgg cctacttcat    48900 tccttttat ggctgaatac tattccattc tatgagtaga ccacattttg tttatccatt     48960
cacccactgg tgaaatttag gttgtttcca tcttttggct gttgtgaata gtgctgctgt    49020
gaatatttgt gtatgagtgt tcgttggaat acctgtctta cgatcctttt gtgtttatac    49080
cttggagtgg agttactgtg tgtcacatgg taactctgtg attaactttt tgaggaacca    49140
aggaatggtt ttctatggca gttgcactgg tgtttttttg ttgttgttgt tttgttgtt    49200 gttgttttga gacagggtct cactcccatt gcccaggctg gagtgcagtg gtgcagtcat    49260
ggttcactgc agcctcaacc tcctgggggct caagcaatcc tctctcctca gcctcccaag    49320
tagctggcac tacaggcctg cgccactatg cccggctaat ttttcatatt ttttgtagag    49380
atagagtctc agtttgttgc ctaggctggt ctcggactcc tgtgctcaag taatcctcct    49440
acctcggcct cccaaagtgc tgggattaca ggcatgagcc accgcatctg gccagctaca    49500
ccattttata ttcccaccag catgagggtt tcaatttctt cacatcttca ccaacacttg    49560
ttttctgttt gtttgtttgt tttaatagc tatcctagtg gatgtgaagc agtatcccgt     49620
tggggtttga tttgcacttc cctgatcact aatacccctca tgtacatatt ggccatttga    49680
ctgtcttctt tggagaaatg tctattccag cctcctgtcc attttttcaat tggattatct    49740
```

```
ttttgttgtt gtgttgtaaa tgttctctct ttattttta ttttttttgag acagagtctc    49800
gctctgtcgc ccaggctgga gtgcagtggc acgatcttgg ctcactgcaa gctccgcctc    49860
ccaggttcac gccattctcc tgcctcagcc tcccgagtag ctgggactac agatgcccgc    49920
taccacgccc ggctaatttt ttgtatttt ttagtagaga tagggtttca ccgtgttagc    49980
caggatggtc tcgatctcct gacctcatga tccacccgcc ttggcctccc aaagttctgg    50040
gattacaggc gtgagccacc acacctggcc gtaaatgttc tttatatagt actagaccct    50100
tatcagatac atgatttgca aatagcttct cctattctgt tacttgcctt ttaactttct    50160
tgataacgtc ctttgatgca caaaaggttt aaattttgat aaagcccagc atatctgttt    50220
tttcttctgt ggatcatgca ttaggtgtca aatctgatca taatgtttta tttatttatt    50280
tacttattta tttattattt tatttatttt tgagatggag tcttgctctg ttgcccaggc    50340
tagagtgcag tggcatgatc tcggctcact gcaacctcca cctcccaggt tcaagcgatt    50400
ctcctgcccc ggcctcccaa gtagctggga ctacaggtgt gtaccaccac gcctggctaa    50460
tttttgtatt tttagtagag acagggtttc accatgttgg ccaggctggt ctcaaagtcc    50520
tgaccgcaag tgatccaccc accgcagcct ctatctattt ttaatttatc tcttttttt    50580
tttttttttt tgagacaggg cctccttctg tcacccaggc tggagtgcag tggtatagtc    50640
attgtacact gcagcctcta cctcctcggc tcaagcaatt ctctcgcctc agcctcccaa    50700
gtacctggga ccacaggtgc ctgccatcat gctggccctg ccaccatatt tgaaattgca    50760
gccctgaccc cttccactgt ctatagtctt caccatctta ctacataaca tagcatatat    50820
gatgtactgt ataacatggt atatgcagtg tactgtatag catagtatac atgatgtagt    50880
catctcattt atttgcttct cctctgggaa gcaggaggaa gcttctcctc ttgtctgctt    50940
tgctctcaac tgtgtcccta gcccagaaca gagtctggca cacagcaggt actgaatgaa    51000
tatgtgttca gtgaatattg tgggtgagat agaaggtgaa tatccacatt tcccttaga    51060
agtcacctga tctgggtttg agatctgcag ggatctactc cagacaggag aacgaataat    51120
tccacctgtg ctgatgagtt ggaaggatct agagggcttg agatcttttcc actgggtca    51180
gtgggggtgg gtgcacctcc aacacccttc ttttctttga acaagatttt tccttaattc    51240
cccaatactc cctttgaata tatgatttta gccaccatca tagcgaattg catcgtcctc    51300
gcactggagc agcatctgcc tgatgatgac aagaccccga tgtctgaacg ctggtgagt    51360
gatgtctttt ctcagggtct tctccttggc tttagcagga cattaatttt tgggggagtg    51420
gagcagggca cagaggaggc tctcagtcct ggagcccaga gccagatcat gggaagccta    51480
aatttccttt tcattttttc ttgaaccaga gtctcgctct gtcacccagg ctggagtgca    51540
gtggttcagt catagctcac tgcagcctcc acctcctggg ctcaagccat cctcccactg    51600
cagcctcctg agtagcaggg actacaggtg ccaccatgcc cagttaattt tcttattttt    51660
atcttttttt gtagagatgg ggatctcact aggttgctta ggctggtctc aaactgccca    51720
ctttggcatc tgacataatt tcaggcagta tactcaaatg aacattgtta atgttaataa    51780
ttatgtcttg gccagacact gtagctcatg cctgtaatcc cagcagtttg ggaggccaag    51840
gcaggtagat cacttgaggt caagagttcg agaccatcct gaccaacatg gtgaaagccc    51900
gtctctacta aaaaaataca aaattagctg gatatggtgg tgcacacctg taatcccagc    51960
tacttgggag gctgaggcag gagaatcgct tgaacccggg aggcagaggt tgcagtaagc    52020
caagatcgca ccattgcact ccagtctggg caacaggagt gaaactccat cttggtgggg    52080
```

```
gggaggcgaa aaaaaagaaa caagaatatt acaaaggata cagatgaaga gatgcaaagg    52140
gtgagatata ggagaagggt gtggctggca gcttctaggt agcttcagga gggggactgg    52200
tcaccagaaa gaccaaggca tgattcgagg gttgcgactt tcagccccac cccccaacct    52260
ctgggagggc agaggggctg aaaatcaagt tgatcaccaa cggtcaatga tttaaatcca    52320
aacctctaat catgccttgg ttttcccggt gaccaacccc catcctgaag ctacctagaa    52380
gctgccagcc atcagtcaat ccttagcctg caaaaagaca tcccttggga gatcccaagg    52440
gttttaggag ctgtacacca ggaaacagtg tcaaagacca aacatacatt tcacaatgtc    52500
acagtcttct aaaaactata actagcctag caaacctatg atttctagat ctttgcattt    52560
tcacttaaaa taaagctaaa taaaaagcgt ccattgaaag actggtaagc aagtagaagt    52620
accagtggca agctaatgtg gaaaaaaaaa atcattcagg cagagtgaaa atgattgtag    52680
ctcgagaaac gttgctgtaa cagatgggaa acattcaca ttgggctct gatggagaag    52740 agcttgtagc ttaattttcaa atatgataga ttagcagctg gaagccagaa ccagccggag    52800
gttctgcaga ggaactggag gtgaggatac tggccactta tcagccagta cagaagtcct    52860
attccaaacc tttaacaatc tacatgccag ctgagaacca tcctaagggg tcagatttag    52920
gagtgaggtc aatgcacaag ctctagcctc aaataccttg aacgctgcat gtgacaagta    52980
aattctctaa accaatgctt tccattagaa ctttctgcag tcacagaaat gatctccatc    53040
tgccctgtcc aataggattg tcacttgaaa tgtagccagt gtgactgcag aactgtgttt    53100 tttatttat tgcatttaaa ttaattttaa ttgaaatagc cacatgtggc ctgtgactgt    53160
cgtattgaat aagacaggtg caaacaaata attctgttta gctgagtgat atgtgaggtt    53220
ggcccaaaag gaatgaagga ggaaggtgcc ttctctaggc attggctttg ctcgcaaaag    53280
gctttggaca agagaactct gcaagaggca gtgaggggtg gtgagtgcag gagggtcagg    53340
ggaagtgaga gggtgatagg tactgatttc taggtgggct ggttccctga tcttgtcaac    53400
atctgcccag cccaagacgc tgaccttgcc ttctctccct tccaggatga cacagaacca    53460
tacttcattg gaatttttg tttcgaggct ggaattaaaa tcattgccct tgggtttgcc    53520
ttccacaaag gctcctactt gaggaatggc tggaatgtca tggactttgt ggtggtgcta    53580
acggggtaag tggcgcgtgc tatacgcttt ggatttaact agctgaagga ttacgaggct    53640
tttggttggt gtggtccggg ccaggctcag gaaggctgag cccttgtgtt ctccctcccc    53700
ttgttatgcg cctgcctcct ttctgccaac accccacctc catgtctcag ctgtatatta    53760
cagcagatgc tttctgttac aattaaaata atagctcatt attgttggct gcttccagag    53820
tgctttatgc ccattctcta atttaatcct tgcaacaacc cactgaatta ggaaatatta    53880
atattcccat ctgaccactg aggaatcaga aactcagagt gtaacttgct taaggccacc    53940
cagcaagtaa gtgatggaac tgggagatga acagaagatt atgcattcca gaactcaagg    54000
ttttaagtgt tgtacgtgca tgggtctctt gatttgcttg aggatatctt gcttttattt    54060
caacttggtg aatgtttttt gagaatgtct gggtgcaagg gattgtgatt atgacaaagg    54120
agaaaagcaa gctaaataag gtacagttac tgtcttcaag gagttttcag atccatatat    54180
gatgaactgt ggttgaaatg tgtatatgct ttcctctaag caccctgtat gaggtagcac    54240
ttgctggtat aacaaaagat ccaaagctag gaaatgactt aaacacggca gaagtttatt    54300
tgtcactcat agaaaattca aaattgagct gggtgtggtg gtgcatgcct gtaatctcag    54360
cactttggga ggctgaggtg ggaggatcac ttgagctcag gagttcaaga ccagcttggg    54420
caacacagtg agaccacccc cccatctgta aaacataaaa taaaataaaa attaaccagg    54480
```

```
catggtggta catgcctggg agaattgctt gagctcagga gttggagggc acagtgagct   54540
atgatcatcc aaccgtgctc cagcctgggc aacagagcaa gacccccatct cgaaaaaaaa   54600 aagtccaaaa taattgttcc tagttgacag gctcatctcc tccaatgact gacggaccct   54660
gacccttgcc atattgtggc tcttcattgt cagcccacat catccaataa ctccatgctt   54720
gtctgtatca aaccaggaag gagaagtgag catagaaggt gatacttgga aaggtttatg   54780
agtttggaag gggtgtgacc catacctgtt ccattcatat cctattggct agaactcggt   54840
cacatgacca cacatcactg caagggaagc tgggaagtat cagattgtgc ttagaagaaa   54900
agggaaatgg atttggagaa tgacctacta gtctgtcagg gaccttaaaa acttttatta   54960
gattccagta gggacattag tatctggtac caatggctgg ttcctcctct tcccactctc   55020
tactctcctc tcagctaagt ctgggctctt ctattctaag accttcttc actgacacc   55080 ttttcatag taatcattta caggatcata gctttccatg ttttgttgct gctccaggtt   55140
ctgtctctct tggcggatgt gatgggttgc agcacccaca ctgtgctggc cgggctctca   55200
caatgcagat ttgtttcaga gcaatgttgc ctctcacaga aggagctgtg gcctattggg   55260
ctgtttctgt agaggccttc agatgtcagc agtctgttgt aaggactctg gctagctct   55320 catgggcttg ggtgttcaca gagggatctt tgttggctgt gctcacagtt cggtggcttg   55380
ggaccttggt gggttccaag ggcatattat ggtactgggc acttttctct tagtctacta   55440
ggaaactcat ctagaaacag cctagtggct aacttttta ttgtttaaaa aatgtaaagc   55500
tgggcagggt ggctcatgcc tgtatcccag cacattggga ggccaaggtg ggaggattgc   55560
ttgggcccag gagtttgaga cgagcctgag caacatagca agaccacatc tccacaaaat   55620
aaaaattaaa agtgtataaa gctgggtaca gtggcacatg cctgtaaccc caattactca   55680
ggaggctgga gagagaggat tgcttgagcc taactagttt gagaccagct tgggtaacct   55740
agcaagatcc catgcaaaac taagtagaga ataatagagc aaacacctgt gtatacattc   55800
atttattcaa tgactattta ttgaacactt ctgtgtgcca ggtcctgttc taggctctgg   55860
gacacagcag taaacaaaat agaaaaatcc cctgtcctca tggagctgag agtctactga   55920
tggagatgga cacaattgat gaatgaatct agtgtgtcag atggcggtga ggggtacaga   55980
ggaaaaataa agcaggggag ggatgggatg tgtggcaggc agggtgagg ggtgctggaa   56040 gccagggaag acttcactgg gcatgtgaca tctgaatgaa aacctaaggg aggtgagtga   56100
gtgagccatg aggagagctg gaacagagtg tcaggcaaag ggaacagcca gtgcaaaggc   56160
tctgaggctg gactgtatct gacatgtttg atcaacagta agaagaccca catggctaga   56220
gaaggtgacc agaagaatgg ggagaattgg ggatagagaa gtaatggagt aacctgctat   56280
caaaacacaa cctttctctt ttttttttt tttttttttt tgacaagagt ctccctctgt   56340
cacccaggct ggagtgcagt ggtacaatct cagctcactg cagcctctgc ctcccagttt   56400
caagtgattc tcctgcctca gcctcccaag tagcttggat tacaggcgtg taccacaaca   56460
tctagctaat ttttgtattt ttagtagaga cgggtttacg ccatgttggc caggctggtc   56520
ttgaactcct gacctcaagt gatccacctg gcatggcctc ccaaagtgct gggattacag   56580
gcgtaagcca ctgtgcccag caaaacaaaa ccttctaac ctttctaatc cctgttttct   56640
ccctccctag acccattcct ttctctcccc catccagggg cactttcctg aattttatgt   56700
ttattatttg catttatgta ttcacacttt ggctgcctaa gtatataaga aatatatgct   56760 acctatttt acacttcaaa atattttta aatagcatca gagtgagaat agtttacact   56820
```

```
ttgactacat gcatagataa gaaatatgtg ggctgggaat ggtggctcac acctgtaatc   56880
ctagcaattt tggaggcaaa gatggaagga ttactttagg ccagaagttt gagaccagcc   56940
tggccaatgt agtgaaaccc tgtctctaca aaatgaaata aaatgtaata aaatattcag   57000
ctgggcatgg tggtgtgctc ctgtggtccc agctactcag gaggccaagg cgggaggatc   57060
acttaagccc ataaggtcga cgctgtagtg agctatgact gcactccagc ttgggcaaca   57120
gagcaagacc ctgtccctaa aaatgttttt ttgttgttgt tgttgttttt tgttttttttg   57180 ttttttttaat aaaggccagg tgtgatggct cacacttgta agcctagcac tttgagaggc   57240
cagggcagga agactgcttg agtccaggag tttaagacca gcctgggcaa catggtgaaa   57300
ccccatctat aaaaaaaatg caaaaaatta gccaggcatg atgacgcacg cctgtagtcc   57360
cagctactca ggaggctgag gtgggaggat cacgtgagcc caggaggtcg aggctgcagt   57420
gatccgtgat tgcaccactg cactccaggc tgggcaacaa agtaagacct tgtctcaaaa   57480
aaataaaata aaataaaaaa taaaaaaaag aaaagagaaa gaaaaaaaga gatatgtggt   57540 actgttttt caaacttcaca tttctctaac ctgacttttg tgttcaacat gagataaatc   57600
tgattaataa aaatagtttc catgcatcca ttttcatgac tgcatagtat tctgtggtag   57660
gagtatgctg ccgtgtattt atctatttgg attgtttcca gctttgggct attttgaccc   57720
aaagtgtccc tgcttttctcc caagtgagtt tctctagggc acgtacccag gagtggaact   57780
gctgagttgt atactgtgtg catcctcagc cccactaggg attgccaaat tgctctgcaa   57840
agtggttgtg ccaattcatg ctccctgggg gctggcttct gctggctgag gctggcttga   57900
ccttgctggc aggaaggagc cttaaaaatc cctgtgtggt ttttttttgtt ttacttttat   57960 tttaagttta ggggtacaag tgcagatcta ttacatgggt aaacttgtgt cttggggtt   58020 tgttgtacag gttatttcat cacccacgta ttaagcctag tacccattag ttatttttct   58080
tgatcatctt cctcctcccg ccctccaccc tccaaaaggc cccagtgcgt gttgttcacc   58140
tctgtatgtc catgtgttat catcatttag cccccactta gaacacgcag tatttggttt   58200
tctgtttctg cattagtttg ctaaggataa tggcctccag ctccgtccgt gttcctgcaa   58260
aggacatgat cttgttcttt tcttggctg catagtattc catggtgtat atgtaccaca   58320 ttttcttat ccagtctatc attgatgggc ttttgcagcc ctgttttttt ttttttttca   58380
taataacacg gttatgggaa cacttaggga agctcatata ttattgagca gtgtgatggt   58440
taatattgag catcaacttg atcagcttga aggatgcaaa gtcttgttcc tgggtgtgtc   58500
tgtgagggtg ttgccaaagg agattaacat ttgagccggt gaactaggag aggcagactc   58560 accccaatc tgtgtgggca ccatctaatc agctgccagt gtggccagaa taaaagcagg   58620
cagaagaagt tggaaagagt agacttgctg agtcttctgg ccttcatctt tgtcctgtgc   58680
tgaatgcttc ctgccctcta aaatcagatt ccaagttctt cagcttttgg actcatggac   58740
ttacaccaat ggttagccag gagctctcag gcctttggcc acagactgaa ggctgcactg   58800
tcagcttccc tactttgag gtttgaggac tctgacggat ccaccactgg cttccttgct   58860
cttcatcctt cagatgggct atcgtgggac tttaccttgt gattgtgtga gtcaattctc   58920
cttataaact cccttcata tatacatcta tcctgttagt tttgtccctc tgaagaacct   58980
tgactaatac agacacctag tgggtcccaa taagtgatca ttaaactgaa ggcagtcatt   59040
cagtaggtca gtttgtcact tgtgtttgta tctccctgct tacaacaagg tggcctttct   59100 tctagttttcc tgtcatctga tggaagagat tctagactca ttcctctaga ggagaaatac   59160
ttcatctaga acagataggt cctaagggtg agagctcatc gttgggatga atgaacccac   59220
```

```
tgaaatttta tgcaagaaga aaattgtgta tatgtatatt ttttttttctg gtctgtagtt   59280 tttattagat tctcagggaa tcctgatcct atcatgaaga ccttctattc tagattgggt   59340
tcctttcaca tccccttctc ctttcttgtt gaattctcca tgcatttctt tcacttgctt   59400
ttcttgctct tatttctctg gtagtcagtt atccttttg tctggtggtt ctatctcctt    59460
caaatgaggc acattgctca aattttatta ctccaaattc caaggtgctg tttagtgtcc   59520
tgttgggttg taagctagga cagggaggg gaaagtaaaa cattctgcat gagctgggtg    59580
cagcgggcaa gcacctggaa ttccagctac tggaagctga ggtgggagga ttccctgagc   59640
ccaagggttt aaggccagcc tgggcaacaa agtgagattt tgtcttaaaa aaaaaaaaaa   59700
tcccagctgg gctctgtggc tcatacctgt aatcccagca ctttgggagg cagaggcggg   59760
cagatcgctt gaagtcagga gttccagacc agcctggcca acgtggtgaa accccatctg   59820
tactaaaaat acaaaaaaaa aaaaaaaaaa gcctggcatg gtggtgtggt gtgcactggt   59880
aatcccagtt atttgggagg ctgaggcagc agaatcactt gaatccagga ggcagaggtt   59940
gcagtgagct gagattgtgc cactgcactc catcctggat gacagagtga gactctgtct   60000
caaaaaaaaa aaaaaaaga aagaaaaaac acgcgcgcac acacacacac atcatgcaga   60060
cctagccttc tgccaatgtc aatggtagag aaacacagta gacacttaat tctatgtttc   60120
agagaggagg ggactcaaat atattaattt gacattgaga cagtgatgac tttaatgagt   60180
actttctttc cttttttttt ttttttttt cgggacagag tgcagtggtg ggattttggc    60240
tcactgtagc ctccacctcc tgggttccag cagttctcct gcctcagcct cctgagtagc   60300
tgggactaca ggcatgcact gctgtgcctg gctaattttt gtattttag tagagacggg    60360 gtttcacact atcagccaga ctggtctcga actccggacc tcaggtgatc tgcccacctc   60420
ggcctcccaa agtgctggga ttacaggcat gagccaccgt gcccggccta atgagtactt   60480
tctgattaac ctgttgccct ctcagattcc tgaagcaaac cacagcgtta aacgtgatt    60540 cattttgtgt ggaccaccac ggtgtttacc ttcttcttgg gtgaagtttg gtggaaaaga   60600
tcttaccccg gacatctgtt tgttctttgt aactcagagc ctcagagaaa tcctaacttt   60660
ataatgttgt caaacccttg taaggcatgt ttttattgta tttgtgttct gatcatgaaa   60720
ctgaaaatgt gtaagaggaa gatttcagaa gcttggctgt atgtctgaga tgacagttct   60780
tttactgtca ttctcaaata tatataaata ttgaagagat caaataacac aaatcgtgca   60840
tgttaagaaa agagactgtg aacctcacca gagaggggtg agcacaattt ttttctttt    60900 ttattcacag ggttagcact gtcccttca cataataaat gctcagtaaa ataaatggtt    60960
gttaagccgg aaaagggtaa cacttctgat aatgagtgtc ctgggaaatt tactaagctg   61020
tttagaagat gggaccaaca cactgataga aatagtcaga tagtccagaa gtctatggca   61080
gatgccctga acatcagatg agatataaga cagagaagct ctgggtcttt gccagctctg   61140
acattttatg actctatgaa acggaaggtt cctttttaga agggtctata aactgtctca   61200
ggctttgggc cattttgttg aagatcagag gcaaggaaaa gacacaacta cacaggaacc   61260
atcagggaaa gatgttgttt tttggtcttg aagcatcatt gaattttttt ttttttttt    61320 gagacggagt ttttctcttg ttgcccaggc tagagtgcaa tggcatgatc tcggctcact   61380
gcaacctccg cctcccaggt tcaagtgatt ctcctgcctc agccttctga gtagctggga   61440
ttacaggcat gtaccaccaa gcccgggtaa tttttttgta tgtttagtag agacgaggtt   61500
tctccatgtt ggtcaggcta gtctccaagt cctgccctca ggtggtccgc ccacctctgt   61560
```

```
ctcccaaagt gctgagatta caagcgtgag ccaccgcacc gggccgcatc attggatttt   61620
aaggctccat ggattctggc aggtccagcc cttctgtttt actcacaaac aagtggtttg   61680
tccaaagtca cacagagatg gtggcaagag atctagaata agaaggtgtc ttcaagtcat   61740
ggagccagga accctggctt tttgggcaat ggaagtggta taaatgttta atatcacccc   61800
tcaggttctg ccactagagc ccagctctct cttccttcct cttgccccct gactagccta   61860
tggcctcttt ccagagaata agaaaggggat cctcagagaa taatcccagt tcctcgcttt   61920
ttattatata gttgaggaaa ccaagtctca gaggggtcag tgtcttgacc atacacctct   61980
catgtcctct ctccttttttg attaattgaa taaatacatg tagttgcttc ttacctcctt   62040
tctttcttca cccctgcccc atgcacctgc tcttagttgc cttcacatgt aaacagcatt   62100
ccaacaacaa caacaaaaca caaccagcat tctaactcat gagaccagca acagttccta   62160
taaataccag cagcatttta ttttaatgtc tctctgcagt agtttctccc ctccatggat   62220
cagtcatcct tggtaccaaa aggattcccc actgtgacac aaatgctttt tgtcattctc   62280
agtgagttat accattgaga gagcatcgat ctttttattg ttcaaagctt ttggttgtca   62340
tgatatttgc tggaccatgt ttcaccagga accacatcac ttcctagcag caggagctat   62400
tttcttccat cttctaacaa caccagcagt gacagtgata ataatgatgt tagctgccat   62460
ggtcgttatt cttatcattt attgagtact tactatgtgc cagggactac attaagagtt   62520
ttatgtgtat tatcacattg agcctcgcta gcctttgtac agatgaatct gaggctcaga   62580
gaggttaagc tgctcacaag ggagtcacac agctggtaag gggtggatca ggatctcagc   62640
ctctctgcta ggacacttct ctaaacctag aataatactg ggcctgtgtt aagttcagca   62700
aagagctgta ttcaacccag tgtccttagg aatgtaatgc ctgttattaa caacagtggc   62760
aacattgata agctgaaact tatgaggtgc ttacaatatg atatactata tattatatac   62820
atacataggc acccacctat aatctcagca ctttaggagg ccaagtcagg aggatcactt   62880
gagcccagga gttcgagacc agcctgagca gcatagcaag atcctgtctc tgtaaaaagt   62940 ttatttttc agttggccag gtatgttggt acatgcctat agtcccagct aatgaggagg   63000
ctgaggcagg aggattgctt gagcccagga atttgaggct gcagtgaact atgatcacac   63060
cactgcactc cagcctgggt gacagagcaa gactgtctct aaaataaaa ataaaaataa   63120 aattatttca actctcaagg ttaaataaat actattatta ttcccatta cagatggagc   63180 aactgaggct caaagacatt aaatgcttac tgtcttagtc tgttttctgt tgcttatagc   63240
agaacacctg aaactgagta atttataaag aaaaagcaat ttatttctta cagttatgga   63300
gactggaaag tttaagatca aggctgcatg agctataatg cacacacact attgcactcc   63360
aggctgggtg acagggtgag accccgtgtc aataaataat aatataaaat aaataaaaca   63420
aatttcaaca tgagttttgg aaggtttgaa atattcaagc cagagcatct gtctcataag   63480
tggtggaccc aggatttgaa ctaaggcaga tctggatcta gaacccattt tcttgaatcc   63540
tacgctattt ctctaaggtc aagtttgcca aggaaaataa acttgagaat ttgaatagag   63600
ctctctgaca tgggaagtca gggtgatcct tccttcccct ccctgatctt gggttccact   63660
atggctgggg gaaaacagga gcagaagaga tttcaagaaa tgagagattg gcctagcgcc   63720
atggttaaga cctggacttc agagtcagag gaagctcctc cctctatgac agtgagaatg   63780
tgggttgaac tcactgaacc tcagtttttct cacctggaaa aagggagtaa aactagtgcc   63840
tagctcctag ggtttgcatc acacacgaaa gttggtgaac tgaaggaaaa aaacttaaat   63900
tcttgtgggg gagcatgtga tagatgctac aaattctcca tgccttattt acctagctta   63960
```

```
cgtctaagtt cacctgcagc ttcctcttgg tacactccca tctctctaca tctctgttgg    64020
agggcagtct ctggcatcac agagtttgct gagccagatg cttaacaacc tcggtagcat    64080
ccctcaacca gtgagctagg gagtcagtgt ataaataccc tggcttcccc attgctcagt    64140
gggaaaacac tgaaatatgt tatacagcat catagaggtg cctcagtaaa attgaatcct    64200
agttgttcac ataaaaccca ttcactagtg tacccttttac caatctctct cttcctcatt    64260
cctcacttgt aattccttgc attacctccc aaattaacca ttggaccctaa gttttgcct    64320 tggggtctac tcggcgctaa ctcaaggagc ggaagttgga agcttagcgg gttacaggtt    64380
tcagcaccct ggacagctcc cagcacaccg tattgtgcta aaatgttctc ttccctcct    64440 ctgcctccag ctggggtgga gagggactga gtaaaggcca gatggccagg tgaccttgtt    64500
ccatactgag cttcttggcc atttcccctg tggggctgga gaagaccttg ccatccatct    64560
ctccgcaggt ttgggggccg actgaggtct tgttttctcg aattgctatg acaaatgcca    64620
gcctgcctcc aagggcatc tgtcccactg cctctacagt ttgcatgcct aatgactcct    64680
ctcctctcac cagggcaggg aggtggctgc ctggtgggcc gcttgaagcc gggagaccaa    64740
gatcatgcca ctggactcgc aacaaaccga gactcttttt ttttttttt tttcctcgag    64800 acagggtctt gctctgttgc ccaggctgga gtgcagtggc gcgatcttgg ctcactgcag    64860
cctccgcctc ccaggttcaa gcactccac ctcagcctcc caagtagctg ggattacagg    64920
cgcacaccac catgcctggc taattttgc attttttagta gagaggggt ttcaccatgt    64980 tggccaggct gatctcgaac ttctccctc aggtgatcca ctcgccttgg cctctcaaag    65040
tgctgggatt gcagctgtga gccaccatgc ctggccaaca aataggact ctgtctcaaa    65100 aaataatttt ttttaaacat tgctttgcaa cccagctgct tcttgtgcag gcatctctaa    65160
atgaggacag ccagtctaca tagacacgta aggaagcata gtggttaaga cctggtcttt    65220
ggggttagag tggattccca acctgactcc actgtttcca agctgtgtga ccttgggcaa    65280
gttactgtac ctccctgaat cttccatttc ttcatctgga aaatgagagt agtagcatcc    65340
cctgacttgg tggggcatgg tggctgatgc ttgtaatcca acactttggg aagccaagg    65400 tgggtgaatc gcttaaactt gggagttcaa ggccattctg gcaacatgg tgaaactcca    65460 tctctacaaa aacaaaacaa agcaaaaatt atctgggtgt gatagtgtgt gcctgtaatt    65520
ccagctactc aggaggctga ggtgggagaa tcacttgagc ccaggaggtc aagtctgcag    65580
tgagccgtgc ttgcaccact gcagtccaac agagcgagac cttgtctcaa acaaacaaaa    65640
caaaacacaa aacaacaaca aaatactacc accttatgga gttgttttca aggttcaatg    65700
agttaatgtc tgacccatgc tgggctgggt ttatggatgt tacttgccca gggacagtct    65760
gaagaaagag aaagtgatat agtccattgg gcctcagctt cctcatctgt ggaatgggaa    65820
taataattgc acctacctca aaaggtaaaa gtcagtgaga tacatataag gcattcagaa    65880
caaaaactgg cacagaataa gtgctcaatt atattagcta ttgtaagact aataactatc    65940
attataatga tgataataat tattactact tccccaggcc cagttccata gaccagttag    66000
ttaactgtag ggaacgtttg ctattattag ttgggttccc aatatctgac ctcccttcc    66060 aatttaggga gaatcctccc cttctctataa agtactgctg gtctatggga tcccaccctc    66120
actaataagt tgaaggtgaa agggattcat tgtcaccca tcacctggta gtcagggcat    66180
gtgatttaaa caaccagggc caggcgcagt ggctcacgcc tgtaatccca gcactttggg    66240
acgccaaggc aggaggatag cttgagccaa gcccaggagt ttgagaccag actgggcaac    66300
```

```
atagtgagac ccctatctct taaaaatttt ttaattagct gggggtggta gcacaggctt    66360
gtagtccccg ctactcagga ggctgaggca ggaggattgc ttgagcccag gaggtcaagg    66420
ctgcagtgag ccgtgatagt gccactacac tccagcccag cctgggcaac agggcaagat    66480
cctgtctcaa aaacaaact aataaaaaac tcaaccagtc acgttttcct acccaggaat    66540
ttgaaaatgg accaagtgat ccaaacatga tggtttggac tctttcatgg cctcctgcta    66600
caggagaagg tcaggctggc tacattgttc ctgctgattt cccaaatccc ctcttctggc    66660 ccctgttga ttatctgagt ttcctaaaaa tcccttttat gcctaagata gccggtcagt    66720
gtttggtttt gcaatcaaga acccagactg ggccaggcac ggtggcccac gcctgtaatc    66780
ccagcacttt gggaggccga ggcgggcaga tcatgagatc aggagatcga gaccatcctg    66840
gctaacgtgg tgaaaccccg tctctactaa aaatacaaaa caaaaaaaaa aaaattagcc    66900
aggcatgatg gcggtcacct gtagtcccag ctactgggga ggctgaggca ggagaatggc    66960
gtgaacccgg gaggcggagc ttgcagtgag ctgagatggc accactcac tccagcctgg    67020 gcgacagaac gagactccgt caaaaaaaaa aaagaaaaa agaagaaccc agaacccaga    67080
ctgatcctga gacaaagatt tgagggcaac gaatcacgag gtcaggaaat cgagaccatc    67140
ctggctaaca tggtgaaacc ccgtctttat taaaaataca acaaattagc tgagcgtggt    67200
ggtgggcgcc tgtagtccca gctactcggg aggctgagga aggagaatgg cgtgaacctg    67260
ggaggcggag cttgcaataa gccaagatcg caccactgca ctccagcctg ggtgacagag    67320
caagactcca tctcaaaaaa aaaaaaaaa aatttgagga caagtggttt gtttggcaat    67380
accaggaaac aggggaacag gatagtcaga aagaaagag aaagctgggc atggtggctc    67440
actcctgtaa tctcagcact ttgggaggcc aaggcaggtg gatcacctga ggtcaggagt    67500
ttgagaccag cctggccaac atggtgaaat cccgtctctg ctaaaaatat aaaaattagt    67560
cgggtgtggt ggcgtgcacc tataatcaaa ataaaataaa atcaggatat tttatttaa    67620 aactctgtct tagtgtaact catatttacc tcttctgtat gctcctttgc atcagttata    67680
tattgccata atacggctgt gtaacaaaca atccccaaga cccagtggct tataatgaca    67740
agcatttatt tagctcatga ttctgaaggg tggcagttta ggctgggccc agttgggtgc    67800
tttatctggt ctcagttgag ctcattcatg catctttggt cagctgcggg tcagctgggt    67860
ggctcttctg tttggctgtt agctggctgc agactggtcc aggatgacct cggctggaat    67920
gactgtgctc cactccctat ggtctttcac cctccagcag gctagcctga gctagttcac    67980
atggcagctt ttcatcctcc agcaggctag cctgagctag ttcacgtggc agcaatggga    68040
ttctaagaga aagaggaagt gttcagcctt cttaagggct agtcccagga atggcacaac    68100
atcgtgttgg ccactgttgt ccaaagcaag caatgaagct ggtccagatt caaggaatgg    68160
ggcaacagag cccatctggt atttacctgg ggccactggg gccccattcc tgttccctgg    68220
ggccttttgc cctgacttct gtgggccctc agagcatatt ttcagattcc tttccatccc    68280
tgaccctcag caatcaatgt agatgacgtg tcattactgt gtcacttgca cagagaaaag    68340
gaggaaaaaa tgtcagcaaa aactctgctg agagcagagg gcccatcata cagcaagctg    68400
gaaagaaaag tgggaatgat tacacagcct cctcagatgc ttccagcttt tatcaaatct    68460
cactgtgata tctgagttct gaaccctcac aggtggttgg cgtgcaaggg aagagatttc    68520
ttgtctgcca tgctgacatg cacagacacg caacctggct ccctctgtcc actgggctt    68580 tggattttgt ttgttgaaat gttacccact cctgatcaga gctggatgga aacctggctc    68640
tgattccatt ggctcagggg ctcaggtggg ggcagaggcc aggctggttg ggtgtctatg    68700
```

```
tggagacctt aactcttctc cctcccgccc caactctttt tgtttctttt tttttttttt    68760
tttttttttg agatggggtt tcactcttgt tgcccaggct ggagtgcagt ggcgtgatct    68820
tggctcactg caacttctgc ctcctgggtt caagcaattc tcccacctca gcctcctgag    68880
tagctgggat tacaggagca cgccaccata cctggctaat ttttgtattt ttagtagaga    68940
cagggtttcg ccatgttggc caggctggtc ttgaactcct gacctcaggt gatccaccct    69000
cctcagcctc ccaaaatgct gggattagag gcgtgagcca ccacctggg ccttttctt     69060 ttcttagctg cctccacctc tcttcccttc tgcagtgtta ggtttatgga aaccgaggcc    69120
ggcgtagaga tcaacttcag agagcatgaa ctgagcatct gctgggtctt agatccttta    69180
catagcttat catcttcaaa ccttctcaca gttctgtgtg gctagagcca ggatttggac    69240
acagctctgc cccactgtag aaccaggctt ccttctgtcc actgtcaaat tttagaggga    69300 gaaaatagg aaagggacac cagccttctc cacgagcagc ttctgcccac tcaccccagg    69360
gactttgcac atgctgtgtg cctgtgtctg agatatgctc cctcctctgt atctgcttaa    69420
ttcttaccca gacatgatac ataaagtatt taacatccag gtggcaggga caccagctaa    69480
cctgaaaaga ggttcccctg ttgtgccaca tgtgtactca ttgtttgctg cattgtgggg    69540
gcagtccagg ggccttgaag aggggccaag gtgccaaagg ggcactctca ggcctcaagg    69600
aagtacatgt ttactgatat gatactgtct cttcctccag gaaggaagcc ttccctgatc    69660
tccccactgc atgcccacta tgataccagt ttaggtcccc tctttatggc catctgtggc    69720
atcagtgtga atcctcttaa tgttgtctat tggttaatc atctgtctcc ttcctctggg     69780
gggtaaagac agaaccacag agcctcgtgt agaacttgag aatggggttc agtaaaaatc    69840
tgttgaatgc ataaatgggt gattgagtga atgaatgaat gagtgaatga atgagtgagt    69900
ggatgaatga atgagtgaat gaatgagtga gtgaatgaat gaatgagtga attaatgaat    69960
gaattcatag ctgataatac aggcttcatg gcttttgtta ggcttgccca gacattgcta    70020
ggggatggac agaaggaaga agagctatac ttaattccag tcctgttgtt ctgtagcagg    70080
aggagaaaaa cagggactgc ccagcctgct ctgggtggat tcaggagcag ctgaggttcc    70140
tctcttattt gcaaacaggg aattcaaaaa gccccaacct cagaatcaca ctcgcctcag    70200
cagctgtacc agccaagggg acaatgtggg aagccttggg caccaggaat gctgagtgct    70260
tcgaaaaagc gaaggctcag ggaacaatcc ctgattttc attcccttgt cctttctgaa    70320
gaaacaggca aaggcaggcc aggcacggtg gctcacacct gtaatcccaa cactttagga    70380
ggccgaggct ggtgaatcac ttgaggtcag gagttcaaga ccagcgtagc caacatcatg    70440
aaatcccatc tctactaaaa atacaaaaat tagctgggtt tggtggtgca tccctgtaat    70500
ctcagctact cgggaggctg aggcatgaga atcacctgaa ctggggaggt ggaggttgca    70560
gtgagctgag tctgcgccac tgcactccag cctggatgac agagtgagac tccatcttaa    70620
aacaaaacaa aacaaaaaca agtaaagcct tgtgtgtttt taaattgtag gttcagcagc    70680
aaagctctgt aataaggagc tggaccctgc agtcagacag tcatgggctt ctccagtgcc    70740
cagccgagtg acccgaggga gttatgataa acaccaacat tcatccacaa tttgtaccta    70800
gtgctattct caatatcttg agtaaattat ctcatttaat cctccaggca catctttctt    70860
ggtaggtgcc gtcattgtcc ccagtgtaca tctgggaaaa tgaggacagg ctggcagagc    70920
acccttcctg ctcacctctg ctgctctgct gacctctggc aagactgttg tctctctgag    70980
cctcagtttc cccatctgaa aattgggggcc tgtattagcc cgttctcaca ttgctataac    71040
```

```
gagatgcttg gctggggctg ggcgtgatgg cttatgcttg taatcccagc actttgggag    71100
gctgagttgg gcagattggg agtgtgagac cagcttgggc aatatagcaa gaccccatct    71160
cttctaaaaa aaaaaaaaaa ttagccaggc atggtgatat gcacctgtaa ttccagctac    71220
ccaggaggct gaggcaggag aattgcttga acccaggagg cagaggttgc agtgagccaa    71280
gattgcgcca ctgcactcca gcctgggaga cagagtgaga ctccatctca aaaacaaat    71340 tattttaaa aaattaaaaa aaaaaatgcc tggctgggca cagtggctca cacccataat    71400
cccagtactt tgggaggcca aggtgggaag attgcttgag cccaggagtt ccagaccagc    71460
ctgggcaaca cagtgaaatc ctgtctctac taaaagtaca aaaattagcc aggtgtggtg    71520
gcacgcgcct gtggtcccag ctactcagga gggtgaggtg ggaggattgc ttaagcctgg    71580
gaggtcaagg ctgcagtgag caatgattat gccactgcac tccagcctgg gcgacagagt    71640
gagaccttgt aaaataata ataataataa taaataaata aaaccctga gactgggta     71700 atttataaag aaaagaggtt taattgactc acgattctgc aggctctaca gaaagcatgg    71760
cagcatctgc tcagcttctg ggaaggcctc aggaaactta caatcatggc agaaggtaaa    71820
gctggagcag gtgtcctcac atggccagaa caggaggaag agagagagtg gggagatgct    71880 acacacctt aaatgtccaa tctcacaaga actcactcac gatctcgaga atagcaccaa    71940
ggcggaaatc tgccccatg atccaattac cttccaccag gccccacctc caacattggg    72000
gattacaatt cgccataaga tttggttgcg gacagacaca gatccaaagt acattaaaag    72060
taatggcaaa aaccacaatt acttttgcac caacctaata tctcaggggc tcattgtacc    72120
tatttcacag gacaaatgaa ggtatcagta ataacagtag cctgtagtcc cagctattca    72180
ggaggccgag acaggaggat cacttgaacc caggaggtcg aggctgcagt gagctatgat    72240
cacgccactg cactgcaccc tgggtgacag ggcgaaaact tatctctaaa aataataata    72300
acaacaacaa tagtgaacac agatataaca tgtgtgtggc caggctgtgc ccttagggct    72360
ttgcagggat tatttcattc actctcaatc tccccatttt acagatgaga aaactgacgt    72420
tcagaaaagc tagaggactt gccccaagcc acacggctag gaagtggtgg aattggggtt    72480
taaatgagga agcttgactt cagtgtcgaa gctcttaact gccacactca atacatggag    72540
tagaggttgc tgattctgtg attatctgat tctggaaagt aaagaccctg tttccagacg    72600
tttgctgctt gacttagttc caggggatg gccactggat gatgcagtgt tgcccaggag    72660
aggttagcta gacacactgc aaccattcca ttgctaatac ttatacttgc tcttgttctg    72720
ctgggtgcta tgcagggaag ggctgtctga gcccttttgca agaattctcc cattggtgcc    72780
tcccagagat tctgaggttg gggctttttg catcccttat tagcagatga gacaccaaag    72840
cccaggtcaa taatctgacc tgcatccccc gcctaccagc cagaccaagg tcacttcccc    72900
acaatgcagg ccctgatcca aggctctggg tgcaaaccag tttccatgtc cctgggggtc    72960
catcttcttc agctgacttt tttttttttt tttttttttt gagacagcgt cttgctttgt    73020
tgccgaggct ggagtgcagt ggtgtgatca tggcttattg cagccttgac ctcccaggct    73080
caagcaatcc tcccacgtca gcctcctgag tagctaggac tatgggcaca cgccatgatg    73140
cctgggtaat ttttttttt ttttttttga gacagagtct cgcactgtag cccaggctgg    73200
agtgcagtgg cgcaatctcg gctcactgca agccccatct cccaggttca tgccattctc    73260
ctgcctcagc ctctcgagta gctgggatta caggtgcctg ctacctcgcc tggctaattt    73320
tttgtatttt tagtagagac gggtttcac cgtgttagcc aggatggtct ccatctcctg    73380
acttcgtgat ccgcccacct cagcctccca aagcgctggg attacaggca tgagccagat    73440
```

```
gcctggctaa ttttttaagtt tttttataaa ggcggggtct tgctatgttg cccaagctgg   73500
tctcaaactc ctggcctcaa aaagtcttcc tgcctcagcc tcccaaagtg ctaggattac   73560
agacatgagc cactgcaccc agcctgactt tttttctaac tgaaaaatta attatatata   73620
ttcatggagt acaatgggat gttctgatat atgtttacat ttttgaatga ttaaatcaag   73680
ccaattaaca tatccactac atcgcatact tattttttgt ggtgagaacg cttaaaatct   73740
actcttttag caattttgaa atatacaata ccttatgttg tatattacat tatgttgtat   73800
agtacgttga aacatacact acaatacgtt atcattaatt gtggtcacca tgctgtgcaa   73860
aagatctcta aaacgtattc ctcctgtctg actgaaactt tgtatccttt gcctaatatc   73920
tccccaatcc ctccaccacc agccctggt  aaccaccatt ctctctgctt ccatgggttc   73980
aaatttttta tttttttgaaa ttttaattt  ttatttattt atttatttat ttatttattt   74040 attttttgaga tggagtctcg ctctgtcacc cagtctggag tgcaatggtg ccatcttggc   74100
tcactgcaac ctccgcctcc tgggttcaag cgattctcca gcctcagcct cccgagtagc   74160
tggggttaca ggtgcttgcc accaggcccg gctaattttt gtattttag  tagagacggg   74220 gtttcaccat gttggctagg ctggtctgga actcctgacc tccagtgatc cacccacctc   74280
ggcctcccaa agtgctgaga ttacaagcgt tgagccactg cacctggcct aaaattttt   74340 ttttttttt  tttttttgag acggagtctc actctcttgc taggctggag tgcagtggca   74400
tgatctcagc ccactgcaac ctcagcctcc cgggttcaag cgattctcct gcctcagcct   74460
cctgagtagc tgggactaga ggtgtgcacc accacgccca gctaattttt gtattttag   74520 tagggacagg gtttcaccat gttggccagg atggtgtcaa tctcttgatc tcgtgatctg   74580
cctgcctcgg gcttccaaag tgatgggatt atgggccacc acgcccggcc tcaaattttt   74640
tagagctcac atataagcga gattgtgtac tatttgcgtt tctgtgtctg gcttgtttca   74700
tcttagtata atgtcctcca ggttcatgca cgttgtcgca aaagatggaa tttgctcctt   74760
tttaaagact gaatagtact tcattgtgta catatacacg ccatattttc ttcatccatt   74820
cctttactga tggacatttg ggttgtacct gcatcttggc tatttgtgaag agtgctgtca   74880 tgaacatggg tgtgcagctg actctgaggt gttagaggga ttacagctcc tccaaaagac   74940
caccgtcacc caaacctgct cctcctgccc tattttctgt ttaggtaaag gcggctttaa   75000 cccccctgcag tgctctggcc tcagacctcc agatcttcct ctatgcctct atgcctcttt   75060
ttctccaccc cctgcatcca atctgttagc acatcttatt ggctctacct tcagaatcta   75120
cccagaatcc accacccacc tctcaccacc ttcacagccc caccccggtc cagccccat   75180 ctttgctggc ctggactaaa ccagttgccc ctccaccca  atctggtctc ttaacttcag   75240 tccttgccc  accccagga ctgttcccca cacagcagcc agagggcacc tgtgagccac    75300
tgagtcagga cctggctcct ctttgctcac aacctcactt ggagaaaaag cccaaattct   75360
cctcacaggg acccacaaac tctgcccctg tgatccccca tccccctcta ttcccactct   75420
cctctccact cactcggctt cagctacaca agttccctgc tgtcccttac acaccaagca   75480
ctccccagcc tcagggcctt tgcacaggct gttccctctg cctggaacac tcttccccca   75540
gatatctgct tggctccccc ctcacttcct ttgggtcttt gctcaagtgt ccttctaaca   75600
tgtaactgcc tcacctgcac tgtgccaccc cactccccgc ctctaggctt aatttccctc   75660
tacacccctg aagagcatct gccaagctat atttacttgt ttattggtta ttgccaatcc   75720
cctgccccca ctagaatgcc agctccatga gggcagggac ttctgtctgt tttgttcact   75780
```

```
gctattcccc cagagcctag aacacagcct ggcacatagt aagtattcac taaataattt    75840
gtaatatgaa ttgtgccagt aaaatcttcc aggggcatca agccctgcc atgactaggt     75900 ggtaacatcc tcaccccctg tccatgtgct atctcctcct gacctgcttg tctcattgtt    75960
ctaatggtgg ctcacgcctg taatcccagc acttggggag gccgaggcgg gcagatacct   76020
gagttcagga gtttgagacc agcctggcca acatgatgaa accctgtctc tactaaaaat   76080
acaaaaatta gctgggcgtg gcattgcacg cctgtagtcc tagctactcg agaggctgag   76140
gcaggagaat cgcttgaacc cgggaggtgg aggttgcagt gagctgagat catgccattg   76200
caatccagcc tgggccacaa gagcgaaact ctgtctcaaa aaatatatat atatatttca   76260
ttgtggtaac atatgcataa cataaaatgt accatttttt aagtgtttag ttgagcggcg   76320
ttaagtacat tcatattgtt gtgcaaccag gaccgccatc catctccaga acttttgcat   76380
cttgcaaaac tgaagctctg cccccaggaa actctcactc cccgctcccc cttcccctct   76440
ccccgactcc cccttccccc ctccccactc ccccaccct actccacact ccccactccc     76500
ccagcccctg gcaccgccg ttctagtttc tatctctgtg aatttggcta ctttgggtcc    76560
cccctgtgag tagaatcata cagtatttgt cttttttgtga ctggtttgtt tcgtggagca  76620
taatgtcctc cagtctcatc catattgtag catgagtcag aatttccttc ttttccaggc   76680
cgaatcgtat tccattgtgt ggatggacca cactttgctt atctgttcat ccagatgggc   76740
acttggcttc caccttttgg ctattgtaaa taatgctgct gtaaacctgt gtgtacaaat   76800
agctgagtcc ctgctttcaa ttcttttgga tatagaccca gaagtggaat ttttttttaaa 76860 tcaagatttg acccactggg gcccttagag gtctcattgg ctctgaagct ttttttttt    76920 ttttttttg gacgctttga aactaaaaat aggagtgagg ggcacagtga gggggggcaca  76980 catctctcgt gtcagcgttt tttaaaaaca ccccgggagg aagatgtgtg aaatccctcc   77040 cttcccccg ctcccacccc ctccaagatc tcaaaatacc tcttgttta ggaagcggct     77100 gtgacatcag gcaggcagcg tgtggcatct gagacacaat atcgcaagtg ctgggagcc    77160 cagagaaacc aggacaggcg tgctggggat gtggactaga gatggagcta attttagtgg  77220
ctgaagaggc tgcaagaaga gagagaaaga ggggtgtgtg tgtgtgtgtg tgtgtgtgtg   77280
tgtgtgtgtg tgtacgcaca gtgatagagg ctggaggggg agaaatgaca gataaatcag   77340
cttgggcaaa gaaagctaat gggcagagga gcgagaccca gctcagaagg tggtcagcaa  77400
atctaaagat gtgtgcccga gggtcaaggt ggtgggggga ttcataggca agtggtagag   77460
aggctattcc atttgcagag gctctctctg tttgaggcgt gattcacctg tgccgtcctc   77520
aaggccattc tgagaacacc actgttgttt cctccttttt atgagtaggg aaactgaggc   77580
attgaactgc ttctattctt cagtaagaag caggggaac atatggtaga agcaaagaaa    77640
tacaaacatg agggctctcg gggtctacgt gattggctgt gacatccatg agagcggatc   77700
gcaggttgaa ggaaacactg gtggcagaaa gtagctgaac atttggattt gggaatccca   77760
gtggacgtgg cgaaaattct ggcttttccc ttcacaggct gcggggccac tctgacctgc   77820
ggtttcctta tctgtgaaat ggaacgatgc cacctgtctc agcgttgttt tgaggatgcg   77880
aggagatgat ccgtgtaata tgcccactag ggggcctgct ccagggtaga ttctcagcaa  77940
atggtagtca tggtttttgt tacatttggg gatattggca ggtaaaaagg aaatacttca   78000
ttcattccaa aattgctcac tgaggttcta ctatgtgcta ggccctgatg acacatcggt   78060
caacaagaca ggcctgcttt ctgccttgt aaaacttcag ttcaactgca ttgcactcat    78120
cagcctaata atccaggtaa attgtgatga gaataacaac tagcatttac tatgagccct   78180
```

```
ttacaaatat taacccattt aatcttctaa agagcctata agataagagc tcttgccctg   78240
cgcagtggct cacgcctata atcccagcac gtcgtgaggc caaggcaggt ggatcacctg   78300
aggtcaggag ttcaagaata gcctgaccaa cagggtgaaa ccctgtctct gctaataata   78360
caaaaattag ccaggcatgg tggcaggtgc ctgtaatccc agctacttgg ctgaggtagg   78420
agaatcgctt gaacccagga ggcggaggtt gcagtgagtc gagatcactc cactgcactc   78480
caagagtgaa actctgtcac acacacaaaa aaaacaacc tgttattatc cacattttac   78540
ctatgaggaa accgatgccc agagaggtta agtaactgtc caaaggtcac acagctacgg   78600
agtggtagag ctgggattca gacccaggag tgtgatccca gagtgtgtgt gtatgtttgt   78660
ttgtttgttt gtttgtttgt ttgttttttac cactgtgttt tcctgcttct gcaatagaag   78720
taatcaccag taacactgag cagttgttat gtgccatgcc cttaacacac atctccttgg   78780
atctttggaa agaatcctaa aagggttgtt tttcatgatc cacattttat ggagagagag   78840
agatcaaagc atagagagag gaagtaactt gcccaagatc ctgcagctga agactctagg   78900
gttgcaaatt tgggacggcc ctggaccctg cattccagct tctagcagct catgggggga   78960
actctttatt tatttattta tttatttatt tattttattta tttatttga gatggagttt   79020 cgctcttctt gcccagcctg gaatgcaatg gcatgatctc ggctcactgc aacctccgcc   79080
tcctgggttc aagtgattct cctgcctcag cctcctgagt agctgagatt acaggcatat   79140
gccaccacgc ctggctaatt taattttttt tagtagagac ggggtttctc catgttggtc   79200
aggctggtct cgaactcctg acctcaggtg atccgcccat ctcggccccc caaagtgcta   79260
ggaatacagg cctgagccac cacgcatgcc ctgggggga ccacttttat cggtgcattt   79320
cttccatttt ccctgtgtct gtgtaaagat aaacacccccc aagccccttg actatgaact   79380
gtgggccata attagttaat ggaaggtaaa tgttttagag acggaaattg ctgtgccatt   79440
tttccccgct aggcattgtt gcctgcatgc taatgcaaca caatgtgcct ttcttctgtc   79500
aggcattttt agacaaattc tatttttccct aaaatatttt gccaaagaaa atagcaaatg   79560
gggaagacat tcagaggctc aggcagagag aggacaccat tcccttgggt ttaaacagaa   79620
tggcagagtg gataacagca cagatcttga gttaggtgga tgccaatttg tgatttattt   79680
cccagcaaac caagatgctg gctctctgtg tgcctcagtt tacttatttg tcaaatgagg   79740
agaataatgg tacctgtctc tcaccagctt accagttgcc tctttagcta tgtctaatct   79800
gctattaacc acgcccacta tgtctttaat tccaagtatt agaattgttt tcttcctaca   79860
agctgtctga tctttttaa tcctgcttca tcttttgcag tattgttttc ctacagcagg   79920
atttctcaac cttggcacaa ttgacatttt gggctaggta attcttggcc gtgagctacc   79980
accctgtgct aagatactta gagcatccct ggcctctcac cctactaaat gccagtagca   80040
gcccctcccc agttgtggca gccaaaaatg gctcagacat tgccaaacga aatgtcccat   80100
ggagggtaga aacgcccca cttgagaatt gttctatagg tattttcaag catgtcttac   80160
atttctttaa gtataatatg caaaagaaaa ggctaaatct aaaaaaagcc cataatatgc   80220
gaagaatttt tataatcagt gtccaataac ttaagtatct aaaattgtta tggcttttt   80280 tctgctgtct cttgtttcct gtgattcctc attctggtgc cttgttttct tgaatgtctt   80340
gttatctttg gttgtgtgaa gctcattttc catgggacac tattttttgt tttgtttttgt  80400 tttgagacag agtctcgctt ggttgccag gctggagtgc agtggtgcaa tatcagttca   80460
ctacaacctc agcctcccag gcccaaatga ttctcctgcc tcagcctcct gagtagctgg   80520
```

```
gattacaggc gtgtgccacc acacccagct aatttttttg tattttttagt agaggcaggg   80580 tttcaccacg ttggccaggc tggttttgaa ctcctgacct caagtgatca acccgcctcg   80640
gccccccaaa gtgctgggat tacaggtgtg agccaccgtg cccggcatcc atgggacact   80700
gttgaaggga gttcattgag gcctgcgatg aaggcgaacc ctccatggac aatttgcatt   80760 tacttttttcc aggtgtctgg gaaactccca gtctaggacc atcttagact tttagaccaa   80820
caatgtgttg agaatttagg tcaccagtgt ctgcaaaagc cagcttgtgg ttataatttc   80880
tcaaaaactt ttgtttttct ccttttctgc aaagtgccaa agtaacttcc tcaaaaatct   80940
ctgggaatgg aaagacggga gtaaattaac ttcaggtttc ttacctgaaa gtgatagcct   81000 attgggccc catcctactt ggggagtggt gtgtctcctt tgagactttc taacacgtgt   81060
gtaccctgga ctttgcccca cccctgctcc ctaggaggcc ataaaacttg aagcagcagt   81120
tccatgggtt agacagatgc ccttggggca aaagtggttt taatgctctg gtagatgctc   81180
aggttacctc tgggaaattc ttgacttcac ttatttattt ggggctgata actactaatt   81240
gtcaggcctt tcttgtttca acaacatgga cttcagattt tatgcaggat ttgtcatcgt   81300
tttcagcaag agagtcagtc ttattaccca gcttactgca ttagaaatag atgtctgggc   81360
caggcgcagt ggctcacacc tgtaatccca gctgtttggg aggctaaggt gggcggatca   81420
tgaggtcagg agttcgagac cagcctggcc aacatggtaa aaccccatct atactaaaga   81480
tagaaaaaat tagctgggtg tggtggtgcg tgcctgtaat cccagctact gggaggctg   81540 aggcaggaga attgcttgaa cccgggaggc agaggttgca gtgagccaag atcgcaccac   81600
tgcactccag cctgggtgac aggacgagac tctgtctcaa aaaagaaat agatgtctgt   81660 tgtgtggatt atttaaaaga gtagatggcc aagaactatg acttatgcct gtcatctcag   81720
cactttgaga ggctaaggtg gagggatcac ttgaggccat gagttagaga ccagcctggg   81780
aaacatagca agaccccat ctctgcaaaa gtaaaataaa ataagttagt gtgcatgatg   81840
gtgcaggcat acctctagtc ctagctactc aggaggctga ggcaggagga tcacttgagc   81900
ctaggagttt gaggctacag tgatctatga tcatgccact gcactccagc ctgggtgaca   81960
gatcaagacc ctgcctctaa aacataaaaa taaatacaaa ttaagttaaa aaataaaata   82020
aataagtaat agaacatcca gcacagttct tggcatgcat tgactgttgt tgtttgtttg   82080
tttgtttgtt tgtgacggag tctcactctt gttgcccagg ctggagtgca atggcatgat   82140
cttggctcat cataacttcc acctcccagg ttcaggtgat tctcctactt cagcctcctg   82200
agtagctggg attacaggca cgtgccacca ctcctagctg ttttgttttg tttgtttgtt   82260
tgttttgtat ttttagtaga gatggggttt ctccaagttg gtcaggctgg tctcaaactc   82320
ctgacctcag gcgatctgcc agcctcggcc tcccaaagtg ctgagattac agacgtaagc   82380
caccacgcct ggccagctgt tttgattgtt aaatgaaggt ggtatgaaag ggaaggaaga   82440
acagtgacat ttgcaaggga cactccctgg agggcagggc aaggggggctg tggaggggag   82500 aagtcagaga gtatgataca ggttgccttg ggtgatgttt tagattttag ccaacattgg   82560
caaagagcct catttatctc tcagagtagc tctggctact ggaaatgctg cacaacttca   82620
ggcggacttt ctagaagaaa actcttggcc aggtgcagtg actcacacct gtaatcccaa   82680
cactttggga ggctgaggca ggtggatcac ttgagctcaa gagtttgaga ccagactggg   82740
caacgtggca aaacctcatc tctacaaaaa aaatacaaa aattaaccag gcgtggtggt   82800
gcatgcctgt atcccagcta cttgggaggc tgaggtggga ggattgcttg agcctgggga   82860
ggtggaggtg gtagtgagcc aagattgcac cactgcactc ccatttgagt gacagagcaa   82920
```

```
gaccttgtct caaaaaagaa aaaagaaaa gaaaagaaaa gaaaattctc tctgggattc   82980
aatcctggcc cacacagcat tggcttcact tcacctcctt ctcccctgag atacacagca   83040
ccattccccc aagcttcatc aacttaatct ctgatctggg tgctgtgact tgtccccatt   83100
cctggccaga atttaaggta gggatgaacc cactagccct ccatcacgca ctctgccata   83160
aaagcacacc acgtgctgat tgctgtcttt ggtctccttt ctgccttgcc ctctagactc   83220
tgagctgctt ggagacagag gccagttttg tccatctcca aatcccctaa agtcctgtgg   83280
ccagcaagca ggtaggacat ctgaaagttc gtcagagagg gaattgcttt tctcttgaga   83340
tgcaactaga acaagaatct tattgacctg gagtagcttc aaggttgtaa gagtatgtgt   83400
cagggttctc caagaccact ctcaggtttg aaggtttgct aaaagggctc acgggaccca   83460
gaaaagctgt gaaattcagt tatggtttat tacagtggaa gaatacagat aatacagatt   83520
aaaatctgca aagcaaaaga tgcacaaggc aatgtccagg ggagatcagg catgagcttc   83580
cagctgttca ctcccagtgg agttatgcaa acagtgctca attctcccag caatggtgtg   83640
tgacaatgta cagtgtaccg ccaaccagag aagctcacct gagccttggt gtccagggtt   83700
tttattgggg ctcagttaca ttgacatgga gcacccatgt gactgacttt aactgctggg   83760
tctccagcac actccaagat caaactgata ccgtgtgtcc cagggcccca gctgaacaca   83820
aacaggcagt caccatagat cccattgtga gcataagcta ccaggcatgg cccaaagccc   83880
tagatataca gatattcttt ccaggagcca gccaagggcc agtccttcct ttggaatatg   83940
cagagtttga actccccaac cccaaggagt taactctttta ctacacagaa tataaatctc   84000
accaagtctt tcttcttgtc aagtcctctc aaggtgaccc attgctttta gcagtgtctt   84060
tgagaccctg cgtcatctgg ccttgaccca tatcacctgt gttatctctc cactctagct   84120
acattgaact tttctttttt gagatgtggt ctcactccat cacccaggct gaagtgcagt   84180
ggtacagtca cagctcactg cagcctcaaa ctcctgggct caagtgatcc tcccacctca   84240
gcctcctgag tagctgagcc cacaggtgca tgccattaca cccagctaat attttttattt   84300 ttagtaaaga tgggttctca ctatgttttcc caggttggtc tcaaactcct gggctcaagc   84360
agtcctccca tcttggcctc ccaaagtatt ggcattacag gggttagcca ccacatccag   84420
cccattgaac tttttaagga tccctagca tcctatactt tctgtcactg gatagccttg   84480
gaattatttt tccttctttt tgaaatactc ttcttctttc caccctttgc tgtcaagtct   84540
cagaataggc attatttcct ccaaaaaccc tctcctgacc ctccaaatct ggatgaggac   84600
acttcctttg cccagagagc acctgtttta atcctctcag gtggctataa taaaatacct   84660
taaactgggt ggcttataca cctcagaaat ttattttcca cagttctgga ggctgggaag   84720
atcaaggcac tgacagattt ggtgtctgat gaggggccat ttcttgtttc gtagaagggg   84780
tcttcctact gcatctttcc atggtgaaaa gagttgaggc agctctctga aacctctttc   84840
atgagagcat gaatccctct gtcttcatga tctaatcacc tcccaaaggc cccacttcct   84900
aatatcttca cattggtgac taggtttcaa catatgaatt tgagaaagac acagacattc   84960
agaccatagc agtgctcttc caccaggttt tttatccccc tgtattataa ttgaggttta   85020
aattatctgc tttccttccc ttagattgta agctccatga gagcagggcc ctacccatcc   85080
agtcattgtc ctatcccccca tgactacaac ttcctgggta cataattaat atttattata   85140
ttatgtagca aaggtatgct gccatactaa gagacccaaa aggccaccgg attaaaacct   85200
taaagaaaaa aaaataattt ctctcctata atagctgcaa ggttagccat gcaggttggc   85260
```

```
agggaagctc acttccacaa agtcactcag ggattcaggc tcctgttgcc ctcttctttt    85320
ctaccaccaa atgatcttca gcaccatttg cacaatcaaa acttaactgg tcttgaatag    85380
gcagaccttg aatttctgaa gtctcagacc caaaagtggc agctgtcact tccactgaca    85440
tatcactgat ggaaacttaa tcatgtgatc ataccaaact gctagggatg ctgggaaatg    85500
tagttttgtt gggaactcca tgacttggct aaaattccat tactgtagaa gatggtgggg    85560
gatgggggag tggtggacat ccagtggttg ctaccatatt tattgaatca aattgtcaaa    85620
caggacctat ctgataaggg gttctttttcc agaattaact gaagtattaa atcagggca    85680
aaggcatgtc acctcatctt tctctcccta tattggcttt ctagggctgt ataacagag    85740
taacatgaac ttggcggctt aaaacaacag aaatttattt tctcttagtt ctggaggcta    85800
gaagcctaaa atcaaggtgt cagcagagcc accttgacaa ctgctctagg aaagaattct    85860
tccttgcctc ttctggtggc tcctggcaac ccttggtatt cttttgtctgg catccacttc    85920
aatctctgcc tccatcttca tttgcctttt ttctctgtgt gtctatgtcc tttcctcttc    85980
ttagaaggat accagtcatt gaatttaggg cttactctaa atccaggatg atctcacctc    86040
aagatcctta attagttaca tctgcaaaga gcttatttca aaacaagatt gcattctgag    86100
gtttcggtaa acacgaattt gggggaaata gtattcaact caattcactg ctttacttaa    86160
gaaaagagac catgaagtga gcctccttct gcttgagaga gagagcgagc ctttctgtgc    86220
aataggtcaa tgaatggatg cagctgaatt ccacataact ttataaaaat agatggccag    86280
cccatggggt ttgctgaccc ctgcccaaaa attccaaagt caacagcagt ctcttttta    86340
atcatttctc tattttttaa tttattttta ttttatgtt gagatagagt cccgctctgt    86400
cgcccaggct ggagtgtagt agtctcggct cactgcaacc tctaccttcc agatacaagt    86460
gattctcctg cctcagtctc ctgagtggct aggagtacag gtgtccgcca ccatacccag    86520
ctaattttg tattttaat agaaacaggg tttcaccatg ttggccaggc tggtctcgaa    86580
ctcctgacct caagtggtcc acccacctcg gcctccaaa gtgctgggat tacaggcatg    86640
agccaccatg cccggccagg attttcttca ttttaacagc attcttactt gtcccacatc    86700
cattctatcc tggtctctaat tagataacaa aatctacaga tcttgtttaa ctgacattgt    86760
cctggggat acttttatc ttttgagaca aggtctcact ctgttaccca ggctggagtg    86820
cagtggcctg ataacagctc actgcagcct cgaccacctg ggttcaagcg atcctcccac    86880
ctcagcctcc agagtagctg gaaccacaga tgcatgccac cacacctggc taattttaa    86940
atttcttgta gaggtggggt ctccctatgt taccaaaggc tggtctcaaa ctcctgggct    87000
caaaagagcc tcccaccttta acctcccaaa gtgctgggat tacagatatg agccactgtt    87060
tccagccttg gaaatatagt ctaagaactg agtcaatagg cgattttgtc attgtgtgga    87120
catcatgtag agaacttaac acaaacctag atggtataaa ctactgcaca cctcagttat    87180
ggggcatacc ctattgcacc taggctgcaa acctgcacag caggttactg tcttgaatac    87240
tgtaggcagt tgtaacacaa tggtaagtat ttgtgtatct aaacatatct aggccgggca    87300
cggtggctca cgcctgtaat tccagatcac ctgaggtcag gagttcgagc ccagcctggc    87360
caacatggcg aaactccttc tttactgaaa aatgcaaaaa ttagccaggt gtggtggcag    87420
gcacctgtaa tcccagctat cgggaggct gaggcaggag aatcgcttga acctgggagg    87480
tggaggttgc agtgagctga gatcatgcca ctgcactcca gcctgggtga cagagcaaaa    87540
ctccatctca aaaaaataaa aaataaaaaa catatctaaa cagaaaaggt acagtaaaaa    87600
tacagttata accatatggg accaccattg tataggcagt ccgctgttga tcaaaacata    87660
```

```
tcaaaacatc gttatgtagc acatgactgt accataaacc acacggcttc aaacaaggga    87720
aatgtattct ctcactgttt tggaggccat aggtctgaaa tcgaggtgtc accagggtcc    87780
ctccaaagga tccgggggag gatccttcca ttggatttgg agttgcttca ctccagtctc    87840
tgcctcagtg gtgacagggc gttctcctct tccctctcaa agttccctct tctgctgtgt    87900
cataaggata catatgactg catttaggcc ccactcagaa aatccaggaa taaactcttg    87960
ccctcatatt cttaactaaa tcgtacctgc ataccttatt ttttctaaat aaggtagcat    88020
tccagggatt aggacatcaa cataacttct ggagggttca ctgttcaacc cactacagcc    88080
agaatgcgct ttgaattcag gttctgacat ctgggactgc ctcccacgta cacacaccac    88140
taccttgtac tgaatgcctg aagggttctg cccccacctc cactccccca aatatttgct    88200
gtggacctga gaaagctgac ttcatggaag cttcattcca ttgttctaag gacttttcat    88260
acattaacaa atgtcttctc tctatgggga aaaccacaga gaaatcaaga cagagtgggg    88320
ttaagtaact cacctgagga ggaacagtaa gtggcagagc caggattcaa accaacatgg    88380
ttttgcacag ttttgacatc atttgcaaca caaatattgt cacagatacc tttttgagca    88440
tctactgtgc taaccgccag gaaggaaaag aacatggggc cgggagagct cttgacaggg    88500
gacagggctg gccatggagg tctgtgtctt ggtggaagat gctatggttc tcttttttt    88560 tttttttttt tgagatggag tcttgctctg tcacccaggc tggagtgcag tagtgcaatc    88620
ttagctcaca gcaacctcca cctcccgggt tcaagcgatt ctcctgcctc agcctcccaa    88680
atatctggga ttataggcac acaccaccac gcccagctaa ttttttgtatt tttagtagag    88740 atggggtttc accatgtggg ccaggctggt ctcgatctcc tgaccttgtt gtgatccacc    88800
cgcctcggtc tcccaaagtg ctgggattac aggcatgagc caccacactg ggcaactatg    88860
gttctctttt aactccttgt gctgaaatta ttgcagaagc ccaggccagt tcatcccag    88920 aaagtgaggc ataaacaggc agagctctac agaaacagag aatccacgac tggtttgatg    88980
gaggctgcct cactacctac agaatgggct ctgggtggat tgttctatct ggggagccag    89040
cccacccacc agtctcagcc cttggcgact cttttcctgct gtcacagcag ctggacattc    89100
agaaaccgaa acatgacagc cttccctccc tgttcctgcc cagtggagtg gaaaccctc    89160 gggacccaca taccgagcgt gcacagcagc acagagttgc acagttaaca cagcgcttct    89220
tctccagccc tccggatgca agctgacaga ttggcagctg gctgacttcc aaggtccagt    89280
gagttcttgg cagtcgcttt ctgacctgga cgagtggctg ccacctcctg gaacatcagg    89340
ctgccccctt ggggagaggg tgacggtctc tctggaaaga ctgtgagctt tgaggtggtc    89400
atcaaaagcc attcttggaa acattctttg agctgtaccg tgcaattcgg tcaccaattg    89460
cacgtatttg gatattaata tccgtatgtg gatattaaat tggttttggg ttttgttttg    89520
ttttgattgt ggcaaaatat acacaacaat cctcctgcct cagcctccca agtagctaca    89580
ggcatgcacc accatacccca gctaattttt ggattttta aatttgtttg tttgttttg    89640 tttttgaga tggagtgtag cactgttgcc tgggctggag tgcagtggcg cgatctcagc    89700
tcactgccac ctccgcctcc tggattcaag tgattctctt gcctcagcct cctgagtagc    89760
tgggattaca ggcgcccgcc aacacgccca gctaattttt tgtattttta gtagagatga    89820
ggttttacca tgtcggccag gcttgtctcg aactcctgac cttgtgatcc acccgcctca    89880
gcctcccaaa gtgctgggat tacaggtgtg agccaccgcg cccggccgat ttttgtagtt    89940
ttagtagaga cagggtttca ccatgttggc taggctggtc ccgaattcct gatctcaggt    90000
```

```
gatccaccgc ctcggcctcc cgaagtgcta ggattacagg catgagccac cgcacacagc    90060
ctaaatgctg tgcctcacgc ctgtaatccc aacactttgg taagctgagg ccagaggatt    90120
gcttgagccc aggagtttga ccagcctg  ggcaacatag gaagacccca tctctataaa    90180
aaataaaaat aaaattagcca ggcgtggtgg tgcaggcctg tggtcccagc tactcgggag    90240
gatgaggcag gaggatcgct tgagcccaag aggtcaaggc tgcagtgagc tgtgattgtg    90300
ccactgcact ccagcatggg tgaaagagca agaccttgtc tcaaaaaaaa ttaagcgaaa    90360
tttaaaattc tgtttctcac tcacacaggc tgcacttcaa gtgcttaatc atcccttgtg    90420
ggtggtggct atcatattgg acagcatgga tagagaatat ttttatcagc gtaggaagct    90480
tcatcagaga ggaccgctca gaggcctgtg gggaccagca cagtgcagta aagacacag    90540
gccagctggt gagagactgg tcttctgatc ccagatctgt ccctcacttg ctaggtgacc    90600
ttggacagct ccctcagtcc ctctggagtt ttctcttcat tgttaaatca ggaaattggc    90660
ctcagtgaat tctgaggccc catctacttt tttttttttt tttttttttt ttttttttaat    90720
tgagacagag tctcgctctg ttgaccaggc tggagtgcag tggcatgatc ttggctcact    90780
gtaacctccg cctcccaggt tcaagcaatt ctctgcctca tcctcccag  tagctgggac    90840
tacaggcgtg caccaccatg cctgggtaat ttttgtgttt tcagtagaga ccgggttttg    90900
ccatgttggc caggctggtc tcaaactccc aaccttgagt gatcctcccg cctcggcctc    90960
ccaaagtgct gggattacag gtgtgagcca ccacgcctgg cctcatctag ttctaaatgt    91020
tatgacccac tcagctctga agacaaggga ggaacatcct ctcagtctag ctctgacatg    91080
cagaagcctc tcaccctgtc ccccaggtca taaaggcagg cgtgttgtga agagcacaga    91140
atgggctgag aaaaatatgc agggattgcg tctatctccc ttccttccgc acgtttcctt    91200
gtcggcacca cctgcctcta ttccgcgccg cacacacacc cgccttctct ctgtctcgga    91260
ggaagacagg atcttccatc ccccaaatcc tgccctgatt cctactctga agcctctgcc    91320
ctgactcctt taagctccct gggaatacag cccatctcct atgccctcct catcccagta    91380
gttcctacct tccccaaaat cgctttggga aagtccccca atgagtaacc agctgtccta    91440
catgggcatc tcagaacttc tcttctgttg ttgttgttgt tgttttgct tttgttttga    91500
gacaggatct ctcttttttca cccaggctcg agtgcagagg tgtgatctca gctcactgta    91560
gccttgacct cccaggctca ggcgatcctc cccctcagc ctctggaata gctgggacta    91620
caggcacacg ccaccacacc cgggcaaatt tttttagga cttttggtag aaatggagtt    91680
tcgccgtgtt gcccaggctg gtctctaact cctgggctca agcgatccgc ccactttggt    91740
ctctcaaagt gctgggacta cagacatgag ccaccacacc cggcagagct tctatttctt    91800
gagtgtgttc tcagccatgc taagacattt tctcttctca gcctgatgat gcttttggct    91860
tgtgtttctt tgtttttaat tacccccttcc cagtcgctgt catgggatca tgagggtctt    91920
ctgtccatct agatgacacc tttcttgtgc cacgtgtctc caacattccc tggttttaa    91980
acccttattg ctttcaagat actatccaag ctccttaatg tggcacattg ccttcgctg    92040
ctatctgcct gctttttttt tgagacagag cctcgctcta ttgcctaggc tggagtgcag    92100
tggcgcaatc acagcttact ctgcagcctc gacttcttgg gctcaagcaa tcctcctgcc    92160
tcagccttct gagtagctgg gaccacaggc atgcaccatc atgcttggct aatttatttt    92220
tatttatttt tatagagaag gagtctccct atgttgccca ggctggtctc aaactcccgg    92280
actcaaagtt cattgcagtt tcaatttttt ccttggctca aggatcctcc cacttcagcc    92340
tcctgagtag ctgggactac agacgggcac caacacacct ggctaatttt tgtatttttt    92400
```

```
gtagagatgg ggtcccacta tgttgcccag gcttctatct gcttttatct caccttccac    92460
tcttccatcc ttcctttctt ttcttttatt tcctttccct tcccttgcct tccttttctt    92520
tctttctttc tttctttctt tcttttcttt tttctttctt tcttttcttt tctttctttc    92580
ttgacagagt ctggctctgt cacccagact gaagtgcaat ggcaagatct tagctcactg    92640
caacctccac ctcctgggtt caagcaattc tcctgtctca gcctcccgag tagctgagat    92700
tacaggtacc tggcaccaca cccggcaatt ttttttttt  ttttagtaga cgcgggtttt    92760
cgctatgttg gccgggctgg tcttgaactc ctgacctcag gtgatcctcc cacctcagcc    92820
tcccaaagtg ttgggattaa caggtgtgag ccactgtgcc tggccttttt ttttttttt    92880 ttttttttta agacaggacc ttgctctgtc actcaggcca gagtgcagtg gcactataat    92940
cactttctgc agccgtgacc tcctgggctc aagggatcct cttgccttgg cctccctagt    93000
agctgggact acaggcatgt gccaccacac tggctaattt ttaaaacttt ttgtaggccg    93060
ggcacggtgg ctcacacctg taatcccagc actttgggag gccaaggcgg gcggatcacg    93120
aggtcaggag attgagacca tcctggctaa cacagtgaaa ccccatctct actgaaaata    93180
caaaaaatta gccaggtatg gtggcgggcg cctgtagtcc cagctactcg ggaggctgag    93240
gcaggagaat ggtgtgaacc tgggaggcgg agcttgcagt gagctgagat cacgccactg    93300
cactccagcc tgggcgacag agcgcgagac catctaaaa  aaaaaacaa  aaaaaaaaa    93360 caaaaaactt tttgtagaga tggattcttg ctaggttgcc caggctggtc tcaagcttct    93420
aggctcaagc agtcctcttg cctgtgcctc ccaaagcctt gggattacag gcgtgagccc    93480
ccacacctgg tcctaaccca ctttctgaac ttccaaccac accattttgt cctaatatt    93540 aagtcacacc ataacatgtc ccacttcaga aatgcctacc aaagtagtct tcaaatcttt    93600
ttaaatcagt ggacccttc  taccaaacaa atgttatttt ttaaatattt attttagagt    93660
aatttagact tttagaaagg ttgtagctgg gcgcagtggc taacgcctgt aatcccagca    93720
ctttgggagg ccgagacagg tagatcacct gaggttgggc gtttgagacc agcctgggca    93780
acatggtgaa accccgtctc tactgaaaat acgaaattag tcaggtatgg tggcacgcgc    93840
ctgtagtctc agctactcgg gaggctgagg caggagaatt gcttgaaccc aggaggcgga    93900
ggttgcagtg agctgagatc gcgccactgc actccagcct gggtgacaga gtgagactcc    93960
atctcaaaaa aaaaaagaa  agaaaaaaa  agaaaggtta taaatatatt ataaagagtt    94020
cccacatacc cttcacccag tttctcctgt tgtttgtatc ttatattatc accatatgct    94080
tgtcaatgct aaggaattgc tgggtgcaga gtggcacatg gctgcagtcc cagatactca    94140
ggaggccaag gcaggaggat atcgcttgag cccaggagtt caagtctagc ctgggcaaca    94200
cagtgagacc tcttttctgc aaagaaaac  aaataaaaca tctaaaaaag aatacactgg    94260
aggcggcgtg gaaacaagga tctcatttgg gagttgtctg caatgttctg agcaagcagt    94320
aacggaggcc tcaagtcagg gctgtggtca tggaggtggg gaggggtggt tggtttcact    94380
atctgtgttg acttaatttt agatttgcag actcaactga gtatgaactt taagagaaag    94440
agagaggcca ggcacggtgg gtcacacctg taatcccagc actttaggag gccaagtggg    94500
gaaggccgct tgagcccagg agtttgacac cagcctgggc aacatagtga daccctgtc    94560 tctacaaaaa aaaattttta aattagccag gcagggtgat gtgtccctgt aatcccagct    94620
actcaggaca gtgaagcagg aggatcattt gagcccagaa agttgaggct gtagtgagct    94680
gtagttgcac cattgtgctt cagcctggga gacaaagtga gaccctgtct caaaaaggag    94740
```

```
aatgggaga  gagagagaga  gagagaagga  gaaagagaga  gaaagagaga  gagggaagtc   94800
aaggagaacc  ccacatttt   tgacatggtg  tattagtctc  ttctcacact  gctaataaag   94860
acatacctga  gactgggtaa  tttataaagg  aaagaggttt  aatgcactca  cagttccaca   94920
tggctgggga  ggcctcacaa  ccatggcaga  aggcaaagga  gaagtaaagg  catgtcttac   94980
atggcagcag  gcaagagagc  ttgtgccatt  tataaaacca  tcagatctca  tgagacttat   95040
tcactaccac  aagaacagta  tgggggaaac  tgcccccatg  attcagttat  ctccacctgg   95100
cgccgccctt  gacacgtggg  gattattaca  attcaagttg  agatttgggt  gggaacacag   95160
ccaaacccta  tcacatgggc  aagtgaaagg  atgggtttgc  catcaaataa  aatggggaag   95220
gagactgact  aggtgggcag  attaggaact  cagctttcta  tgaagtgcct  actgatggat   95280
agagatattg  tgttggccat  ctattaggtt  ggtgcaaaag  taattgcggt  tttgccatta   95340
aaagtaatgg  caaaggaaat  aacctttgca  ccagcctaat  aggaattgga  gtctaaaatt   95400 caaaaaggt   aagtcagagc  tggagatcca  aaggcaggag  tcagcctcct  gtggaggcta   95460
tttaaggaac  tgaataaggg  catagatgca  ggagagcacc  caggactgag  cccagggctt   95520
actctccatc  attaaagagg  ttggggaaga  tgaggaggag  ccagcagaga  agactgaatt   95580
ggagcaaatc  agaagaatgt  gggtgctggc  tgtcatgcaa  ggaaagtgct  aagccatttc   95640
aagtatgagg  gaatgatcaa  tgatgtccac  tgatgctgat  gtgttgactc  aaatgaaaaa   95700
tgagaatcaa  ccattggatg  tagtggcatg  gagatctttc  gtgacctgag  ccagagctgc   95760
ttaggtgaag  aggtgaaggc  aagaggctac  tggaaggatt  actactagct  cttttaaaga   95820
gttctgctgt  gaagggtaga  ggaagagaga  tggggcatgt  gttagctggt  ggggaagtg   95880 gatttcagag  gtttgtttcc  cttaaaaaaa  aaaaaaaaaa  gaaaaaagaa  taagaaaaa    95940 aaaaaggcca  ggcacaatga  ctcacacctg  taatcccagc  attttgggag  gctgagacct   96000
cgggaatttg  agactagcct  ggacaacata  gtgagacccc  atctctacaa  aaaaaattt    96060 tttttaatta  gctgggcatg  gtggtgcatg  cctgtggtcc  tagctacttg  ggaggctgag   96120
gtgagaggat  ctcttgagcc  tgggaggtcg  aggctgcagt  gagctatgat  cacaccactg   96180
cactccaggc  tggacaacag  agcaagaccc  tgtctcaaaa  aaaaaagatg  ggagacctaa   96240
cagcagattt  tatgctgata  ggaataacct  attaggggag  aaaaacatga  ggatgctgga   96300
ggaagaagag  tgtcaggagg  acatctcttg  gtggacgaga  ggggatggca  tttggtgtac   96360
aggtggaagg  tttcactta   gatgacagca  cacacagtta  tctatagaaa  caggagaaaa   96420
tgcactatat  gggcatacat  gctgggaggt  agagagtaaa  taatagtggt  ggttgcttgt   96480
ggaaattctc  ttctaatgtt  tttatatttt  tatggtttat  caaggacaat  ttatattttt   96540
acagtttact  gcaaacaaca  agttctaatt  tattcaataa  ttatttgtgg  gtagaccgag   96600
tgcagtggtg  catgcctgta  atcctagcac  tttgggaagc  caaggtggga  ggattgcttg   96660
aactcctgat  tcacttctga  gcttgaatca  ggagttcgag  atcagcctaa  gcaacatggc   96720
aaaacactgt  ctctacacaa  aatacaaaaa  ctagccaggt  atagtggcat  gcacgtagtc   96780
ccagctattc  gggaggctaa  aacgggagga  tcatttgagc  cctgaaggtg  gaggttgcag   96840
tgagccaaga  gcgagccact  gcactccagc  ctggtgata   gaataagacc  ctgcctcaaa   96900
aagaaattct  tattcttctt  cttcttatta  ttatttgagg  agacatttac  tttgtaccag   96960
gcgctgtgct  agatgctgga  gatacagaca  tcaacaatga  caaggctaag  tgcctggcgt   97020
atttgtactt  tgagtctaat  aaaagacatc  acacagacac  acaacacaca  cacacacaca   97080
cacaggattg  tcaaaggatc  aaccatttca  catgtcaaga  tcaggaatga  tattggtcta   97140
```

```
ctactgcctt accatatctc ctaccatgac ctcatcttcc tcttgccaga ttttaagtct   97200
ttatacctca actcccagaa ctctcttcgc ctcacaccct atcacaatgt catccgtacc   97260
ccacggccaa tactccatca ttcgggaaag caaagttcca aagcgtcaag attgtatcaa   97320
tggacctgtc tctatggcaa cagtcctgaa tgagccaagc aaggtaaccc tggagatggc   97380
gtgaatgaga aagtggcctg ttgccacgga gacgtgctga atgggaaggc ccccacgagc   97440
caggctatgt cacgaagccg aaacagtcag catgaagtcg gtatgtctat tttcaactcg   97500
gaattacaaa aatacatttt aatagagctc atgacccatc tccttcctcg tccctgcctc   97560 ccacccccact cttcagcctt catcctacaa cacaatcgag cctcaccagg aacccttcaa   97620
acccctcaag gacaccttac tgttccttca gtacacagtc cccttcctgg gctgaggtgg   97680
tattcctttg accaactact gtctcccctt tgggaccaac agtattctca aaagccatga   97740
gcttatggga agaacattaa ctacattctt tggggcaaga acagttgctc acctgtgaac   97800
cagctcagct tgcatctgtg agaatgattg caatgggtag accagttctc catcaaagaa   97860
tggccctagc accccacaca cagtggtata atctgatcat gctggtgtat tgaacatata   97920
atgttagtgc cacatgaaag gaatttgtaa aaggacttag tgcctagaaa ggtaccttttg   97980 aagatcttgg aatctctgaa acttacccag gttccttata ccctgctcaa agtattcctc   98040
catttatttc ttcattcatt agttcttttg tttcaccaca tatatatttt tgaaacgggg   98100
tctcactctg ttgcccaggc tagagtgcag tggcaagatc gtggctcact gcagcctcaa   98160
cctccccatc tcaagcagtc ctcccacctc agcttcctga gtagctggga caccacaggt   98220
acaagccacc acgccaggct aattcttgta attttttgtag agacgggggtt ttgccatgtt   98280 gcccagtgta ttcgtttgtt ctcacattgc tataaagaac tacctgagac tgagtagttt   98340
ataaagaaaa gaggtttaat tgactcacgg ctccacaggc tgtgcggaag gcatggctga   98400
ggaggccaca ggaaacttgc aatcatggcg gaaaatgaag gggaaacaag cacatcttca   98460
catggtggca ggagagagag agtgaggggg ggagtgctac aaaaccaggt ctcacgagaa   98520
ctcactcact gtcatgagaa aagcaagggg gaaatctgct cccaggatcc aatcacctcc   98580
taccaggtcc ctcccccaac attggggatt acaattcaac atgagatctg ggtggggaca   98640
cagagccaaa ccatatcacc caggctggtc tctaactcct gagctcaagc aatctgcctg   98700
ccttggcctc ccaaagtgct aggattacag acgtgaacca tatttattaa gcattgttac   98760
agcaaagaga agcattgttg cagcataaca attggaagac tccattgatg gacgtctcca   98820
tcaacaagaa ctgtcggata aactatggta cacccatccc ttagcgtgtt atgaagtcat   98880
tacaaaaaga agaagcagat ctctgagtgt caataagagc tagtacttat agggtgtcta   98940
ctgtatacaa gtgctgttag aaagtgagta ttaactcatt taattcttgt aacaagcctg   99000
tgaggtggat tctttcatat ccccatttta cagagaagga aataggaatc tctatatcca   99060
agatatgtta tcaggtgaca aaagcagttt ttgaatggtg ccgccatttt ctcgtaagag   99120
caaatctgga agattccatg agaaattaat aattgtgttt gcctctgtag cggcaccctg   99180
aaagatttgg aagtaggtgt ggaaaggaaa cttactttct tgtgtctttc tgaattttgt   99240
actgtctacg cgttttgtct ttcacaaaac caaacagaaa atgaccattt ggtgcatttt   99300
gtgtgtcagg cattcttcta gtctagagaa gcacaggaga gcaaaatatt ttactgacga   99360
gaaaaatgag gcatggagaa gttaagtgac ttgcccaggt agcagagctg ggattccaca   99420
tcatagggtt tatacaggaa acaggtaaac agagctgtgc ttgtgtgtgg gtatgtgtgt   99480
```

```
acacatgcat acatgtgtgc atgtgtgtgt gtgtttgtgt gtgtgtgaat gtgcttgtgt    99540
gttgggagag ggaaatggca agagaagaac ctacagaagg tcagcaggaa ccaacccatg    99600
ttttgaggag tttggacttt atcctgaagg cacaagggag ccatggaagg atttagacaa    99660
ggggtggttg tgcttagctt tttatttaga aggatgactc tggctgaagg gtgatggccc    99720
agaatacagg tatatgtgaa ggactcctcc tgccctagta ggaggatgcc cacccaccct    99780
ctctgcccag tgcagtatca aagggcaaat tgggtacaga gaattctcac caagctgggg    99840
agaatccact ctgatgctgg ggagtggaca ctgaatgcac cagcctctcc tcctgctcaa    99900
tccctgaatt gaagctgttc cactaatgtt agggatcaga ttcccttcat atatatat    99960 atatatatat atatatatat atatatatat ataaatttt tttttgaga cagagtctcc   100020 ctctgtcacc caggctgaag cccattgtcg cgatcttggc tcactgcaac ctccacctcc   100080
caggttcaag caactcttgt tcctcagact cccaagtagc tgcgattaca ggcacccgcc   100140
accacacctg gctaattcta tatttttagt agagacaggg attcacctat gttggccagg   100200
ctggtcttga gctcctgggc tcaagtgatc agtctgcctc agcctcccaa agtgctagta   100260
ttacaggcat gagccaccat gcccgtcctt tttatattac ctttttttat agagatgtgg   100320
tttcactatg ttgaccaggc aggtcttaaa ctcctggcct caagcgatcc tccctcctca   100380
gcctcccaaa atgctaggat tacaggtgtg agccactgca tctgtccaga ctctgttctc   100440
cataaagctg gcatatggaa agagggaaga ccatccaggc aatatcgaag tcccattggt   100500
gctgatgtgg ctgctgagac cacatgaatg gatgcattct gactctgcca cctctcagct   100560
atgtgaccct gggccagtca gcaagtccct ctataactca gttttctcat ctgtaaaatg   100620
gcgtcaacag tagccaaccc cagcaaatac tgtgaaatat acagaacatc attataatgg   100680
tgaggatgat agagatgcta tgttatcaga atacctgggc ttgaaccagc tccccttctt   100740
gcaagctgtg tgacttggag ctgatgccca aacctctgtg ggcctcattt gtttcatctg   100800
ttcaatgggg ataataacac tcttacttca tacagttatg gaggatttat tgaaataatt   100860
gacatacagc tcttagaaca gtatccggct ccttgtaagc gctcaagaaa tattacagac   100920
tgttgataat aatgcaatac tactaccaat aatatggcca ggagcaatgg ctcacacctg   100980
taatcccagc acttaggag gcagaagcag gctgattgct tgagcacggg agttcgaggc   101040
cagcctgggt aacatagga gactctgtct ttacaaaaaa taaaataaa aatcaaata   101100 attagccagg tatggtggtg catacctgta gttccagcta cttgggaggc tgaggtggga   101160
ggattgcttg agcccaggaa gttgaggcta cagtgagctg tgatcacacc actgcactcc   101220
agccagggca acagagtgag accctatctc aaaaataata ataatggccg ggcgcgctgg   101280
ctcatacctg taatcccagc actttgggag gccaaggcgg gcagatcact tgaggtcagg   101340
agtttgagac cagcctggcc aacatggtga aaccccatct actaaaaaca caaaaattag   101400
ccgggtgtgg tggcgggtg cctgtaatcc cagccactca ggaggctgag gcaggagaat   101460
cgcttgaacc cgggaggtgg aagttgcagt gagccgagat cacaccactg cactccagcc   101520
taggtgacac agtgagactc catctcaaat aataatatga gtaataataa taatatcatt   101580
tttatcatca ttcttactaa cagtctctca ctccttgccc tgcagttttg cctgttttct   101640
tggaataaca ctcttccaca ccttccccct cagggatggt tcacgtttag catcatgacc   101700 caccccctggg gattagttag ctcatttctg gaaagcactt tggagctgta ggtgctttgc   101760
aggctggaaa catcacggga cttgtaccat atttaagcaa tgccagatta ttctgcctgg   101820 caggggagg acacagagga tacggccctg gtatcttttc tccctgccta cctcagcttt   101880
```

```
gctctgaacc attttctgtc ctgttcaggg cagcctgggc cacttgccac ttccagcttt    101940
ctcgggagag gatgccttcc tgatggcacg cctcttaaca cacacctggt gctgttgttg    102000
aaaaagcaac aattgactcc agcgccagca ctgagaggct tgtccttaaa attagcagga    102060
gctgttggaa ggtcgctgtt agctcttttg actggaacac actgttcccc aggtggcatg    102120
aggctgaata cagtgcaggg attggctctg ctctcaggtg gcctgctcca cgctcctgag    102180
ctccgggtgg aagctgtgac cattatttcc ttaacagaaa catatatagc agcattaact    102240
atgaacctta ttactgtgtg tgtgtgtgtg tatatgtgta tatatatata tgcacatatg    102300
tgcatatgtg tgcctatgaa cctgttctga gcactttaca aatgtcaatg tattttatcc    102360
tcccaacaac ccattttata aataagactt gaggcacaga gaggttacgt tactgcccca    102420
agatcacaca gctggagagt ggtgaggcca agatttgaac atatgtacca ttgtaccata    102480
tgtaccaact ttttttttct ttttgggatg cattcttgct ctgtcaccca ggctggagag    102540
cagtggcatg accacggctc attacaacct caacctccag gttcaagcta tcctcccacc    102600
tcagcctctc aagtagctag gaccacaggt gcataccacc atgcccagct aatttaaagt    102660
ttttttttgt ttgtttgttt gtttgtttgc agagatgggg tctccttata ttacccaggc    102720
tggtctagaa ctcctaggtt caagcaatcc ccccacctcg gccttccaac atgctgggat    102780
tacaggcatg agccactgca cccaggtcct ccctccttat aaaggtcgcc aagcacaatc    102840
ttgtgagcct ggccctatcc acacccatac gcaacatggt gtgtattttt caaacaaaaa    102900
ctgaatgaac acctctggtt tgggttcccc tcacacttgt cccgggtttg ttgactctgt    102960
gttgtgggcc tagacaaagc agtgtctgga gctcctagac ccagggacca gacagtctgg    103020
gttcaaatcc tggctcttcc acttctgcct gagtgctctc tctgaacctg tctttcttta    103080
tctataaaat ggagataatt tttttaaact catcacttgg tcaaactgct ttgagcatgc    103140
aaatgagttc atatgtataa acctcttaga atgtcccagg caaagaacaa cacttcactc    103200
agatcaacat ttatttagca tctactgtgt acccatgact attctaggtg atgaggagac    103260
cctctggttc ttatgaggta gtgaggtggg ggagggtgag aaccctaaac attaacgatg    103320
gtgtgttcgc aggtgggaaa atcagtaaag tcgggtaaag ggaatttggg agtgctgtgc    103380
tcaagtcctg gccctgccac tttctggggt gcaagataca gcattgaata gggtggtcag    103440
ggtaggcctt attgggaaag tgatatttga gcagacgatc tagatgtcgg cacatattgc    103500
tactgtttga tggtactaat atgagtttga gtttcacttg caagtatata tatatatata    103560
tatatatata tatatatata tatatatgtg tgtgtgtgtg tgtatatata tatgtgtata    103620
tatatgtata tatatgtgtg tatatatgta tatatatatg tgtgtatata tgtatatata    103680
tgtatatata tgtatatata tgtgtgtata tatgtgtata tatatgtata tatatatata    103740
tgaaatttgg tccatttatt tatgctgatc aattaattga tgttgaaatt ataattgaat    103800
gttttattaa taaacagata cccacatact atttttttcag aaattgttag gttttggggt    103860
tttctttaga ttttgattat ttttatttgc ttaattttct tttttctttt ttttaatttt    103920 attttttccat aagttattgg ggtacaggtg gtatttggtt gcatgagtaa gttcttcagt    103980
ggagatttgt gagaacctgg tgcacccatc acccgggcag tatacactgc accatatttg    104040
ttgtctgtta tccagtgctc acctcctact cttccccccca agtctctaaa gtccattgta    104100
ccattatttt actcacccac attctttggc ctgagatgct gagtggtcat gactcccaga    104160
tcccttcttg tttctgtatc aaagatcttt actaagatcc tggcctaggg aacctattcc    104220
```

-continued

```
ctttcctcat ccccaatggg agaaggggct tcttccccag cttatttgcc aactcatagg 104280
aaaggtatga aggagaggac tgtagttgtc ttgaagctgg tcagatgttg aagagatgat 104340
aatatttgct gatcaagaga gacaaagcaa tgctggaaga agaggctgtg ttagttaaca 104400
ccagctgcaa taaccaataa aaccaaaaat ctctggctta agagtatgca tgagtgaaaa 104460
atcaacttct aaagtacaac tggtggccgg atgtggtggc ttatgcctgt aattctagca 104520
ctttgggagg ctgtggtggg agggtcgctt gacccagta gtttaacgcc aacctgggca 104580
acacagtgag acaccatctc tactaaaaat aaaaataat aaagtgaaac tggtgagggg 104640
tgcaatgagg tggagtggtg ggtgactcaa atatggctcg actccatgca gtcactcagg 104700
gatccaggct gttggaggct ctccctgctt aaacatgtgg cttccaaggt tgttctaaga 104760
gcctacattg agacagcagc tggggaaaag ggaaagtgga gtgggaggta cttatgaggg 104820
ttcctggaag tggtgaacaa cacttctgcc tgcattctat tgggtggaat ttagtcatgt 104880
ggcccaggct agctgcatgg gaggctggga aatgtagtct ctgattaggc tgccatttcc 104940
cagtcccact tgtgaatctt tagtgggaag ctcaccatgt ttgcaccagg gattcagtct 105000
acctcccact catgcctcaa ctatgtatca ggcactgtcg taagtacttt acatatcagc 105060
ctacctaatg caaacaacta ctcagtgggt gctttattgg tcacatgtat tagtgagaac 105120
atggaaaccc agagccgtta aatatcttgc ccaaggtcac acagctagga agtggcagag 105180
ttggaatttg aatccaggaa atctggctgc agagccccac gcttagtata aattcattgt 105240
agtttagaaa gaggcagaag gaccctaaaa ttggcataat ccatttttg gtccctaagg 105300 aactgactga attgactact tgtaaaagtg agtcctggac aggcaacagt ggctcaggtc 105360
tgtaattcca ggactttggg aggctgaggc gggcagatca cctgaggtca ggatttcaag 105420
accagcctgg ccaacatggc aaaaccctgt ctctaaaaaa atagaaaaat tagctgggtg 105480
tggcggtggg tgcctgtaat tccagctact caggaggctg aggcaggaga atcgtttgaa 105540
cctgggaggt ggaggttgca gtgagcaaag atcacgccac tttactccaa cttgaatgac 105600
agagcaagac tctgcctcag gaccgccatg gcccctggg ttctaggtca gagtttctcc 105660
gccacagcac tgatgacttt ggggctgca ttattagctc caaatggga gctatcctgt 105720 gcactgcctc aacttacttg atgccagtag cgcccgcgcc ccagttgtga gaaccaaaaa 105780
tgtctccaca cattgccaaa tgtccctgg gaggtgaaat caccctggt tgagagtcac 105840 tgttctagat tgttaaatat tatcttacac tctagcacaa gtccaaggca aactgactta 105900
gaaattacca accttgcaaa aaatagaaga tttcttaaag tcagtgagca tgatggtggc 105960
aagctgctga atcacaccc ccagacatta gcagatggga tctggacagt attcatctag 106020
ttaaaaattg acaaggactg ggacactgca ggctcttcaa aagagaatca tttgaataac 106080
aaggggtcaa gacaggggta attggtgaaa gcccctgctc ataatttgaa aatataaata 106140
ggcatcatga aaattcatcc tgcaaaagtc aaaagtcgaa tgtgcagtgt tatacatgat 106200
cagttgattt gggaggggaa attgcatgca cacacatgag agcttgcaca cccacacaca 106260
cacacctgtt caagtgtgtg tgccagtgct cagtgaggac catctcccca acctgtctga 106320
tcatcttgct ttggggtgac cctatgggtg aggcagaaat tcttgatca tagttttcta 106380 atgaatatta taattgttaa cttctgatgg gtgctgactt tttcatcttt gcaacactgc 106440
gtaggtattt ttactctccc cattttacag atgagacaac tgaggctcag aaagattgat 106500
tagctctaca cgaagccagg atccaggctt agcctggctc caggaatcat gttttgagtt 106560
acgtagcttc cctgattctg agggacctcc ccacttctga aatcttctac tgttactccc 106620
```

```
catggcccett tcctattgac cggaggcacc ccagctcctc actcgtccct tatcttatga  106680
aacatgacca tgatgtctga attcaaagga gagcctgggc tttgtgggga aaacgaagca  106740
gaaaaagaaa ggtggaggtt ggtggttgtt tttggcatgg tgaggagcct gtcgttgctt  106800
gaggaaagca agaaaggaga ttgctggggc ttggatccat ctctgggtgc ctgtgggtct  106860
gtctgtaaaa atgagaactg gtcgtgctca ttagaggatt tgaccgttag gccttgggat  106920
agcgatttgg gaacttttt ctgctaagac aaagaataat atggttcagg ttcattttgc  106980
tcctgctttc ccaagcccta catctcttct gggctttttt ttttttcctt ttctctcctt  107040
cttcttcttc ttcttcttct tcttctcatt tttggatctg gacttctgct gactcatctc  107100
tctgagcaag gaaggaggga ggaagtcaga attgctcatt aaccgttttc tttagtgact  107160
cagctgtgat tcacatttta attaatggag gagaaaaacc tgatcagtcc taaggcatct  107220
gcccaatcac gcataactcc aggctggtga taataataat acttgaaaaa agtggggtgt  107280
cctgaattaa actatggctc attccccaca ttagtcttga ggactccacc aggccctcta  107340
agttccaggt ctcaatgggg ctccctgaac cagagcagct agtccaagcc ccgagcagca  107400
tttctgcaga gttagtctga ggtcaggaca agaaacagag gctcaagccc tcctgggatc  107460
gcaggaggat catgggaatg taatattgtt tcctgagctg gtctttggct ataatcccag  107520
gctcaagcct ggcctccctc ccctcggggc ctgaaatttg tcagagccta ttgcaggggc  107580
agcttctgtg cttttttgttt gcccagagaa tgagaaaagt ccagataatc atgaccgcta  107640
cttcctgagc acttactatg catcaggtgg tgtgctcagc acttctcatg aatgatcacg  107700
ttgaatcctc actctgtcca caaaagaaa gagctttat ataattctcc aacctcccta  107760
tgaggaaact gaggcttggc aattgcccaa tgtagacaat tagtaaataa tcaggcagga  107820
tataaaccca acccttccc acctgggagc cagagcttgc atctactata cttctctgct  107880
ttccagtcag ctgcaaagaa aaattggaag ctgatagctc attcaacaaa cacttattga  107940
acccttccac ctgctcagcc ctgttctaga caccagagat ccatcagtga accaaagagg  108000
caaatccatg gtctcatgaa actgacaatt tacctgccca agtgtattag ttactgttta  108060
taagttccta ttaagtgtat tagatatgct tgcagctgta acaaagaatc ccaacatgca  108120
taagggctca aaacaataaa aattccgttc ttgcacagat aaagttcaaa aggtgtattc  108180
tttttttttt tttcttttgc gacggagttt tgctcttatc ctccaggcat gagtgcaatg  108240
gcccagtctc ggctcactgc aacctccacc tcctgggttc aagcattctc ctgactcagc  108300 ctcccccagta gctggaatta caggtgcccg ccaccacacc tggctaattt tttgtatttt  108360
tagtataggt ggggtttcac catgttggtc aggctggtct taaactcctg acctcaggtg  108420
acccacctgc ctcggcctcc caaagtgctg ggattacagc cgtgagccac cgtgcctggc  108480
caaaaaaaaa atgtattctt aaacagcagg cacctctcct ctaagcagta agtcagggc  108540 ccaggcttgt tccatattgt agctcctcat cttcaaccca tggcttccaa agtctccatg  108600
cttcttgata tcaagccaca gaagggaaaa gagcatgaga agggcacagg agaaatgttt  108660
ctgggacaga cccagaagta gtccatatga cttccatcta cctcccactg gctagagctt  108720
acatggcggc acccacttgc agagctggga aatgagtct aactgagcat ccaggaagga  108780
gagacagaca tgagtctttg cgtgggtcct cactgagaat caagctccac attttgatcg  108840
atgtcaccag agcgtacatg gcggcgccca cttcagagc tgggaaacgg agtctaactg  108900
agcatccagg aaggagagac agacatcagt ctctgcgtgg gtcctcactg agaatcaagc  108960
```

```
ttcacatttt gatctgtgtc acctccttgc aagccctacc ttaggacaat tttaagggac    109020
attcctatct tcttccaccc ttaggacagt tttaagggac actcctgagt tcttccaccc    109080
acctcctctg tttcttgggc ttccagctct caggatttgc ctttgcctta caatggggtg    109140
aagcaagaat ctggaagaat gtctctcccc acaatttgaa gtcttatttg aaaaaaagca    109200
gtagagcatc cctccctctt gaggtaggga aatctagaat caaatcctgc ttctccagac    109260
tttgacctca gaaactgggg ggacttcaag gtcttcaggt gggcagcttt catgaaccat    109320
tcattcctcc cacctcatac caatcagggt cctaacagga aaagaattaa acttctagat    109380
ggttcaaaag aagaccatgc catgaagaga ctccttaaag ataggaac aggtgagaga     109440 aatagataac ggctgtttga ggtcctcaga gagaagccat cgcgagccct acatttcctg    109500
gaacccagtg gaggcagagc tgtgcagaag ggactactgt cagaaccagg gagggagcag    109560
ggaagcaata ttccaatctc tttccctccc ctcatcttct gccagcgctt ccctcagcc    109620 aaaccaaacc ggaaacggag caaagcattc tgggagttgt agtcttcaag ggtccgcctc    109680
gagggcacag agcccgctgg agcattgacc tagagggcac acaggaatg actagtttgc     109740 accatcatgt gacggactgc acgccctcga ttatgtaatc cactctataa ttcaactgca    109800
gagctgcatg gtacagcagg atagccacta gccacacgag gctatttaaa tataaatgta    109860
cattcattaa aatttaacca aatgaaaatt ttagccactg agccccattt caaatgctca    109920
ttagccacac gtggctcttg gctaccatat tggacagatc agaatagaac atttccatca    109980
tcccagaaag ttctaggggc cggcgcagct gtggtgtaac ctgagcccat gcatgttatg    110040
gaatggagaa gagagaaaac agcacaagag gcagttttga agggagacag agagctgtgg    110100
atcagtaggg aggagactct ctaggcaaag gagcagttga gaagcaagaa agttgagtga    110160
gctgctttgc tgcgatggag gcttccctca cggggaagag tagagtcaga aagctttagt    110220
tcaagttcag ctctgaaatg aaccaatgag tgttctgaca agacacctgg ccttccggaa    110280
ccttggtttt gtagtggcca agggcttgac cctctgaagg ttcactgaaa aaatcaact     110340 cacaaggcat attaattgga gaaaaggcag gcagatttat ttaatgtgtt tgcacgagag    110400
ccttcagaat gaagacccaa agctgcaggg gaaattgtcc gttttttaag cttaggttca    110460
acaaagtatg gacagcggtg tagaaatatg attgaacaaa aagtgtacaa tgtaaatgct    110520
aatagactga gtggggaaac ccaaaaaggg ctgtcttgat tctccttggt ctctctgagc    110580
atgcatttct tccgggtatg ggacaagacc ctctctggaa tggaggggg gctctcttgg     110640 ttctccttgg tctctctcag catgcattcc ttccgggtat ggggcaggac cctctctgga    110700
ataagggggc tgtcttgatt cttcttggtc tctcagagca tgcattcctt ctgggtatgg    110760
ggcaggaccc tctctggaat gggatcctta aacctacgg tcaaataacg taagttagat     110820
aatttctttt ttttttttt cttttttttg agacagagtc tgattctgtt gcccaggcta     110880
gagtacagtg gcacaatctc ggctcactgc agcctctgcc ttctgggttc aaatgattct    110940
cctgcctcag cctcccaagt agctgggact acaggtaagc accaccatgc ccagctaatt    111000
tttgtatttt ttagtagaga cagggtttca ccatgttggc caggctggtc tcaaactgct    111060
gacctcaagt gatccaccac ctgggcctcc caaagtcctg ggatttgtaa tcccagcatg    111120
agccactgtg cccagccaga tcatttcttt ttctttttct tttcttttc tttttttttt    111180 ttttttgag atggagtctc actctgttgc ccaggctgga gtgctgtggt gcaaactcag    111240
ctcactgcag cctctgcctc ctgggttcaa gcaattctcc tgcctcagcc ttccaagtag    111300
ctgggactag aggtgcgcgc caccatgccc agctaatttt tgtattttta gtagagacag    111360
```

```
tgttttgcca tgttggccag gctggtctta aactcctgac ctcaagtgat ccacccacgt   111420
cggcctccca aagtcccggg atttgtaatc ccagcatgag ctaccacagc tggccagata   111480 attttttat aactagtttt tacaaagaaa ggtggaggga agttagagt aacattttta    111540 ggtgttaggg ctgactttgg ggaaaagagg tctggtttct acgacccgcc ttagggaaga   111600
gggattctag tttttgtggc tagccccagg ggagaatggg actaagagat agaagggcag   111660
gagaaggtca gagaaaaact tttgcttctg tggctgcttc ggagaacttc attttggggt   111720
attgttttct gagccccaac agtttgctta tcagtgaagt gggtataggc gcccacctcc   111780
cacagtgacg atgctgtgaa cagggctttg gaagagtaga actatgaaat atttgttgtt   111840
gccttgtggg gaaatggtcg ttaaagccaa aattgttcaa gagaagaagc aggaagagtt   111900
cctttctttc ctgcaggtat cctcttaagc tgagtcttca gaatccctg acaacgttta    111960 atcaacactt tattaaattc accccaaccc tgcttcaaac cttcacctgg tcctcgagat   112020
cttccaactg tttcttgatg aagttagcag gcaattgtat ggcgggatca tcatctcatg   112080
ttttgttttg ttttttttcct ttttaccctc tgactttgag aaatccttgt ccttttactt   112140
ttccaaacct gagagcattg cagagaagtt agaattgagc aggacatggg cttaagaccc   112200
agcccagcca tgtgctagct gtgtgaactc gaagcagtga ccccacctct ctgacctgga   112260
aagtagaggg aatgatagga cccaccaccg ccacacttgt agggtcatca tggggattga   112320
ataaaataat gcataagact tggcccacag caagcactca agaaatgtta gctacttcct   112380
aaatatattt ttaaccttt attgaatata acatacatac agaaaagcac atgtatcata   112440
caagtagagc ttgagtgatt ttcaaaaact gagcccagtc atgtaaccag cgcctagttc   112500
aagaaacaga acatagccga gtgaggctga ggcaggagaa tcacttgaat ctgggaggca   112560
gaggttgcag tgagcagaga tcatgctatc gctccccagc gtgggcaatg ggggcggagg   112620
ggaagagaga gagagagaga gagagagaga gaaggagggg agggaaggaa ggaaggaagg   112680
agggagggag ggagggaagg gaaggaaggg gagagagaga aaaggaaaga aaagaggaag   112740
acagaaagag agagagaaag gtaaagaaag aaaaggaaag aaagagaaag aaagaaaaga   112800
ggaagacaga gaaagaaaga gaaagctaaa gaaagaaaaa aaggaaggaa ggaaaatagg   112860
gagggaagag gaggaggaag aagaagaaga aggggggggag ggagggaaca gctgcagctt   112920
cgaggaagga aggagggagg gaaggaagga aggaaaggaa ggaaggaaaa aaaacagca   112980 ccaacgttta gaaacccccct tgtgcctctg aggtcaccag taactccatc ctgacttcaa   113040
acagtctaga ttagttttgc ttgttttga actttaagca catggggtca tacagcatgc    113100
atgcattgac ttctttccct tgacgttgta tgtgtgagat tcatctgtgc tgttgctgtt   113160
catttgttct catcgctgtg tgtgctgaac cacctgttca tttactctac taatggtggg   113220
cagtttggtg ctttctactt tggggctatt ccagagaaag ctactttgaa cacactcaga   113280
tatgtctgtg ggtgaccact cttcatattt ctatgggaga tattcctagg accggaacat   113340
ctgagtcaga gggaggaatt ggtttagctt tggtaggaac tgcctaacaa ttggccgggc   113400
acagtggctc atgcctgtaa tcccagcact ttgggaggct gaggggggca atcacttga   113460 gctcaggagt tcgagaccag cctggccaat gtggcaaaac ccctggccaa catggcaaaa   113520
ccccgtctcc gcaaaaaaat acaaagatta gccgagcatg gtggcgtgtg cctgtaatct   113580
cagctactca ggaaactgag gcaggagaat tgcttgaacc tgggaggcag aggttgcagt   113640
gagcagagat tgcactactg tactccagcc tgggtggcag aatacatgaa actccatctc   113700
```

```
aaaaagaaga aaggaaggaa ggaagggaag gaaggaaagg aaactgccca acagttttcc    113760
caagtgtttg ggatggaagg aaggaaggaa ggaaggaaaa gaaactgcct aacagttttc    113820
ccaagtggtt ggaccagtta aaactcccac cacctgtgaa tgagagtttg ttttattttt    113880
gctcctggag tgcctctcct gtagcaggtt cccactgaat gtctgggaat tcaaatgtaa    113940
tgcacttgtt catttcctca agagcttcac tccatcaatt ggattcatcc attggctctc    114000
ccatctccac tgacactatg ttctcacctc tatttggaag acatcctgcc tccacctgcc    114060
caagtcacat tatcttctca ttccagcctc tcaaggagag ttttctcttt caccacctcc    114120
tctagccctg gtgattggca aggtctcgca acagtaccct tcaaaacact catgactgtg    114180
aatgcactgg ccttcactaa gtttcccatt cttctctttc tttctttttt cttttctttt    114240
cttttttttt gaacagagtt tcactcttgt tgaccaggct cgagtgcagt ggcacaaaca    114300
cagctcactg tagcctcaac ctcctgagct caaggtatcg tcctgcctca gcctccttag    114360
tagctgggac cacagacatg caacgttgtg cccagctgat tttcttttt ttcttttttt    114420
ttttttttt gagacatggt ctcaccctgt caaccaagtg cagtagcatg atcacagctc    114480
actgcagcct tgacctcccg ggctcatgcg attctcccac ctcagcctcc cgagtagctg    114540
gggctacagg cacaagccac catgcctggc taatttttgt acttcttgta gagaccaggt    114600
ttcaccatgt tgcccaggct ggtcttgaac tcttgggctc aagcagtcct cctgcctcag    114660
cctcccaaaa tgctgggatt acaggtgtga gccagcacgc ccggccatgg ctaatttctt    114720
catttttggt aaagacaggt ctcactttgt tgcctaggct ggtcttgaac tcctggactc    114780
aagcaatcct cctgtctcag cctcccaaag tgctaggact accgatgtga gccaccgcac    114840
ccggcaattt ccccttcttg acttctccag agctctcatc cctctcgagc tcctgtctct    114900
tctagaatca cttacctcac caccttatgg ggttttgcc tctgttccta ctcctcttta    114960
tttaagaaaa cactgtactt taagagggct tcagaaacca cccgaaatag aaacatgtcc    115020
ttttgttcaa tccttactt taaaagacaa ataaaatgaa gaattgctct ccatgtagaa    115080
ggttaaggag cttgggagga ccttctgtga gtggggagaa ctttacatta aaggaaaaaa    115140
aatgctggag aatagctgtg aacccaggaa gggagaagga cttcctccac tgaacttgta    115200
aagcacaaac tctaaggcaa aaaaagacat gattacatga aaactaagat atttgttcaa    115260
ataaagatgc aattgggggcc aggtgcggtg gctcacgcct gtaatcccag cactttggga    115320
ggccgaggca ggcgaatcac gaggtcagga gatcgagacc atcttggtca acatggtgaa    115380
accccatctc tactaaaata caaaaaatta gccaggaatg gtgtcacgtg cctgtaatcc    115440
cagctacttg ggaggcttag gcaggggaat tgcttgaacc agggaggtgg aggttgcagt    115500
gagctgaaat cacgccactg cactccagtc tagcgacaaa gcaagactcc gtccaaaaaa    115560
aaaagatgca atagcaggtg gttcgggaac caaaccttac atccagatgc tggttgtccc    115620
atttcctgtg aatccttggg tgagttatca acctctctga gcctcagttt cctcgtcaat    115680
aaaatggaga aaatagtatc tacctatgga attgttgtga gttttgaatg agttaatatt    115740
tataaatcat ttagaatagg aattagcaca tggtaaatag tggatagaat cataaaaaaa    115800
aaattgatca ggggttaact tctaactgct gtttgttata gaggtcccta gcactgtgtg    115860
gtcattttaa atttagatga tttagaatta aatgaaattt aaaactcagt tcttcattca    115920
cactagccac attttaagtg ctcaaaaccc acaggtgact agtggctacc atatttggca    115980
gcacagattg agaacagatt tatcatccag aaagttctgt cagacagtgt tgatcaaggc    116040
tacatgaggg tctgggtgca gtggctcaca cctgtaatcc cagtgctttg gaaggccaag    116100
```

```
gtgggaggat cactggaggc caggggtttg agaccagcct gggaaacaga gagacctcat   116160
ctctaccaac attttaagaa ttagccaggc aaagtgttgc atgcctgtag tcccagctac   116220
tcaggaggct gagacaggat tgcttgagcc caggaatttg aggctgcagt gaactatgag   116280
cgcaccgctg cactccagtc tgggtgacag agtgagacct gtctctaaac ataaaaaata   116340
aaaatgtagg tggggcatag tggctcccgc ctgtaatccc agcactttgg gaagccgaga   116400
tgggcagatt gtgaggtcag gagatcgaga ccaccctggc taacatggta aaaccgcgtc   116460
cgtactaaaa ataaaaaaaa attagccagg catggtggcg catgcctgta gtcccagcta   116520
ctcgagaggc tgaggcagga gaattgcttg aacctgggaa gcagaggttg cagtgagctg   116580
agattgcgcc actgcactcc ggcctgggcg acagagcgag actctgtctc aaaataaata   116640
aataaataaa taataataaa gtaaaaataa aaatgcaaag actacctgag ggaatgtctg   116700
caagtcaacc agaataacac agcaaccccca ataggaaaac aggccgaaaa tgtgaacagg   116760
cggatcaggg aagtgaagtc tgaaaagcta atcagcctat gacatggtac tcaaagtcat   116820
ttgtaaccag aaagatggaa atgaaagcag tatctctgta cacctttaat attggggaaa   116880
aaatatgtga ataagccaag ggtttccagc gatgcgggca cagaggaaag tcttgcacca   116940
ctcaaagggg tgtggcccag ggaggccact ctggagacat atcggtagta ctcagtccag   117000
tgaggtccag caccatcagc gcttatgtcc ccaggcatcc atcccaggga cattcttacc   117060
aggtctgtta ggggcaggta cgagaatgct tactccagca ccatctatat aaggggagct   117120
gaaggccacc tggtgtccct cctggagacc aggaggcggc atgtgacagc ggcacccatg   117180
gagcaccaga atgagtgaga gctccagacc gcatatccga cagatactac gggatggggc   117240
ttttagaaat atggttgttg ccgggcacgg tggctcatgc gtgtcatccc agcactctgg   117300
caggccaagg cgggtggatc acctgaggtc aggagttcga gaccagcctg gccaacatgg   117360
tgaaaccctg tctctattaa agatacaaaa attagctgga cgtggtggcg ggtgcctgta   117420
atcccaacta ctcgggaggc tgaggcaaga gaatcgcttg aacccaggag gcagaggttg   117480
cagtgagccg acatcgtgcc actgcactcc agcctgggtg acaagagcaa aactctgtct   117540
caaaaatttt aaaaaacaaa aataaaaat atggttctgg gtgaaaacag gaaacaacag   117600
aatgtgtcta acttcatcct gcttatgtca gttaaaaata gacacactca aaatatcgca   117660
cgtgtttttg cgagaatgca ctcctataag gccaaattaa acattctctc agttgtctct   117720
gggagggaga agaatgaaag tagggtatag agagatatag gggaattaat gcatgaatga   117780
atgaaggtat aaacaagaga caggcgtcat acagaccaaa ggtaaagata tcccgtaacc   117840
tgaggagagc aaagaacttg actctgcatt tgaagattca gaaatgaatt tcagaaata   117900 gttttctcgc caggggtgg ctcacgcctg taaccccacc actttgcgag gcgaggcag   117960 gtggatcact taaggtcagg agttcgagac cagcctggcc aacatgatga aaccctgtct   118020
ctactaaaaa tacaaaaatt agccaggcat ggtggcatgt gcctgtaatc ccagctactc   118080
aggaggctga ggcaggaaaa tcacttgaac ccgggaggca gaggttgcat tgagctgaga   118140
tcacaccatt gcactccagc ctgggtgaca gagcaagact tgtctcaaa aaaaaaaaa   118200 aaaaaaaaa aaaagaaga ggaagaaatc gttttttcaa gaaggggaaa gctgggtgat   118260
ttaagaatga acttgaagag gatcactcag tcctcaacct aggagtggca agaatataga   118320
ctgtatggga agtggttctg ctccttggta cccatcttag aaatatttgg cctgagtctg   118380
taagaggcag gtactttatc taacctgagg ttaggggggcc actacatccc catcccctcc   118440
```

```
cctgctttct aaccatgcta acatcttctc actctcctgt ctcctctcct tctcactccc    118500
ctaatctgcc tattcacatt ttgggcctgt tttcctattg gggttgctgt gttattctca    118560
ctgatttgca gacattcctc tgtgtcatct ttttaatttt gttttaattt ttagaggcag    118620
gatgtcattc tgttgcactg gctgtagtga cgtagctcac tgcagcctca aactcttggg    118680
ctcaaactcc tgtcctctgc ctccacttct caactggtaa cctcacttct cttcatgagg    118740
tctctccagc cccagggcct ttgcacatgt tcccctctct tctgagtggc atatggtagt    118800
tgctcctctg taaatattta ttgacatcct gacttccaac cagcagagaa ttgacctcct    118860
tcccatgctc aggctagtga aggcatgagt ttggctgagg tcccagtggg aaggtgagt     118920
ggggtggcag agttaaccag gagcagcatg gtagaatggg taaaaccaga cgtagcacgc    118980
aggcaccaca tgttagctgg acaagtagtt taaccccatg ggtctcaatt tccccatcaa    119040
tgaaagggag aatagaacaa gtccctggta agcagcataa aatgagctct cagaatgtaa    119100
agtaacaagc acacaacctg gaagagaata catttagtga atattggctc ctttaatcag    119160
caggttctga tatgacttag ctacaattaa gaaaataaaa atggaggccg ggcgcagtgg    119220
ctcatgcctg taatcccagc actttgggag gccaagacgg gtggggtgga tcacctgagg    119280
tcaggagttt gagaacaggc tggccaacat ggtgaaaccc atctctacta aaaatacaaa    119340
aattagccag gcgtggtggc gcacgcctgt agtcccagct actcgggagg ctgaggcagg    119400
agaaacattt gaacccagga ggtggaagtt gcagtgagcc cagattgcac cactgaactc    119460
cagcctgggc gacagagtga gatttgtctc aaaacaaaa gaagtctgga ggccaggagg    119520
ttggttgcag ggttggttcc ttggctcaac aatgtctcca aagagtcctt ccatctttcc    119580
actctaacat cgtcactgta aggactttt ttaacattta ccactcacag ccccaagacg    119640
actgcgtcag ttctttcttt ttttccttca gacagagtcc cgctctgtcg cccaggctgg    119700
agtgcagtgg catgatctcg gctcactgca acctctgcct cctgggttca gcgattctc     119760
ctgtctcagc ctcccgagta gctgggatta caggtgcctg ccactgcatc cggctaattt    119820
tttgtatttt ttttagtaga tagggtttt caccatattg gtcaggctgg tctcaaactc     119880
ctgacctcag gtgatgcacc tgcctcggcc tcccaaaggg ctgggattac aggcgtgagc    119940
cactgtgccc ggccgatgac tgcctcagtt ctaaggtact tacccagcca tccacgtaga    120000
cagacacaaa agcatccggc caaagaagag ggagaggaag ggctgtctct taccatgtga    120060
ctcatctcac ggggaaaaaa tccttttcca gaagcaccca gcagattttt cacccagatc    120120
ctgttaggcc tacgaatggg tcatgtgaca agtgctctta ttgcaaggaa tcttgggaaa    120180
aagagactat taggcatttt ctgcctcttt gatgggaggt gggctctgcc agtaaggcgg    120240
gtagtggtgg tggctcttgg atggacaact gtgtcttcca ttcttcttct tctttttttt    120300
tttttttaa gagacaaggt ctcactctgt tgcccaggca gaaatgcagt ggcacaatca    120360
cagctcactg ctgcctcgac ctgccaggct caggtgatcc gcccaccta gcctcacgag    120420
cagctggagg agtgtaccac catggccggc taatttttat attttttgta gagatggggt    120480
ctctttatgt tgcccaggct ggtcttgaac tcctgagctc aaacaatcct cctgcctcag    120540
cctcccaaag tgctgggatt acaggcataa gccaccacgc ctggactctc ttctttaaat    120600
actgagcctt ccacctcttc tagaatatac tctgttaatt atcaaccaca cttttctaca    120660
tttttgcttc attattcatt cagtaaacat ttattgagtg cctactgtat gccaggcaca    120720
gctttaggtg ctggagatgc tatgaacaaa acagatgaaa atttctaaaa aataaaataa    120780
aaaataaaaa taaatttgc aaagccaggc acagtggctt aggcctatag ttccacctac    120840
```

```
tcaggagtcc aaggcagtag gatctcatga gactgggagt ttgagtccag cctgggcagc   120900
atactaggac tctgtctcta aaaagaaaa gaaggccggg cgcagtggct cacgcctgta    120960
atcccagcac tttgggaggc cgaggcaggt gaatcgcaag gtcaggagtt tgagatcagc   121020
ctgaccaaca tggtgaaacc ccgtctctac taaaaatgta aaattagcc aggcatggtg    121080 gcaagtgcct gtaatcccag ctacttggga ggctgaggca ggagaatcgc ttgaacctgg   121140
gaagcggagg atgcaataag ccgagatcgt gccactgcac tccagcctgg gcaacagaat   121200
gagaccctgt ctcaaaaaaa aaaaaaaaa gaaagaaaga atagaaaata tctgccctac    121260
ggggatggac atgctagaac atcaaagtcc aatggaactt tctgcactga tgaagtatgt   121320
atgtatgcac cagccacatg tggcttggga gcacttaaaa cgtgactggt acaagcgaat   121380
ttttcattta atttaaatga atttaaatct gtatttaaat agccatgtgt ggctagtggt   121440
tactttattg ggcggtgcag ctctctaaag gccaagagat acatcatcaa cttctctccc   121500
ttgacccata ttcagttctc tcccaccctg aaaatctcct ctcctaccca ggctcacatt   121560
tccagttctt ctcctcttgt tctccctcaa ccatcagccc ccgcaagact gacgtgaccc   121620
tgatgccgta tgaaatgcat tcttcatcct ttactcttac tcacctctgt gcggccctgg   121680
agaccagtga cctctccttt ctcaaaatac tttatttctg tgtgttttg ttgttgctat    121740 tgttttggg gggttttctt gagatggagt ttcactctca tcacctaggc tggagtgcag    121800
tggtgcgatc tcagcttact gcaacctctg cctcccaggt tcaagcgatt ctcctgcctc   121860
agcctcccaa gtagctggga ttacaggctc ccgccaccac ggctggctaa ttttcttgta    121920
tttttggtag agacggagtt tgccatgtt ggccaggctg atctcgaact cctaacctca    121980
ggggatccac ctgcctcggc ctttcaaagt gctgagatta caggcatgag ccaccgcacc   122040
cagcctcaaa atgcttttga acttgactgt caggtatgcc attctccaca ccagtctcct   122100
cccatgtctg tgtcttctcc ctctccactg gggacccttg gctttttcca cttcactcat   122160
ctaccctggg ttatctggtc ttccataacc ctgtcctctg ccacacctca cttattcacc   122220
caccacaata tttattgagt actcactagg ccatgaaaga tgctatacaa aaaaagcccc   122280
tgtcctcgtg gagctgacat tctagaagaa agcatgaata ataaatacga cttaataaac   122340
agtacggcca ggcatggtgg ctcacgccta tcatccaaac actaagagac caagatgaga   122400
ggatcacttg aatccaggag tttgagacca ccttgggaaa cgtactggga ccctgtctct   122460
acaaaaaaaa tattaaaaat tagctggata gggtaatgca tgcctgtagt tccagctact   122520
tgggaggaca aggtggaagg attgcttgag cctgagaggt caagtccgca gtgagctgtg   122580
actgtgcact gcacgccagc ctgggtgaca gagtgagatc ctgtcttaaa aataaataaa   122640
taaacaaaca aacaaacaat ataattccag agagtgaaga ggcaggatct ctttagctag   122700
gaagttgagg gatgttctct ctgagaaggc agaatctgag tttcaacctg aagaattcga   122760
agaggccagc taggcaaaag atgagagttg aaggaatggg gacggcagag gagacagcca   122820
atatagtaat tctcaataaa gcagaaagtg agcttttcct gctggcagaa cagaaaggaa   122880
gtcggagtgg ccagggtgtt gtgggacaag gtggtcagca ggagtcacat cacgcaaggt   122940
catgtggtca tggtagactt taaattttac tccaagcctg atggaagcca ttggaagatt   123000
ttaactaagg agtgacggaa aactggcatc tcaaactcaa catgtctaca acccagttct   123060
tgatctttga aaccttcttc ctccatcttc cccatctcca ttgacagcaa cttcatcctt   123120
cagttagctc aggccaaaac cctggagtca cccttgatac ctctctcctg ctccacactc   123180
```

```
agtctttcca ttggaagccc tagggctgc catattgttc tccatagcac ttcacaccgt    123240
ctgacatact atatctttc ccactattgc tttgtccttg gtagcatctt taggcactct    123300
ctgaatatct ggcacatagt acgtgctcac taaatccttg ttgaataaat gaatgaacat    123360
cactccgtgg tcctttcaga accagagcca ttcttctctt tcttcaccac cgttgcccct    123420
caccccgccc aactagtcac aggagttgaa ggatgacaca gtagagaact gggattctgg    123480
agtcctgtgg ctggtctggg gttcgagttc ttactcagtg gtaggaacct ccatgtggga    123540
ttaacttatc tggtctttag tttcctcctc tgtaaaatgg gcctcaaact gccaaccgct    123600
gggatgcagg gaggatttga tgagcccagg caggctccct ggagcacagc aatcaatggc    123660
agctatatat aaaccggggc ctcttttgta ctcccactgc ctttgtccta gttccagccc    123720 tcattcacc agcctgctct tgcggctccc tcctaacttc tgctccatca ccaccaatct    123780
gtcctttcag ctgtcaggct tgtcttctga acgccaaccc taatcacatc ccttcctgct    123840
ccaaaacctt acatgactct cactgtccac aggacaagac ccagcctcta gttgacagcc    123900
tccactgtcc agcttaccca acctctcccc taccacatac cctgagtgga gccttctgcc    123960
tccatagggc tttcttagcc agagaagcct cccttatctt cctgttctcc tcctaattcc    124020
ttcttatcct tccagggagg aggctgtgag gtaatgcatc ttgggagcca gctgggattg    124080
cacagggtgg tgagattatc tgcatttccg aggcttgaac aagttaaggc aatgggaaag    124140
gtcacacaat gagaaaatgc agggccagga tttaacccgt ctgagatgtt ctgactgtgc    124200
tatgctgcct ccccggacat gagctctgcg ataatgctgt ccccaggctg taatcattcc    124260
ctctttcatc cctgcctcct ctatccctgg ggtcagaggg acttgtagtt gaatctctca    124320
ctcactcatt ggtgtggtct ctccctaaag cagggtggag tttgtcttag cgttatcact    124380
gcatccagca caacctccct ggtccaggct tatcagcgtt caactgcgtc aatgcagttg    124440
cctcctcctc aatctcccag cttccggcct tgccccctag agagatcata ttttaataca    124500
agtcagatta catccctcct cccctcagaa ccctccatgg ctcacacctt actcagaaga    124560
aaagccaaag tcctctccac aacccacaaa gccctgcacc atccatcacc tcactgcctt    124620
cgtcccctca cacccctcccc cttgctcgct ctgcttcagc cacaccaact catctctgtt    124680
tctcaaatac accaggcatg cctagctat taaatgcacg gtccagcctg gtgcatttga    124740
agaacacgga tgaattggtg tggctggaac agagtgagtg aggggagag cgggaggagg    124800 accttttgcac cagctggacc tttgcaccgg ctgttccatt tgcctagagt tttccctgac    124860
atattcatat ggctcactct cttgcttccc ttgctttctc ccagtctttta ttcaaatgtc    124920 tatttctctg cacttgtgct gtttgataca gtcaccgctg gccacatgtg gcctttgagc    124980
acttcagttg aaacacatga aagtgtagaa tattgaccag attccaagga aaaccatgtg    125040
caaaatatct tttatctctt aagatacagg gtctcgctct gtcttccagc ctggaatgca    125100
gtggcacgat cacagctcac tgcagcctca aaatcccaaa ctcaagtggt cctcccacca    125160
acagcctccc gagtagctgg gattacaggc acacaccaca atgccccgcc cattttttta    125220
attgttatta ttttttttaa tagcgacaag gtcttgccat gttgctcagg ctggtctgga    125280
actcctggcc tcaagcgatc ctcctgcctc agcctcccga gtagctgaga ttacaggcag    125340
gagcttttgt gcccagcagg tctacgatct tcttagaatg cttcaggctg gcatagtgg    125400 ctcatgcctc aaataccagc actttgggag gccaaagcag gcagattgct tgagctcagg    125460
agttcgagac cagcctgggc aatatggtaa aaccctgtct ctccaaaaaa aatacaaaaa    125520
ttagctgggc ttggtggctc ccacctgtag tcccagctac ttaggaggct gaggaaggaa    125580
```

```
gatcacctga gcccaggagg cggaggttgc agtgagccaa gattgagcca ctgcactcca   125640
gcctagacaa cagggagacc ctgtctcaaa ataaataaat aaataaataa ataaataaat   125700
aaataaataa acaaacaaac aaacaaacca ataaatgaat tttacctgtt tcttttttact  125760
tttttaatgt ggctactagc aaattttaat tttttttttt tttttttttt tttttgagac   125820
agagtcacgc tctgtcaccc aggctggagt gcagtggtgt gatcttggct cactgcaacc   125880
tccacctcat gggttcaagc agttcgcctg cctctgcctc tgagtagctg ggattacaga   125940
tgcccaccgc cacgcccagc taattttttg cattttagt agagatggag tttcgccatg     126000
ttggccaggc tggtctcgaa ctcctggcct caagtgatct gcctgcgtcg gcctcccaaa   126060
gtgctgggat tacaggcatg agccaccgcg cctggctata aatttcata agtagctctt     126120
aatagatttc tcctgggcag tgctggtcta aacacttttt tttttttttt ttttttttga   126180
gacggcatct tgctctgtca ccaggctgga gtgcagtggc gcgatctctg ctcactgcat   126240
cctctgtcac ccgggttcaa gctattctcc tgccttagcc tcccaagtag ctgggactac   126300
agacacccgc caccacgccc agctaatttt tgtatttta gtagagacgg ttttcacca     126360
tattggccag gctggtctcg aactcctgac cttgtgatcc gccagccttg gcctcccaaa   126420
gtgctgggat tacaggcatg agccaccgca cctggctata aatttcata agtagctctt     126480
aatagatttc tcctgggcag tgctggtcta aacacttttt tttttttttt ttttttttga   126540
gacggcatct tgctctgtca ccaggctgga gtgcagtggc gcgatctctg ctcactgcat   126600
cctctgtcac ccgggttcaa gctattctcc tgccttagcc tcccaagtag ctgggactac   126660
agacacccgc caccacgccc agctaatttt tgtatttta gtagagacgg ttttcacca     126720
tattggccag gctggtctcg aactcctgac cttgtgatcc gccagccttg gcctcccaaa   126780
gtgttgggat tacaggtgtg agccaccgcg cccggccctg taacactttt aacactgaac   126840
tgtttgcctt ccaggtggta aagagcaggt gcctttactg atagaaatgt caccactccc   126900
ttcatcccgc cagccccatg tcactgacgc gtcctttccc cttgctctgt ggtaactttc   126960
tcctaagcac tcatcgccct aacatctgtc atacaggtat acctcagaga cactgctggt   127020
ttggttccag gtcgccataa caaagcgaat attgcaataa agggagtcgt gccttttttg   127080
gtttcccagt gcacataaaa gttatgctta cactatagtc tgttaagtgc atgatagcat   127140
tatgtctaaa aaaaaatgta cataccttaa ttttaaaatc catcaaggct gagcacagtg   127200
gcttgtaatc ccaacacttt gggaggccaa ggcaggagga ttgcttgagc ccagggattt   127260
gaaaccaggc aacaaagtga dacccgtttc tacaaaaaa attcttttta aaatagctg     127320
ggtatggtga cgcatgcctg tggtcccagc tacatgagag gctgaggtgg gaggctcact   127380
tgagcctgag agattgagac tgcagtgagc tgtgatcaca ccactgcact ctagcctggg   127440
ggacagagtg agaccgtatc tctcaacaaa aattaaaaaa aaaaaaaaaa aaggctgggc   127500
acagtggctc atgcctgtaa tcccaacagt tgtgaggcc aaggtgggtg gatcacttga     127560
ggtcaggagt tcaaaaccag cccagccaac atggtgaaac cccgtctcta tgaaaaatac   127620
aaaaaaatag ccgggtgtgg tggtgcacac ctataagccc agctactcgg gaggctgagg   127680
cacgagaatt gcttgaacct gggaggcggg gggagattg cagtgagccg agattgcact     127740
gctgcactcc agcctgggtg acagactgag actctgtctc aaaaaataaa taaataaata   127800
aataaataaa taaatgtttt attactaaaa aagttaacaa tcatctgagc cttcagtgag   127860
tcctcatctt gctggtgaag ggtcactggc tcagtgttga tgggtgctga ctgatcgtgg   127920
```

```
gggtggttgc tgaagattgg ggtgcctgtg acattttctt aaaataagac aagaaagttt    127980
tccgcatcca tcgactcttc ctttcacgaa agatttctct agcatgagat gcttgttgac    128040
agcaatttta cccacagtag aactttttc aaaattggag tcagttcttt caaaccctgc     128100
cactgctttg tcaactaagt ttatgtcata ttctaaatct catgttgtca ttttaacagt    128160
gttcacagaa ttttcaccag gagtagaatc catctcaaga aatcactttc tttgctcttc    128220
cataacaagt aacgcctcat gcattgaagt ttgatcatga ggctgcagca attcagtcac    128280
atcttcaggc tccacttcta actctagttc tcttgctagt tccatcactt ctgcagtgtc    128340
ttcctccagt gaagtcttga actcctcaaa gtcatccatg aggatcggaa ttgacttcct    128400
caaaattcct attaatgttg atattttgac ctgttcccac gaatcacaaa tgttcttttt    128460
gttgtttgtt tgttgtggat tgttttttta tttttaattg agttgaggtc tcactatgtt    128520
gcccagactg gtcttgaact cttggcctca agtgatcctc ctgccttgat ctccctaagt    128580
gctgggatta caggcatgag ccactggaac agccacaaat gttcctaatg gtatctagaa    128640
tggtgaatgc ttttcagaaa gttttcaatt tcctttgccc agatgcatca aaggaattta    128700
tctatggcag ctatagcctt atgaaatgta tcccttaaat cataagactt gaaatagaga    128760
attacttctt gatccatggg ctacagaatg aatgttgtgg ctgggcatgg tggctcacac    128820
ctgtaatccc agcactttgg gaggctgagg caggtgggta acttgaggtc aggagttcaa    128880
gaccagcctg gtcaatatgg tgaaacccca tcactactaa aaatacaaaa attagctggg    128940
catggtggcg tatgactgta atcccagcca cttgggaggc tgaggcagga gaattgcttg    129000
aaccctcttg aagacagagg ttgcagtgag ccaagatcac accactgcag cgacagagtg    129060
agactctgtc tcaaaaaaaa aaaaaatgt tgtgttagaa gtcataaaaa caacattcat     129120
cttcttgtac atgcccatta gaggtcctgg ataaccagtg cattgtcagc agtaatattt    129180
tgaaagaaat cttttttctg ctgggtaca gtggctcgca cctgtaatcc caccactttg     129240
ggaggccgag gcgtgtggat cacctgaggt cgggagttca agaccagcct ggccaacatg    129300
gtgaaacccc aactctacta aaaatacaaa aaaattagcc aggcatggta gcaggtgcct    129360
gtaatcccag ctaccctgga ggctgaggca ggagaatcgc ttgaacctgg gagtcagagg    129420
ttgcagtgag ctgaggtcgt gccattgcac tccagcctgg gcaacaagag tgcgacttca    129480
tctaaaatac atatatatat ataacatgtt atatgtaata taaattatat atataacata    129540
tatgtaatat aaattatata tcacatataa catatatcat gtgttatata tatcacatat    129600
aacatatgtg ttatatatca catataacat gtgttatata tcacacataa catatattat    129660
gtgtatatat gtcacatata ttatgtgtta tatatgtcac ataatacata ttgtgttata    129720
tatatcatat ataacatata ttatgtgtag tgtatcatat gtaacatata ttatgtgtag    129780
tgtatcatat ataacatata ttatgtgtag tgtatcatat ataacatatg tgtagtgtgt    129840
tatatataac atatattatg tgttatatat ctcatatgtt atatataaca tatattatgt    129900
gttatatatt atatatatat tttttctga gtagatctca acagtgggct taaaatatca    129960
gttatccatg ctataaacag acgggctgtc attcagtctt cattgttcca tttatagagc    130020
acaggcagag tagattcagc ataattctta agacctaggg actttaggaa tggtaagtga    130080
gcattggttt caacttaaag tcaccaggag cactagctcc taacaagaga gtcagcctgt    130140
cctttgaagc tttgaagcca ggcattgact tctcctctct agctatgaaa gtcctagatg    130200
gcaacttctt ccaatagggc atttcatcta cattaaaaat ctattattca gtgttgccag    130260
cttcattaat aatctcagct agatcttctg gataacttac tgcagcttct ccatcagcac    130320
```

```
ttatcacttc accttgcact tttatattat ggggacacct tctttcctta aacctcatga    130380
accaagatct tctagcttca gattttttctt ctgcacttcc ccacctctct cagtcttgct    130440
gtgggcttgc tgtggattag gctttggctt aagggaatgt tgtggctggt ttgatcttct    130500
atccagacca ctaaaacttt ctccatgtca gcaagaagcc tgtcttactt tcttatcatt    130560
catgtgttta ctagagtagc ccttttaatt tccttcagta attttttcctt tgcattcaca    130620
acttggctaa cctctagctt atggccttttt gtttgtttgt ttgtttttgtt tttgagacag    130680
ggtctcactc cgttgcccag gctggagtgc agtggtgcaa tcaccgctca ctgcagcctt    130740
gacttcctgg gaccaagtga tcctcccacc tcagcctcct aagtagctga gaccacaggt    130800
gtgcaccacc acacccagct aattttttta ttttctgtag atagagggtc tccctatttt    130860
gcccaagcta gtctcaaact cctaggctca agccatcctc tcacctcagc ctcccaaaat    130920
gctcggatta caggcatgag ccaccatccc tggccctatc tcagctttttg acacgccttc    130980
ctcactgtgt ttaatcattt ctagcttttta atttaaagtg agagacgtgc aactcttctt    131040
ttcacttgag cacttaaagg ccattgtaca gttatacact gacctaattt caatattgtt    131100
atgtctcggg gaataggaag gcccaaggaa agcgggagag atgggaaat ggccagttgg     131160
tagagcagtc agaacacaca caatatttat cgatcaagtt tgccatcttc tatggatgtg    131220
gttcgtggca cccccaaaca atgactatag tcacatcaaa gatcactgat cacagaccac    131280
cataacagat gtaataatta tgtaaaagtt tgaaataccg taagaattac cagagtgtga    131340
cacagagacg caaagtgagc acacgctgtt ggaaaaaaa tggccctgat agacctcctt     131400
gacacagggt tgccacaaat cttcaatttg taagaaacac aatatctaca aattgcaata    131460
aagcaaagca caatgaaatg aagtcttcct cggccggtgt ggtggctcac gtccataatc    131520
ccagcacttt gggaggccaa ggcaagagga tcccttgagc ccaggagttg gaggccagcc    131580
tgggcaacac agggagactc catctctaga acaaaacaaa acaaagcctg cttatatta     131640
ttgggtttac tctcagtctc ccccacacag agatagggcc tggcttgtta ttagtgctca    131700
gttgatgttt gtgaagtgaa atactaagga cttaaccact gcctgttctt tgctgttcat    131760
gccctgacag cttttatgtg ccagcacaga agaaacaag gtgcaagaag agaatagtga     131820
tctctaagtc agaatttgag gaacccaaat tagtaccaga aagctgggag gagaagagaa    131880
aaataaagta aatcaaatta aaagttgaat gggccaagtg cagtagctca tacctataat    131940
cccagcactt tgggaggctg aggtgagagg atcacttgag gccaggagtt ctagaccagc    132000
ctgggcaata tagcaagacc ccatctctac aaaaaaaatt ttttaatttt ctgaatatgt    132060
tgttgtacac ctgtagtccc agctgcttag gaggcagagg tgggaggatc gcttgagccc    132120
aggaggttga ggctgcagtg agctgttgtt gcaccactat actcaagcct gggtgacaga    132180
ataagtccct gtctccaaaa ataaaaataa ataaattcat tttttgtaaa gttgtatgtc    132240
atggcccctg cctactctgg cttcatgact tgctgcttga acctcaccat ccaaatccca    132300
gtggtgacac catgtcattt cttgaatttg ccaagccctc tttcagtccc aagctctctg    132360
tcatggccac tctcagcctg gaaagttctt tccccactgg ccagatttct cccctcatc    132420
tatgggaact tgacttgaag taggggtat cccaggccct ggactagtta acacgacctg     132480
ctgtgtgccc ctcaaagcca ttgtcttcct agctgagaag gcatcacacc tgcaacagat    132540
tcactcattg tgtgcatgtt tttcttaacc acttctcttc tgcatcagct ccatgggca     132600
gggatagtct catatgtcac tctacccagc acataggata cgctcagacg cccacttgtg    132660
```

```
gatggtggaa aaggtcagcc caacctaata tgcccatctc tcctctaggg gtaatcttga  132720
gaaaaaaagt tgggaacttg ctttgtgtta gtttaggatg acccagaata gatcctgaaa  132780
caagaattta gggcaatcct tgtgcaagta gttcatctga gaggtgaccc cagaagggtt  132840
ggagaaggag aggggaggtg gggcaaggaa gggtgagttg tcctgtaggc aactgagctc  132900
cgtcctactg ggagcccacg tggaactcac ctcttaagtg atccagaatg aagggtgagg  132960
gagctgcggt attgatccac caactcccag caatctttgg ttgagggctg ctcccttaaa  133020
gttcattccc tgggcctgcc ccagatttgg agacagccct aaggcaagag gtacagatac  133080
cagttggcca cagactgaag tgttaagacc caagccctg gataaaactg aaaaatcaag  133140
ccagatgtgg tggttcccac ctgtaatccc agctactcag taggctaagg caggaggatt  133200
gcttgagccc aggagttcaa tgctgtagcg agctatgatt gcaccactgc attccagcct  133260
gggcatcaga gcaagacccc atgtctaaaa taaaataaa ctgaaaaatc cccaagttat  133320
ttgctgtgac caaccttcca ttaaccacag accctctggt attcagcatt tcttgtccat  133380
tatatgaagt tctgatgaca gtctcttta ttgtattgtg ccttgaccac gcactgtaca  133440
tcacttagct ctgaaatgga catgttcagg aaacagggcc aggtgggacc ctgtgtttca  133500
acagcaatac ttttacaaat gaggtctcat gacagggtct tgctcggagg gtttctatgg  133560
aagcctcatc ccacctactg ctatcatcct tactaacttg catttacaaa agggactctt  133620
tttgaccaga ggcttggggt ctgtagctgc cttctagcca gctgatgctg gctggtccac  133680
acaagcagga tcacacccat tttttttgttt tcttatttat ttctgaatag gttagcatac  133740
cggtaacctg tgtgcctggc attgtgctga ccacttttg tcaacttact gaatcctcac  133800
aacccttgga ggtattgata ctattgttat ccaggttata caaaggggg aaactgaggc  133860 acagagcagg gatgtccctt gcccaaggtt acccaactgg aaagtggcag atctgggatc  133920
tgaacccatg caggctgggc tcttaacact gaactacttt cctgccattt gttaaagagc  133980
cacaaaccag gccaggcacc atggctcacg cctgtaatcc cagcactttg ggaggccgag  134040
gcgggtggat cacctgaggt caggagttca agaccagcct ggccaacatg gtgaaaccct  134100
gtctctacaa aaatacaaaa aaaagtaccc gggcatgatg gcgggtgcgt agtaatccca  134160
gctactcggg aggctgaggc aggagaatcc cttgaacccg ggaggcagag gttgcagtga  134220
gctgagatca caccattgga gatcgcactc cagcctgggc aacagagtga actctgtct  134280 caaaaaaata aaataaaata aaataaagag ccacaaaccc cgaaaggtct gccattcccc  134340
cagggcccca ggccacccca caatctattg tcattgtagg ttgtgaaata tactgaatgt  134400 cacccccaacc ttgagccatg gggaagattc catttctctc attgcaacat tgtgcaaca  134460 tgaaccatct gttgggggtc ttcgtaaatc accttttatc ccgtgaggca ggtactgtta  134520
agaccatttt acaggtgaca aaactgaggc cagtggtgtc gagtcacctg cctgtggtca  134580
cccaaccaat acaggacagc ttggaatccc aagcaccccc gccctgctgt ctgaccccca  134640
aaacccaccc tctgttctcc attctggctt ctttctttca gcatcttggc gacagttggg  134700
acggagtttg acctacggac gctgagggca gttcgagtgc tgcggccgct caagctggtg  134760
tctggaatcc caagtgcgtg agtttccgac cctgacaagg ggtttgctca cgggcccag  134820 gagccctcag tttcccctat gcagagcatc tcaggaggcc acatcctgcc accagcctgt  134880
gtgagggcag tctcttcttt gggactccct atagggaacc ccctaggaat atgactgtag  134940
ctccccatga gctcctgaaa gcaaactagg agccacaccc atttattgag cacctactgt  135000
ctatcgggag ccatgctaag caccacgtgt gatctcattc agtactcaca gccctatgaa  135060
```

```
gttgatagga ctgatgtctc tattttatgg agggggaaac tgaggctcag agtggctgaa   135120
acattggagc agggttttgt ggctgagaag tggcagaact aggagtgagc aagtgtgact   135180
ccaagcctgg gccgtaccac tggtggcaat gaccattccc atttaatgag tgcctgctgc   135240
gtgcagggca ctacagaagg actttacatg aattacctta tttcatcctc acagtcaccc   135300
agcgaacacc cattttacag atgagacggt tgaggcttaa ggaggttaaa ttactcacct   135360
gaattcttag agtggacagt aatgagctct aaaattcata ctcattcctt gctgctttct   135420
cattctccac agatacatct agtccccgtt taagggtggc tgccatatgc agggtcaaga   135480
ttaagtgtag gttgagccaa aaaaaaatgt aaaaagcaaa aataaaacag ggctgtcctt   135540
tttctatctt cttgtcttgg ttaataataa taatttagcc aggcatggtg gctcatgcct   135600
gtaattccag cactttggga ggatcacttg aggccacaag ttcgagacca gcctgggcaa   135660
cattgtgagg aacaccaccc ccaccccccc gccaatatct acaaattttt ttttttttt    135720 tagaaattag ccaggttgac tgggcacagt ggctcacacc tggaatccca gcactttggg   135780
agaccgaagc gggcagatag agcgagctca ggagttttaa gaccagcctg gcaacatgg    135840 cgaaccctg tctcaaaaaa aaaaaaaaat tagcaggcat gatggtgcac acctgtagtc    135900
ccagctactt aaaaggctga ggcaggagga tctgagccca ggaggtcaag gctgcagtga   135960
gctgtgatag caccactgca ctccagcctg gacaacagag tgagaccttg tctcaaaaaa   136020
acagacaaca aaaagtttaa aaacaaacaa tttataggct gggtgcagtg gctcatgcct   136080
ataatcctag cactttggga ggccaaggtg gatgggtgga tcacctgagg tcaggagttc   136140
gagacctgcc tggccaaaat ggggaaaccc cgtctctact aaaaatacaa aacttagccg   136200
ggcgtggtgg cgggcatcta taatcccagc tactcgggag gctgaggcag gagaatcact   136260
tgaacccggg gggcggaggt tgcagtgagc tgaaatcacg ccactgcact ccagcctgga   136320
tgaaagagtg aaactccgtc tcaaaaaaag aaaaaaaaa attaaaaagc acttactatg    136380
tgccagacat tattctaagt atttccatt ttttaaagtc ctttatcctc ccaacaagcc    136440
tgtgaagtag tctcttttat tatcaccatt ttacatttta ttggcttcgt tcttccggtt   136500
cattgctacc caggtttaaa gagtaagatt tcccagagga tcaccagcag gatctttttg   136560
tagaaagaag acacttctat ccaaggtctc tgcaagatcc cagcagatgc ctgcatcata   136620
ttaaattaag ggccatccca aatctaatag tcaaaagagc caggtgcagt ggctcacacc   136680
tgtaatccca gcactttggg aggccaaggc aggacgattg cctgaggcta ggagttcaac   136740
accagcctgg gcaacaaagt gtgaccctgt ctcaaaaaat atatgtatat tataatagca   136800
gtagtaacaa gagtctctgt ttaatgacca cctatgactt accaggtact tcactgtgtg   136860
tgaactctct catctaatcg tatgagggag gtactattgc agtccccatt tacagatgga   136920
gaagctgagg tttggaattc actagtaagt ggatgactag gtcaggttcc cttgaagcgg   136980
atacttaggt gggtgttcag atgcacctgc tttattgggg acggctctt gggagagaca    137040 gcaggagatc agcagggtgg ggctggggaa tggatagagc agggacgcaa tttcagctgg   137100
agtgtgtgtg acaccagagt tgtcctccaa tgcatggcaa ggatgccggc cttttgtact   137160
tctatagtca gtcactgtgg atgggaggta gagacgcagt agctcccagg tgagatagct   137220
tttgatcacc aagggcaatt ctactaagaa gagaggcagc tgggaggcat tagcaaccaa   137280
catccatagc agctggaggg cgggtacacc agaaagaaaa tgggatcttg ccagacacc    137340 aagagtatcc agcaccttaa ccactgcacc acactgcatc tgttagcacc cacattacat   137400
```

```
tttttttttt tttttttttt tttgagacgg agtctcgctc tgtcgcccag gctggagtgc   137460
agtggcgaga tctcggctca ctgcaagctc cgcctcccgg gttcacgcca ttctcctgcc   137520
tcagcctccc gagtagctgg gactacaggc gcccgctacc acgcccggct aattttttgt   137580 attttttagta gagacggggt ttcaccgtgt tagccaggat ggtctcgatc tcctgacctc   137640
gtgatccgcc cgcctcggcc tcccaaagtg ctgggattac aggcgtgagc caccgcgccc   137700
ggccagcacc cacattacat ttttaagccc ttggagtggc atggcccctc gagctatcct   137760
gacagcttcc ctctcttact gtggtctcca cccatcaaga gccatgggaa gttcctgcaa   137820
tcaagaagca aagcctcagg ctatatgttt gaaccttcat tttgatcata gactttccta   137880
gtagatacca tagtggttac aaacatagga tgttgtcatc gttcagacct gagttaatag   137940
cctcaagaaa aaaatggtag tggaaccagg tatggtgaag tgtgcctgta gtcccaccta   138000
ctcgggaggc tgaggcagga ggctcgcttg tgcccaggag gtcaaggctg cagtgagccg   138060
tgatcatgcc actgtattcc agcctgggtg acagagcaag cccatctcaa aaaaaaaaa   138120 aagccaatga taggcagaga aatactaact aaggctcttg ctctgtcgcc aggctggagt   138180
gcagtggtgc aatcacagct cagtacagcc tcaacctccc cagactcaag caatcctacc   138240
atctcagcct cccaaatagc tgggactcca ggcacacagc accatgccca gttaattttt   138300
ttgtattttg tagagacagg gtttcaccac gctgctcagg ctggtctcaa actcctgagt   138360
tcaagtgatc caccgcctc agcctcccaa agtgctggga ttacaggtgt gagccaccac   138420
gcttggccag ctattattat tattaacatt cttcgagtct tacaacagtg gaacttttag   138480
tgcaggatgc gaatttcagt attaacccct tcctctccca aaaggatttg aagcccagag   138540
taattcagcc gccatgaatg aaccatttgt tagatgagag gctactggag gctgagcttg   138600
gtaggataag agcttgcatg gggtccctga ttgatgacaa taccccccaga tttaggtctt   138660 cagatgccca gttgggtgtg tcttctgttc cactgtgtcc cttcggggac tgttccctgc   138720
cttctttctt tttgagatgg aatctcgcac tttcacccag gctggagtgc aatgcgtga   138780 tctcagctca ctgcaagctc cacctcccgg gttcacacca ttctcctgcc tcagcctccc   138840
gagtagccag gactacaggt gcccgccacc acgcccagct aatttttttg tattttagt   138900 agagacgggg tttcaccata ttagccagga tggtctcgat ctcctgacct cgtgatctgc   138960
ccgcctcggc ctcccaaagt gctgggatta caggcgtgag ccaccacacc tggccccctg   139020
ccttcttatt caccaccatc tttctgaatt gggttgctca gaacagagaa agcaacatca   139080
gcacatgggc aaacatgggg cttcatttca gatggacctg ggttcaaatc ctagttctgc   139140 ctttttttt tttttttt tttttgaga cagagtcttg ctctgtcacc cagactggag   139200
tacagtggcg tcatcttggc tcactgcaac ctctgcctcc caagttcaag caattctcct   139260
tcctcagcct cccaagtagc tgggattaca ggcgctggcc accatgccca gataatttt   139320 tgtattttta gtagagatgg ggtttcacca tgttggccag acttgtcttg aactcctgac   139380
ctcgttaatc cgctggcctc ggcttcccaa agtgctggga ttagaggcgt gaaccgccgc   139440
cgcgccctgc ctagttctgc catttctcat gcattctctg ggtgaatcac agcatctctg   139500
ttagccttgc ttcccacttc tgtaaaatga gagtgacttt acatgtatgg ccacctcagg   139560
ggcttgtcac tagaagccag tgaaataatg ttgagtctgg ttccttgggg ttgaaattgg   139620
gaccgccaac cgcttcccta cccagagcag caactagcct atatggcggc cttttatgaa   139680
tgaggaaaag acaccgcctc ttggcagaaa aaaaaaatta agaaaatggc tcctctcttct   139740 gggtgcaagt tgcccaacac ccaggaatat ggctccaaaa gcaatggact cccaccccctt   139800
```

```
tcttgcccaa aagatcatca aatggaacag catgtcaaat acctttatta agtactttaa   139860
agttggctgg gctctgtggc tcatgcctgt aatcccagaa ctttgggagg cagaggctgg   139920
aagatcgctt gaggtcagga gttcgagacc agcctggata acatagtgag accctgtctc   139980
tataaaatat atatatagat ttatttgaga cagcgtcttg ctctgccact caggctgggg   140040
cgcagtggca caatcatagc tcactgcagc cttaacgatc ctcctgcctc agtccctaga   140100
gtagctagga ctacaggcat gcaccatcat gcctggctaa ttaaaataaa taaataaata   140160
aatactttaa agttaaaagt gcttttaaa aataataag gccaggcgtg gagactcacg     140220
tctgtaatcc cagaactttg gaagaccgag gcgggtggat cacgaggtca ggagatcgag   140280
accatcctgg ctaacacggt gaaaccctgt ctccactaaa aatatgaaaa attagctggg   140340
cctactcggg aggctgaggc aggagaatgg cgtaaacctg ggaggcggag cttgcagtga   140400
gccgagatgg caccactgca ctccagcctg ggcgatataa caagactctg tctcaaaaaa   140460
aataaataaa ataaataata ataataatag gggccaggta tggtggctca cacctataat   140520
cctagcactt taggaggctg aggagtttga gtccttggag accaggggtt tcaggccagc   140580
ctgggcaaca tagcaagacc ccatctctac aaacaagttt taaaacttag ccaggcatgg   140640
tggtgcatgc ctgtagtcct agctattgca gggactgagg caggaggatc acctgagccc   140700
aggaggttga ggctgcagtg agctgtgatt gtgccactgc actccagcct gggcagcagt   140760
gcaaaaccct gtctcaaagg aaaaaaaaaa cctaggaagt gttgttccca tgataaggat   140820
cagcctccgt gtggtgcttc cttcaccatt gcccaatccc caggctcctg ggtgcttaat   140880
attccctcag gaacacacct gctttgtctg ggagagacct gggcgtcttg gtggcggggt   140940 ttggggtac ttgctcatgg gcttatgggg cctctctctg tgtcccccca ggtttacaag    141000
tcgtcctgaa gtcgatcatg aaggcgatga tccctttgct gcagatcggc ctcctcctat   141060 ttttgcaat ccttattttt gcaatcatag ggttagaatt ttatatggga aaatttcata    141120
ccacctgctt tgaagagggg acaggtaggt ccacggagca tgatgcatct ttccagtttt   141180
ctccttcagg acaagctct tgggaggatt aggcaggggt gtgcttcttt ctcctggcag    141240
ctgggaggac cgtctccttc agagagcact acaggagagg cagtgagtga aatagcctct   141300
gagatcttag ctgttgaaag gggtgggggtt ccacagaagg tgacccagca gagaaagagt  141360
ttatttggga atgatcccag gaagcaccat cgggggaatg aggaagtgag cagagaaaga   141420
agggatcttt taaagagtgt gctatcaagc gggttaccac ttaaaactgg gactggatcc   141480
ccctgggcac ctctgggaga cagcaaagaa cacacaactc agctggtcac ggtggctcac   141540
gcctgtaatc ccagcacttt gggggggccaa ggcgggtgga tcacctgaga tcaggagtca  141600
gagaccatcc tggccaacat ggtgaaaccc catctgtact aaaaaataca aaaattagct   141660
gggtgtggtg gcaggcacct gtagtcccaa ttactcagga ggctgaggca ggagaatcac   141720
ttgaacccgg gaggcagaag ttgcagtgag ccaagatcac accactgcac tccagcctgg   141780
cgaaagagtg agactccatc tcaaataaat aaataaataa aatataaat aaaaaaagaa    141840 cacacacctc agagccgtcc cagccaaggg gcaagggagc tggggtattt atacactggc   141900 ttcttttga cattggtgag gactgctcct agagtggaa ttaatgcctg gcacatctgg     141960
ctgagtggaa caggtattct gggtgctttc agacctcgac cagtcctgac ttctaaagca   142020
agcaagaagt ggggagagtt gggccagaaa agggttattg cctcaatgca ttgtgagtgg   142080
taccttgtgg aaggtgagag acagagaaga ttccaggcac aggtgccatg ctaaacgata   142140
```

```
gttctcattt attataggaa cccatggatt tattttgttc tctgccctga gtgctgggtg    142200
agagtactgg atgagtcctc ctggtctccc ccaaccccca ggatgtacca gagataccccc   142260
aattgggagt cctggcacca accaatcaga acctagcact cagcagcatt ctgcccctcc    142320
ctgactatgc ccacattaac ccttcagtgg ctgggtctgg gggtagggtg agccccggaa    142380
aagccaggca gcgcagagac actctcccag ggctcagctc tgaaccagca gtgtggaagc    142440
agtgtgtcca ccacgatcca cactcaggaa ccaaatagcc cttggatacg ttttcagtta    142500
aatctttgcc atccaaactc tagctgcttg ctctctaaag ctccagaatg aaatggaatc    142560
aagtaggaag ggatgccttc agtatttcag tatttggacc actggccatc tgggtgcaga    142620
cagactgaat agcagttctg gttctgatga tttgggtcaa gggagctgtg aattgaagga    142680
gtggatagaa ggaatcaaga agcccaaagg ggaacccagg tgggcagaga aagaggtttc    142740
aggccccttta tttgggaaag gcagccacag aagaagattc tgtctgggag tggatttcca   142800
cccaccctct ccacccagtg accccaagt ggatccgcag aggcagcccc tgagccctcc     142860
ctccccactc ctccccacgg ggaggaaaa cccactgggg aaggtttatt tgcaatggtt     142920
ggaggtttgg gttttttttgt gggttttggt ttgttggttt ttttttttcct cttttttctct 142980
tgctcctcct gtctctttct ctcctgggct tgtgaagttt gctcaatatg gaatgtccta    143040
attatttctt tccccgatga agaaggtgtt aattgaggca gagctatttc tgctcctggc    143100
ctcgtcaccc aggcggaaat gcgagagaga gagagagaga gagagagaat gaatatgggg    143160
cagggcctct tggaaaaatc agccgtgagc agagaaacca ggactcctgg atcctaggtt    143220
tctgtgaagt tttatttttat gtttttctac cctagactag ctaaaggaga agaggccatg   143280
gggttggctt gggtccgagt gggggttttga ggggacagat gtgggtggtg ccaccagagg   143340
ggaggaagcc tcgatttagg agaaagactg aaaagctagc tcacgattaa aaatataaga    143400
cgtgtgagta agagacagat atatacagac acccaggcag tgggttaatt ttaaaatgta    143460
tttataaccg aattcctcag acactctgga cgcttgtttt tctagaagca acgctcagag    143520
tgtttcgtgt cggtggttgg ggggttgagg gggattgcaa agctgctaaa gatagacccg    143580
ttttcagtag cattcctcag tgtcgggagc ccagttcctg tgtgcccagc accgtgccaa    143640
tcgcttagaa ggaagcaaag ataaagtgga aggcttcctg cttttctaaga gcttccaaaa   143700
tagttagagg aaacaagacc cctcatttgc agccattttt aacagtgaag gctaatgtgt    143760
gattataccc acgccccct aaatatgaaa attcagtagc tattgtatgc ctgaaagggg     143820
ccaggtgcag tggctcacac ctgtaatccc agcactttga gaggctgagg tgggagtatc    143880
ccttgaggcc gttagtttga gaccagccta ggcaacatag ccagaccctg tctctgctaa    143940
aataaaaatt taaaaattgg ccgggtgcag tggctcacgc ctgtaatccc agcactttgg    144000
gaggccgagg caggcggatc aaaaggtcag gagttcaaga ccagcctggc caacatagtg    144060
aaacccgtc tctactaaaa atacaaaaaa aataaattag ccgggcatgg tggcgtgtgc     144120
ctgtagtacc acatacttga gaggctgagg caggagaatc acttgaacct gggacataga    144180
ggttacagtg agccgagatc acgctactgc actccagctt gggcaacaga gtgagatttt    144240
gtctcaaaat aaaaaaattt aaaaattagc catgagtggt ggtacatgcc tatagtccta    144300
gctactcagg aggctgagga agaaggatca cttgagccca ggaattggag ctgcaaggc     144360
tgcagtaagc tatgatggtg cccgcactcc agcctgggtg acaaagtgag accctgtctc    144420
aaaaaaaaaa aaaaaagag agagaggaag gaaagaagga aggaagggag ggagggaggg    144480
actggggctg tgttaactgg gctacacaaa gaggctacat ggagggtggg aattgagcca    144540
```

```
gacttggaca tggcgtggag acagagaaga ttccaggcac aggtgccatg ctaaacgata   144600
gttctcattt attataggaa cccatggatt tattttgttc tctgccctga gccttatgtt   144660
taaaagattt ttgccttcca acctgtattt atcaaataat agttcatgta ccaagtccag   144720
cataagtgag gaaggcgttt ccaacaactt aagttcatgg cgaggctaga cttggagttt   144780
ctattcagcc agagcttgaa aggccaacaa gattcattca ttcagcattg gtttatttcc   144840
ctctgctgtg tgctcagtca agggagcaga gaattggtgc tgcgaagtct gtagcacata   144900
cattgagaga tattttttgtt gagtaggaag cttgagttta cacacactca gctgtttgtt   144960
ttcttgtccg acaatgccac ggtcgtcttt gaaaaccttc aaaagcatcg ctcacagaat   145020
aaggtcctct cagacccgct gtgctggtaa atgaggaca  ctcccagatg tgagctttcc   145080
tgcctcccta ccccatcaat accttaagat ttggactgac ctttagcgtt cagcctgact   145140
gccacctccc caggaagctg tctttggttt ccagcaaaag gggtgtctgt tggcacgttt   145200
ctctctcctt gtggcatttt cacagcctgc ctcctgctat ttggggagaa agctcagctc   145260
ctgttcctta cccttaggca agggtaggaa ctgtgtgtac tggtgtccct cacccccaga   145320
acagctccct gagcccagta catcccaaga agaaaaaaat cagcaaggct tataggagaa   145380
taacacaatg cgcttgacaa atttgtccta atggatgtcg gaagaaggct gcacttacca   145440
gctacaccat gcacacggca catttactaa aactgactat attatggacc ataaagtttg   145500
tctcaacaga ggtcaaaaag ctgaaaaaaa tacaaataca aacatatttt tctgaccgta   145560
atgcaattaa gctggaaatc agtaacaaaa agagaactct aaaagtgttt gcagattaac   145620
agacatgcct ctcatttatg gatgaaatga tatgatgtct gagctttgct ttaaaaatat   145680
tctaggctgg gtgcagtggc tcacgcctgt aatcccagca cttggaggc  cgaggcgggc   145740 ggatcacttg aggtcaggag ttcgagacca gcctggccaa catggtgaaa ccccatctcc   145800
actaaaaata caaagattat ccaggtgtgg tggtggccac ctataatccc agctacttgg   145860
gagcctgagg caggagaatc ccttgaacct gggagtcgga gattgtagtg aggtgagatc   145920
atgccattgc actccagcct gggtgacaga atgagactcc gtctcaaaaa aaaaaaaaaa   145980
aaaaaattct agtggcaagg caaagtgttt ggaggggata cagaggaata gatgaaacaa   146040
aatttgccag aagtaaatag gtaagtgtct aaattggtga taggtacatg gtgaatcatt   146100
atattgtttt atacttctct ctcgctctct ctctccccc  gttctctccc tgtcttcctc   146160 tccctctgt  cttcatatat atatatatat atatacacac acacacacac agacacctaa   146220
taagtttttt taaaaaacaa atacatctaa attacccata ggtcaaagaa gaataataa    146280 tggaaattag aaaatatttt acttgaacaa taatgataat gcatgacaaa atgttgagat   146340
gcaggtaaag ccacacttaa aggcaatta  tagccttaaa ggcagttaat ccatccatct   146400
caaaagttta ggaaaagaat agaaaaaaaa aaaaaactca tggaaaacat aaagagaaaa   146460
gtagtaaagc tcagagaaga aattaatcaa tagaaaacca ataatagacc cccaaagcca   146520
aacattgatc tctttgaaga ctgatcacgt ttgtcccaaa agttattcgt tccaacagca   146580
ttatagagtc actggtccct atttctcaga gctggttttc cctgctcctt ccctgactt   146640 ttctccccctt ccctttttgta gatgacattc agggtgagtc tccggctcca tgtgggacag   146700
aagagcccgc ccgcacctgc cccaatggga ccaaatgtca gccctactgg gaagggccca   146760
acaacgggat cactcagttc gacaacatcc tgtttgcagt gctgactgtt ttccagtgca   146820
taaccatgga agggtggact gatctcctct acaatgtaag tgatgctggg acagtgtgtg   146880
```

```
tggacaatca gagtctcagg gaggtggcct cctgggacca gtgagactcc aaggctgcaa    146940
tggagggacc ctgagctggg aaaggcagcc caaggacaac acagccccac tgaagctggc    147000
ctgaggctca ggcttttgaa gattacaggg gctcatgagc agaactctaa ctatagggca    147060
tagaagtctg gagggccccc agatgcaaca tcattttca ttgtgcaagt gtttagatat    147120
aattttagat ttttgaatac ggaaaggtta tgtgatccaa aaaccaacac agataaaaga    147180
tagagtaata tctttggacg taggcgaggg gtccctgccc tgaggctcac ccagtccttc    147240
tccagccata ccactccccg tgggatgaga agttcctgga gccaaggggga tgtgtctacc    147300 aagagcttgt gccccacttt gtaggccatg ttttaagtta ccaggatcct ggaattccct    147360
gcccatggcc agattccatg aacttgcgtg caattctcat atggatctgt tcgtaaccca    147420
actgagggcc aaggacatcc gaggggtggc tgttaacaca aatgtggcca gagcttggat    147480
gtacaagctg gaatgcccac acatatgtgt ggagcccctc tggcaggaca gagccatgac    147540
taagaagaga aagggacagg acagggctgg ctctccccac accttgaccc agtgcagata    147600
tccggattct aaattccacc ctgaccttcc aaagtgtaaa ggaaggtata tttgcaaagt    147660
agaagcacac agcatgtttt atttagttac cttttcaata tttccccgta gtatgtggtc    147720
tgcttttgta ctcttgccct agatcttaaa aatgttaggg atgtttctgg aaagatgtat    147780
ccctgccccc acttgcatgc tacttcctct tcccacaata tgcaaccccct ttagttcctc    147840 agaatatcct tccaatgttt atttatgcaa ttataattat aagcataatc gaatctatgt    147900 cctccccct ctttcttatc ccaaggagta gcattctata catgctgttc aattctgtga    147960
tttttgtttt ctcataacca cacgttctag agatcttcc actgcaggac atggacagtc    148020
tcttcacggg tgcacactag tatgcccagc taattttgt agagacaggg ttcttccgtg    148080 ttgcccagge aggtctggaa ctcctgggct caagcaatcc tcccgcctct gcctcccaaa    148140
gtgctgggat tacaggcgtg agccaccacg cctggccttc tttattcttt tgcacagctg    148200
catagcattc tattgtgtgg ctgcccatag ttttattttgt ttgccattaa gagaaatgct    148260
tgactggctt cctgtccact gacatggaac atgatgctgc tctgccagga gcatgttgca    148320
cgtacctctt catacttttg cagatatagc tagggggttg gagggtctcc attcccagaa    148380
gtgggattgc aggatcaaag actaaatgca tttataattt tattttttggg gaagattttt    148440 gttttgtttt tttggagaca aggtctccct ctgtcgtcca ggctgagcg cagtggtgta    148500 atcatagctc actgcagcct taaactcctg ggctcaggtg atcctcccac cccagcctcc    148560
tgagtagctg ggaccacagg cacacaccac catacctagc taattttaa gaacaatttt    148620 atagagatgg ggtctcacta tgtttcccag gctgctctca gactcctggc ctcaagcaat    148680
cctcctgcct cagcctccca aagtgctagg attacaggtg tgagccactg cacccagcct    148740
aaatgcattt ataatttga tagatattta ggtgtgcaag ttttaaaccc cactctgtcc    148800
tcaccacagt tcaccttccc tcacctacta tgcaggtaag cagtcccag gcaggtcact    148860 tgtcagcagc tggagtgggg cagagccaag gattcaggat caaacacaag gatgccacaa    148920
ctgtagtgac cccatagagc accctggggc tgctccatac acacagctct gttgaccagt    148980
ggaggtctcc tcttcacctg ccctaagggc tgaaattacc attgaagttt aggccagcgg    149040
ttggcctgac ccgggagcaa tacctggctt cctcctcctg tacatagaga agctgaactt    149100
tcctcttggt cctagtgtat gttccttaac aacccattta tgcctagtgt tccattattg    149160
gaatgctaat cctgtgggag ttatttacat cctgctgctc aaggtcatca ctaaggtcgg    149220 attttttcaca cacacaaaaa ttgcaacctc cggcataaat gggttaagga atttccccac    149280
```

```
ttgtgggtgg agggagattt gcaaaaactc atccttgtaa tcctgatcaa caaaggcccg  149340 tttagttgg gagtaggcag caaaaggagc cacatgaaca gttgcgcctg tcacgcactg   149400
cacaagaatg tcattcatat catagacaac atacgatttc tactgttatc ctgataattt   149460
attgacagaa aaaaggatgt ggggaaggga catggtgttc taatttgcat gaaaacctcg   149520
tctgagtgta gcatctctgg gaacatgcag cagatccgag ctcaggccct ctcttggccg   149580
tcacctgcaa acagcttgga caaagggtca gcccaattgg ccaaaactca ctggggaatt   149640
tttgtgggtt ctaggttttt actttgcaag gctggtgtga gaggaggttc cagcaggaaa   149700
tgaaccctcc tgagagggaa agagactggg aaatggagaa ggctgggaac tcagggagag   149760
aatgggagtg gggaatggga gctgaaaaaa attgtgagca taaaaagggg atatgtcaca   149820
gggttggatg accagagaaa gcgtctgggg gttcagatta agatgctggg ggcgtgccca   149880
gtggtgggac aggaagcatg aatttccaga gggctcggtt ataaacatca ttgtccaatg   149940
ggtgtttccc ttggaagcct ctaagcttag agctaagcca cctctgggga cacaaactga   150000
gtggttaaga gcagagactc aggtgtcagc ctgtctgggt tccttccgac tcttccactt   150060
ccttgctgtg cagccttcgg caaggtgctt ggcctctctg tgccactatt tccacatgtg   150120
caaaacgaag agaagcatag tcccacctca caaggcacga ggactaagta aggtggattc   150180
gcatgaagtg tttagaactg atcctggccc ggggtgacct ccgtgtaagt caaattcccc   150240
accctgcatg gtgttccttt tagaaatgtg catgaatttt tcattagaac agctccagca   150300
gtgcctgagg aagtggagtg aggtgtgaga ggtcttactt tattccctc gctggccctg   150360 ctattaacca ctaactcaga gtagctttct agcactttcc acacatttac atcccaccct   150420
cgtcctttgg ttagcagccc atgcaatgat ttggccttaa tgtgaaccta gaacacagct   150480
tctcgcccag ggatgatttc tgcccccagg ggacacttgg cagtggctgc agacattttt   150540
ggttgtcaca actggatggg aagaaggagg atgctattgg catcaagtgg gtaaaggcca   150600
cggatgctac tcaacattct acaatgcaca gcatccccca cctctgcccc accatagaga   150660
atgatccagg cccaaatgtc agtaaggttt ctgtcaggaa accctgggtc agaagaccaa   150720
ggttccttga ggacggggat gccttatact gcaatcagct gtcactctct gcctctctct   150780
ggggctgctg tgatcacctg gcctgcatgg acaacccta ggagcagccc ccatccagtg    150840
cctggagaag tcagtggata aatacccag ctccctccct gtcgggcgtt ttgctctgcc    150900
ctgcatctct ccagtgggat caggctctgg ttgcccgcag ggttaacctg gtcacgtaca   150960
cacccttcac ttgccacctt cccttccctg tctggtattt cctgggatga acttttagat   151020
ttatttcctg gggctgctat aatgaagcac cacagactga gtagcttaaa acaacaggaa   151080
tttatggtct gacagttctg gaagccagaa gtccaacccc aagatgttag cagagctgac   151140
aacacgcccc tcaaaagcct ccgggggagg atccttcttt gcttcttcct ggcttttgct   151200
ggtttcccac aatctttggg attccttggc ttctagagcc ttcattctcc attccagtct   151260
tctgtcatct aatagcatcc tcccagcccg ggcacagtgg ctcacgcctg taatcccagc   151320
actttgggag gccgaggcag gcagatcact tgaggtcagg agtttgagac cagcctggcc   151380
aacatggtga accccatctc tactaaaga tacaaaaatt agccaggcgt ggtgggcggg    151440
tgcctgtaat cccagccact tgggaggctg aggcaggaga atcacttgaa cccgggagat   151500
ggaggttgca gtgagccaag atcatgccac tgcactccag cctgggtgac agaatgagac   151560
tccgtctcaa aaaaaaaaa aaaaaaaaa agaaaaagaa aagcatcctc ccttcgtgtg    151620
```

-continued

```
tctgtgtgtg ttctcctctt cttagaagga catcagttgt attggatcag aacctaccct   151680
actccagtcc aacctaattt taactaatta cgtctgcaat taccctattt ccaaataaga   151740
tcacattctg aggtaccagg gggttaggac ttaaacattt ttgtgtgtgt agcaggagga   151800
cgtaattcca tttataactc ctcctaaata aaacgacttg catgtgaact cttgtctggg   151860
gcttcccaaa gtgagataac ccctctctct accccctaaaa caacgagtag cgtctgtcaa   151920
tgccagggtg caggggctaa ggtgcccatc tttgagtttc tgctgaggag gacacagctg   151980
ctacgttgga gcactcttgg gttctgcctt cgtgcccagc catctccctt gggctagccc   152040
tgccctgggt ctatcctaga atgagcctcg atctgtttgg ccataggcaa gcagagtgtc   152100
tggaaatctt tgtcctccat gactggtgct ggagccgaag ccagtgggtg tggccttgcc   152160
agccaactcc atttacccag ctctgaacaa gctagtagtt gagatcaacg gagagtccag   152220
acagtcgctc caagcatctt ggaatccatg gacacaggtg taccgcagag gcttcccacc   152280
tgggtaggca gcccttttgta agatcctggc accacattta ttctcttaac atcctttcag   152340
ttatccagta atcatttatt gagcacctac tgtgtgccag gcaatgatta ggtgattgga   152400
gacactgcaa cgaagaagac agactaaaat ctccaccctg gtaggagaga cagatgcaaa   152460
tggtaaacat gataaataat caatcaccca gaaagcagga gacactaagc aaatgtgtat   152520
gtactatggg aagcccaata ggaacgaaag ctacacaaga gaacaagtga tgggtggttc   152580
cttagtctag gtcaggcaat cagggagggc ttctcagagg aggtgatgtt tgagcagaga   152640
aggagggagc caggcagatg tttttggaaac agcattctca gcatggagaa cagtggcagc   152700
tcacctacag gatgtgtttg attcccttcc agattttgta ttcgtttctt gttttttctcc   152760
cttggcttcc tggtttaaat gccttttgaa gaaatctaag ctcaactaat cagcgatgct   152820
gttgaaggtt tatatcagga tatgcatccc agagttattt acaaaattag aacaaaactg   152880
gaagcaattg aaagcctgac aataggagat cagttaaata ccgtatggtc cttccgtatg   152940
atggcatatt atgtcatcat taaaaatcgt ctgctgggag aatattaagg atacaggga   153000
aaggctcacc atataatgat gagtgggggt gctgggcgca gtggttcatg cctgtaattc   153060
cagcaatttg ggagtctgag atgggtggat cacttgagcc caagagtttg aggccagcct   153120
gggcaacaca gtgaaaccca atctctacaa aaaaaaaaaa acaaaaatac aaaaatcagc   153180
caggcatagt ggcgtacatc tgtagtccca gctactcagg aggctgagac aggaggatag   153240
gatcacttga gccctggagt cagaggtggc aataagccgt gatcacgcca ctgcactcca   153300
gcctgggcaa cagagtgaaa ccctgtcaaa aacaaaaca aaaaaaatga tgagtgggag   153360
aaacaagttt ttaaacaggg atcaaggagg ccaggcatgg tggctcacac ctataatccc   153420
agcactttgg gaggccaagg caggcagatc acctgaggtc aggagtttga gaccagcctg   153480
gccaacatgg cgaaaccctca tctctactaa aaatacaaaa attagccagg catggtggcg   153540
ggcgcctgta atcccagcta cttgggaggc tgaggcagga aaatcgattg agcccaggag   153600
gtggaggttg cagtgagctg tgatcatgcc actgcactcc agcctgggca acagagcgaa   153660
agctgcacga gagaagaagt gatgcatggt tccctagtct aggtcagcca atcagggagg   153720
gttcctaaga ggaggtgatg tttgagcaga aaggaggaa gccaggcaga tgttttggaa   153780
acagcattcc cagcatggag aacagtggca gctcaccctg tctagaaaag aagaaatgat   153840
aagaggggaa aatgagtttt taaaaggaa tcaggggag gtaaacctta tgatctcaaa   153900
ggtacaaata tgaaaatata agtaaagaaa aactggagga cactgtacca agctgacctt   153960
cgggtggtgg gatttgggaa tcttgatatt ctcaatactt cttttgtatct tcaaatttct   154020
```

```
ctatgatgat cacagtttac tttttttttt tttttttgag atggagtctc actctgttgc 154080
ccaggctgga gtgcagtggt gcgatcttgg ctcacttggc tcacctctgg ggttcaagca 154140
attctcctac ctcttcctcc caagtagctg ggactatagg catgcaccag catggtcagc 154200
taattttttg tattttttagt aaaaatgggg tttcatcatg ttggccaggc tggtctcgaa 154260
ctcgtaagtt caagtgatcc accaacctca gcctcccaaa ttggcttgag ccaattaaac 154320
ttgtcttgct aaatggttag cggggagaaa gaagaaggtc tcgggtcatt cctagaccag 154380
gaggcaggga gaaagggagg agaatgaacc tttcttaggc aaacagtgtc ctaggtgtcc 154440
ttatcttaca taatctgtcg agagagtcac actaaaataa atcattgatt gattgattga 154500
tacatcaata ataaatggcc agccttggtg gctcacatct gtaatcccag ctacttagga 154560
agctgaggtg ggaggattgt ttgagacaag gagttcaaga ccagcctggg aaacacagca 154620
agactcatct taaaaaaatt ttttttttta attagccaga tgcggtggct cacgcctgta 154680
atcccagcac tttgggaggc cgaggcgggt ggatcacgag gtcaggaatt cgagaccagc 154740
ctggccaaca gggtgaaacc ccgtctctac taaaaataca aaaattagcc aggcgtggtg 154800
gcacacgcct gtagtcccag ctacgcagga ggctgaggca gaagaatcat atgaacctgg 154860
gaaacagagg ttgcagtgag ctgagatcac gccattacac tccagcctgg gcaacaagag 154920
caaaactaca tctcaaaaaa aatgtttttt aattagccgg gtgtggtggt ccatgtctgt 154980
agttccagct acttgggagg ctgaggcagg aggattgctt gagcccagca gttcaaggct 155040
gcagtgagct atgatcccgc cactgcactc cagcctgggc aacagcaaga ccccatctct 155100
taaataaaca cataagtaaa taaatgatca ttttttatttt attattaaat acacaagata 155160
aatgaaaaac aggcaaatct ttcttacaaa agaattccat ttaaagtatg taaacttcac 155220
tccccactgc cccaggaggt ggagactaat ctcccctact ttgagagtgg gctggattta 155280
gtgactcatt tccgaagaat agagtaggta aaggggaaaa tagaagtttt atagcggagg 155340
aacagataga taccacttta accaaatgat gaagattagt atcccccagg gatgtggata 155400
ttatgtaacc cttgatttta tgcctatata gcgttcttcc caaaaactcc taatcccagt 155460 ttttggggt tttgctctgt cttctaagct ggagtgcgat gatgcaatca tagctcactg 155520
cagctcaaac tcctggtctc aagcgatcct cccacctcaa cctcctgaat agctagggct 155580
gtaagcacat accatcatgc ccagctaatt gtattttttt ggtagagaca tgttctcaca 155640
cattgcccac gctgtcctcg agctactggc ctctagtgat cctcccaccc cagcctccag 155700
agtcactggg attataggca tgagccactg tgaccagccc agaattttt ttaaggagt 155760 tgtgatgtcg tttaagagat gtgattcttc ataacacatc aacaacaagt cccagcgatg 155820
ggttggataa gtcttgggat ttcatgggag tattaagctt aaaagacttt gcatgatatc 155880
tgtgaactat atgtgatttc tgttggtaat ggggtcact gattctgcgg tttgccacct 155940
ccaatcatca tggaagaaaa tgttccactt ccagtgaaag taagaggaag taaagggta 156000 attattttct atctaaattc acgaactcct tgaattctgt ccacagaccc ctaagtgttt 156060
cctccccaag gtgaaactga gagaatcttg ccagtgcctt ccgcagtcac tgtggctaga 156120
aaacccctca gaagaggtga tagtttagca ggtaactgga gttctcacca tccgtgtctg 156180
gctcagcccc catcacaacc agttacccag cccaaaatgt cagtagtact gaggttgaga 156240
ggctctgctc taggaggcca ggcctctcag aggaaggagg attggggtac tggctgggcc 156300
tcaagatgaa cctaccccct aagagctttg ggatggcgtg agtttctgtc catacccaag 156360
```

```
gactacaaat gcaggtttac tggaaattct gtgccaaaag tgaggtccaa ctcacttcta   156420
actgctacaa aacaaacctc catcaacata gcccatctct gttcttgacc tggaagctcc   156480
aaggtatcca catggctccc atgcccacta gacgggcctc ttccctggac cttcctgggc   156540
cagagaaggc tctgggtagc cttgtggaat caagatgggt gatcagccac ttcctctgtg   156600
ccaccctgtt ttggctactt ccctaggcat cagcctggga ttccttgatg gtaaaaatat   156660
aaaactctct gagctagggc ctttaatatc cccattttac agatgaagaa actgagtccc   156720
agagctgtgc acagcgattg agagtcagaa ttcagctctg tctcactcag tgtcaacatc   156780
ctcagattct gccatttata gcctcccaca gcaaatagga ttgagggctg cttctctgag   156840 ctcaaggggga tagaatgggg aaccccatga gtactgcaac aaaactgttt gctggagaca   156900
agagctggtg gctctgtgtt gttctagtga caggtggcct catttcacag ggaccccctc   156960
accctatgtg ccccatgtgg ctcagaaaag ccagaaattg tctccactct cacaggggaa   157020
ggtccctgac cccctctttg ccagctgggc caaggcaaat tggggtcact tcatgggggta  157080 caggacctac cctctcttgg ttgccccaa ggaggggatg tggagggggct ggggacctgg   157140 caggaccagg gtgtcttgag ttaatttggg gctgcctttta gccgagggct tctgtgtgcc   157200
tggcatcagc tttacattgt gtcttgatcc gtaaaacagc cctgtgagga aagatatttt   157260 taacccccatc ttccagatga ggaaacggag gcccacaggg tgacgtgacc tgccaaggtc   157320
ccctagccaa gagtgacaaa gccagggttc acacacagct ctggacacaa ttcatcaccc   157380
ttcatccgtc tctctctgac tcttctttt tcctctctc tctttgtctc tctttttttt     157440
tttttttttt tttgagacag cgtctcactc tgtcacccag gctagagtgc agtggcgcaa   157500
tctcggctca ctacaacctc catctcctgg gttcaagcga ttcttgtgcc tcaacctccc   157560
aagtagctgg gattacaggt gcgtgccacc acacccagct aatttttggg ggttttgttt   157620
tgttttgaga tggagtcttg ctctgtcgcc aggctggagt acagtggcgt gatctcggct   157680
cactgcagcc tctgactccc aggttcaagt gattcccctg cctcagcctc ctgagtagct   157740
gggactacag gcatgcacca acacgcccag ctaatttttt gtattttagt aaagacgggg   157800
tttcaccatg ttggccagga tggtctcgat ctcctgagct catgattcgc cgccttggc    157860 ctcccaaagt gccgggatta caggcgtgag ccactgtgcc tgccaatttt ttgtattttt   157920
aacagagact gggtttcaac atgttggccg ggctggtctc gagctcctga cctcaagtga   157980
tctgcctgcc ttggcctccc aaagtgctgg tattacaggc atgagccacc atgcccagcc   158040
tttgtctctt ttattcttgt gttctctctc tctcttcctt ctctttctcc acctcctcct   158100
ccttctctcc cttctcctca cccttctttg tgcttttctc tgtgagtttc tcttcttctc   158160
tatttctctc ctttggtgaa tgtcaattag aaaagcagaa aaactgcgtt taatttgtga   158220
tcataaatgc atgtccctgg ccaggcgtgg tggctcacgc ctggaatccc agcccttttga  158280 gaagctgagg caggaagatt gcttgagacc gggagttcaa aaccagcctg gtcaaaaagc   158340 aagacccccat ctttaaaaaa gaaaataat taattagctg ggcatggtgg tgtgtacctg   158400
tagtcccagc tactcgggag gctgaggaag gaggattgcc tgagcccaag ggtttgaagc   158460
tgcaccgagc tgtgattaca cccctgcact ccagcctggg tgacagaacc agaccctgtc   158520
tcaaaaaaaa cctaataatt aaaaataaat aaataaataa atgcgtgtcc cctggccagt   158580
ggttgctaat gtttggaatc acccttttgacc catgcccttt ttcattcata gatgtttgtc   158640
ttgaccaaaa tcaaagcatt agactttgga ctataaatca ctggttcatt caacaaccat   158700
cattgaatgc ctactgtatg cagacactct tctggacaca gaggagttga cgtgttggtg   158760
```

-continued

```
gggaaagcca gtgatcagtt gggataaaaa gggcagacag cagacattaa atagtttagg   158820
ctttgtgggc cagatggtct ccatcgcaac gactcaatct gctcctgtag cgtgaaagta   158880
acgacagata aagcgcgtaa gtgaatgagc atggctgtgg gccaattaaa cgttaaccta   158940
taaaaacagg tggctggccc gcgggctgta gtttgtggat cactgcctta gagatagtgt   159000
tagagggtgg tgagaggtcc gggatagaat aaaacagtag agagtttgtg cattgtcaag   159060
atgagaggtt gcagttcttc ttatacaccc cgaatggccg ggcaccgtgg ccattatgat   159120
ctataattct aacactttgg gaggctgagg caggaggatc ccttgagccc tagagtttaa   159180
gaccagccta ggcacatagt gagacccat ctctacaaaa aaaaaatt aaaaattagc      159240 tggacatggt ggagcatgcc tgtaggccca gctacttgag aggctgagat gggaggactg   159300
cttgagcctg ggaggttggg gctgcagtga gccgatcatg ccactgcact ccagcccgga   159360
tgacagagca agaactgtct caaaaaaaaa aaacaaaaaa acaaaaaaaa cagacctgaa   159420
ggaacaaatc atatgaatgc attaaagtat cacatgtatc caaaaaatat atacatctat   159480
cagcctggca cggtggctca tgcctgtaat cctagcacat gggaggcca aggcaggcag    159540 attgcctgag ctcaggagtg caagaccacc ctaggctaca tggtgaaacc ccgtctctac   159600
taaaatacaa aaaattagct gggcatggtg gcaggcgcct gtagtcccag ctacttggga   159660
ggctgaggca caagaattgc ttgaacccag gagacagagg ttacagttag ccagatcgt    159720 gccactgcac tccagcctgg acaacagagc aagactctgt ctcaaaaaaa aaaaaaaaaa   159780
aaaaaaaaaa aaaatatata tatatatata tatatatata tatatatata tatatatata   159840
tataatcaat taaaaatttt ccttaataaa taaacatttc tctccttctc tcccttggtg   159900
aatgtcaatt aataaagcaa caaaactatg tttagttagt gatcattaat gtatgtccct   159960
ggctgggtgt gatggctcac acttgtaatc ccagcacttt gggaggctga ggcaggagag   160020
gatagtttga ggccagcaat tgcttgaggc tttttgaaag acatgaagga gatgaaggga   160080
gccatggaga tatctcaggg aacagcagcc gaggtagatg gaacagccag tgcaaaggtc   160140
ctgaggcagg atgttcctgg catttgtgag gacatgtagc tgcccagatg tccagtgggg   160200
agtgagtgag gatgaaggaa ggagctgatg aaggaagatg ataaaaatact tcatggatca   160260 gccaggcatg gtggctcccg cctgtaatcc cagcactttg ggaggccaag gcgggtggat   160320
cacaaggtca gagttccag accagcctgg ccaacatggc gaaaccccgt ctctactaaa    160380
aaatacaaaa aagttagcca ggcgtggtca tgcacgcgtg tactctcagc tacttgggag   160440
actgagactc gagaatcgct tgaacccagg agatggaggt tgcagtgagt tgagatcacc   160500
ccactgcact ccagcctagg tgacagagcg agactctgtc tcaaaaaaa aaaaaaaaaa    160560 aaaaagactt cgtgaacaga cagcctatat aatttatgat ccaaccagg acagttttga    160620 gagtgaaagg ggaaaaagag cactgaaaaa ataattagca ggcctggcat gatctataac   160680
gggtataaag tgggacacac agcctctctc acggtcactg tcagacttca gcttttttcac  160740 actcaaatcc accccccatgt ttatcccata tactggagaa acgggtgttc tcctgagctg   160800
agttttgggg tttttttcctt ttgttttgtt ttgttttgt tttttttaaca tcctgtatac    160860 tttttctcaa tgaaccatgc tcaaaaaaat tagaggaaaa taaaccataa aacagaaggc    160920
actgaaggat tttgctggga ctcagccatt agtttgtttg atgagtattt atggagcgct   160980
ttctaagcac caggcaccac cagcgatact gggatgaatc agtaacatcc ctcacccttg   161040
aagctctctt gggcccattg ttatttactt aaaatactat gcaagtacgg agaaggggtg   161100
```

```
aagtgggaaa aaatcagttg gttgtaaagg ccagaatgac gggtctagtc ccacccatgc   161160
catctgcacc ctgtgtgatc caggcacatc atgttgcctc tctcagcttc agtttctcca   161220
tccaccaggc acagagatgg cgggaatcga ggaagatgtg gggagtattt catcagccca   161280
aaaagacttg gctaatgcga ccataattct gccttctgcc tctcctttcc cagaaaaata   161340
gcttaatcat ttggatttgg gataaacaca tttcctgtgt ttattattta aatgatccac   161400
caagctgggc atggtggctc acccctgtaa tcccaactct tgggaggct gaggagggcg    161460 gattgcttga gcccaggagt tcaagaccag cctggccaac atggcgaaac cccatcttta   161520
ctaaaaaaat acaaaaaaat tagctgagcg tggtggtgcg tgcctgtaat cccagctact   161580
tgggaggccg aggcacaaga atcacttgaa cctgggaggc agaggttgca gtgagcctag   161640
atcgtgccat cacactccag tctgggcgac agagtgagat tctgtcccta aataaataaa   161700
taaataaata aataaataaa taaataaat gatccaccaa caggaacccc aggaacattt     161760
gtattgacta tgcaactaat gcttagtgag cacctactat gtccctggtg ctgatctgga   161820
cactgggatt tagacaggaa aaatctctac cctggaggag ctgatgatca agatgacaat   161880
cttgaaatgc ataagttgac aagatgattc agacagtgga acgtgctggg aagagaatga   161940
gatgtctggc tgagctgcag gaaggggcaa gtccttttga ttgagaggtc caagaaggct   162000
tctctgatgg gggcacaatg gatctaaggt tgagtgataa aagaaattg gccaagccaa    162060 gacctaaagg cagagttgct ccaggcatag gttcagagaa tggaaataat tggctgattg   162120
tgatcttgaa cttgaccttt cttttcttct gctaactttg ggtttggttt gttcttgctt   162180
ttctggctcc ttgaggtacg tgttgggttc ttaatttgta attttttttt ttttttttg    162240 ctttttgag acagagtctc actgtggtgc ccaggctgga gtacagcagc atgatcttga    162300
ctcactgcaa cctctgcctc ctaggctcaa gtgaacctcc cacttcagca tccccagtag   162360
ctgggactac tggtgcacag caccacaccc agctaatttt tttatttta ttttttagag    162420 atggggtctc actgtgttgc ccaggctggt ctcaaacccc tagctcaagc gatcctcctg   162480
ccttagcccc ccaaagtgct gggatgagag cgtgagcca ccacatctgg cctctgtttt     162540
ttgtgatgta ggtatttgat gctataaact tccctcttag ttgcttcttg gcccttttagc  162600 taaggtcaag tgtaaacttc cctcagcact gcttctgctg catctcacag gtgttggtgt   162660
gttgtgtctc tattttcatt catttccaaa attttttaag tctccatctt aatttctgca   162720
ttgacccaat ggttgttcag gagcatgttg cgtaatatcc atatatttgc atcatttctg   162780
aaattcttct tggtattgat ttctagtttt atcccacggt agtctgagaa gatgcttgac   162840
agaattccag tattttaaaa tttgttgaga gttgttttgt ggcctaacat gtggtctgtc   162900
ttggagaatg tccatgtgct gatgagaaga atgtatgttc tccatcagac atgcaagaga   162960
cagacacttt ctcacctgcc tcatgggatc cataaaagag tcaatcagaa gttggcattt   163020
aagaaagacc agaaggaggc tgggtgcagt ggctcatgcc tgtaatccca gcactttggg   163080
aggctgaagt gggtggatca cctgaggtca ggagttcaag accagcctga ccaacaaggt   163140
gaaatcttgt ctctatttta aaaatacaa aattagcta ggtgtggtgg cgggcacctg      163200
taatcccagc tactctggag gctgaggcag agaatcactt ggaccagga ggtggaggtt     163260 gcagtgagct gagatcacac cattgcactc cagcctgggc aacagagcaa gaccccatct   163320
caaaaaaaaa aagaaagaaa aaaagaaag aagaccaga aagaggtgaa ggagcaagct      163380
acagagatat caaactgtat caatctggct gggcgtggtg gctcatgcct gaaatcccag   163440
cactttggga ggctgaagca ggaggatcac ttgagcccag gagttcgaga ccagcctggg   163500
```

```
caacagagac cccctctcta caaaatataa aaatttaatt aaaaagatgt attggtcagg    163560
gcagccaagt tatgctgcag taacaaacat ccccaaagcc tccatgactt ttgacaacag    163620
atgtatttcc tgctcatgct acatgtccag tgcaggttgg cagtggggaa gaagggggct    163680
ctgttcagtg cagtcacttg agacctagct aatcacctag aacattgcca cttgctattc    163740
cagaaggaaa aaaggaatgc tagaaggtcc cacactgaaa gttcaatgct ctggctccaa    163800
aatgacagct atttccactc actcctcatt ggccagcact tagcatgtgg tcctcagcca    163860
accccaaagg gactcaggaa ggaccatccc accatattgc tggaaatatt tgatggcagc    163920
attaatgggg aacagtgttc caggcagtgg aagtctttga gcccttggaa gaaagacaag    163980
gcgatctcta gagcacatcc ttcccaatat taatgaattt aacaaatgag caagccatcc    164040
tcccccactc tccttcccga attcagactt gtgcatatcc ctcccttaac ttgaactgcc    164100
aaagaagaga tgagaaccag gagaagagat ctgtgacccc atctttgctg atgaactacc    164160
acagaacagc catggcatct ccagtccttg tgcttgtaaa atgtactttt cattttgctc    164220
ctgaacgaaa tccacccacc cccaccccca aaccagggaa agctcatctc ctaatccaaa    164280
actgcaccca gccttccacc accttcttcc ctgggaattg ttgattccag agtatggaat    164340
tgaataattg gatgagtttg gaagagaaaa agtgtctcta aaatcaggca gcagaagccc    164400
actcccagga ggaggatggtg cagatgagag ttcaggaggg agcttggctt ggggttgacg    164460
atctgagcta tgcagggaac ttggacacac ctctcaatca gtcattcaac agacaccact    164520
tattgagcac cgactgtgtg ccagatgttg tcctaggggg ctgggaatac aggaatacag    164580
cagggaacaa aaaggacaaa gcccctccct cttgtcgaat ggacattcca gccaggaaga    164640
cgagagaaca agagaaataa gtaaagtata taggcggtga aatgcaaatg ggaaaaaaga    164700
aacaatgggg accagaaatg agggtgcaa ttgtaaaggg ccatcagggg aggcctccct    164760
cagaaggtgg catttgagta aaaaacctga aggaggtgag gggaaccat gtagcaatct    164820 caggaaagag cattccaggc agggagggac agcctgtgca agggccgagg taggactgtg    164880
cttggcgtgg ttgagaaact gcaaggaagc caggtggctg gaaccgaatg agcgagggaa    164940
aaggggagga gataaaagca aggagatggg agggttggag gcccctctg ccattcagta    165000 actgagtaac ttcatttatt tcctgtagct tgaaccacaa agaaccacaa atagagtagc    165060
tgaaaacaac agaaatttat ttattctctc gcagttcagg aggccaggag tccacagacc    165120
atcaaggtca gctgggccac agaccatcaa gatgtcagct gggccatggt gcctcctgag    165180
acttggtctg aaatcccttc ttgcctccct cctagcttct ggtggtttgc caacagtgct    165240
tggtggtcct tgtcttgtag acgtatcacc ctgatcccgc cttcatctcc atttcacatg    165300
gccttctccc tctgtgcaag gttgtctctg tgcccaggtt tctccttttc ttattattta    165360
cttatttgtt tgtttgtttc tttattttag acacagggtc ttgctctgtc tcccaggctg    165420
gagtgcagtg gtgcgatcat agctcactac agcctcaaac tcctggcctc aagcaatcct    165480
cctacctcag cctcctgagt agctgggact gcagatgtga gccactgtgc tctgcccaga    165540
tgtcctcttt ttataaggaa acccgtcatt taggatgagg ttccacccta atgacctgat    165600
cttaacttga ttccatctgc aaagacccta tttccaattc ataggtacca gggattagga    165660
cttcttcaat gcatcttttt ggagagaccc actgcaaccc acaacagaac tgtgggcatg    165720
taacttgacc tctcggccag gcgtgatggc tcacacctgt aatcccagca ctttgggagg    165780
ccgaggtgag tggatcgcct gaggtcggga gttcgagacc agcctggcca acatggtcaa    165840
```

```
accccgcctc tactaaaaat agaaaaatta gctgggcatg gtagcaagca cctgtaatcc  165900
caactacttg ggagggtgag gcaggagaat tgcttgaacc caggatgtag aggttgcagt  165960
gagccaagat agtgccattg cactccagcc tgggtgacag agtgagactc catctcaaaa  166020
aaaaaaaaaa aaaaaataga cctctctgtg cctcagcttt ctcacccggg aggatgggga  166080
taattatata cccactcctg gggttcatga gaggattaaa tgagctcaaa cagtccaagc  166140
ctccacgtgt gtctgttgtg gtgctgggta gcatgtcctg tggccagagg ttcccaagct  166200
tgtcgaggac ccaggcaagg gcagattcgg gtcttgttgg cagcacctga gatggacggg  166260
ctgccttggt atggaagggc ctcggctgtt tttccctttc agtcctgtcc ctctccccca  166320
tcctccaccc tgtccctgtc atctgagcct gctcctcgtg atggctcaga gtctccctac  166380
tggcggccgg tgcagagttt cgttccctgg gctatattta gccctgagaa atgggaacga  166440
gaaccctcag ccgccaaagt gatggagaga ggagcacaaa gccagtgctg ccttctgtcc  166500
agcaatgttc cgctgactcg gttctttctt ccagaacctt ccagaagcaa agcattggca  166560
tttctgagct cgttaaaaca aggatgtggg ctggtggctg gcacattcat tgtccccaga  166620
acctgtctgt gtccatgatt aaagctgact tgttagtttt tattttcagt gctttttttt  166680
ttttttaatc catggcaaaa cacacatgac ataaaattta ccatcctaat atttttttta  166740
actttgtaac atttttaat tgacaagtaa ttgtacttat tcatggggta catagtgacg  166800
tttcaatgca tataatgcgt agtgctcaga tcagggtaat tagcatatcc atcttctcag  166860
acctttattg tttctttctg ttaggaacat tcaagctcct ccttctagct atttgaaacc  166920
attaatatat tgttgtcatc ctaaccattt ttaaggatac agtttcgtga aattaagtat  166980
aatacattca cattgttgtg caactgtcac caccatccat ctcccaaact tttccatctt  167040
ccaaatgtaa ctctgtcccc actaaacgcg aactccctgt tcccctccc ccagcccttg  167100 gcacccacca tgctactttc tgttttata aatctgacga ctctagggac ctcctataaa  167160
tggaatcata caggattttc ccttttatga ctggtttatt tcacatagca taatgccctc  167220
aaggttcacc catgttgcag cacgtatcag cattttcttt ctttttaagg taaagttgac  167280
tattaaaaaa aaacttctgc cgggctcagt ggctcacgcc tgtaattaca gcactttggg  167340
aggccaaggc aggcagatca ggaggtgagg agttcaagac cagcctgacc aacatggtga  167400
aaccccatct ctactaaaaa tacaaaaatt agccaggcat ggtggcgggc gcctgtaatc  167460
ccaactactc aggaggctga ggcaagagaa ttgcttgaac ccgggaggca gaggttgcag  167520
tgagctgaga tcatgccact gcactccagc ctcggcaaca gagtaagact ccgtctcaaa  167580 aaaaacaac ttttaagaa ttgaagtaga ataaacatac agaaaaatcc gcggattata  167640
agtgaagagc ttgattaatt gtcacaaact aaacacatcc atgtaaccag cacacaaatg  167700
aggaaacaga aacttctcag ccccagaagc ccccctcata tcctgttcct agtcactacc  167760 tcccgcaag ggtacccta ccaggacttt gagcatcatt caccagttta gcctgttttg  167820
tattttgcat aaatgaagtc tggcttcttt tgcttgacgt taactttta agatctcatg  167880 tgacctgtgg cattgttcat tgcatgtatc ctctctctcc tattgataac agtgtggatt  167940
gtttgcaatt tggagctatg atgaatacca ttgctatgaa tgttcttgtg tgtgctttct  168000
gttgtgtaat tattcagaat tactatttcg gaattactat ctaattgtag tgatcttgga  168060
tcagtaacta tccaagaatt actgggtgtt ggcaaaggta catacagtta tacactgcac  168120
aatggcattt tggtcaacaa cagatcaaat atgtaacagt ggtcccataa tggaccgaat  168180
acataacagt gattatcata cagtattttt actatagctt ttctgttttt agattctttt  168240
```

```
tttttttgaga cgaagtctcg ctctgttgcc caggctggag tgcagtggtg tgatctccgc 168300
tcactgcaag ctccgccttc tgggttcacg ccattctcct gcctcagcct cccaggtagc 168360
tacaggcgcc cgtcaccagg cccggctaat tttttttgta ttttttagtag acacggggtt 168420
tcaccatgtt agccaggatg gcctcgatct cctgacctca tgatctgccc gcctcggcct 168480
cccaaagtgc tgggattgca ggcgtgagcc accgcacccg gcctgttttt agatatttt 168540
agatacacta tagagttaca attgcctaca gtattccata gaataacatg ctgtatgggt 168600
ttgtagccta ggagcaatag gcgagaccat gcagcctagg tgtgtagtag gctataccat 168660
ctaggtttgt gtaagtacac tccatgatgt ttgcacaaca aaatgaccta gtgacacatt 168720
tttcagaatg tatgcccatt gttaagcatg acttaatttt agcatagaaa ctctcaacca 168780
atttttcaag tagttgtacc atgtgttatg ggttttattg tctcaccca aaattcatat 168840
gttgaagtcc taaccccccag tacctcagaa tgtgacctta tttggaaata gattcattgc 168900
acatgtaaag gttttgccat tggcaaaact gccgttattt ttgcaccaac catagcagtt 168960
aagatgagat cattagggtg ggtcctaatc taatacgatg gtgtccatat aaaaagggga 169020
gattttggca cagagacagg cacactcaca ggaagaatgc catgtttaaa caaaggcaga 169080
gctcaggatg atgcctctac aagccaagaa tcagcaaaga ttgccagcaa accgccagaa 169140
gctaggagag aggcataaaa cagattctgt ctcacagctc tcagaaggaa ccagcccttc 169200
tgacaccttg agcttggatt tttggcctct ataactgtaa gacaataaat ctttgttgtt 169260
taagccacct aggttgtggt tccttgttac agcagccaca ggagatgaat acagcatggt 169320
gccctcccat tggcagatta tgagggttcc agttgctcca cagcttcaca gacacctggt 169380
agtaatgacc tcatcttaac ttctttctca ttttagcctt tcttccaggc agcagcagtg 169440
tcatacatgc tttaaaggt gggcttttaa agccacactt gagagccctg cattctgcag 169500
gtgtcacagg gtgatcaact attcaaaggc taccctgcc ctgacagctg gaggcaaggc 169560
ttcccagcac agaggttaag cccatggact ctggggccag gtggttagtg caaatcccat 169620
gtccactagt gaataactct gtgatcttgg gctgatgatt ttgtctttct aagcctcagt 169680
ttcctcaata gtaacatggg cattataaca tagaggcatc atgaggatta aatgactaag 169740
tgagctaaca tacataatgt gcttaggaag gtgccagcac accataaata ctctgtaagt 169800
gctggctttt atcattcttt tctctctctc tctctctctc tctctctctc tctctctctc 169860
tctctccctc tctctctctg tctctctttc tctctccacc ccccaacctc ctctccttga 169920
ttttcttccc ctcatcttac ttccttcttg ctatagtgtt ctattttctg tttcagagag 169980
tattctattt gtggactttt ttcctcttga aaattgagct gaaacttctg agaatttttt 170040
gtgattggca ttaaggctgc agggaatgga gcagggagac acttgaggaa agggctcatg 170100
gaccatctgt ctggcttggt gatttcacca ggccatcaga ctctgtggtc atgcatctcc 170160
tctaagggga gtctatgact gtgttgggag aagagaagga accagggatt aattaatcca 170220
tttcaatagg ttttgtgttt tgtttggttt acttttttcct tctccttctg gactgtggtc 170280
tgggaagtcc tcttgtgttt cttactccat tcccaggtca attatgttat gtgaggagaa 170340
cataattaag agagagcttt accctttgga tgttttcttc agaaaacgtt cctccatttc 170400
cccctctggg atgccagagc cccagaactc cacaagccaa gaacatttaa gacagagcca 170460
caagagaacc gagcttcccc ttccctcacc tgtcaggttc tatctgagtc ccagtcaact 170520
ctcacctgct ttccctcctc acaccctaca gagcaacgat gcctcaggga acacttggaa 170580
```

```
ctggttgtac ttcatccccc tcatcatcat cggctccttt tttatgctga accttgtgct   170640
gggtgtgctg tcagggtaag tttctgctac tccccacccc atcccactca ctcctctttg   170700
ctaacttctt tccaagtaga ggccattgaa gctttgtttt cattcactag acagagaaaa   170760
ggcttcttcc cttgtttggg ttaccagact gttattagca agccatgcac aggtgcagag   170820
gttgtgtact gctaggggta cccagtgaga gggttcatat gggctttact ttctttacat   170880 ttttttttaaa aaccaatagt ttgggtttac ttctccccca ttttccaaat ataaaatcat   170940
agcatatgct ctaacggtgt attttcctga cccatattgt cctctatccc caagattttt   171000
ttggcttaat cataaatggg cttcattttt cttaccataa gaagtctggg cacttgtatg   171060
gtggctctat ggcaccatca gcaaccccag attcttccag ctttccattc tgacatcttt   171120
accagaggct tccaatctcg tggatacctc atggtcttaa gatggctgcc tcacgccctc   171180
cggatggcca cttcatgttc caaacaggaa aaggaagaag ggaaacagga agaggtggga   171240
cctatggcag agaagccaac ctgctgcaga aatctttcat tcatggctta ttggtctaac   171300
ttaaaagagg gctgaaataa ttattagcca aaagtatgaa gagaatgaga atgaggtatg   171360
cagccagtgg tggttggcat ggcatggttt tatcctttcg gttttttttct tttttattgt   171420 tttttttga cacggtgtct agcttttatta cccagactgg agtgtagggg gcgatcatag   171480
ctcactgtaa cctagaactc ctaggcacaa gcgatcctcc tgcctcagcc tcctgagtag   171540
ctaaggcaac aagtgtatgc caccatgccc agctacattt tttattttttc atagagatgg   171600 ggcccactgt gttgtccagg ctggtctcaa attcctggcc ttaaatgata ctcccatctc   171660
agcctcacaa agtgctggga ttacagacat gagccactgt gcctggcctt tttcttttacc   171720 taggcacagt tgtcgggaaa tgtgtgaagc tggcagaagc acccatcact ataatatccc   171780
agtcttttcc cagaagtcct gactcctcct gttgaaaact cctgacctcc agggacttct   171840
gaatccccaa acacacacac acacacaaac acacacacac acacacacac acacacacaa   171900
acacacacac aaacgtttcc taacattttc aaaacagcca tactctggct tttctatgct   171960
tctccaggga gtttgccaaa gaaagggaac gggtggagaa ccggcgggct tttctgaagc   172020
tgaggcggca acaacagatt gaacgtgagc tcaatgggta catggagtgg atctcaaaag   172080
caggtgaggc cctttcatcc tggggcccag ggatggagat cccaggccac ggagtacaaa   172140
gagagtcatg cagtttggag aaggctaagc tgggagggtt atgatgggag gagaaagaga   172200
acctgaattg gtagtcccaa attttatcaa caagaatcca gagtctgata tgaagaagtc   172260
taagatgaag ccaggatctg acatcacgta acttgaattc tgaaatcaga cgctggttta   172320
catcccggcc ctgccacttt ttacccatgc accacacatc cctgtacctc cgtttcctca   172380
gctgttacat ggaggcgatg gtagtgccta agtcatagta ctattggagt atttagtaaa   172440
ataatctcag ctgagtcact tggggagaga agtgcctgat acacggtagg cacatattta   172500
tttgttcagc catttaacaa acatttaggg agcacctgct gtgtgccagg cactgatcta   172560
agcactgagg atatgggagt aaacaataca caccaaatcc ctgccctcag agctctgata   172620
ttctaatgag agagataaag caaacaaata catgtcatgt tgggaactcc caaattcaga   172680
gaaggaagat aaaacagact aggaagataa aacagagtag gaagttggcc gggcgcggtg   172740
gctcacgcct gtaatcccag cactttggga ggctaaggcg gcagatttc ctgaggtcag   172800 gcattcgaga ccagcctggc caacatggtg aaaccctgtc tctactaaaa atacaaaaat   172860
tagccaggca tggtggcgca cgcctgtaat cccagctact cgggaggctg aggcaggaga   172920
attgcttgaa cccaggaggc agaggttaca gtgagctgag gtcgcaccac tgcactccag   172980
```

```
cctgggcaac agagtgagac tctgtgtcag agaaaaaaaa aagagtagga agttagaggc    173040
agggtggtca gggaaggctt ctctaaggaa gtaccctctg agcagagaga cctgaaggac    173100
gtgaagaagg aagctgtggg gatgtcaagg gaaggggcat tccaggcaga gacagcaagt    173160
gcaaaggccc tgagctagga acgtatttga gacacagcaa ggaagccagt gcagctgaaa    173220
cagagtgaga ggtggggaca gctggaggag aggaagacag gaaggtgatg gagatcagat    173280
caagcagggg cttataggct gtggtgtgga cattggtttt tattttgcgc gaggtgggga    173340
gaatgttggc tattgctact gttgcggagg tggggcttga agtcacaaac cacccagcag    173400
catgtttttt ggtcggttga gctgtcacca tcagtcagca gagaatgggg gtggccgggc    173460
agacccttct tcctggtcca agggagaact catcctccaa atgcaggagc ttaactctgt    173520
gctcttcctc ttcagaagag gtgatcctcg ccgaggatga aactgacggg gagcagaggc    173580
atccctttga tggtaactgc tctaaaccca cctcaggggt gggtcccagg ggagaaggga    173640
gaagctgtgg tggggagtcg ggggagagca ggtgactggt tctaaggatc ttgcagaggg    173700
tagacgttcc tcttggagga attttaggac ttccatgcag agtttcccta ttctggcctc    173760
cacttttttg tttaaccat ggacctggtt ttttctgctt tgtgccttgg ttttctcat     173820
ctgcaaaatg ggtatgatat aaacaatacc ctagctcacg agattgtttc tcagaatgat    173880
attcgttatg gcaaatagaa cacctgggat agtgcctggc atggggtcag cacgtttctg    173940
tttgctaaat aagtaataat tccaccaata atccagttta ctgtgaacgg ctgctgtctc    174000
ccatgttaga aacttaacga gacagaacca tgactttctt tcttttcttt tttttttaat    174060
tgagacagag tctcgctctg tcacccaggc tggagtgcag tcacacgatc tcacctcact    174120
gcaacctctg gctcccaggt tcaagcaatt ctctgcctca gcctcatgag aagctgagat    174180
tacaagcatg agccaccatg cctggctaat ttttatattg ttgatagaga tgggggtttcg    174240
ccatgttggc cgggctggtc ttgaactcct tgcctcaaat gatctgcaca ccttggcctc    174300
ccaaaatgct gggagtgtag atgtcaattc atggtcccct ggaaacctga atatgaaagg    174360
agggaccatt aaaaaggtgt ccaaaagccc aacctcccca gcatagctgg gagtcagggg    174420
acagactgta agagtcactg tgtatccaac ctgaggcttc atgaaagtaa agtttcctag    174480
aatttagaga tagggttgga tgcggtctgt ctgtggctca catctgtaat cccaacactt    174540
tgggaggcca agacaggagg aacacttgag cctgggagtt caagaccagc ctgggcaaca    174600
taatgaggtt ccgtctctac aaaaaataaa cttagccaga tgtgggggca cacgcaccta    174660
tggtcccagc tactcaggag gctgaggtgg gaggatcact tgagcccaag aggtcgaggt    174720
tgcagtgggc accactccac tccagcctgg gtgacagagt gagaccctgt tcaaaagaa    174780
aaaaaaagaa tttagagata ggccagaata atatgtctgc aatataataa taacagcaat    174840
aagaaaaata atagtactcc ctgaaaaatg caacttcttg cttgagattt atcttctcat    174900
actttagaaa actggttaga caggggctgg gcgtggtggc tcatgcctgt aatcccagca    174960
ctttgggagg ccaaggcggg tggatcactt gaggccagga gttcaagacc ggcctggcca    175020
tcatggcgaa accccatctc tactaaaaat acaaaaatta gctaggtgtc atggcacacg    175080
cctgtaatcc cagctactca ggaggctaaa ctacgagaat tgcttgaacc tgggagacgg    175140
aagttgcggt gagccgagat cacaccactg cactccagcc taggcgacag agcaagactc    175200
tgtctcaaaa aaagaaaga aagctggtta gacagggtga tgacttttga ttaaaaatct     175260
gagagatttg agggaaataa aagaactggc actgcgtccc agaaggttat aaaatgaatt    175320
```

```
ttattatctt agttggggag gggagattac ctaactcccc taaatgagtt aggtaatcta    175380
actcatttag ggtacctaaa tcttttcatt ggaagtctac acctgaactt gtctgctgtg    175440
gagcccctgg ggtgtatagc ttgaatatgg gggcagaatc ccaaaattgc agcctgccta    175500
gcgagtatgc tacaggtcaa ggggtggact gttttcataa gaaagtgagg tttcttagaa    175560
tttaaaaata gaggctgagt ggggcggctc acgcctgtaa tcctagcact tttggaggcc    175620
aaggcaggca atcacttga ggtcaagagt ttgaccagcc tggccaacat ggcaaaaccc    175680
catctctact aataatacaa aaattagcca ggcgtggtgg tgcatgcctg tagtctcagc    175740
tactcaggag gctgagggag gagaatcgct tgaactcagg aggcagaggt tgcagtaagc    175800
caagatcaca ccactctctg ggtgacagag caagattctg tctcaaaata aataaacaaa    175860
taaataaata aaccagaagg aaaatagtgg ctgagggccc agacctggag tcggactgaa    175920
cccgacttga ttcttgtctt tacccctta agcaaagtga tagtgccacc ttgaacctca    175980
gtttacacat ctgaaaaatg ggtatactat tagttcccgt gagaacagtt gccgtgagag    176040
ttaaatccaa ggacacactg tgtccatatg gtctgtgttg caaaagggt aacgtctttt     176100 tctcttgcca tgtttccatt gttggagctc tgcggagaac caccataaag aaaagcaaga    176160
cagatttgct caacccgaa gaggctgagg atcagctggc tgatatagcc tctgtgggtg     176220
agtcccttcc tctgccacct atcagttgtt catcacctat cgcccaagag acatggtggg    176280 gtggggcag agggcttgca aaccgtgctg cctggatttg ggtctcagct ccaccctttc     176340
ccacctgtgc gtgtgtcctg ggcagattac atcattatgg gaataacatc cgtgcctagc    176400
ttctcattat tttgtgggaa ttcaactaaa tgatccccat gaagcatggc aaaccagcac    176460
ctggcaggga cgaagctccc agtcaagttg gtgaatgttt gtgactcatt cgggaagtat    176520
tcatggggga cctgcttata ttaggtgctt ggttgcaaac aagacaaggc agtcacgagg    176580
ctgagctggg aggatcactt gagcctggga agtggaggct gcaataagcc attattgtgt    176640
tactgcactc cagcctgggc acagaaaaaa aaaaaagac acaaactgag ccaggcacag    176700
tggctcacgc ctgtaatccc aacactttgg gaagctgaga tgagcggatc acctgatgtc    176760
gggagttcga gaccagcctg gccaacatgg tgaaaccctg gctctactaa aaatacgaaa    176820
aaaattagcc tgtagttcca gctactctgg aggctgaggc gggagcatca cttgaacctg    176880
ggaagcagag gttgcagtga gctgagatct catcactgcc ctccagcctg gcaacagag    176940 caagatcctg tctcaaaaaa aaaaaaaaaa aaaagacaca aaccaaatcc ctacctacat    177000
ggagctcaca gtccagtgca ggaaatagaa attaaacaga gaattacaca aataaacctg    177060
taatggtaat ggcacttcag ggagaggctc tgggcttagc ttgctctaga aggatgggga    177120
gcagtcaggg aaggctacct ggaggaagtg acggttaagc tgggaactga aggatgggta    177180
ggagatcact gtggtggtga tagcagaagg aacagtgtga gaggcagggc tcagaccttt    177240
gccaccacaa gggccagagt tcgagggagg agggaacatt tattctttcc cttctcactc    177300
ctctgtccta ttgattcatt ggctgtgatg atgttgattt tgaccttcta aagtgagaat    177360
gtattgttat tgttgttgtt gttctttaat gggttttgt ttttaatgga aggaagagca     177420
tccaggcaga ggaaataaga ctggaataag attgagggga gaaggaattt aggctgcttg    177480
ggaaactgtg tggccgcagt ttagaggaag aaaggatggc aagagaaaga ggaagggagg    177540
aagagaagga gggagagaag tgaaggaagg agggaagtta gtacatccat gtgtttctga    177600
tccatagttt ctgatccact atttcgtatt ccccttttat cgctcgcccc tagttttataa    177660 ccttattgct gagtttaggc ataatttcca ttgcgatcac atatctcgta gggtggatac    177720
```

```
actatggttt gtttagccat agctctatta tagggtgttt gagttgtttc caataatttc 177780
tcttacgaag aacactgctg tgcacattta cgtacaatga ctcccccac cctttgggcg 177840
tatttccttg gggataatta taggatcaaa gatattaaca gcttttcaac tcattattca 177900
aagagccatt ctgagtttca aaacatgga acccatttat aaacctgcca agtatgcata 177960
tgttcatgga ttccccaccc aggccatcga atattaccaa tttaatttcc tttcccagtt 178020
aagtgggttt gtaatgaaac cttaaagctt gttttcattt gcattttaa tttccagcca 178080
aaacacgctt ttctttgtaa tggagaactc attctgcttc cactcgtgtg tgcatctgtt 178140
taatttcctg taagcaaatg tcaagaattg gagcgctcag taggtgtctt gagtatttga 178200
tcaattatgt ctgtctcacg tgttacgtta cctccattgt ttaaaatctg ttttatgacg 178260
aggtacagtg gttcacgcct gtaatcccac tgctttggga ggccagtgca ggaggatctc 178320
ctaagatcag ccgttcaaga ccagcctggg caacataaca aggctccatc tctgaaaaac 178380
aaaatgttga aaaacttagc caggcattat ggcacacacc tatagtccca tctatttagg 178440
aagctaaggc aggaggattt cttgaaccca ggaattcaag gttgcagtga gctatgattg 178500
tgccactgca ctgcaacgtg ggcaacagag tgagaacctg tctcttaaaa aaataaaata 178560
acatacattc ttaaaaatct actttgctgg ccgggcgcgg tggctcacgc ctgtaatccc 178620
agcactttgg gaggctgagg cgggtagatc gcttaaggtc aggagtagga gaccagcctg 178680
gccaacatgg tgaaaccgtg tctgtactaa aaattcaaca attagctggg tgtggtggcg 178740
tgagcctgta atcccagcta ctcaggaggc tgaggcacaa aatcacttga acccgggagg 178800
cggaggctgc agtgagctga gatggcgcca ttgccctcca gcctgggcat caagagtgaa 178860
actccatcaa aaaataaaa aatctgcata tacatatata tgtatatata tttttaattt 178920
ttttaatttt ttttttttt tctgagatgg agtcttgctc tagcacccag gctggagagc 178980
aatggtgcca tctcggctca ctgcagcctc cgcctctgtt aacaaggcag gtgacattgc 179040
agctttctaa acagacccaa aacccaggcc agtggcttgt tctttcatag ccacgtttgc 179100
tacaggcaaa tccaccaaaa cccacctcat cagcctgatt actcaaaaag acaaagaaag 179160
gagccccaa tctagccagt ggttttctag accaccccaa aagagatctc tggaattcca 179220
ggattctggc aaggaatcac atttagcttt atttatttat gtaaagaatg caacaataca 179280
ggctgggtgt ggtggctcac gcctgtaatc ccaacatttt gggaagctga ggtgggagga 179340
tcgtttgagg tcaggagttt cagaccagcc taggcaacat agtgagaccc tgtctctatc 179400
aaatattagc tgggcattgt ggcacacgcc agtagtccca gctactcgtg aggctgaggt 179460
ggatcacctg agcccaggag gtcaaggctg cggtgagcca cagcatgccc ctgcactcca 179520
gcctgcgtga cagagacttc atctcaaaaa aaaaacaaa aaaagtaat aatacagtaa 179580
tgcatatttc aaagtaaggt gggagctatg tggtatttgc gttcacgttc acattatacc 179640
acagtatgca cagtcctttt ttttttttt ttgagacagt gtcttgctct gatgttcagg 179700
ctggagtgca gtggtgcagg catagctcac tgcagcctca aaccctggac tcaagtgat 179760
cctcccacct cagcctccca agtagctggg actataggtg tacactgcta cactcagcta 179820
agttttttat atttttact agagatggga tctcaatatg ttgcctaggc tggtctcaaa 179880
ctcctggcct caaacaatcc tcctacctcc acctcccaaa gcagtgggat tacaggcgtg 179940
agccaccaca cctggcccac atgcagtctt atataattgg tgattctact gcgctgttga 180000
atcagttgat aaacgcacta taaagcaggt tcattcctaa ttgatgaact tactgctgaa 180060
```

```
ataaggaact tgaatcattt acatgaaaag ttgagccatg ttgctgaaag gatatcaatt   180120
tttttttctt ttttttcttt tttttgaga tggagtctta ctctgtcgcc caggtgggag   180180
tgcagtggtg cgatctcggc tcactgcaac ctccaccttc caggttcaag cgattctccc   180240
acctcagcct ccaagtagct gggactacag gtgcacacca ccacgccctg ccaattttg   180300 tactgttagt agagatgggg tttcaccatg ttggccaggc tggtctcaaa ctcctgacct   180360
caagtgatct gcccacctca gcctccgaaa gtgctgggat tacaggtgtt agccaccgcg   180420
cctgacagga tatcaaattt catttagact gcaggaatac gttcaagaga tctattttgt   180480
acagcctggc gactgtatta ataacaatgt attatatact tgaaaattgc tcagagagta   180540
ggttttaagc attctcaccg tgagaaaagt gataagcata tgtaataatg catatgttaa   180600
ctagctcaac tgagccactc catagtgtat acatatggtc aaaatatcat gttatgcact   180660
ataaatagat acagcctgta tctgtcaatt taaaataaat gaataataac tttaaaaaga   180720
aaaataacag tatggctggg cacggtggct cacacctgta atcccagcac tttgggatgc   180780
caagacaggc ttgaggccag gagtttgaga ccagcctggc caacatggcg aaactttgtc   180840
tctaataaat atacaaaaat cggctgggca tggaggcggg cgcctgtaat cccaactact   180900
tgggaggcag aggcatcact taacctggga gatggaggtt gcagtgagcc aagatctgca   180960
ctccagcctg ggtgatagag tgagccttta tttatttctg taaagaatgc aataatacag   181020
gcctggtgcg gtggctcatg cctataatcc caatgttttg gaaggccaag gtgagaggat   181080
catttgaggc tacaggcgca tgccacagtg cccagctaat acttgataga gacacggtct   181140
cgctatgttg cccaggctgg tctcaaaacc ctggcttcaa atgagcctcc caccttggcc   181200
tcccagagtg ttgtgattac aggtgtgaga cactgtacct ggcctgtatt aaaaaaaaaa   181260 aaagaagaa gaagaagaag aggaggaaag aagaagaagg aagaaggaag aagaagaaga   181320
ggaggaggag gaggaatggg aaggggaagg ggaagaagaa gaggaggaag gggaagggga   181380
agaagaagag gaggaggaag gggaagggga agaggaagaa gaagaggaag aagaagacga   181440
agaagaagca caatgataaa taagtaaaat gtggagcata tgaaaacaaa acaaaaaaaa   181500
gttgatccat tatgaatgga agctgccatt gtaactctgc ttttttagga aaaccagacc   181560
ccatttagat gatttttattt gttttttaaag gcaggttctt gctctgtcac tcaggctgga   181620
gtgcagtgat atgatcatag ctctctgcag cctggagctc ctgggctcag gcgatcctcc   181680
cagcttagcc tcccaagtag ctgggactac aggcaccacc acacccagct aatttgttgt   181740
tgttgttgat gttgttgttg agatggggtc tggctatgtt gcccaggctg gtctcaaact   181800
cctggcctca agtgatcctc ctgccctggc ttcccaaagt tctgggatta caggcatgat   181860
tttttattaa tttatttgca gctgacaaat ggtaattgtg tatgtttatg gagtgcagtg   181920
tgatgtttta atctatgtat acatcataga atgattcagt catgctaatt aacacatcca   181980
tcgcctcacc acctcaccgt tttttgtgtg tggggaaggc attaaaaatc tcttagcaat   182040
tttgaaatat gcaacacatt actatttatt aataatgcaa tataaataca caataatgta   182100
ttaatgcatc actaaatgcg atgcaatgca atgcaatgca atagatcact aaaacttact   182160
cctccagtct aactgcaact tatacccttt gatcaacatc ttctccttct caatccctcc   182220 tcctccctg cagcctccag gaaccacctt cctgctcttt ctatgagatc aattttttt   182280 agttttaagc tcccacatgt gagatcatac tgtaattgtc tttctgtgcc agcttatttt   182340
actcagtata atgtcctcca gttctgtccc tgttgtcaca cattacagaa tttctttctt   182400
ttagggctgt atagtattct atttgtatac ataccacatt ttctttatcc attcatccat   182460
```

```
tgtgggacac ttagtttgct tccatatttt ggctattgtg aataatgctg aagtgaacgt    182520
gggagtgcag atgttctgaa aagacttaaa tgtcagacct gaaatggtaa agatgctcca    182580
agaaaacata aggagaaagc tccatggcat tggtctcggg aatgattttt tggacaggac    182640
ctcaaaagca caggcaacag aagccaaaat ggacaaatgg gatcgtatca aactaaaaaa    182700
tttgtgcaca gcaaaggaag cgttcagcag aggaaagaga caacctaagg aatgtgagaa    182760
aacgtttgca acaatacat ctgataagga gctaatatcc aaaatatata aggaactcaa     182820
acaactcaac agcaagaaaa caacccaatt aaaaatgggc aaagacagct actcgggagg    182880
ctaagatgtg acgatccctt gagcccggga ggaggaggtt gcagtgagct gacattgcat    182940
cactgcactc caccctgggc gacagaagga gaccgagacc ctgtctcaaa ataaaaaata    183000
aaaatgtgca aaggatctga acatacatat cccaaaagaa aagacataca agtggccaac    183060
aggtatatga ataaaatgct gaacatcact catcatcagg gaaatgcaaa tcaaaaccac    183120
cattagctat caccctcacac ctgttagagt agctattatc tttttgtttg tttgtttgtt    183180
ttttgttttt tgttttgttt ttgagaggga gtctcactct gtcacccaag ctggagcgca    183240
gtgttgtgat ctcagctcac tgcaacctct gcctcctggg ttcaagggat tctcctgcct    183300
cagcctcccg agtaactgaa attacaggca cacgccacca tgcccagcta acttttgtat    183360
ttagtttcac tatgttggtc aggctggtct tgaattcctg acctcaaatg atctgccctc    183420
cttggcctcc caaagtgctg ggattacagg tgtgagacac tgtgcccagc ctagagtagc    183480
tattatcaaa aagacaaatg aggtttgttg aagttctaac ccctggtacc tgcaaatgtg    183540
gccttacatg aaaatagggt cttttgcaggt ggtaatcaag ttaagatgag atcaaactta    183600
attagggtgg gtcctaaatc caatgactgc tgtctttata agaggagaag caggctgacc    183660
aacatggtga acccccatct ctactaaaaa tacaaaaatt agctgggtgc agtagtgcac    183720
acctgtagtc ccagctactc aggaggctga ggcaggagaa ttgcttaaac ccaggaggtg    183780
gaggttgcag tgagcagacg tcatgccact gcactccagc ctgggtgaca gagtgagact    183840
ccatcttaca agaaaaaaaa aaagacaaa tcataacaag tgctggcaag gatgtgggga    183900 aacgggatc catttacatc attttaataa cacaggctct atatgggtgg tattgagttc     183960
ccagagttgc cattacaaaa tgtcacaaac ccagtggctt aaaacaacag aaatttcttc    184020
tctcacagtt ctagaggcca gaagtccaaa ctgaaatcaa ggtgtcagca gagccaccac    184080
gttccctcag aaggttttag gggagaatct gttccatggt attttcttag tttctggtgc    184140
tgccagcgat acttggtgtt cctcagttca tagatgcata attccagtct ctgcctctgt    184200
tgtcatatgg tcttctttct gtgtttctgt atgcgatttc tttttttttt tttttttct     184260 gagacaagtc tcactccatc acccaggctg gagtgcaatg gcacgatcac agctcactac    184320
aaccccaacc tcacaggctc atgccgtcct cccacctcag cctcccgagt agctgggatt    184380
acaggcgtgt gccaccatgc ccggctaatt tttgtatttt tagtagatac ggggtttcac    184440
catgttggcc aggctggtct cgaactcctg accttacgat ctgcccatct cggcctccca    184500
aagtgttggg attacgggca cgagcccacc gcacctggcc ctaattactt tattttttg    184560 taaatttttt tttgtaaatt tcatgtagcc tgagcataca gtgttataa tatatacagg    184620 agtgtacaat aatatcctag gccttcacat tcactcacca ctcaactcac tccctcacca    184680
agagcaactt ccagtcctgc aagctccatt catgccaagt accctatgca gctgaaccac    184740 ctttttctctt ttatactgtg tttttactgt accttttcta tgtttagata tgttcagaca    184800
```

```
cacaaatact atgatgttac agttgcctac agtattaagt acagtaacat gctgggcagg   184860
tttgtagccg aggagctaca aaccacgtag cctgggtgtg gagtaggcta caacatctag   184920
gtttatgtaa gttcacttta agatgctcac acaaggacaa aattgcctaa caatgcattt   184980
ctcagaacac gtctccctca ttaagccaca catggctgta ttacaattta catataattt   185040
taagcgtata taaattgcca gaaatcacca gatgaatcct tggcggtgac ataccccttc   185100
ccccaccata gaacattgca gactggcccg gacgcccagt atctcatgcc tgtaatgcca   185160
gcactttggg aggctgcagc gggcagatca cttgaggtta ggagttcgag accagcctga   185220
ccaacatggc aaaacaccat ctttactaaa aatacaaaaa ttattcggac gtggtagtgg   185280
gcacctgtag ttccagctac ttgggaggct gaggcaggag agtcacttga acttgggagg   185340
cagaggttgc aatgagccaa gatcgtgcca ctgcactcca gcccgggtga cagaatgaga   185400
ctctatctca aaaaaaaag aaaaaaaaaa aaaaggaaa agaacatttc agactggtac   185460
cagttacacc ggctcttgat cccttgaatg tggctgaccc tgaactagga tgtacttcat   185520
aataacacgt ccggctggga atacttagta caaaagaaag agtataaaat atcttttgaa   185580
tccaccttga tattgattcc atgttgaaat ggtaatattt tggatgtatt gggttgaata   185640
aaacatctca tgaaagtgat ttttaaaaat ctagaaattg tctgcaatta taattccaga   185700
ccacagagaa aaacgagaga caggaatgta tagaaaagg gaacgtggga caaagtgagt   185760
atgaaattca actaacagaa gtgacagtgc ctagcatggg gtccagcact tagtaggtgt   185820
tcaattaata ttcatttccc tctcccttac cagtgaaggg tatgcctgtc gtgggaatg    185880 tgtcttcagg ctgagtgatc aggaaggact ttctcaatgg ctggcacgtg aacctagtca   185940
tgatttcagc tcttgaggtt gtactagaag atttatatcc aataatcgta aggtaccact   186000
tagcatcacg ctaagatgta ttaattcatt tatgcctttg gatggcccttt gaggtagga   186060 agtgtggttg tctccagttt accaaggtgg cttgcccaag gtcatctgct ggttggtgat   186120
taagccaggt tttcagtgtg gctccagcag gagtgggggc tggggacctt ctacctgctg   186180
tggtttctct ctctctctct ctctctctct ctcgatctgt ggaacatccc               186240
ccctgtcccc caaggtccca agggtcttat ttcttttggc caagcccttt ggagacctgc   186300
agatctggac acatctttga gagtttcagg aactagggcc agaaatgctg gcagggtca    186360 tgaggagctg ccactggggt tgagaaggtg atggacatga ggggaagggt ctttgcagaa   186420
aggagaggcg tccctgtaag caggtcacag ccactgggcc tggccaactg cagccgagtg   186480
gaatgtgccc ctgccccatg accatatgcc ccaggtgtgc aatgtggcgg cccagagcac   186540
acactctgaa ccatcttgac acatcttcac tggttactag accccctca gcctgtttcc    186600 ttggctgtaa aatggggatg acgctggtcc ctacttccta gggctctgag caggagtaag   186660
tagcttgtcg tataaaacat gttccctgca gtgcctggtg cctgctaaat gttccataaa   186720
cgtcagctgt tattttcatt caggggaagc tgaaatccat attttcatgg aaaatctccc   186780 agttttttaaa tgtggaccaa taattttcagc tttcacaaac ccagtatgag tcggtatggc   186840
ccctagggtg ccaactcaaa atctctgttg agaatttgc tgataggaag tggcctcctt   186900
ggaggtgttt gctgtgtcct gtgtctggca agtggggtgg ttttgataaa cgtgctggat   186960
ggatgtatgg gtgaatggat aaatggagga atgaatggag aaacaaatga gcaaatgaat   187020
aatgaatgga tggatgaatg gatgagcgaa tggatggatg aatggatgag caaatgaatg   187080
atgtacacac aaaggaatgg ataaatgatg aatgtgctaa tgaatttaag aatgatgaaa   187140
gaatgaatga ataaatgaac aaatggatgg atgaaagaat gaatgaatgt actaatgaat   187200
```

```
gaatcaatca atgaagaacc atttaaaaat gaatgcaact gagggtttat aagaaaaggt 187260
atcttaagcc tgggcatggt aattcatgct ggaatcccaa tgcttaggga cgctgaggcg 187320
ggaggatcgc ttgaacccag gagttcaaga ccagcctggg caacacaggg agacctcatt 187380
gctaccaaaa acaaaattgt tttaattaag cgggcatggt ggtacgtgcc tgtagtcata 187440
gctacttggg aggctgaggt gggaggatcg cttgaaccca ggagttcaag ctgcagtga 187500 gctaggatca agccactgca ttccagcctg ggcaacaaag caagatcctg tctcaaaaaa 187560
aaaaaaaaaa gatgtatttt agaaggtaaa ttcaatctgt ccaaaactga gctctgacct 187620 tccccctaaac ctgtgcccat tcagtggatg agagctccat cccttagggg gttcaccaat 187680
tcatccattc ctttgtatgt acatcattca ttcaccttgg ctcatccctc tctcttacat 187740
ccacaccgtt ccatcagcaa atgttgaatc tgtcttaaat gattcatccc aaatcctccc 187800
cgcttaacta ccacccaact ccagccccca tccatcatca tcatcacttg cctggatggg 187860
ttcagtcacc tccagcctgg tctcccagct cccgtcctca cctctcactg tctactctcc 187920
cactcggcag ccagagggtg cctgtgaaca cccaaatcag gttccatccc tcctctactc 187980
agaaccctcc acggctcccc cctcactcag ggtaaaagcc aaagtcctcc ttgtggtcca 188040
ccaggccatg catgatctgc ctgtcacctc cctgccttca ccacttcct cttttcccct 188100 caaccactcc actccagcca cactgacttc cttgtgctct tccccaaaaa tgtcgggcag 188160
acacattcat gcttcaggac cttaaatttg ctgtttcctc tacctaagat actaaagtga 188220
caagtcaaca cactcacctt gaccatgcaa tttaatgttg cagcctaccc tgtggactct 188280
ccaagggctc ccagtccctc tgtgatgctt tacttttct cttaaaaaaa aaattgttat 188340
ttaaaagaac ttgtctcgct gtgttgccca ggctggtgtc aaactcctgg cctcatacag 188400
tcctcccatt ccagcttccc aaagtactgg gattagaggc atgtgccact gcacccatcc 188460 caacttttt tttcccatag cacttttcat tttccatccc actgttaatt tacttattac 188520
gtccactgtc tgtctcctcc ccttagaggg tcagaccccg gaagtccagg ctctgttgcc 188580
taatgtatcc tgagcccctg gaacagagcc tggcacaaaa taggtactca ataaatgcat 188640
aagagcaaaa ctatatgtag gcagaggaca cacccagctt attcctcagt gatcacttct 188700
aaagttaaat gtccatggaa aacagtctca tccacatctc tttctggagg ccttccaagc 188760
gtgctccatg cagctctgtt gcctgccct gcatcaggga atggaggctc tgctttatcc 188820
tgccctgtgg tgtgactccc agaggcatca gatgtggctg ggagtgggag acatggaaaa 188880
ttggctcctg caacagagaa ctatcagcct tcccatcaat tggttacttc taattctgtt 188940 attttcagg ggcactgtct tctcataagc tccatctatg caaaactaag cccatgggtc 189000
atgatggttc cctcaggcca gaggcttgct ggagagacta atggatcccc tggctaaaat 189060
ctgtgcttgg gctgcacatt ggttaatttc ttctgaagga acagcctgag cctgacattc 189120
tccatctttt ccctggcagg ttctcccttc gcccagccca gcattaaaag tgccaagctg 189180
gagaactcga cctttttca caaaaggag aggaggatgc gtttctacat ccgccgcatg 189240
gtcaaaactc aggccttcta ctggactgta ctcagtttgg tagctctcaa cacgctgtgt 189300
gttgctattg ttcactacaa ccagcccgag tggctctccg acttcctttg tgagtatcac 189360
ccagccccac ccctgccaac tccctgatcc ctccctcaca ccctttttcc acttctcttt 189420
ctctggtagt atgtgtatct tctttggtcc tcattgaatc tgcccttcc tttagccatt 189480 tctataactg tcactggggc caatgttact gttgctatga caatggaacc catctcccctt 189540
```

```
agacctgaga gctggaagct ggaattcaga ccaacaaatg ctcctgtgat tcctttctaa    189600
gagagaggga cagaggggtg ctggtgaagg ggatgttgga agagagacag agaaagacgg    189660
agctcataag atagacagat agaaacagaa acatacatgt attaataatt tttatgtaca    189720
tctctggaaa tgttcataac ttatggttaa gagaggatgc cttagaaata aggagtggct    189780
tatatgttgc cctcattttc tctacttatt tctgactcta cttctctctt ctttcaaacc    189840
ttctgcttct ttcctgttag gttggtgcaa aattaattgc gttttttgcc ttttttttt    189900 ttttttttaa ccacagttac ttttgcacca acctaatact tcctcccctg cccttttgg    189960 cttccttatt cattcataga acatcccctc cagtatctgc gagagcgttt tgctccctca    190020
aggtacaagg cccactaagg ctttgccctc tgggcctatt cccagattct atgtgagtta    190080
gcatgagata gtatcaaaat tgagggccaa gtgagggtga ggaaaagcag caaaagatgg    190140
ggagatgtct gagcaggatt taaaaagtaa agagctcgag gaatcaacaa gagcagcgac    190200
tggggccagg catggtggct cacacctgta atcccagcat tttgggaggc tgaggtgggt    190260
ggatcacttg aggccaggag ttcaagacca gcctggccaa tatggtgaaa ccctgtcttt    190320
acaaaaaata caaaaattag ccagatgtga tggtgcacac ctgtaatccc agctactcag    190380
gaggctgagg cactagaact gcttgaatcc aggaggcaga ggttgcagtg agccaagatc    190440
atgccactgc actccagcct gagcaacaga gagagtgtct gtctcaaaaa ataaagtaaa    190500 ataaataaa ataaaataaa gagtagtgat tgggcagtga gggggcagg tggatgccct     190560 ggctttggct cacaggcccc aagtaaggac ttctcaaaac gtcttttgcc tactggctgt    190620
ctaatttatt cactgaccct ctgacctggt tcagaattga cttaggacag caagaagaga    190680
cagtctagtc tttgacctag aaaggcccgt gagcctagtc caggccattg tcttcttata    190740
accctccttg ttcccagtca cgttggctga ccccccagga caccectcag gaaccagttc    190800 tccttcccag ggccctgacc tagtttcaaa cttagtaatt gttttttagtc cctctggagt    190860 ctcttataaa tgaggactct acttcgtgtt ttaacttcct ctaatactct attttttaatc    190920 tcctatattc tctctactaa tcatcttgta cagtctgtcc tggttcagga acaagggact    190980
gagacttcct gcctgggtcc tcagtgtcta taaaggtcct ttactcattc ccactttccc    191040
tttgagaaaa ctgagacaca gagaggttaa gtagattgcc caggatcaca cattagcttg    191100
gcatgatggc gggcgcctgt aatcccagct acttgggagg ctgaggcagg agaatcgctt    191160
gaacctggga ggcagaggtt gcagtgagcc cagatcatgc cactgcactc tagcctgggc    191220
aacagagcta gacgccatct caaaaaaaaa aaaaaaaaa aaagataca cattaatttc      191280 agagatgtca aaatataaac aaaaatgtat atcttggcat cagtgaagtg tagttgtttc    191340
tctggatctc agactccaca tctatgtggt agaaaccgga tttgatggtc ctgaaagttc    191400
ttccagatgc aacaatgcta aggataagta attctttcaa gtcttgtgca tcacctgcta    191460
tcatgttttc atggtaactg aggaacaaga tcttcagaaac tcttcagtcc tcccagagtt    191520
acttctggtg ggtctaggaa tgtgtcagat gttacaaaca gacttcctct gctgatattt    191580
tggtcctagg aaccctagag ttcccctcag acactaagat ctccttagcg tcctataaat    191640
aaggagaaat tttggtgata aatactgtga aggactttga cggtcagttc aaaacacctc    191700
ttaaaagcat gacatagcaa acaccettgg caaatatctt agttcatttg tactgctata    191760
acaaattacc cgagactggg taatttgata agaacagaaa tttattttct cacagttctg    191820
gaggctggga agcccaagat caaggcattg gcaggtttcc ctgtctggcg aaagctactc    191880
tctgcttcca agattgcacc ttgaacactg tatcctctgg aagggaggaa cactgggtcc    191940
```

```
ttacatggca gaaggtggag gagcaagagg gacaaacttc ctctgtcaac ctctttata   192000
agggcaccta atcccattca tgagagctct accgtaatga cttaatcacc tcctgaaggc   192060
cccacctctt aatactgtta cattggcaat taagtttcaa cgtgaatttt ggaggggaca   192120
caaacattta aaccatcaca accaccaaac acaattagct ttgtggcctt aattagctat   192180
atgaaattca tggaagttag tttcagtcct ctgtctcttt cctttctgta tgctttctgc   192240
tcctcagaaa ccctcctcat ctctcctttc tatccattaa gtacccacgc ccttcctaac   192300
tcctcatctt cctaccctac caagaaagcc ctctcagaaa aggatctgat gtcagccatt   192360
tatttgctgg agcaaatgca tatccatgtt ttaccctcc ctgaggcatt tgcaatttta    192420
tgcttgctca tcaaagaaca aaaggctttg tcttactcaa gacttttag gtcactcaca    192480
acacaggatt tctagggac ataagacaag ttttctgagt taggagaaaa gccatacctt    192540
aggtgggttg cctgtgtcgc tccaactaag tacttaactt caggattaca aataggatat   192600
cattatgatt tctatttcct tttatccttt ggagctcagt cacgtagaag tagattaaat   192660
ataattgtta gatcacagca ccctggcatt atggggccgt tatggtccat tgttattatg   192720
tgaattattc agttaattag tttatttttt aaatgtgata aacacccagg aacccaccag   192780
tcaacacaaa agtccttggc aataatctat atccgatcct tctcatcgaa ccagggcaaa   192840
aactacaaga tggagaccca ctgatatttt tctcattcct tttaaaatcg gcctaaggtt   192900
ggttagcttg ttggttggag ggtagggcat aattgttgct tttttttttt tttttttttt   192960
ttagacaagg tcttgctctg tcacccaggc tacagtaggg tggcccaatc ttggctcact   193020
gcaacctcca cctcccaggt ttaagtgatt ctcatgcctc agcctcccaa gtagctgggt   193080
ttacaggcat gtgtcaccac actggctaat ttttgtattt ttagtagagg cggggttgc    193140
catgttagcc aggctggtct caaactcctg acctcagttg atctgaccgc ctaggcctcc   193200
caaagtgctg ggattacaga cgtgagccac catgcccagc cagctcttcc tttttaacag   193260
aggggaaact gaggcccatg ggaaggacac cttgacagg gcgtggccac agtgggtcat    193320
gtatataatc ccagcacttt gggaggctgt gctgggagga tcacttgagg ccaggagttc   193380
aagaccagcc agggcaacat agtgagaccc ccatctccac ataaaaattt taaaagaaa    193440
aaagataagt cagaagttgg gtgtggtgac acatgcctgt agttctagca tgttggaggc   193500
caaatcaggg aaactgtttg aggccaggag tttgaaacca gcctaacagc atagcaagac   193560
ctcatctcta caaaaaataa aaagtttaaa aatgataata aaggaaagt cagagccacc    193620
tggaacccct accctcagca agcctaacct cctctctgtt tcctccttct cccttctaga   193680
ctatgcagaa ttcatttct taggactctt tatgtccgaa atgtttataa aaatgtacgg    193740
gcttgggacg cggccttact tccactcttc cttcaactgc tttgactgtg gggtaagtgc   193800
tcttgttct aagagttcat ttctccagct cttgcctgga atgacagata cctggacaca    193860
ttaaaggag aaggtaaag tcacccctga atatgagaga ctcagatgga tgcagaagga    193920
atgagaaaac aatcccaaac actggcaagg atacagtgta cccagaaccc tcaaccaccg   193980
ccagtgggag gaaaacgtat agaccccctt tggaaagcta agtgggggac ataagacaag   194040
ttttccaagt tgggagaaaa gccatgcctt aggtgggttg cctgtgtcgc tccaactaag   194100
tacccaactt caggattaca aacaggacat caatatgatt tctatttctt cttttccttt   194160
gtagctcagt catgtggagg tagatgaagt ataattgtta gattacaaca ccctggcatt   194220
atggagccat tatggtcctt tgttattttg tgaattactc agttaattaa tttatttttt   194280
```

```
aaatgtgatt aacacccagt aacccactag tccacacaaa acctaagtcc tggagaataa  194340
tctacgtcca atccttctca tcgaaccagg gcaaaaacta caagatggag atatgaccca  194400
gcattccatt gctaggaatt catcctagaa aatctcaccc agatacctag gagacacagg  194460
ccagaatgtc cctgcagctg gaagtgaaat taaggttgtt cgcaaataag tggagaatgc  194520
ctggcccagg gcagccctaa tcatttacca tagtcctgtt ggtctcagaa aggcttaata  194580
atttatttat ttttttttat tttttgtttt tattttttgt ttttgagatg gagtctcgtt  194640
ctgtcaccca ggctggagtg cggtggcgcc atctcggctc actgcaagct ccgcctccca  194700
ggttcactcc attctcctgc ctcagcctcc cgagtagctg ggactacagg tgcccgccat  194760
catacctggc taattttttg tattttagt agagatgggg tttcaccgtg ttagccagga  194820
tggtcttgat ctcctgacct cgtgatccac ccgccttggc ctcccaaagt gctgggatta  194880
caggcgtgag ccaccacacc cagccagctt aataatttat aataactgaa tgttgtactg  194940
ttttctgcca ttatagaaaa ttatgttgtt ggagaaaaca aatacatac aaacaagcaa  195000
accttcccta cataaatgac ccaagtagtt aaagaataaa accaatttct ttccattaaa  195060
aagaaaagaa agccgggtgt gatgcctcat gcctatagcc tcagctattc aggaggctga  195120
ggcagcagaa ttgcttgagc ccaggagttg aaaaccagcc caggcaacat agcaagaccc  195180
tgtctctaca aaattaata ataattagcc aggtgtggtg gtgcacacct gtagccccag  195240
ctactcagaa ggctaaggtg ggaggattgc ttgagcccag cagtttgagg ctgcagtgag  195300
ctatgatcac accactgccc tccagcctgg acaagagagt gagacccat ctctaagaaa  195360
taaaagtagg ccaggcacag tggctcacac ctataatccc agcactttga gaggcggagg  195420
caggtggatc acctgaagtc aggagttcaa gaccagcctg gccaacatgg cgaaaccccg  195480
tctatactaa aaaatacaa aaattagcca ggcgtcgtgg cacatgcctg taatcccagc  195540
tacttgggag gctgaggaag gagaatcact tgaactgggg aggcagaggt tgcagtaagc  195600
tgagattgca ccactgcact ccagcctggg tgacagaatg agactccgtc tcaaaaaaaa  195660
aaaaagaaaa attttaaaat gtcctgagca accttgtttg taatagttcc aagtctcaat  195720
atccgtgtat ccctttgctg tagaacagat aaatattttg tggcatatct atataatgaa  195780
atactctgtg acaatcaaag tccaccaaca gcagccacat gcccaacaac aggaatgaat  195840
ctcacccatg taacatggca cagaaggagg caggagctag caacgtaagt ccatacagtt  195900
catgcaaagt tcaagtggac aaaattaaac tctctctctc tctctacata tatatatata  195960
tatatatata tttttttttt tttttttttt tttttttttt tttttgaga cagagtctca  196020
ctctattgcc caggctggag tgcagtggcg caatcttggc tcactacaac ctccacctcc  196080
cgggttcaag ccattctccc gcctcagcct cccaagtagc tgggattaga ggcatgcacc  196140
accaccccg gctaattttg tattttttgt agagaccggg attcagcaat tgcccaggc  196200
tggtctcgaa atcctgatct caggtgatcc acctgcctg gcctcccaaa gtgctgggat  196260
tacaagcgtg agccaccacg ccccgcctta aactgtattt tttaaggatg atacttgaat  196320
acgttaaaaa ggcgaggacc ttgaaaacac aacgctcggt aaaagaaacc aaacacaaaa  196380
ggtcaagtat tgcataattc catttgtatg aaatgtccag agcaggcaaa tccatagaga  196440
cagaaagtag attagtggtt gctagggtct gggtgaggga gagtggggag taactgctca  196500
tggggacagg gcctccttg ggggtgatga aaatgttttg gaacttgata gaggtgatag  196560
ttgcagaata ttgtgcatgt acctaaaggc actgaattgt gtaattcaaa gtgtgaattt  196620
tatgttatgt gaatttcacc tcagtttttt ttaaggtaag aaaatggtta ttacaaaatt  196680
```

```
caggatggta gttatatcac agtgtctctg gaaacttcca gggtatccac atgtcccttt   196740
ttattttatt ttattttta ttttatttga gatagggtct tgctctgttg cccaggctag   196800
agtgcagtgg caggatcatg accctctcct gtctcaaatt cctaggctca agctatcctc   196860
cctcctcagc ctcctaagta gctgggacta taggcacatg ccaccatgct tgactaattt   196920
tttttttttt tgtaaagtca gggtttccct gtgttaccca ggctggtctt gaactcctgg   196980
gctcaagtga tctgcccacc tcggcctccc aaagttccag aattacaggc atgagccact   197040
gccctagcct tctcctaatt gttgacatag gtagtagttg catgacattc actttgtaat   197100
tatgtgtttc aggaattctc aggcctgtgg gagctcttaa taaataaaaa agaggccagg   197160
tgtggtggct cacgcctgta atcccagcac tttgggaggc cgaggcaggc ggatcacgag   197220
gtcaggagtt cgagactagc ctggccaaca cagtgaaacc ccgtctctac taaaaataca   197280
aaaaattagc cgggcgtggt ggcgggtgcc tgtaatccca gttacttggg aggctgaggc   197340
aggagaatcg cttgaacctg ggaggcggag gttgcagtaa gctgagatcg cgccactgca   197400
caccagcctg ggtgataaga gcaagactcc atctcaaaat aaatgaataa ataaaaataa   197460
ataaataaat aagaggccgg gtgcagtggc tcaatgcttt ggaaagtgga ggccaacagt   197520
tggagagacc aaagcaggag gatggcttca gcccagaagt ttgaggccag cctgggcaat   197580
actagcgaga cactatctct ataaaaatgt tttaaaatta gccagatgtg gtggggcaca   197640
cctgtaatcc cagctactca agaggctgag gtgggaggat cacttaagcc caggaggaca   197700
gtgctgcagt gagctatgat tgcgccactg cactccagcc tgggtgacac agtgagaccc   197760
ggtctctata gataaatgaa tggatgaatg aggggggtcaa ggatcctcac ccggcttcca   197820
tttggaggga ggagtttggt tgagttcttg caaggttggt acctaggaaa tgcttgccag   197880
ttctggagcc cagacactgt ccctggacat gagaccaggt tctctgccct aggttatcat   197940
tgggagcatc ttcgaggtca tctgggctgt cataaaacct ggcacatcct ttggaatcag   198000
cgtgttacga gccctcaggt tattgcgtat tttcaaagtc acaaagtaag tctttggggt   198060
tcctggacat ttgtacaggg ggtgggggatg ggggacatgg tggggccgcc tccagaaagt   198120
tgggaaagtg agcctcgtgt ttcgagggct gactccgggg ccctgcctcc ccgcctggc   198180
ctgagtcctc gcctggcctc tgtcggcagg tactgggcat ctctcagaaa cctggtcgtc   198240
tctctcctca actccatgaa gtccatcatc agcctgttgt ttctcctttt cctgttcatt   198300
gtcgtcttcg cccttttggg aatgcaactc ttcggcggcc agtaagtcct tcacaggaat   198360
tccaactcct ggttccctgg ggtcaggctc agggaacaca cagtcccctc caccgtgcag   198420
gctgccttcc tcgtagccca gacacccatt gcggtcaccc aaatgggcag ggccctgggt   198480
accactcagg gttcctggg gacagagatg atggagacgt tcgtttcctt ggagatgaga   198540
tactgagcca caccctcaga gcaccccggg tggggccaac gtgaaatgtc tgtgtcctcc   198600
ctgcaggttt aatttcgatg aagggactcc tcccaccaac ttcgatactt ttccagcagc   198660
aataatgacg gtgtttcagg tacagcctcc acctggcccc acgggccaac acctctcagt   198720
gtcacagatg aaagtgcctg ctccacatcc aaggggcttc cctgaactcc tccttctcta   198780
cctggccttt tcacaccact ttgaaacaca gatttttatgg ttatcattat tcaattatgg   198840
tgaggccaac agatcaggag atgaatgtca ttggaaagat agtttgtggc tgggcacggt   198900
ggctcacacc cataatccca gcactttggc caggtacggt ggctcacacc tgtaatccca   198960
acgctttggg aagcccaggt gggcggatca cttgagatca ggaattcgag accagcctgg   199020
```

```
ccaacatggt gaaacccat ctctactaaa aatacaaaaa ttagccgggc gtggtagcac    199080
atgcctgtaa tcccagctac tcgggagatg aggcacaaga attgcttgaa cctgggaggc    199140
agaggttgca gtgagccaag atcgcgccac tgcactccag cctgggcaac agagtgagac    199200
tccatctcaa aaagaaaaa gaaaaaaaaa accactttgg gaggtcaaga tgggaggact    199260
acttgaggcc aggagtttga acaagtctg gcaacatag tgagactccg tctctgcaaa    199320
aaaataataa taataattag ctgggcatgg tgatacatac ctcctagcta ctagggcagc    199380
tgaagtggaa ggattgcttg agcccaggag gttgaggctg cagtaagcta caatcacacc    199440
actatactcc agcctgggcg agagagcaaa gccctgtctc aaaaacgaaa agaaagtttg    199500
ttatactcac agatcctcag agaaggagca caccatgcag gaccaagcag agaagcaaca    199560
gggtcaagca ggaagagaag gaaaatgtgg gcaagaggct tgattgtggt ttccatggga    199620
cggaatgggt gaggcagagt aaacagctcg agactggcta gtttggatca tttcagtggg    199680
ctctggggca gaggagctgt tcctacttgt ctaggacctg gccttggggt gattagggca    199740
ggtggatagt gctgggaaga taaggagggt ggttgggata tgggctggtt gggatattgt    199800
ttggtttgct tttaaaaagc ctgctcaggg ctaaattgtt tactacctct agggactggc    199860
tagtgctgga ccgggcagtc cctccagagt cagcaagacc ccagatgcat cagaataaag    199920
aaaataaaat gcgtggccag gccaatgagg tggttcatgc ctgtaatctc agcactttgg    199980
gagaccaagg cggaggatt gcttgagccc aggagttcaa ggctgccgtg agctccagcc    200040
tgcaccacag agcaaggccc tgtctcttaa aaaaaggca gagaaaaaa atggctaata    200100
cacccatcaa atctgaagat accttggtct catattccag ggtgatcaac ccaaagcaac    200160
ttctgcaccc atgtgggcgc attccctgag gcttgggact ggcccagccg ggaccttcag    200220
agcatctttg gtggattctt tctctttgag ggactgagag tgtatagaaa atgtgacttc    200280
actctctcct tctcctgggg aggtagtttc taaatgagac cccaagacag ggagttgaag    200340
aggaaaccttt ccatgaaggg aagttctgag ccccccacata agcgattttt ttttttttt    200400
tgagatggag tctcgctctg ttgcccaggc tggagtgcga cggcacgttc ttggctcact    200460
acaacctctg cctcctgggt tcaagcgatt ctcctgcctc agcctcccga gtagctgaga    200520
ctacaggtgc atactaccat gcctggctaa ttttttgtatt tttagtagag acgggtttc    200580
actatgttgg ccaggctggt ctcgaactcc tggcctcgtg atctgcctgc ctcggcctcc    200640
caaagtgctg ggattacagg catgagccac cacacctggc ccataagcga ttattaatag    200700
cactgatcgc tagtcatgta tctttagctc agaggttctc acccaaggac aagtctgtcc    200760
tccaaggaca tgtagcaatg tctgcaagca ttgttggttg tcacagctag ggagagggtg    200820
ctactggcat ctggtgggtg gagactagga atgctgctca atatcctaca atgcacagga    200880
cagccccaaa tagaataatc tggccccaaa tatcagcagt gctgaggctt agaaaccctg    200940
ttttagcaga ttcatgtttt tggagttctt taacatttac tttatcctca tgggatatg    201000
gatagaagga aggaagttgg atcttttta aaggagcatg taggtgctgt ttgaatatcc    201060
ccttggttct ttcagtatgc atcagcacaa cttgcgtctg tcaacaccta atcctttgcc    201120
ttggtctttc tctggtcccc tgctctgccc caaggaact gcagtccagc agtactgtga    201180
atttttgtg ccacaccta aaaggagcag ccgttggtgg ataaataccc cagctccctc    201240
accctcaggt gggatgaccc ctagagctcc ccagcaagac caagcccgg ttacctacag    201300
tggaaactcg cttgatcaca tactgtttac gttccaccct ctttccctt ttctcacttc    201360
tcctctcccc tactggtgct tcctgagatc acctcccaga caaaccactt gcacccgaac    201420
```

```
ccttgttcca gggtctgcct caggcagggg gaccccaaac gtgtccttgt gctacatttg  201480
tgctatccac gtagtagctt gtttaatcat caccatgacc acatgaggaa cacaggtaaa  201540
tattaaaatc ctgtcttagt ctgctcaggc agccataaca aaataccaca cactgggtgg  201600
cttatacagg aaacatttat tctctcatag ttctggaggc cgggaagtcc aagatcaaag  201660
tgttagcagg gttagttagt tcctggtgag ggccctcttc ctagcttgca gatagccacc  201720
ttcttgctgt gtcctcatat gtcaaagaga gagagagaga gttgtgatgt ttcttcctgt  201780
tctttttttt tttttttttt tgagacaaaa atctcaaaaa aaatctatt ttttttttag  201840 gcaaatcaca ttttttttgtc acccagcctg gagtgcagtg gcacaatcat agctcactgc  201900
agcctcaaac tcctaggttc aaacgatcct cccacctcag ccccttgagt agctgggact  201960
acagatgggc accagctaat tttttttaaat tttttgtaaa gatggggtct tgctatattg  202020
cccaggctaa tcttgaactc ctgggctcaa gtgatcctcc caccttggcc tcccaaagtg  202080
ctgggattac aggcatgagc catgcatgc ggtctcttcc tgttcttata agggcactaa  202140
taccatcatg aagtccccca tgacctcatc taaccctagt tacctcttaa aggccccatc  202200
tccaaatacc atcccatcat aggttagggc ttcaactcat gaatttggag gcgggcacaa  202260
tttagtccat aacaaatccc cttaatcaca tcaagtaaga cagagttaca ggagggtctg  202320
tgactcctcc agggtcccat tttcctagaa gccaggctaa gagccccacg acgcaggaac  202380
ggccctttct actcgcaaac aaagagaaaa gccaaggaga agccaacacg gagtctggct  202440
ctgcaaaccg ggcaggattg ttaaagacct cctgggctcg gggatggggt gggcggattc  202500
cggctccaca gctgcatctc caaggggccc gtggctgaga gggggttgg ctgtgtgttt  202560 cttcctcccc tttcagatcc tgacgggcga agactggaac gaggtcatgt acgacgggat  202620
caagtctcag gggggcgtgc agggcggcat ggtgttctcc atctatttca ttgtactgac  202680
gctctttggg aactgtatcc ttcatggaga gagagaaggg gacaggcctg gacctctggc  202740
agaggagagg ttgcaggggc tcaagggagg gtactgagag acccagatac ccagggccca  202800
agtggtgtcc caccagtggt tgcttttcct gactcagaca tttgcagaca ccctcctgaa  202860
tgtgttcttg gccatcgctg tggacaatct ggccaacgcc caggagctca ccaaggtgga  202920
ggcggtggga gaatgtttct ctggcaaagt taccacctgc ccatggcaga tcaggacggg  202980
ggtgggggtg gggtgggg tggggtggg gcatgggaa caggggttaga acttttgccg  203040 gggatgcacc atgcaaagag aaggcgcctc tccccccact cccagaaaca gactgtccct  203100
catcaagcaa attctacagc caagagggtg ggaaggggga aggcagtgag gtcgctgcag  203160
gaaacggatg gcaaactcaa ccaaaaggcc gtttacaggg agtaagcagg gtttccaagg  203220
aatggtgtag cccccaggct agtggatggg agagggagtg ctgttatggg gacccagtca  203280
gagctggggc caaggaaaaa gggctgccac cagccctggg accttagaga acccagaacc  203340
atggcaaggc acagatggag tggccaataa atgtccccac cttctctctt cctctggctt  203400
cccgctggag cctcccctta gccaaacgca gcatgttaag agctagcctc cgtccagcct  203460
aagcctctcc ccaaggaccc tattaagtta agattacatg taacaggtac agggtcttcc  203520
tctcagccct ggggtctccc tcagcattgc agccccacct ccagtgcctc gaggtattca  203580
ggacatgttt gtgaaattga accaaaccaa gcagacgttg ccaacgctcc atctgccggc  203640
cctggcagga gggagagaga gtttcccggc cccagctccc agtggaggga agcggaagtc  203700
tctgccatcc caagcacacg gccacaagcc tggccactgt ggagctggct ggcatggctg  203760
```

```
agccgagggc tgatccagcc atgagctcat ccaagttcca agagtccatc cttagggct  203820
ggtgcaggag ggtagcagaa ggggagggag aaaggccagt tcgtttatct cctgggaggt  203880
gtggacattc ctctccagat ccacattctt tctttcattg atcctacaag catttcttgg  203940
tcatttaata cgtgttttta atcctattca gtcctcatgg aaaccttagg agccaagttc  204000
tctgagcccc attttacaga tttcatcatt cagtaagcac ttaatgagca cctactgtgt  204060
gaccaaggcc ctggtctagg acttagggat taagcagtga acaaaaaaag gcaaaaatcc  204120
ctgcctccgt ggagcaggga ttcaagaggg gagacagaca agaaacaaga taaatttgta  204180
aacatacgta gcttgtcagt tggtgataaa cacaacagag aaaaattcag tagggaaagt  204240
cagggagagt tggaattta tgatgagatgt gtgtcgcaca gagaggttga gagacttgcc  204300
caaggccaca cagcagtaag ttgtggagct gggatttgaa cccaggccgt ctgggtctgc  204360
agcttgtgct cttaactgct gtgtaccagt tgcttgaatt tgggcatgtt ttatgctcac  204420
ttgggaacct gtgggaaatg cagattccag ggcccagcac tggttctata gattatttgg  204480
ggagcctgag gatctgcatt ttaggtgttt ctgaggcaga tggtccagag acctagctct  204540
gaaaaatgct gggaatggtg ccaggagggg tggggtggc cctatgagag cagggtggcc  204600
agccagatcc catctccatg ttgtctctga cagtgtcctg atctgaccat ttccaaggtg  204660
gtaaggttgc tccccgttcc agtgattcgg agcacagcgg gagagctgcc tgcaatggca  204720
tgacttttct tatgggcggg ttcatttctg gccattctt tctcgttgcc ttttctttgc  204780
tttttctttg ttggcttttc tgttttacga atgaggccct gcatgaaggc tgaagaagga  204840
tttaaagtcc aaaaacgtct ttttctgtat gtatttttaa aacctcttcc cccattctcc  204900
tcctctctga acctaaccac cagtgagcag cagcaccctg ggcagttggc tgtagcccaa  204960
gtgccctgct ctcctctccc caccgccttc ctgtcatggg ggctgggaat ataaattcct  205020
ctcctcattc tccttctggg ggctgttgac agtgcatggc aggggccatc ggatgccagg  205080
ctcttctgtg tgtgagggta gttggtgttt tttgaaagtt ggttcagaga gttcacatgg  205140
ctcagaaagc ctagtgagag gaaaatcttt gcactgcttt ccagctcatt aagacaggat  205200
gcagggccca ggcatggtgg cacatgcctg gaatcccagc actttgggag ccgaaatgg  205260
gaggatcatt tgaggccaga agttcaagac cagcctgggc aacatagtga gaccctgtct  205320
ctacaaaaaa aaaaaaaaaa ttaaatgtat acaggcatag tggcatgcac ctgtagtccc  205380
agttgcttgg gaggctgagg tgggaggatt gcttgagccc aggagttcaa ggttacagtg  205440
agctatgatt gtgccactgc actccaggct gggcaaccaa gggagactct gtctctgaaa  205500
acaaacaaaa gaaaaaaaaa taggctgcag gaaagtcttc attgtaggaa gagaagggac  205560
atttttattt tttgttatct ggctgtgtgt taaaataggc ttcataatga gttagatgtc  205620
aaacttatac acagagggga tagcaataca cttaaccaat agcaggtacc cattccaatt  205680
ggggagcctt ggttctgatt ggtcgaaata tttcaaatgt tgcccctggt cagcaacagg  205740
gtcagaagtg agtccccaag gcctagttca tgttttgtga acaaagattc cacgtgcctt  205800
ttaggacgag caagaggaag aagaagcagc gaaccagaaa cttgccctac agaaagccaa  205860
ggaggtggca gaagtgagtc ctctgtccgc ggccaacatg tctatagctg tgtaagtgcc  205920
cctaatccct gggatgctac cctggctcct gaacgtccac actatcccag gcacagattt  205980
gggaagcagt gggggtggtc cttgacagaa ctgagcttta ggaagagaca cttcttgtcc  206040
ttccacccac tttcactcaa taatatttg gttagcagct gttatgtacc cagcactgtt  206100
ctaacttctg gggatacagc attaacaagg aggaaaaaaa aaatcccacc tgtgtgtagc  206160
```

```
cattctagca agggaaggag tcaataaatt agataaataa gtaaattata tattgtgtta 206220
gaaggcgatg gaactacaga gaaagtaggg gagggaaata gcaaatgctg ggagtgaaga 206280
gagttgtgat tttaaacgaa gttgtcaggg aaggcatcac ctagaatagg ggtccccagt 206340 cccgggggctg tggactggta ccaggccgag gcctattagg aacggggctg cacagcagga 206400
ggtgaacagt gagcaagcaa gcattaccgc ctgagctcca cctgccgtca gatcagcagg 206460
cagcattaga ttctcatagg aacacaaaca ctattgtgaa cggtgcatct gagggatcta 206520
ggttgcgtgc tccttttaag aatcgaatgc ctgatgatct caggtgaaac agtttcatcc 206580
caaaaccacc ccccacacct aggtctgtgg aaaaactgtc ttccacaaaa ctggcccctg 206640
gtgccaaaaa ggttggggac tgctcaccta gaaggttaca tggcctgaag gaggtgaggg 206700
aggagccact gggggggcctg ggaagggca tcccaggcag agggaacagc ataggcaatg 206760
gccctgaggc aggaacatgc ctgatgtgaa ggaggcctgt gtgactagaa tcgaatagta 206820
agtgtgagga ggtgaaggca aggaggtgac aagcagatta cacagggcct tctgggtcag 206880
gggggaggac ttgggctttt gccctagcc aggtgggagc catggagggt tcttgagcag 206940
aggaggctgg gacctgactc agatgctcac agactcctag cattcagtgg ggagtagagg 207000
gtggagagca ggagtgggag gctgagatgt gggttggttc gcctgggtca tccatccaag 207060
ctacagtgcc tagcaatgct ctaagtcctg tgaccatgcc actgcaggaa agagcaacag 207120
aagaatcaaa agccagccaa gtccgtgtgg gagcagcgga ccagtgagat gcgaaagcag 207180
aacttgctgg ccagccggga ggccctgtat aacgaaatgg acccgacga gcgctggaag 207240 gctgcctaca cgcggcacct gcggccagac atgaagacgc acttggaccg gccgctggtg 207300
gtggacccgc aggagaaccg caacaacaac accaacaaga gccggcggc cgagcccacc 207360 gtggaccagc gcctcggcca gcagcgcgcc gaggacttcc tcaggaaaca ggcccgctac 207420
cacgatcggg cccgggaccc cagcggctcg gcgggcctgg acgcacggag gccctgggcg 207480
ggaagccagg aggccgagct gagccgggag ggaccctacg gccgcgagtc ggaccaccac 207540
gcccgggagg gcagcctgga gcaacccggg ttctgggagg gcgaggccga gcgaggcaag 207600
gccggggacc cccaccggag gcacgtgcac cggcagggg gcagcaggga gagccgcagc 207660
gggtccccgc gcacgggcgc ggacggggag catcgacgtc atcgcgcgca ccgcaggccc 207720
ggggaggagg gtccggagga caaggcggag cggagggcgc ggcaccgcga gggcagccgg 207780
ccggcccggg gcggcgaggg cgagggcgag ggccccgacg ggggcgagcg caggagaagg 207840
caccggcatg gcgctccagc cacgtacgag ggggacgcgc ggagggagga caaggagcgg 207900
aggcatcgga ggaggaagta agtggaggtg acctcgaatc cgcagaatga cggtaacatt 207960
aataatgaca acagccaaag tagcacgtgc tgtgtatttg tttataaaaa tatattataa 208020
aatgctgtat ttggccaggc gcagtggctc acgcctgtaa tcccagcact tgggaggcc 208080 gaggcggatg gatcacgagg tcaggagttc aagaccagcc tggccaagat ggtgaaaccc 208140
cacctctaat aaaaatacaa aaattagccg ggcacggtgg caggcgcctg tagccccagc 208200
tactcaggag gctgaggcag gagaatcgcc tgaaacagg gggcggaggt tgcaatgagc 208260
cgagatcaca ccaccgcact ccagcctggg cgacagagtg agactctgtc tcaaaaaaaa 208320 aaaaaagtg ctgtatttgg ccaggagcag tggctcatgc ctgtaatccc agcactttga 208380
gaggccgagc cgggcggatc acttgaggtc aggagttgga gaacaggctg ccaacatag 208440 tgaaaccccg tctctactaa aaatacaaaa attagtggtg gtgcccacct gtattcccac 208500
```

```
tactcaggag gctgaggcgg gagaatcagt tgaacctggg aggtggaggt aggttgcagt   208560
gagctgagat cgtgccatca cactccagcc tgggcaacag agcaagactc tgtctcaaaa   208620
aaaaaaaaat gctgtatgtt tttgttttt tgacacaggg tctcgcctgt tgcccaggct    208680
ggagtgcagt ggcagtcata gctcagtgca gcctctacct cccgggctca agccatccgc   208740
ctcagcctca caagtagctg ggaccacaga catgtgccac atgcctggct aattttgta    208800 gagacagtgt tttgtagaga cagggtttca ctgtgtttcc caggctggtc tcaaactcct   208860
gaactcaagc attccgcctg ccttagcctc cctaaagtgc tgggactaca gggttgagcc   208920
accacactca gcctaatttt tttacccttta gtagaaatga ggcctggctc tgttgcccag   208980
gctggtcccc aactcctggc ctcaagcaat catcccacct cagtctccca aagtgttcgg   209040
attagaggct tcacagatgg ggaaactgag agattgagtg agctcctcaa ggtcattcct   209100
ctaaccagtg tccttgaacc caggctctct ggcaccagag gccttgagca tttcagggaa   209160
actattaaga gaagcccac tgtcgtccag aattatatag tcttctgtgt tcttgctgtg     209220
tgacttttgc aaagtgactt catatctctg ggcctcacac aatggaaata gtgggatcta   209280
attgggtcat tgccaggatt gaatgaggta atgtatgcaa agggcctgga agagcagctg   209340
acacataata agtgctcggt aaatttagag catttttggc catttcagc caactctatt    209400 tacctaatgc tattctttgg aagtttgaaa agccactctg ttgggaggcc aaggtgggag   209460
gatcacttga taccaggagt tggagaccag tctgggcaat agaggcagac cccatctcta   209520 taaatataa aaaattaaac agatgtggtg gcatgcacct gcagtcccaa ctacttggga    209580
ggctgaggca ggagggtcac tggagcccag gatgtctagg ctatgatgag ctatgattgc   209640
accactgcac ttcagcctgg gcgacagagc aaggctttgt ctcaaaaaat aaaataaaaa   209700
ataaagaaaa agaaaaggca ctttgggccg ttagaattga agggagagca gagtttcaaa   209760
gctttggatg cagcgggatg tggtggctca tgcctgtagt cccagcactt tgggaggcca   209820
aggtgggagg atcccacttga gccccggagt tcaagaccag cctgcgcaac atagtgagac   209880
ctcacctttt aaaaataaat aaaaatgtta gaaagctttt gaggcatctt ccaggccagc   209940
aacttatcca ttcagaacca gcatcctctt tttcataacg acattttgta atactttcta   210000
gcagatgcta tagtgattct gcatataggg actcaacaac ttacccatta aaatagacat   210060
cgtagacatt gtcctattac aaattaacct gctcttagtc ctcttttata ttaccatcag   210120
ggcataatat tgattttttt aatgatgggt ttaagtgatc ctgttgtatg acatatgagg   210180
taggccagca cttctcaaaa tctaatgtgt atgtgaatcc ccaggatct tgttaaaaca    210240 caaattgtaa ttccgtaggg ctaaggactc agtggagcct gagattctgc atttgcaacg   210300
agctcccaga tgaggctgat actactggtc cagggaccac attttgagta atgagactct   210360
ggaggacata gtgaagtaat tctgatatgt acaccataca caaaatcacc atgaagtgac   210420
aggcacaaat gatggctaac tctgggttgt gtggacaatt caaccacat gaggggagtt     210480 gccagcagtg tcaagatgtt ccacaatgtt gaacacctct tggcaaagtt ccatatacaa   210540
aagagtctag tctttcttcc atttatttaa tagttgcatt gcaggaaaat gcaatgtata   210600
ttaaaaacat acaaaaaata tgttgtgttc ttatgtaaaa gagttaggtt taaactaaaa   210660
gcacaggatc aggtgcagtg gctcccacct gtaatcccag tgcattggga ggctgaggaa   210720
ggagaatcgc ttgaggccag gagttcgaga ccaacctggg cgacataagg agacctcgat   210780
ctctacaaaa gaagtttttt aattagccag gtgtggcggc aggtgcctgt agttctagct   210840
acttggaagg ctgaagcagg aggattgctt gagcccagga gttcaagatt acagtgagct   210900
```

```
atgattatgc cattgcattc caacctgggc aacagaacaa gtccttgtct caaaaaaaaa  210960
aaaaagaaag aaagaaagaa aaacccaaa caaacaagca aactaaaagc acaggtaatt   211020
acaagcaaga tttttcacct ctttgaggga cattagaaag tcatgaagag gaaagataa   211080 gtctttccca tatgggactg tcatgtacat ggtagggtat ttagtataac tgcctaccat  211140
tctctaagtg cctgcagtgc ccctcaatca ttatgttatt aggtttccac gtagttctac   211200
aacagttttc tgaaaaccat tgttctaggt cattctttcg cttcaatctt ctcctatggg   211260
tttatgcatt cattcagtta gtatttacta agtgcctact atattctaag ctcatgctgt   211320
gagttcagtc acacaactgc aagtgaagtg gtctgagaca ttctgagaaa tacgaccaag   211380
aaactgctcc cagggtctca gggcaggttt ccagaggagc aatctgagaa gggagtagag   211440
tgtttcagtc taacaacagc atgtgcaaag gccctgggt ggaccagaag gaggccagtt    211500
tgcaggacat gactagtgac gagaaagtga caaagaaatt gaaggtgcat tgatgagact   211560
ctggggctgt cagtcactca ggggaatgag agatcaaaac gggagtttag gtggaataaa   211620
gtgtttacca cagcactctc tgtatagtaa agaccaatga agagccaggt acaggccagt   211680
gtgatggttc acgcctgtaa tcccagcact ttgggaggca gagacaggtg gatcacctga   211740
ggtcaggggt tcagaaccag cttggccaac atggcaaaac cctgtctcta ctaaaaatac   211800
aaaaaattag ccaggcgtgg tggtggacgc ctataatccc agctactcag gaggctgagg   211860
cacaagaatt gtcctgcgag gcagaggtta cagtgagctg agatcacacc actgcactcc   211920
agcctgggca acagaacaag actctgtctc aaaaaaaaaa aaaaaaaaaa aaagccaggt   211980
acagtggtat gcacctgtaa tcccagctac tcaggaggct gaggcaaagg attgcttgag   212040
cccaggagtt cgagaccagc ctgagcattt agagaatggg aggccagtat actaaatacc   212100
ctaccatgta caagacagtc tcatatggaa aagaattatc ctttcctctt catgactttc   212160
tagtgctcct cacacaggtg aaaaatcttg cttataatta tctgtgcctt tagtttgttg   212220
gtttatttag ggttttgttt gtttttttt tttttttgag gcagggtctt gctctgttgc     212280
ccaggttgga ttgcagtagc attgctcatt ttagagatga gcaagacctc atgtctaaaa   212340
aaaaaagaaa gaccaatgat tattaattac tcttgctatt attactaata ttactgttat   212400
tatcagcctt attaacagat ctactgttat tgaaggaggc agagtgacag ggacaaaatg   212460
tctctcccta acaatatgcc aggaagagtt tttgaaagac aacagtaaac attggaaact   212520
acaagagcag caaagcctgg ttgtgaaagg caaggacttt ggggcaggca gtcacattcc   212580
tgccctatca cttccaggct gtgtgacttt cagaatttca ctcctctctg ggcctccatt   212640
tcctcatcta taaatgaag ataagaatag tagctacctc cttctctggg tataagattt      212700
aactgagccg ggcgcggtgg ctcatgcctg taatcccagc actttgggag gccgaggtga   212760
gcggatcaca aggtcatgag ttcaagacca tcctggctaa tatggtgaaa ccccatctct   212820
actaaaaata ccaaaaaaaa aaaaaattag ccgggcgtag tggtgcacg cctgtagtcc     212880 cagctactcg ggaggctgag gtaggagaat ggtgtaaaac ccgggaggcg gagcttgcag   212940
tgagccgaga tcgcaccact gcactccagc cggggagaca gagcgagact ccatctcaaa   213000
aaaaaaaaaa aaaaaaaaaa agatttaact gagttagtac gtgtaaaatg ctttgagtgg   213060
ttcctggctt ataccaagag ctcaataaat gttagcaatt ttttgtagca ttttggggtc   213120
tcactatgtt gccaggctg gtgtcaaact cctggcctca agaaattctc ccactttggc     213180
ctcccaaagt gctggattta cagacatgag acaccatgcc tggccatgtt agctattatt   213240
```

```
aatatgaata ttattaagta ctcaatgaat gctattttta gcagtaatag taagcactca  213300
ggaagtgtca gctaatactg ttagtaatac tctcatcaat aaacataaaa agcaataagg  213360
acccagcttg cccaaatccc acagatggtt cctgctccct ctcttcttca gaggaagaaa  213420
ctatctcccc actttcaccc ccatagcctc agctggccag accccattc tgaaccaggg   213480 gagtactgct aattccatta ttaatagaca catcaaacaa tctggccggg agagacatta  213540
ttcatttggc tgataaagag gttctaaggc tcttttggaaa taaaagttca tgaagattca  213600
tgcactttaa gagaaaaaaa ttcaagatca gtcattcatc tgctttaaaa aaagtggcaa  213660
agataaaact ttatttgaga atataaaata ataaaaagac attttcgttc tctgttgtga  213720
caaagccagt ggccttcgga ggtctgcctt gtacatttt cctcttcttc agtcattcct   213780
tgaggctttt tgcaaacgta ccctgtgttt ttcattctcc agcatattga aatttttttt  213840
tttttgagac atggtctcgc tttgtcatcc aggccccgga gtacagtggt acaatcatgg  213900
ctcactgcag ccttgacttc ctgagctcag gtgattctcc cacctcagcc tcccgagcag  213960
ctgggactac aggtgtgcat gaccatgcct agctaatctt ttgtatttt tgtagacaca   214020 gggttttgcc acattgccaa ggctggtctc caactcctgg gttcaagcga tcctcccacc  214080
tcagcctccc aaagtgctgg gattacagga gcgagctacc ttgccaggcc gatcatattt  214140
ttttcctttt tattcacttt gtcttctcct cattcctacc ttcatctgtc tttcagtggc  214200
tcactccagt gaaaagtgga ctgacgcaca ttctatttca tataattcaa tggctgctgg  214260
ccccagatcc cccataccag gtggccgagc ccagtggccc tgcagggtgg acaaaatgag  214320
ggtggaactt tcccagactg tcagtaaaaa tctatgaagg acagagcttc tgcctctccc  214380
ttgcaaccag gcagtgcctt ctcccaggcc tatctgcttg caagggaac ttttgccaag   214440 acctgctcca ctctagaatt cttatctctg ctgttcgcat cctaattcca cctgcatctg  214500
tcaccatgac aacctgctcc ccaaaaggaa caggaagaga gatgctggac ttttgagctc  214560
cacagtttat cctgcatggg ggtagggagt ggttaattac ttagcactct aattcttacg  214620 gtaccccaa tgggcccaag ttggtttttt taaaaaaaa cagtcttgct ctgttaccca    214680
ggctggagtg cagtggcaca atcatagctc actgtagcct caaactcctg gactcaaatg  214740
atcttcccac ctcagcctcc caagtaactg gaacaacagt ctcgtgcaac tacgcccagc  214800 taatttttt ttttttttt tttttttaga gatgggtct cactatgttc cccagactga     214860
tctcaaactc ctgggctcaa gcgatcttcc ttcctcagcc tcccaaagtg ctaggattac  214920
aggcgtaagc cactgtacca agctgcccca ttaaagcttt gaacaccaga gagcccagct  214980
cagctgtttt ccagctgggt aactctgggt aactttgcct ctctgaacct cagtctcctc  215040
ctgtgtgaaa tggggctgat cactataccc atctcggatg gtggtagttg cagggattaa  215100
atgagttaat acgtgaggtc cttaggacag ggggtgggga cacgagataa gcaataaaca  215160
ggaactgctg ttattatcac ccccacataa tccgatctca gggtctgagt gtgcccagg   215220 caaggtgtcc acagccctct gcagaaggat gcccaagtga tcagctggca caagaacgcc  215280
acgcacagca ggtgttatgc aactggccac ctattccagg cagaggatgc cagatcccca  215340
gggagaaggg ggtaggggtg cagcttcaaa gttttctgcc cctttgagt tctccttgga   215400 gacactttgg aaatgaaacc tcccggaaat tgatattagg cctctgcagg ctgagcttgt  215460
taaaatttcc caacaaacag agccaacaga cgctctacaa ggaagcaaaa acaagacaaa  215520
acacattggc agacccttt ccatctgctc ttggtagatg gtattcctct aagaaaatgc   215580
cgccacgagt ttctccatgg cttcttgagc tggtggccaa aggatttagg ttctctttga  215640
```

```
aattataact taactgggcc tgctttatgg cagggatatc actctctgaa atgtgtatat   215700
atatgtgtat gtatatatat acacatatat acacatatac atacacaggg ccaggcgtgg   215760
tggctcacac ctgtaatccc agcactttgg gcggccaagg caggtggatc tcttgagccc   215820
caggagttca ataccagcct gaacaacata gtgagaccct gtctctacaa aaattaataa   215880
aaataaccag gcatggcagt gtgtgcctgc aatcccagct acccagggtg ggaagatcgc   215940
ttgagcccag gagttaaaag ttgcagtgag ctatggtcat accactgcac ttcagcctgg   216000
gcaacagagc aagaccctgt ctcttaaaaa tatattatta ttattataca cacacagaca   216060
cacacagaca cacacacaca ttacagatga tgagaaaata ctctcagcca ggttttcatg   216120
atacacaact tctcaaaaag catcacaagc aggttagaat tagggatttc tttgtggact   216180
gtccaagatg ttgaggaaat attggtttag aatttacctc atttaggcca gaaatggtgg   216240
ctcacgcctg taatcctaac actttgggag gccaaggcca atggatctct tgaagccagg   216300
agttttagcc tggccaacat ggcaaaatcc tgtctctact aaaactacag aaaaaaaaaa   216360
aaaaattagc cgggtgtggt ggcacaggcc tgtagtccca gctactctgg aggctgaggc   216420
aggagaatca cttgaacctg ggaggcgagg gttgcagtga gccgagatcg tgcattacac   216480
ttcagcctgg gtgacagagc aagactccat ctcaaaaaat aagatagata agataaatat   216540
atataatata tatgttatat atataatata gaaactacag aacaagtgat ctttgtatgt   216600
ttccagaata taacagcggg acaggcatag gatagacgtt cccattgcaa aagggagaaa   216660
ttggaaggga taaagaggtc accagtccta agcaagtgct aaatccagca agacaaatcc   216720
cattaggttt caaggcctga gaataatcct cggtgactct cagctcatta acatacttag   216780
ttctcagagc cagactcaat gaggttacgg cccgcatgtt atgggtcagg aactgaggct   216840
aagtaactca ctggagatta tgtggtaaag aaggtccagg atcattgctt cagtctccag   216900
gatatgggga aggttctact cctgttatcc caaattttaa aatgtgggaa ctaaggctca   216960
gagaggttaa gcaaatcaca cagggttgca cagctagtga tgttgctgag atttccctgt   217020
gtgtagtggc tcatgcctat aatcccagca ttttgggagg ctgaggcaag agggtcgctt   217080
gatcccagga gtttgagacc agcctgggca atatagtgag acctcatctc tacaaaaaga   217140
aaaattaaaa agttagccag gcgtggtggc aggcacctga agtcccagct actgggaagg   217200
ctgaggtggg aggattgcct gagcctggga ggtggcgatt acagtgagct gagatcgcgc   217260
cactgcacta caacctgggc gacagagtga gaccctgtct caaaaaaaaa aaaaaaaaa   217320 gacattgccg agattcaaac ccaggtcagc ctgtcttctg aaatgtccct ctatgaccca   217380
ctcacaaaac tgagaaggca gaaagttgct tggacctgtc tatttcccct gtgcagtctc   217440
agagaaacag tggaactgcc tcggtttctc cttccgggaa gtattcatag aagcatccca   217500
cttacctact ttggtctgaa aataaattag cttgtctctc ttccacttac taaaaacacc   217560
gtgggttttt gcaagttaaa atgcaaaaat aaaatgagga gaatggtgct ggtagtttag   217620
ccagtgggaa gccctctggg gaaagccagc cttttattta ttacttattt atttatttat   217680
tctttctaga tagattttatg ggaaaccagg gctgtgttgt ccaggggtct gtagtccaga   217740
aggcatcaga tgggctacta agtgagtctt tgtccacctg tagatggcaa gaggcagggc   217800
ccaggtgtcc atggcttgga gaggcagggg ttgatgggag gtttgaggct gtgggatctc   217860
tcctggggcc tcagtatcct catctggata atggggacat tctggccagg cacgtggct   217920 ctatatatcc agcacttagg gaggcctata atcccagcac tttgggaggc tgaggtgggt   217980
```

```
ggatcactgt aggccacgag ttcaagcagc ctgggcaaca tggcgaagcc ctgtctctac 218040
tgaaaataga aaaactagct gggtattgtg gtgcacgctg gtaatcccag ctattcggga 218100
ggctgaggca cgaggatcac ttgaatccac gaggcagagg ttgcagtgag ccaagatcct 218160
gccactgcac tccagcctgg gcaacagagt gaggctctgt ctcagttaaa aaaaaaaga 218220
aaaagaaaa agaaagaaag aaaagaaaa tgggggtatt catttatcat ttgacagtaa 218280
gtttacccag cattgactgt gtgagaggcc ctgtactagg cagtgaaaac tcagctaaga 218340
ataagaaagt taaaaacaag ctgggcattg tggtttacgc ctgtaatccc aacattttag 218400
gaggccgagg aggaagaatc acttgaggcc aggagtttga accaccctg gcaacatag 218460
tgagacgcca gtctctacaa aaaattgtaa aattagccag acatggtggc gtgagcctgt 218520
agcctcagct acctggaggc tgagatggga ggatcactgg agcccagaag ttcaaggctg 218580
cagtaagcta tgatcctgcc actgctctcc agcctgggca acagagtaag accctgtctg 218640
aaaaaaaaaa aaaaaagag gccaggtgca gtggctcaca cctgtaatct cagcactttg 218700
ggaggctgag gtgggtggat cacttgaggt caggaattcg agaccagcct ggccaaaatg 218760
gtgaaacccc atctctactg aaatacaaaa aattagccgg tcgtagtggt gggcacctgt 218820
aatcccagct actcaggagg ctgaggcaag agaatcgctt gaacctggga gccagaggtt 218880
gcagtgagcc gagatcacgc cactgtacga cagagcaaga aaaagaaag aaagaaagaa 218940
aagaaataag atgatgggga gttgtggaaa cctgtccatg gcacgtgaa ggtcttgacc 219000
tctgaccaag aagtgaacag gctcctctca attccaggca ctgcagggat ctgggacatg 219060
acttctccat gaccaaactg tacccttcc tttctttt tgttttttg gtgacagggt 219120
ctcactctgt cacccagact ggagtgcagt ggggcgatca cggctcactg cagcctcaac 219180
ctcccaggct caagcaatcc tcccacttcg gcctcccaag tagctagaac tacaggcaca 219240
cagcgccacg cccgtcaatt tacacatttt ttgtagaaat agggtctcac tatgttgccc 219300
aagctggtct tgaactcctg gccttaagca atcctcctgc ctccgcttcc caaagtgctg 219360
ggattacagg cgtgagccac tgcgcccagc ccaaattgta ctcttgaaag atggaatctt 219420
agctaggatc ctgaactgtt gccttttatc ctaaatcagt tgttggttct ttttcattca 219480
cttgccttcc tcagagagaa ccagggctcc ggggtccctg tgtcgggccc caacctgtca 219540
accacccggc caatccagca ggacctgggc cgccaagacc cacccctggc agaggatatt 219600
gacaacatga agaacaacaa gctggccacc gcggagtcgg ccgctcccca cggcagcctt 219660
ggccacgccg gcctgcccca gagcccagcc aagatgggaa acagcaccga ccccggcccc 219720
atgctggcca tccctgccat ggccaccaac ccccagaacg ccgccagccg ccggacgccc 219780
aacaacccgg ggaacccatc caatcccggc cccccaagaa ccccgagaa tagccttatc 219840
gtcaccaacc ccagcggcac ccagaccaat tcagctaaga ctgccaggaa acccgaccac 219900
accacagtgg acatccccc agcctgccca cccccctca accacaccgt cgtacaaggt 219960
gagaccctct gctctcacat cactgggcag gggacctggc gtccctggag ccagaggctc 220020
tgctgagtga ccctggactg tgaccccatc tctctggcct cagtctcctc ccctggaaaa 220080
tgggcatagg cgtagtttcc tacccacag ggctgtggag ggttcagtga gataattgt 220140
gcacagtgcc tggcacgggg ttgtgttcag tcgggttagc aatatcttct acgtccttcc 220200
ttcccaaggg gagccaggaa gccaccccat ttgaggagca ataggtcct ctgatggaag 220260
cttgaggggg tcagatgatt gattctctcg gcccagcact gtccaaaaga aatgtaacac 220320
aggccacatg caaatgtcag tttaaactct ctagtcgcca cattaaaaaa ggggccagat 220380
```

```
gtactggctc atgcctgtaa tcccagtact tcaggaggcc gaggtagagt gagccaagat    220440
ggcacctctg tactgcagcc tgggtgacaa agcgagactg tctcaaaaaa aaaaaaaaaa    220500
aaaaaaaatg gtgaactgct gggtggatta tgtcttaagt tcatctagtg tcagttctat    220560
gtgagagatt ttcatgagtt tgctggataa aggctttcca tggtcctgag acctaagatc    220620
ctaaggtctt gtcactgtgc ccattttata gatgtaggga ctgaggctca gagaggctca    220680
gcctgcccgt gggcacataa gcaggctggg ctgcagaatg gaagctccag aggctgatgg    220740
ctcctccccc tgagtcaaga gagggtgct aatgggggca tgccatgcag tttatgggag     220800
gtctcagtat ttctatctgt tcagtgggtc tcttggcact ctccctacct gcctgcaagt    220860
gagggtgtga aggtccaacg aggatagggg caggtctgtg ttaatatccc atgagggccc    220920
caccgcactc aaggctatag agtggttgag agcaggctct cggggccag gccgcctggg     220980 ttccaaatgc cagctctgcc acttcctgct gtgtgacctt agacaagtca ctttacttct    221040
ctgtgcctca atttcctcat ctgtaaacag gagatcagaa tatatcaacc tcagggctat    221100
acaagggttc agtgatgtca taagatgcct ggtatataca gcaggcactt tagaaatgtc    221160
agccgcttct tgcctgccct gggagtacac aggagttccc agagacttgt gggaaattgt    221220
ggagggagcc ctgtgttggt tcttgtccca acagtgaaca aaaacgccaa cccagaccca    221280
ctgccaaaaa agaggaaga gaagaaggag gaggaggaag acgaccgtgg ggaagacggc     221340
cctaagccaa tgcctcccta tagctccatg ttcatcctgt ccacgaccaa cccgtgagta    221400
tggcccccag caagggcagg gggggcctgg ggctcccacc agggtggcgg aagtcaggcc    221460
agatagaggg caatgagtga gtgttgacca ccatgagtcc agggatacct ttgaacaagt    221520
tgaaaatgga tgctccttcc gtaagtcagg taagatgatt tgtcacaata tactttgttg    221580
gaagagaccc ctgtcctgcc atccactaga aaatcattgt tatttatgac aataaataaa    221640
caaatttgtc ataaataaac aaataaattt gtcctaaaca acaaataaat ttgtcataaa    221700
taaacaaatc ttcactgtga tgtaagaggc accccttag aaatggctgc cttgtgcagt     221760
acacagcctg aacaactgca cgtggcagcc ctaggacctg aactctgttt ctaacctaga    221820
ctctgtaagg gtttagattc tgggcggata gtgtctgagt tccatggcct tctgtcttgg    221880
gcatctttga aatggataga ctatttaggg gagaaattta tcccatgaat gtcgtagtgg    221940
ctcggaggtt gttttagaat tgaatgtctc ccagggatat ttcttgaaag cctgaccgct    222000
caaaatgctt cttgacaatg aaggatcatg tcagataaga tggggagaa gctgctttct     222060 ataatctgcc tcttggcaac tcaccctggg tagtaataaa taaaagtacc tttaaagtac    222120 tttttttattt agttgactta tcgattttac taaggaaaca cttatgtggt atctactcag    222180
tgccaggcac tgttctgagt gccttaaaat ttttttttaat ttctctgagg ttgttactat    222240
gcttagctcc attgacaga tgaaaaaact gaggtccaga gacgtgaatt cacctgccca     222300
aggtcacaca gcaagccagt gggagagctg gagtttgagc ccagacactg gctctagcct    222360
ccttgttctt aaccactcag ctctgctgcc attcacacaa ccttatgaac tatttattat    222420
tggctccact tattaagagg ttaactggca catcccattg gcacattcaa ggctctgata    222480
aggcctgcaa ttcataattt caataactaa cttttggag ccctatcat gagccaggca      222540 taaattaagt cttgggtctc atgattttgt gaagtaagca ctagtattac ggctatttta    222600
cagatgaggg caccaaggca cagagggac aagtaacttg cccaaggtca cacagctaat     222660
ttttaaaaag aaagaaagaa atctacttaa cccatagatt cacaatattg tttggccctg    222720
```

```
ggacatttaa tatcgaaaag ccttttatc tcctacagaa ttaaggaccg tatttcttca 222780
acctagcttg gggatcaaga tacttcaaga gggtcgtttg ggagtgatag gaactttgct 222840
aaacagggca tgtgaatgtc ttctctcacc gaggtcccct ctgccttctt ggggttccag 222900
gacccagaga gggcccccac ctggaggagt ttaatagttt gttgtgtagg aggccttggg 222960
ggttggagat ctcagtagtg gtaggtaaca tgagattatg gaagaaaagg gtttgtgagc 223020
ctgtggtctg agtggacctc tgcacgccca tctgtctcca acagccttcg ccgcctgtgc 223080
cattacatcc tgaacctgcg ctactttgag atgtgcatcc tcatggtcat tgccatgagc 223140
agcatcgccc tggccgccga ggaccctgtg cagcccaacg cacctcggaa caacgtgagt 223200
cccacagagc acacccttc ctagcctggc tgctctgcct caggccactt tctcctgcat 223260
ccaaaatgct cataggtagg gtgggatgtt gggtcaccc ctaggcatag cccttatggc 223320
tgctggttga gaggggaagc tctgattcct tggggatgct cttgggagca agacattcct 223380
tgaggcagtt tctctgtgag cctggtgggg tggaggtggc ccagagtgac tggggctgaa 223440
aattgctgga ttctctaatg gaggcgtgag actagcagga tatggatgtt gcacattctc 223500
tacatggaat aggggggtta ctggggcagg ggcggtgctc agaggtggtc ccctccgcag 223560
tagacatttc cctttgtaca cgaagctttg aaagaaacaa ctatttggct cagaaacaca 223620
gcctaagctt ttggttttta tgaaagcaag cccctttgcg gatggtgggt ctgttgacaa 223680
cccctgttaa ttgagcactt gctgtgtccc aggaagaaac tcagcatgca gtatctcatt 223740
taatcctcac aatgcgcccc cccaaccccc cgcccaggca tccccatttg acagatggga 223800
aaactgaggc tcagggaat gagagagtgg taagtggcct gtccagggtc acacagcaga 223860
attccaactc tgcatccccc aaagctccca ctgcttcccc caactgtctg catttactaa 223920
tcacctactg tatgctacgg atgggtgtgc atagccccctt tgagtcctga caagcaggaa 223980
tgagtgcatg cttgtggttg agatggggaa accgaggcac caacaggcaa gggcgtgcct 224040
cagtcatggg ctgcgggcag aggcttgacc ccagggcctg gtagagggtg gactggtggc 224100
tcctgtttcc ctccccagct ccctccccca accttccct cccaacccag agccaaaaaa 224160
gtgtgttttc tgctggtcca aggctctgct gccctggcta agtaggttag gacccaggca 224220
aagctggcga gccccatccc tcaagcccgc ccacagctta ccatgcactt tcccttcctt 224280
cccaggcctg gcaggccccc ctggggacct gatgggggag atggaaggaa ataattagaa 224340
cgcagctcct ggaggaagct agagccagtg ctcagcctcc tcacagtccg cttagttgct 224400
tcccgcagcc tggtttcccc caggggcctc caggagccag gcgtggggag gaggtgtccc 224460 tggagggggtc cacaaacccc ctgctgacgc gaggatgctg aagaaggcgt tgccttcggc 224520
agggagggca caggcatgga tgatccaggg ggcacggcag ctcccagggc tgaagggaat 224580
ctaggcagtg ctcagaccag gccccaggga ctgtttgcaa agagcgttca gctcccggc 224640 cccctccctc gtccatctcg cagtcgaaac ttctctacaa gaacactgtg gccccataac 224700
gttcacacca cgtaaccacc atccagggca agaaatagaa caaaaacgcc ccacgcggca 224760
tgtgcctcct cgatccccca ccccaccgc cttctttccc tctagagctg ctggggacac 224820
tgtctggaga cattttggt tgtcacgaca ggagggggga ggtgctcctg gcatctggtg 224880
ggtggaggcc agggatgttg ctcagcaccc gccgatgccc aggacagccc ccactctaga 224940
ggatgatcca gacccaaatg tccacagagc ccagcttgag aaaccctgcc ttaccggtaa 225000
ccacgacccc agcttctgga atgagcgttt ttggcttctc tcttttcccc acctgcacag 225060 gcttttttt tttttttttt taagagacaa tgtctctctc tgtcgcccag gttggggtgc 225120
```

-continued

```
agtaacgtga tcatggctca ctgcagcctc aacgtcccgg gctcaagtga tcctcccacc 225180 tcagccccc  aggtagctag gaccacaggc atgcaccacc acacccagct aattttttaaa 225240 tgcttgtaga aacgggcctc gctatgttgc caggctggtc tcgaactctt gacctcaagc 225300
aatcctccct cctcagattc ccagagctct ggaattacag gcatgtaatt ccaattctta 225360
catgcctgta attggccaac actggccaat tcttaaaaac tgaatttatg tttgctcttc 225420
tgtaacattc aataaatgag acacttctat gcttcgcatt aaatgagtac atgttgcttt 225480
tgcaggattg atgggcattc tttttttttt ttttttttt  gagatggagt cttgctctgt 225540
cacccaggct ggagtgcagt ggtgcaatct tggctcactg caacctccgc ctcccgggtt 225600
taagcgattc tcctgcctca gcctccagag tagctgggac tacaggcagg cgccaccaca 225660
cccggctaat ttttgtattt ttagtagaga cggggtttca cactatcagc cagactggtc 225720
tcaaactcct gacctcaagt gatccgcccg ccttggcctc ccaaagtgct gggattacag 225780
gcgtgagcca ccacgcccgg tcaatgagca ttctttatga tgctgttttg agatttactg 225840
tgtggcatgg gatgtgttat ccatccctg  ttgacagatg tttgggttgt ttctaagtgt 225900
gaatactgtc cccatgccac gcccctcaac atgtttcctg agtcacctgg acagtaattt 225960
ctccaggagg ccagatgcag tggctcacgc ctataatccc agcacttcga gaggccaagg 226020
tgggagcaat gcttgaggcc aggagttcaa gaccagcttg gcaacatag  tgagaccccc 226080 acctctacca aaaaaaaaa  aaattttttt ttttttaatt aaccgagcgt ggtggtgcac 226140
acctgtggtc ccagccactt gggaggctga ggtgggagga tcacttgggt ctggaaggtc 226200
aaggctgtag tgatccatgt tcataccact gcactccaac ctgggtgaca gagcgagacc 226260
ctgtctcaat aaataagaat tcctccaggg tataaaccaa aagcgaagtt tctagagcat 226320
ataatttgca agtggttggc ctcagtaaat gcagcttgaa tgtttattgg acaataaaca 226380
cagtgaccct ttgggaggcc aaggcgggtg gatcacctga ggtcaggagt ttgagaccag 226440
cctggccaac atggtgaaac cccgtctcta ccaaaaatac aaaaattatc tgggcgtggt 226500
aacacacaac tgtaatccca gctactcggg aggctgaagc acaagaatca cttgaaccca 226560
ggaggtggag gttgcagtga gccaagatgg cgtcactgca ctctagcctt ggcgacagag 226620
cgagaccctg tctccaaaat atatataaat aaataaaaat aaacacagtg ggccgggcac 226680
agtgggccgg gctcgcacct gtaatcccag cactttggga ggccaaggtg ggtagatcac 226740
gtgaggtcag gagttcgaga ccagactggc caatatggta aaacctggtc tctactaaaa 226800
atacaaaaat tagccgggcg tggtagcatg cgcctgtaat cccagacact tggaggctga 226860
ggcagaagaa ttgcttgaac ccgggaggca gaggttccag tgagccaaga ttgtgccact 226920
gcactccagc ctgggtgaca gagtgagaca ccatctcaaa aaaaaattaa aaaataaatg 226980
aacgcagtgg cccttgcacc agtagctcat gggaactcct gttcttccac atccttgtca 227040
acacttggta ctgtcgactg tttcatttgg ccgatctgct gggtgtggag tgagatctta 227100
ttggggttgt gcttggcatt tccctgtaat gaatgagatc aagcactttt ttggattaga 227160
ctgagccaca ggaaataaca ttttcaaata gatgaaaaag atctaagtat taggaatact 227220
tgaacctaat ttattggtct tttgatttcc tcttgcacag cttattaaga gctccagaat 227280
tagattcacc tgacccccac ggcctgccct ttcccagctc cctctcttcc ttctttcctt 227340
ccattcattc ctttagtaag tatttgataa gcaactacta tgtgccaggt actgagcgag 227400
ccagggagga ttgacagggt atgagatggt ccctgcactc ccagagccca caaaccacca 227460
```

```
ggcctttgac caggctgtgc ccactgcctc gtgcacctga atactctcc caccaccatc  227520
ccctctgccc acccaggtct ttcaagccaa tccccttgca ccagcccctc cctccaggaa  227580
gtcacctcac cctgacccca ggcactctgg tctctgattc ctcttcaagc accacatata  227640
acaggaatat aagttataac cacacagatc acagagccca gctcctccag acccagtac   227700
agccccaact gttgatgcat tcattcaaca aacatttctt gagcacctac tgtattcctg  227760
accctgtatt ataagctgga gacgccatgg tgacagacag acatccctgt ccttgtgggg  227820
ctgacatttg ggtggggag atggacaatg agattatcag taactacaac aaatgttcag   227880
ggagtgataa gtggccgggg gtgtggtggg cagagggaag gagagacttc gtaaagagga   227940
tctcaagcac caggagatgg aatttaaaca gccggtcagg ggagtcctca ctgggaaagt  228000
gttatttgag ctaagtcata aaggaggaga aagacggaat caaatgggat gtggggaaa   228060
gcattccaga gagacagaac agcctgtgca aaggccctga ggtggaagca tcttgggaa   228120
caaaaggaag tgagcaaggg agagaatgag aggaagtgag ggcagggagc tgaatggtca  228180
gatcgtgcag gggcttgagg gcctcgggga ggactttgac ttttatccct gaatgaggtg  228240
ggagccacgg aggattgtaa gcaggggaag gatgtgcctg acttctttgg tgttcacagc  228300
gccctctggt ggccatgttc agtaatgctc agcccttgca gcttctgggt ggatctgatt  228360
tttttttttt tttttttttt agacagtctc tgtctcccag gctggagtgc agtggcacga  228420
tctcggctca ctgcaacctc cgcctcccac gttcaagtga ctgtcacgcc ttggcctccc  228480
aagtagctgg aattacaggc acacgccacc atgcccagct aatttttttat atttttagta  228540
gacacggggt tttgccattt ggttaggctg gtctcgaact cctgacctca gtgatctgc   228600
ctgcctcagc ctcccaaagt gctgggatta caggctcgag ccaccgtgcc cagccggtgt  228660
ccaccccatg tctagcacca gccagacact gtgccggcgc accctcatct tcaggcctgg  228720
gtgacaccag aggtgtgcta tggtgtgtcc tggacagggg ctgggccaga ggacattgct  228780
cgtccaggca gaaacatcag gcctggggag gggcacagga aaaatcaacc taccctggca  228840
ggggcctggc cttgaagcag gaagagatgc cgtggcagga agttggcccc agtgtttaaa  228900
aaaaccacgt agcaactatt tctcgcccag gatgcccagg aaagcaaggg tactggggga  228960
ttagatccat caccaagaag gatacagtca gccctgaact tctctggggc cgcttctaat  229020
ccactacagg gcttggggca aattttaaaa ggtacccttc ccgtgggtta gcgaactggc  229080
ctagtacagt gatttttttg ttaggatttg ctgccatctg ctggacaatt tcattcacaa  229140
catacaaatc tgcagtatga aaagagatgg gaggggccct tgtgcagtgc acgccctgcg  229200
caactgtata tagcagctgt gtttcctctt ctgggtagaa actctgctcc ccagtaggcg  229260
atcgttagtt ttaccggggc tctgctggaa caggccagtg atccactgct ctcttgcttt  229320
tatcccttac aggtgctgcg atactttgac tacgttttta caggcgtctt tacctttgag  229380
atggtgatca aggtgagtgc agattataag tgagaacaca cggtaatttt tttttttaag  229440
caagtgcagg gctgggcaca gtggatcatg cctgtaatcc cagcactttg ggaggctgag  229500
gcaggcagat cacttgagat caggaggttg aggccagcct ggccaacatg gtgaaacccc  229560
atctctacta aaaatacaaa aattagccgg gcatggtggc acatgtctgt aatcccagct  229620
actcgggagg ctgaggcagg agaatcactt gaaccctagg ctgcaatgag ccgatgtgga  229680
ggctgcagtg agccgagatc ttgccactgc attccagcct gggtgacaca gcgagactct  229740
gtcaaaaaaa aaaaaaaaaa aaagagctgg gattccagga gatcctgagc ctccaagaat  229800
gccccccttg agaggatgag tctcccagag gattagaaat gcctggtgtg tttgaagagc  229860
```

```
agcaaggaag ctggtgtggc tgggcggagt gagagaacag tggggaaacg aaggacagag   229920
agatgagtgg ggaggtgagg gggcaccttg tgccggggat cacagagagg gctcttcggc   229980
tcttactttg agtgaggtga gggccataga gtgttctgag cagaggaggg acttgatcca   230040
ggtgttcaca ggtgcccttt ggcatctgtg ggaagccaga ggacctgtga gcaggtgatc   230100
acactggtcc ccatgggcga tgacggggac aggatcaggc tggtgaccaa agaagaggtg   230160
agaagtggac agattcttgg aaggttctgg aaatagagcc agtgagtttt gctgatagag   230220
ccaccaatga gggatttggg acaaagaggc atcaaagagg atcccaaagt ttggatctaa   230280
gagccggcaa gccagagctg gcttccatca ggcaaagggg ggccgcctca tggggcaggg   230340
gctccccact cctccctgga gtcctctggc cactgcccat ccctgcaaga tgaggtggcc   230400
tcattggctt ccctgcctct ccccgagagg ctagagagtg ggtggcagca ccccagggtg   230460
gggatcaggt gggggttctg agcaccctct cttctccccc acagatgatt gacctggggc   230520
tcgtcctgca tcagggtgcc tacttccgtg acctctggaa tattctcgac ttcatagtgg   230580
tcagtggggc cctggtagcc tttgccttca cgtaagtctc ctcgcaaggg ttcctcttgc   230640
ctcttttccc ccaaccccca gcctgggcca cacatcggat tacaggacat gttctcaggg   230700
tctagggatg gggtgtgtgg gctccgggga cgtgggagat atcagcatgc caccaggaag   230760
agcttcgatg gctttttgca tgatgtccat ggaggaagaa ggagaaggga ccccccctcc   230820
tgccaacctt ctacctcctc acacagcaac gggcctcagc cacatcactg gccccttgct   230880
gtgcagcttc ctgtagacta gcctcgccgg aacatctcat cccctactac tccacaagc    230940 gccgcccaaa ccgctgtctc tttggaaagt ccctaaagag acaatcagga aacgaatgtg   231000
catgagaatt ctgaccccct ccctatgcct gaaggcccg tagttgtaga cctggtgact    231060 cccttgtgt gtctttcact tctcctggca gtcctaggat tctctgccct ctgaaaggcc    231120
atgtgtcatc ctgcagctcc aagatggcgc cccagttgta ggcagccatt tcaggatggc   231180
acccaagctc ttagtagtca tcccaagatg gcatccaagt tctgggtggc cattccaaga   231240
tggcccctga gttctgagct atcattccaa gatggcctct gaatttgggg tggtcattct   231300
tagatggtcc ctgagttcca aggtgacctt caagttctgg gtagccattc caggatggtc   231360
cccaagctct gggtggctat tccaagatgg ccccaagttc taggcagcca ttgcaagatg   231420
gcccctgagt tccagggtgg cccccaagtt ctgggcaacc attccaaggt ggcatccaag   231480
ttctgggtgg ctattccaag atggcctctg atttctgggc taccatgcta agatggcctc   231540
tggattcttg gtggccattc ttacatggtc cctgagttcc aaggtggcct tcaagttctg   231600
ggtagccatt ccaagacggt ccccaagtct tggatggcta ctcgaaggtg accccaagt    231660 tctgggcagc catctcaagg tggcacccta gttctgggta accattccaa aatggcaccc   231720
aagttctagg gcaaccattt caaaatggcc cccaagttct gggtgactat ttcaagatgg   231780
tacccaacag gtgagtggcc attagcccct agggccctga tagcagactt agcagtacat   231840
tcctgaagtt gtagacattt ggagcgggat gaaaaatatc taatcagtct ttaatcaaga   231900
aacaaatctt ggggaccctg gctgtgccca tcatggtgaa tgattccctg acaggttttg   231960
aaaggatctt gacacattca ctcccatcgt gagagaatca ggggcttcct cctgtgcctc   232020
tgcctctagg ctccctcctg agccaatctg gaggggccct tgaatggtct ccctcaccaa   232080
acaatgagga cttggtttgt caggagggcc aaaaatagtg cccatttcca gtagaagggc   232140
tgttaagtag gccacactta gattcttctc tgggaacaca atgaggtcaa gttgtgttag   232200
```

```
aacaaaaaat ctccagagtt tttggatgcc tcagagctgg agatgtatca tgaaggttgg    232260
gaggctgatt atacttcttt ctcttttctct ttcactcctt cctcctcttt ctcctctctt    232320
tttgttcgtt tactctttc tttttctctt ctcctctccc tccccacatc cttccctctc     232380
ctcaaagctt ttcagtgtct atttgactac tagagcaatg cacggtggct tacacctgca    232440
atcccagcac tttgggaggc tgagacaggc agattgcttg agcccaggag gccaagacca    232500
gcctgggtaa catagggaga ccccatctct aaaaaaaaaa aaaacaatt agccaggcat     232560 ggtagtatgc ctgcactagc agctacacgg gaggctgagg tgggagaatt gcttgagccc    232620
aggaggttca aggctgcagt gagccgaaat cgcaccactg cacccagtc tggggaacac     232680 aggaagaact tgtctcaaaa aaataaaaag tttaaaaat taaaaatcaa tgaatttgct     232740
atttagaata ttatgcttta tatggttact gaataattt aatagtgatg agtacaaaaa     232800
aaacaggttt agcaagctgt tctgtaggtt aaaaagtaaa taaataaata attaattaaa    232860
caaaatacaa tgcacatcaa attaggggac aaagattgtg acgaataaga caaggagtcc    232920
atgtctttaa aatatgaaaa gcagttacaa atcaataaga aacactactt ctcaatggat    232980
aaatgggcaa aggacataaa cagaaatctg atagaatgct ggcaactagt aaaaatggag    233040
gtaaatcaac ccttggaatt cagagaaatg taaaataaaa acgagataca attcattccc    233100
tatcaagtta gcactgttcc cgccgcaccc ccacacacac acaaaaaatg attttttag     233160 ctaataaaca gcatatataa gaatgtatta taataggctg ggcacagtgg ctcacgcctg    233220
taaccctagc attttgggag gccaagggag ggggatcacc tgaggtcagc agttcgagac    233280
cagcctggcc gacatgacaa aaccctgtct ctactaaaaa atacaaaaat tagccaggca    233340
tggtggcgga tgcctgtaat cccagctact caggtgggta aggcaggaga attgcttgga    233400
cccaggagat ggagactgca gtgagccgag atcatgccac tgcactccag cctgggtgag    233460
aaagcaagat tttgtctcaa aaataaaaaa aggaatgtat tataataaaa tatacttttc    233520 tcccctcta tcacctattt aagcaggtcc ttcaagttgt caggtagaca tcatgctatg     233580
agaaaattta aatcctgaaa agccagaatg ttttaccacc ctcagcctgg aatgaatcct    233640
tctcctatgg aaataaccta cgggtttctc caccctctc tgcctttcag cccttccct     233700 ccctctcccc tcctttctt tctccctctt tctcttcctc ctttcccctc tcttccctct    233760
ctcttcttcc ctctctctgt ctcttttctgt tcgtctttct cctttaccc cctctcagtt    233820 tctatctttt tattttcctc tttctctctc tctctccctc tctttctctc tcactccctg    233880
cactgttgat gacctatgtc cttgggtgat gtgggcctcc cctggaccgt gtagcttgga    233940
gaaagctgac cctctgtcat cggtctggca acagggactt ggcccccta ccctgcattc     234000 tgatgaggaa tggtattcag acaaaggcag atcccaggac acaggaggac atgctcaggc    234060
agggaccccc gccccttcc tctggggcaa ggtctgctca gcagcctcca agattcctag    234120
ggctcaagag gtggcaggta gctcagggca ctagggcagg cagtgggtg aatatgtcac    234180 tcatatccac ctgtccacac acaatgctta ccttggccac ctgtgcccag gggaatgggt    234240
tttatcctgt gaatcctccc agtgaccacc actgagtgtg gcacagataa atggtaccaa    234300
gcccaagctg ttcaggtctc caatgtcact ttcctctcag acctctgttg tagctgacat    234360
actgtaatgc tgaggagggc cgggcacagt ggctcatgcc tgtaatccta gctctttcgg    234420
aggccaaggc agatggatca cctgggggtca ggagttcaag accagcctgg gcaacatggt    234480 gaaacccag gcaacatggt aaaccctgt ctctactaaa aatacaaata ttagccaagc     234540
gtgatagcag gcgcctgtaa tctcagctac tcgggaggct gaggcagaag aattgcttga    234600
```

```
acctgggaag tggaggttgc agtgagccaa gattgcacca ctgcactcca gcctgggcaa   234660
cagagcaaga ctctgtctca aaaaaaaaaa aaaatgctga ggaggtgact gtcccacctc   234720
catcctccga gttgaccatc acaatttagg gaggggaatg acctacaaag gacccagaag   234780
caagcctttc aattgttgag cttttgccat tatgggccat cgtttacaac atgctgtttc   234840
taggttctct ggaggtaaaa ttagcctcct cttttaaaca aagctaatct gcaaaagcga   234900
accaaaaatt cttttccacc agagatcaat tagcagaatg agctgggtgc gatggctcac   234960
acctgtaatc ccagcacttg gggaggccga ggcaggtgga tcacttgagg tcaggggtcc   235020
aagaccagca tggccaacat ggtgaaaccc catctctact aaaaatacaa aaactagctg   235080
ggtgtggtgg ggagggcctg tagtcccagc tactcgggag ggtgaggcag gagaattgct   235140
tgaacccagg aggtgaaggt tgcagtgagc caagattgtg ccactgcact ccagcctggg   235200
tgacggagca agactccatc tcaaaaaaaa aaaaaaaaa aaaaacagc agaatgattc   235260 ttttggggag ttgactttt ttttaatttc tgagttttct ttttaaatat caagttatac   235320
aagggcattc aaattggcct acaactcaca ggaatttggc agcctgtttg cagagtcaag   235380
cttttacatt gttctcatga aattggtaca ggcataaagc cacccttcac tcttgaaaat   235440
ccattttgaa tgttgttgtt ttaattctta tgcaagaaaa ggatctggat agggatttca   235500
ggccatcctg tcaaccctgg caggcttgta gatcatgcag gaactgggag gtgtgagatt   235560
ttgccagtag gatcctggca agtgcctggg actctcccag ggttttggaa gagccgacgg   235620
acatgagtcc aacagggagc atctttatat catggccgaa gggatgagag aggagaccct   235680
caaacctcac gcctaccaca ccctccccac cccactgtca agagtccatc tggtactgct   235740
gttcctcccc cagggcaggg ctgcaggccc agcacagctg gccaggtgcc ttgatcaagc   235800
cattcctgca cacctaagag ccaaactgct agaaaaccag aataggagct actgcttttt   235860
tccctaaaaa gttttggaat cttctccccg ttacaggttt ctggcctctt ttgcctgaga   235920
aggtctctca ccctatgagg actttgctta ttgtctttcc ttgttatcgg atagttggca   235980
cattggaagg agcatggatg ctctgaggtt ctcagcctga gcgctgaact ctccacccgc   236040
cccccacccc ccacccccagg gtcctctgct tatttccttt ctggtctttt aacttgcttt   236100
gtctgtcctc tgtgcatatc ccctcataga caaggctgag agccccacaa gtattagatt   236160
gaccttattg ttttaagaaa ttgtccctcc aggtctgttt gatttctctc tagatgtgca   236220
agtcctttag cctctctgtg cctcagtttt tcccatctag atgaggaaac tgcggcccag   236280
agggactgtg gagggaagta agtccgacaa gatcactgag gttgggttca gctgtcagat   236340
gctacccatc tcccagccct gaatacggag gctcacagtg agcagaatga tgctcagcag   236400
cctggccagc ctgggttctt tgaggcctgg cagggctgcg agatccaggg gaagggaata   236460
ggggaaggga gcataaggtt attcccttcc ttgttgaaag gaaccttgcc attctggcct   236520
gttggggtca aagcaaggat tcttccccca gtgctgtgat tgtggcctcg tctccgatat   236580
gggagaaaac tatccctgtg gtcccaccaa gggatgtatt gaagctcttc tgaagatgtc   236640 caccctcct gcacctcacc caaatatctg tgtgtgtgtg tcctgctcaa ttcactgact   236700
gtgtcccttg tatccatgcg tctaccataa acacccatt tcatgagcca tcacgcgtgg   236760
tatcacgctc tgtgcccatg catcagggcg gccaactgac atttctcagc agctggcaga   236820
tcatgatcct gccctcaccg ccaagagtcc atctggcgcg gctgttcttc ccccaaaggc   236880
aggaccgcaa ctggcagagc gccttgatca agctgctcct gcatacccag gagccaaact   236940
```

```
gtcaggaagc caaagatgga gccctcaggc tgctatctct tgatcctcat cttcaaaaca 237000
gcccccaccc ctgaaggcat tattttcctt gtgtatgatg aaatggaaag aagattagag 237060
tgcgagatac ccacacctgg gtttgaatct tagtctgtct tcccagctgt gtgcctgccc 237120
ttgggcaggt cactcttttt ctctaggcct cagcttcctc atctggaaaa tggtcataat 237180
ggtgctgtct tcccataggc aaatgcagtg atgtccagaa gactcccata ttaaacctaa 237240
agtcagcaga ttaggcaaaa atcactgtca ttgaaaactc cctcaatcat ccgtaaagaa 237300
gctgggtgtg gtgtctctca cctgtagtcc cagctacttg ggaggctgag gtgggagaat 237360
cacttgagcc agggagttca aggctgcggt aagctatgat tgtgctactg cactccagcc 237420
tgggcgacag agcaagacca cgtctctaaa aatataaaat aaagccgggt gcggtggctt 237480
acgcctgtaa tcccagcact ttggaaggct gaggcagcct ggcaacagag tgagaatcca 237540
tcaaaaaaaa aaaaaaaaa aaaaaagta gaatctatat gattctacgt atgcaataat 237600
tcctagatac actgaatttg agaacccaa gtcagactac aggaaaagga gatgaggggg 237660
tgtggaggag aatccacttg gaatatttgt agacatttaa accattctgt gttttaaaaa 237720
atatcacagc cgggcgcggt ggctcacacc tgtaatccta gcactttggg aggccaaggt 237780
gggcggatca cgaggtcaag agatggagac catcctggct aacacggtga aaccccatct 237840
ctactaaaaa tacaaaaaaa attagctggg cgtggtggtg ggcgcctgta gtcccagcac 237900
tcgggaggct gaggaaggag aatggcgtga acctgggagg cggagcttgc agtgagccga 237960
gatcttgcca ctgcactcca gcctgggcga cagagcgaga ctccgtttca aaaaaaaaa 238020 aaaaaatcac taacttccag aggggtcgtg gatggaaaat tccatagagt ccgcttggcg 238080
acagggtttc cgccattctg atggcggtca agtctttcta acctggatct ccagtcattg 238140
ttgaaggcgc ctaatgagcc ccaagcctga ttccaatgaa tcacgagagg accagctgct 238200
aggtgctgat agcttttcccc aggcccgcat ttgctcagag ggcttcagag ttgcttctaa 238260
ttccatccca agtcagaact ctttgctgac ccctccttc ataaagagca aagccaaggc 238320
catagctttt gttaatcaaa catcagaatt ccacagacct gagttggttg gttgtttgtt 238380
ttaagagaca gagtcttgcc caggatgcag tggctcacac ttgtaatccc agcgctctgg 238440
gaggcctagg caggaggatc acttgagccc aggagtttga ccagcctg agcaacataa 238500 tgagaccccc gtctctacaa aaaatggaaa aatttgcctg tatttccagc tacttgggag 238560
gctaaggtgg gagaatcacc tgagccctgg aggttgaggc tacagtgagc caagatcccg 238620
ctactgcact gcagcctggg caacagaggg agacctgcc tcaaaaaaaa aggagagaag 238680
gagagagaca gggtctccct atgttgtcca ggctggtctc gaacttctgg cctcaagcaa 238740
tcttcccaac tcgtcctccc aaggtgctgg gattatagct gtgagccacg gcacccagtc 238800
tgggcctgtt ttgcagatga ggataacgag aggcagagtc aggattcaaa cccaggtccc 238860
ctcaacttca aagctcacaa ccttttagac attctaaaac cttgcagctc cacaacgcct 238920
ggagaagagg ggtttctccg gctcttggca gtgactttcc gtggtgaatt caccttggt 238980 aactgacagc tttgcagctg tcctgctacc tggaaatttg gctttcttag tgctttcttg 239040
ggcagtgcca ggtgcctgcc aagggcgggg gactgaatgg aggtggggc ggcttccaga 239100 tggaaggatg gacatcggcc agcgccatga gcctgaggct cccccaactg ctgcccgggc 239160
gggactcggg ggtgctcagg ggtgcgtgtg tgtacgtgcg tgttctgtgt tcttttttct 239220
gaggccactt acgatctgtc tctccctccg atgccacatc accaggagca gtacacggta 239280
aagtctctct ctatctttct ctctctctct cttctctct ctctctctct catattctgt 239340
```

```
ctctcgtgat ctgtcccctg gtgcagcctc gttagttctg ggcctgtttc tgtggccttg   239400
tgtccttgct gccgctgtcc tgtcgcttca aatgaccaga actcactccc tgcgaaggag   239460
gcatcccaaa gggtcttgcc aatgcctccg cccatgcccc accagttctt gcagagaaca   239520
gaaggggcag aggttcagtt tcaataggca agctgggtgg agcagttatc agaagcaatg   239580
aaagtgggcc agacacggtg gctcacgcct ctaatcccag cattttggga ggccgaggcg   239640
ggtagatcac ttgaggtcag gagtttcaga ccagcctggt caacatggtg aaaccccatc   239700
tctactaaaa atgcaaaaaa ttatctgggc ttggtggtgc acacctgtaa tcccagctac   239760
ataggaagct gaggcaggag aatcacttaa acctgggagg tggaggttgc agtgagctga   239820
gattgcacca ctgcactcca ccctgggtga cagagtgaga ctctgtctca aaaaaatata   239880
taaaataaat tgaacaataa aaaaataaaa tggccatgga atcgttttca gatgaggaga   239940
tgcagaatgc ccatggagac atgctcccaa ttgtcacttg tttgggacat caagatttta   240000
gccagttcca tgtgcaacct ggatgtacag ttccttgact tttttctat caacatgtat    240060 tctaaagttc aatttcaaaa ggaaacttta gccaggtgca gtggtgcatg cctgcagtcc   240120
cagccatttg ggaggctgag actgaaggat cacttgagcc caggagttgg aggctgcggt   240180
gagctatgat cgtgccactg cactccccc tgagattcca tctctttaat ttaaataaaa    240240
aaaaaggaaa ctatattatc cacttacaac cagcattgct aacctaagat aaatctgcaa   240300
ctgcaaaagt aaatgtaggc cagacatggt ggctcacacc tataatccca gcactttggg   240360
aggccgaggc aggtggatca cttgaggtcg ggagttcgag accagcctga ccaacatgga   240420
gaaaccccgt ctctactaaa aatacaaaat tagccggacg tgatggcaca tgcctgtaat   240480
cccagctact cgggaggctg aggcaaaaga atttcttgaa cccgggaggc agagactgct   240540
gtgagctgag atcacgccat tcactccagc ctgggtaaca agagagaaat gccatctcaa   240600 aaaaaaaaa aaaagtaaa tctaacagaa accagacaat gttgttgcct tcaagctggg    240660
ctctttgtta aaaggaaaat tactaagtgt tagggaggtg ttaaaggcct attagcatct   240720
acctgaggct tcctttctcg caaaagcaga gcgtctgaaa gatacgtgga aagaaactt    240780 aaagtataat aaaaaagaaa gaaagaaaaa gaaatgatta tgcccctctg agatccaatt   240840
atttaatctg tgcccctgtt ctgcctaaaa ttatctcagt gactgtccaa cgtgtgtctc   240900
acacttgggg gcacagcctt gagatgataa tgatgatgtt agttttaaaa agaaaaaaaa   240960
aggttcagag ttctgaatcc tggagtatat ctctgcctag caggctaaaa tacaattatc   241020
gtctttgttc cctgaaaaat gaaaaaatg gagtcctta aaaagcaaat ggtgtgaaga     241080
atgatgtttt tgcactggat actgagaccc atcgtgatgg gggtctctgg ggcagctctg   241140
ctcatgacct gggaggtcac tgtagggaga tgttttctag gtgacctccc cacccaaata   241200
ctccaaccgg aggcattcac gtgtcctgag accacacgcc aggcgcaggc tagggctag    241260 gacaagaatc aagattaaag gggaaatggc caggtgcgt ggctcatgcc tgtaatccca    241320
gcactttggg agtcaaggcc agtggattac ttgaggtcgg gagttcgaga ccagcctggc   241380
caacacggtg aaaccctgtc tctactgaaa atacaaaaat tagccaggtg tggtgactca   241440
tgcctgtagt cccagctatt cgggaggctg aggtgggaga atcacttgaa cccaggaggc   241500
agaggttgca gtaagccaag atcatgccac tgcactccag cctgggcaat agagcaagac   241560
tccatctcaa aaaaaaaaa aaagattaaa gggaaaatga acacagagaa gagtagatta   241620
cactgtaagc ctttgaagag ttttctgtct aaaaccagag accgaagaaa caaacaaaga   241680
```

```
ttaactccga aatagcacat aggagctggc aggagccaga ggtaggcagt caggaaatgc   241740
tgtcggaggg agcaacaggt aatttgggct ttgaggaccg ggtagttctg tgactggaga   241800
agtggaggaa gggcatttct agcagcggga acagtatatg cataagcaga cagaggcaaa   241860
agaatgtggc tggggcttga gatatgtagc cataaatggg aatgcaaagg tgaaggtaag   241920
ttggactaga ttttcaagag cattgaatgc catgcccaga agtttgcact tgctcttctg   241980
agaattcacg tgctccagaa gaattctgag caagagaaag agtgacaagg tcattggctt   242040
tagccactgt gtgcataaaa catggaagaa aaggcaggga atgaggagca agttgggaga   242100
cgggtgaggg gggatggcac ccaggaatgg atggcgggat gttaaggaag gtgacccact   242160
ggggatgggg atgggatag agggcaggca gttgaccatg actctcaggt ttctggtgtg   242220
gacaactgga tgggtcatga gtgccatgaa ccacaagcta ttcatggtcc cactcaatac   242280
cctcctcttg gggggcctga gtcatggttg gccaagggtg tcatggcatc tctgggtct   242340 gcattgctaa gctcagttcc aacagacctt ggactgaact tctgtgcagt cctctctggc   242400
aaagatgggc tcagagaccc ttggagcaat gcagcagaga ccatgcagc agccacatca   242460 gcatctgaaa acagcggcac ccggttattt tccctccttc agactcaggg aatatggtgg   242520
gggaggggag atttggtata agggccactt taagtatctt ccagaatccc attggaaggg   242580
ggagaaaatc ccattttttt aagagcccac tgataccacc tttaaaaaga atacacaggg   242640
ggccaggcgc agtggctcac acctgtaatc ccaacacttt gggaggccaa ggtgggtgga   242700
tcacctgagg tcaggagttc aagaccagcc tggccaacat ggtgaagccc catctctact   242760
aaaaatacaa aagttagctg ggcatggtgg cacgcacctg tagtcccagc tacttggaga   242820
ggctgaggca agagaatcac ttgaacctgg gaggtggagg ttgcagtgag ccaagatcat   242880
accattgcac tccagcctgg gcaacaagag tgaaactcca tctcaaaaaa aaaaagaat   242940 acataggga ccactaaact cctagaccaa gggctttttt gaaaatagct gtgaccaggt   243000
gtagtggctc acacctgtaa tcccagcact ttgagagggt gaggagggca gattgcttga   243060
gctcaggagt ttgaaaccag cctgggcaac atggtgaaac ctcatctcta caaaaagaca   243120
aaacaattag ccaggcgcag tggcgtgtgc ctgtagtccc agctacttgg gaggctgagg   243180
tgggaggatg gctttagccc aggaggcgga ggttgcagtg agccgagatc gtgccactgc   243240
actccagcct tggtgacaga gccagaccct gtctcaaaaa agaaaaaaga aaagctgtgc   243300
agaaatgggg gtggggaatc agccaacccc cttgtgctgg gtctcaggga cacccaatac   243360
agctgctcag gccagccag atggcaaagg gccctcaacc aaccctggga ccagaaccac   243420
aaaaagccac gtacttactg gctcccgagc ccaagcttaa caggtgaaat ggaccactct   243480
tcaccaggaa gggcagggct gtgccaagct caccccagac ttctaggcct gggagggtag   243540
ggtcccatgg agctgtgggc tgcccctac ccaacctgac ctctgcttcc tctcttccct   243600
tcttcccacc taaacattcc tccacagtgg caatagcaaa ggaaaagaca tcaacacgat   243660
taaatccctc cgagtcctcc gggtgctacg acctcttaaa accatcaagc ggctgccaaa   243720
gctcaaggtg agattgggag atggtggggt gcggtggggg ggactgtcag ggttatcatg   243780
tacagctgag caggttgtac actgctcaag gacaacacat taaggaggt gctgataaca   243840 tcctagccat cgtgtatgga tatttgtatt attacaactt cccagcagat ggcagtaaag   243900
tgagctgacc taaaataatc tgtgtattat ggcagttttt ctttagatga agtgtcttgg   243960
ggttaagatc cttttcccta attcgcatga aggcatcata tggatttaaa agggtataac   244020
cgtgatctgg gaagcaggaa ctagatttct tgttccataa aattttgact tttcatctac   244080
```

```
ctattctagg ctctagtatc tcccattcca aaatagcatg aaccagcatt tcccaaaagc   244140
ctgtcattca aaaacatata tatatattaa gggaaataaa atccagtcat tagagcaccc   244200
actttcactc tatgcttcac ctgggggtcc ccagtattat ctcttatgta atatgtttct   244260
ttaaatcaag tcacacccgt aatccctgca ttttgaaaga ccaaggcagg agtgttgctt   244320
gagcccagga gaatgagacc agcctgggca acatagttag actctgtctc tactaaaaat   244380
taaagacaga aaacagatac tgttatggaa atctaaccaa atatggctgc ctgcctaagg   244440
ctttgtgcat tgacaactgc tctttcttgg ttaaagaggg aaaatgtcaa tggtaggtgt   244500
taacatggta gcaactaagt aaaaatttct ccttcactca aaaggattga gagagttgga   244560
aaggaagtaa ctttgttacc ttgttttttct gtgttgggct cctgtatcac ttaaaagcat   244620
ctctggtatc ccatctggga gttttagatc catagaatgc caggattgag tccaactcct   244680
ccaacgctta tttctgaaag ctgggggggac cttaccctag tgacttgact tatgaccttg   244740
cctgtaaaat gggaatgatc atggcagtat tttggtatga tgggccactg gaggcagaag   244800
gttgggcagg tccccagccc ctcatgctct ctgtcaactc caccccacag gctgtgtttg   244860
actgtgtggt gaactcactt aaaaacgtct tcaacatcct catcgtctac atgctattca   244920
tgttcatctt cgccgtggtg gctgtgcagc tcttcaaggg gaaattcttc cactgcactg   244980
acgagtccaa agagtttgag aaagattgtc ggtgggtctc cactttccag cacattccca   245040
ttggaaccag caggtgggca gggggggaagt ggctagaggc attggccact tgggctcaga   245100
gactggagaa gtgatgagcc ttggaagtga ctcagttgca accagcttgg atcttgggta   245160
gaaagaaaac cggttttaga atttgagtca ccacccagag ccacagaatg agtcataagc   245220
aaattgattg acctttcagc caccgccttt gtcatgtgag ggatattaat acacatccac   245280
agttccttac ttgaaatcgt tacaggcaga tgtgtttcaa agttgagaat attttgagat   245340
tcccatgtgg gacatgacac cctcagctgg gtctaaggca gccctataat caaacacaat   245400
atttctgcca taaaatgtgt aactatttac atcaaatggg gtaaataaca agtataaaga   245460
gcttcatgtc caatcagatc aggtttcatt accaaataag ttaggtaaga ggccaggtgc   245520
agtggctcac acctgtaatt ccaacacttt gggaggctga ggtgggagga tcacttgagg   245580
ccaggagttg gagaccaggt tgggcaacat aatgagagcc catcctacaa aataaatttt   245640
aaaagttagc ggggcatggt agcacacacc tgtagtccca gctacccggg aggctgaggc   245700
gggaggattg tttaaacaca ggagttcaag gctgcaatgc actatgatgg taccactgca   245760
ctccagcctg cgtgacagag tgagaccctg cctctcaaaa atatatacat ataggccggg   245820
cgcagtggct catgcttata atctcagcac tttaggaggc cgaggcgggc ggatcatgag   245880
gtcaggagat cgagaccatc ctggctaaca cggtgaaacc ctgtctctac taaaaataca   245940
aaaacctagc tgggcatggt ggcagacgcc tgtagtccca gctacttggg aggctgagac   246000
aggagaatgg cgtgaacccg ggaggcggag cttgcagtga gccgagattg gccactgta   246060 ctccagtctg ggcaacagag ccagactcca tctcaaacaa acaaacaaac aaacaacaac   246120
aacaaaaata tatatatata tatatgtata tatatatatg tacacgcaca cacacatatg   246180
tattatatgt gtgtgtgtat atatatgtat gtgtatatat agtgatattg ttaccagtgt   246240
aaagtggcat tttgcaacac atggtagcct gttgttatct tgatggctat ttattgaaat   246300
taggaggatg ccagatgtct ggataggagt ctggaactaa cccttgtttc ctgccttgaa   246360
aaggagtagc aacctcccctt agcctgatga acctctaaat gtcccctatg tctctctgcc   246420
```

-continued

```
tcctcctaaa ctccctccac cccacccccca gcaagcctga ggctctcacc ctgaggacta   246480
gaagttatca cgttggaaga gggtgctgga ccctgggtca gctctcccac caggagtaag   246540
gttgtgccat cacccatgga tttatctcaa agtagatgca cacgtcatcc cctatgaagc   246600
acaggaacac atggtggcag gatggggagt cactgcttcc caagcagtct aggctggtgg   246660
accactcttc cttccctcc ccctgtctct gataaccaaa gacaagtgca agacagcccc   246720
tctttcccat ttactaacag tccccactct ctgtggcaga ggcaaatacc tcctctacga   246780
gaagaatgag gtgaaggcgc gagaccggga gtggaagaag tatgaattcc attacgacaa   246840
tgtgctgtgg gctctgctga ccctcttcac cgtgtccacg ggagaaggct ggccacagta   246900
agtggcccga ctggaaatct atccaggagg agccctgggg agcaggagga taaagggcct   246960
gagagcttag caataagaaa ggtcttggag gccgggcatg gtggctcacg cctgtaatcc   247020
caacacttta ggaggccaag gcagatgtat cacttgaggc caggagtttg agatcagcct   247080
ggccatcatg gcaaaactcc atttctacta aaaatcccaa aaaaaaaaa aaaaaaaaa    247140 aaaaaaagc tgccaggcat ggtggctcac acctgtggtc ccggctactc aggaggctga   247200
gacacgagaa tcacttgaac ccaggaggca gaggttgcag tgagccgaga ttgcaccact   247260
gcacttcatc ctgagtgaca gagcaagact atggcctccc cgccttcaaa aaaaaaaaa   247320 agtgaggctg aatcatggac ttagtctta tttaaatt tgagccactt gtggtggctc     247380
atacctgtta tcccagctac tcaggaggct gaggtgggag gatcgcttga gcccaagagt   247440
tcaaggctgc agtgagctgt gattatgcca ttgtactcca gcctagacaa cagaaggaga   247500
cccctatccc tgaaaaaaaa aaagaagaag aaattgatat ttgttcatca tggacttttt   247560
gcattaattt tgattttta aaatattgga gcaaagatt atcttgatta ctgagatttt    247620
cagtaccccc ttaatttgca cccaaaacaa atgcctccct ccctcacctc gtccaagtaa   247680
tggtctttct ctcagaggtc ttggaaatgc caggctggaa gcttggtaga ttccagcatg   247740
tgccctcagc atcctcacct ccctccctct ctcagcaaat atgccaacct gaacatgccc   247800
tactacccac tctcagacac atccagtact cacacatgtg ggaataatgc taacccacaa   247860
ggcacctttg agcaaagttt ttttaaacac ctttctcaac agacttcatt tccatctgtc   247920
tgaaaatcat cgcaatagac ttaaatgatt ttgttcaaac aaggcactga aggaccacct   247980
gccaaaaaat tgtcatcatg aatacacaaa tctatcatgc ctatcatgtg aaggtatcgc   248040
ttagacacag agcctttgag cagtgtgcaa cctgcactac tgtacagagc tgctgtgcac   248100
ttacccactc tcatatatat ccccattgta cctcctgagc acccagcacc acctgtgctc   248160
aaatacccac tctacatgca tacacccacc tctactccct ccattgccac aacctgtctt   248220
taaatcccaa cttggccact tataagtggg tggtcttcag cacgtccctt taaattgctg   248280
aacctcaagt tcctcatgtg caaagtggag ccagtaataa cctccctggg aggggttgctg  248340 agccggtggg gatgaattgt tgaatattgt ttccagcaca cagcaagccc ttcatgcaca   248400
gcagtagaaa tgactgacat tggccaggcg tggtggctca cacctgtaat ctcaacagtt   248460
tgggagaccg aggcaggtgg atcacctgag gtcaggagtt caagaccagc ctggccaaca   248520
tggtgaaacc ccgtctctac taaaaataca aaaaaattag ccaggcttgg tggcgcatgt   248580
ctgtaatccc agctacttgg gaggctgagg caggagaatc atttgaaccc gggaggcgga   248640
ggttgtagtg acccaagatc acgccgttgc actccagcct gggcaacgag agcgaaactc   248700
catctcaaaa aattaaaatt aaattaagaa ataactgac attgttgtca gccttttcaaa   248760 aaacagcgac tacttaaatt tcttttttcat ttccctctgt tcctgttctg ccatctcact   248820
```

```
tccaccctct ctccaccttc ctcatcaccc cttgggtccc tgtctctctc cttcctgccc   248880
cttccctctc cctgccccat tccttgcagg gtcctcaagc attcggtgga cgccacctt   248940 gagaaccagg gccccagccc cgggtaccgc atggagatgt ccattttcta cgtcgtctac   249000
tttgtggtgt tccccttctt ctttgtcaat atctttgtgg ccttgatcat catcaccttc   249060
caggagcaag gggacaagat gatggaggaa tacagcctgg agaaaaatga ggtgccactt   249120
ccaattccat ctgtccttta aaaactgggg acacacacaa actttaaaac acacacaaca   249180
cccaggaacc cctttctagg ggtacctggg ggagggaaca gaagcattgt cccaaccgaa   249240
tccagtcttc agggcagccc ttcatggagt ttccagagga aacacatcat atagtgtatg   249300
tatcagtcag tttagactag gttatgccgc agtaacaagc aaccccagat ttcattgcca   249360
aatatccaca aagggactta tttttgctc acactgcatg tcaacatcag ttgtggatct   249420
tgccatcttt attctggttc ccaggctggc agagcagcag agcagcctcc ctctgagatg   249480
ctccagatga aaagagagt atgtcagact gaggttcagt tcttcaggct tgtgctcaaa   249540
aattacacat gtcacttctg ctcacatttc atcagccaaa gcaagtcaca catccattct   249600
gacatcagtg gagtgggcaa atacaatctc ccctagcgaa gggtggtgaa tatttatgaa   249660
tgaaaagcca agccaggtgt ggtggctcac acctgtaatc ccaacatttt gggaagctga   249720
ggcaggagga tcacttgagc tcaggagttt gagaccagcc tggccaacat agcaagaccc   249780
catctctact acaaatcaaa aaattagcc aggcaggatg gtgcacacct ttagccccag   249840
taacatggga ggctgaggtg ggaggatgct tgagcttggg agttcgaggc tgcagtgagc   249900
tatcattatg ccactgcact acagcctggg caacagagca agaccctctc tcaaaaaaag   249960
aaaaggaaag aaaatccagt cccctgtcta ccagagagta tagacatgac tctttgcctc   250020
tctggcatca tccaagctaa atagaggacc tagaatatat cctctgctcc cttgacccttt  250080 aagacttaat aaccactatt cctccttctc tctccctcaa agagaaggag aagacgcagc   250140
aaagtattca gtaagaaaga atgggctggg cgcagtggct cacgcctgta atcttaacac   250200
tttaggaggc caaggcagga ggattgcttg agcccgaag ttcaagacca gcctgagcaa   250260
catagtgaga ccccatctct atgattaaaa aaaaaaagtt ttaattagct gggtgtggtg   250320
gtgcacgcct gtagtcccag ctactcagga ggctgaagcg ggaggatcac ttgagtccag   250380
gaggtcaagg ctgcagtgag ctgtgattgc actgcactcc agcctgggtg acaaagcaag   250440
cccgtgtcaa agaaaaaaaa aaaaaagga aggagggagg gagggaggga aggaaggaaa   250500
tgagagagag aaagaaagga gggagggaag gaaggagata gggaagaagg aatgaagaag   250560
aaagaaaggg agcgaaggaa agaaggaaga agagagaaag gaaaggagaa aggggaaagg   250620
gtggaaggaa tgaagggaag gaaggaaaaa ggaaagtgaa ggaggagggg aggaaggaag   250680
gaaaggaggg agggaaggag ggagggaagg agggagggag ggaaggaggg agggagagaa   250740
ggagggaggg agggaaggaa ggagggagga aggaaggaag gagggaggga gcgagggagg   250800
gaggaagggg aagaaggatt aggcttcaat ttgatttggc acactcggta gctgtgtcac   250860
ctcaggcaag tggtttaacc tttctaagcc tctatttgg tgatctgcaa agtgaggcca   250920
ttgatagtac ccacttccca tgtttgtatt agccatgcaa taatgggaa atgtcagtgc   250980 aagttttggc agttggtgac atctcaagca actgtagctg ttgggataag aaagcaatgg   251040
tgagaaggaa gagagagccc aggaatcctg gctgggggca agagaggcag agactcaagc   251100
agaagcactt gagaaccgcg acgagttaga cagagggtgc ccggtgtaca gccaccttcc   251160
```

```
tcctgcctct gccgctctca ccactggcct ctctcccgca gagggcctgc attgatttcg   251220
ccatcagcgc caagccgctg acccgacaca tgccgcagaa caagcagagc ttccagtacc   251280
gcatgtggca gttcgtggtg tctccgcctt tcgagtacac gatcatggcc atgatcgccc   251340
tcaacaccat cgtgcttatg atgaaggtaa gtgccccaca ccagccccca gcactactta   251400
acccccacct cgttcctgcc tctaccctga taaaatgaaa ccatctgcag tttcccagac   251460
agaccacact ctggatcacc tctgagattt tgttcctgct gttccctcta cctgacacac   251520
tgttcccacc actcccccgg ccagcttctt cttcccagct gtacctgcag acctcttcct   251580
ccagaaagcc ttccctgacc acccaagact gcttgaggtg cccatcttag caggcatcct   251640
atctttatgt cgcctgccac aaaaatctgc gtcaggttgc atgacagtgt cccccaccca   251700
tttatgatga cctcagccct gaattcctag aggccaacaa ggatctggct cagacggaac   251760
aagaagctct ctataaatgt ttgattaatg aaatgagggg gctgggcgcg gtggctcatg   251820
cctgtaatcc cagaactttg ggaggccgag gcgggcggat cacctgaggt cacgagttcg   251880
agaccagcct gaccaacacg gagaaaccgc atctctacta aaaatacaaa attagccagg   251940
cgtggtggtg cgcatctgta atcccagcta ctcgggaggc tgaggcagga gaattgcttg   252000
aacccgggag gcggaggttg ccatgagccg agatagcgca attgcactct agcctgggca   252060
acaagagcaa gactccatct caaaaaaaaa aagaaaagaa aaagaaagaa atgagggaga   252120
aggggtaggt gaggaccota aaatccccag ggctaaggag cggcttccaa aaaaaaactc   252180
tgaaaacctt tcaccctgtg ctttggactc caaagcgtgg attcaagccc agctcttcca   252240
tttaattcat ttacctttgt acaagcaacc agtgactttc tggggactca gtttccctgt   252300
caataaaatg ggaatgataa taagagcaca tttgccccct ccagaggagg tgagaggatt   252360
gaatgagaaa gttcatgcaa ggaccttagc tccttctcgg cacttcaaaa acgatcaata   252420
gtggccgggc aaggtggctc acacctgtaa tcccagcact ttgggaggtc gaggcaggcg   252480
gatcacttga ggccaggtgt tcgggaccaa ctggccaaca tggtgaaatc ccgtctctac   252540
taaaaataca aaaattagct gggcgtggtg gcgcatgcct ataataccag ctgcgtgaga   252600
ggctgaggca tgagaatcgc ttgaacccag ggggcggaag ttgcagtgag ctgagatcac   252660
accactgcac tccagcctgg gtaacagagt gagactccgt ctcaaaaaaa ataaggaagc   252720
cggggacggt ggctcacgcc tgtaatccca gcactttggg aggccgagga gggcgatcac   252780
aaggttagga gatcaagacc atcctggcta acacggtgaa acgctgtctc tactaaaaat   252840
acaaaaagtt agctgggcat ggtggtgggc acctgtagtc ccagctactt gggaggctga   252900
ggcagggaa tggcatgaac ccaggaggtg gagcttgcag tgagccgaga tcgcgccact   252960
gcactccagc ccgggtgaca gagtgagact cctcaaaaaa aaaaaaaaaa aaaagtata   253020
attcagccaa gcacaatggc gtatgcctat agtcccgact atcaggaggc taaggtagga   253080
ttgtgagttc aagcccagcc tgggcaaaat aggaagaccc cgtctaccaa aaaaaaaaa   253140
aaaggttgg gggaggtttt tgtttttttg gatgtgaaaa gaagagccta gtccggcgga   253200
gagcggggct ttcctgaact gtgcctccta ccagtgaggt tgctcagacc ttgcctgggg   253260
ctggagtgtt gcctggagaa cagccatgaa gctgcctccc cacttcccac ttcccacccc   253320
tgctcgctga cccctgctac tcctgcttct ttcccctagt tctatggggc ttctgttgct   253380
tatgaaaatg ccctgcgggt gttcaacatc gtcttcacct ccctcttctc tctgaatgt   253440
gtgctgaaag tcatggcttt tgggattctg gtaagtacca ccttggggct acagctatgg   253500
gcttgggaga agcccaaggg ggaacaatgg gtcctggatg atggtctccc aacgtggccc   253560
```

```
caagaacccc aacctcaagg gtggcttcag tatcctgcca gtggccacag atcctactta 253620
ggcattcttg tgtttgccaa ggagtcccag ggagacccaa cctgtgagtg ttaccatatg 253680
gctgcttatg tatccagttc ctcaaaatga tgggagtcat catggctggg agtctttagc 253740
atccatttta gagataagaa aactgaaatc aggctgggcg aggtgtctca tggctgtaat 253800
tccagcactt tgggaggcca aggtgggcgg atcacctgag gtcgggagtt cgagaccagc 253860
ctgaccaaca tggagaaact ctgtctctac taaaaataca aaattagccg ggtgtggtgg 253920
cgcatgcctg taatcccagc tactcgggag gctgaggcag gagaatcgct tgaacctggg 253980
aggcagaggt tgtggtgagc cgagatcaca tcactgcact ccagcctggg caacaagagt 254040
gaaactctgt ctcaaaaaaa agaaagaaag aaagaaaact gaaatcaggc tgagcacagt 254100
ggctcatgcc tgtaatccta gcacttcagg aggccaaggc aggaggatcg cttgaagcta 254160
ggagttctca accagcctgg gcagcaaagc aagcccctgt ccctacaaaa aaaaaaaaaa 254220
ttttttttta attagccagg catggtaact cgtgcctgta gtgccagtta ctcaggaggc 254280
tgaggtggga agatattttg agcccaggag gtggaggttg cagtgagcta tgatcatgcc 254340
actgcacccc agcctgggca acagcaagac tccatctttta aaaacaaac acagaggtca 254400 ggcacagtga ctcacacctg taatcccagc actttgggag gcagaggcag gcaaatcact 254460
tgagcctagg agttcgagac caccctggcc aacatggcaa acccccatct ctactaaaac 254520
tacaaaaaat tagcctggcg tgcttgtggg tgcccatgat cccagctact caggaggctg 254580
aggcaggaga atcgcttgaa cccacaaagt ggaggttaca gtgagctgag atcacaccac 254640
tgcactccag cctgagcaac agagcaagtc tcaaaaaaat aataataata aaataaata 254700 tgtctttatt tttcaccagc cactaactaa attttaacat ttccttccat cttaaaggga 254760
gataacaaac ccttagtatt agtattatca acccttaata ttatcaacat gacctgtgtc 254820
acttataaac atcagatatt ttcatactgc attataagag ctgcagatac cttaacatttt 254880 aatttgcatt catcattgct ttaaaatgtt gcttgtgatt aaacctacag ctagaatttg 254940
ttactcagtg tttttttgtt gttgttctgt tttgttttgt ttgagacagt ctcgctgttg 255000
cccaggctgg agtgcagtgg cgcaatctcg gctcactgaa agctccaccc cctgggttca 255060
cgccattctc ctgcctcagc ctcccgagta gctgggacta caggtgcctg ccaccacacc 255120
tggctaattg tttgtatttt tagtagagat ggggtttcac catgttggcc aggatggtct 255180
tgatttcctg acctcatgat ccgcccgcct cggcctccca aagtgctggg attacaggcg 255240
ggagccaccg cacccggcct actcagtgtg ttaatggaga agtatattca ttgttagatc 255300
gccattttta aaactttttt ttttttttg agacacagtc ttgctctgtt gcccaagctg 255360
gagtaccgtg gcacaatctt ggctcactga aacctccacc tcctgggttc aagcgattct 255420
cccatctcag ccttctgagt agctgggact acagatgcac accagcatgc caggctaatt 255480 tttatattt tagtagagac ggggtttcac catgttggcc aggctggtct cgaactcctg 255540
gcatcaagca atctgcctgc ttcagcctcc caaaatgctg ggattacagg catgagacac 255600
tgtgcctagc cttaaaaaat attttgatag ctatttttatt acaaaaggta accttgaagc 255660
ccttgctatt tgttatgca tttacaagcc tttatgcata aaataaaata gccagcacta 255720
ttctcacatg gccaaggttc atagcacaca cacaaaagta tagttggctg agtgcggtgg 255780
ctcacacctg taatcccaac actttgggag acagaggtgg gtggatcatg aggtcaagag 255840
atccagacca cccttgccaa catggtgaaa ccccatctct actaaaaagt acaaaaatta 255900
```

```
gctgggtgtg gtggcgcatg cctgtagtct cagctactcg ggaggctgag gcaggagaat   255960
catttgaacg tgggaggcgg aggttgcagt gagccgagat cttgccactg cactccagcc   256020
tgggtgacag agtgagactc catctcaata aataaataaa ttaaattaaa ttaaattaaa   256080
attatttttt aaaaaattgg gggctgagtg tgatggctca cacctgtaat cccggcagtt   256140
tgggagcttg aggagggcag atcccttgag gtcaggagtt caagaccagc ctggacaaca   256200
tggtgaaacc ccgtctctac taaaaataca aaaattagcc aggcatggtg gcgtgtgcct   256260
gtaatcccag ctactcgtga ggctgaggcc caagcatcgc ttgaacctgt gaggcggagg   256320
ttgcagtgag ccaagatggc accagtgcac tccagcctgg gtgacagagt gagactttgt   256380
ctcaaaaaaa aaaaaaaatt aaggtgaaga aggcttatac tagtgggctg ggacttgaag   256440
tgaagtgaat tcttgaaggt ccccagtgag tggccaaggt gggacttgaa ccaggacatc   256500
tgttctcttg accaccagct tagtccatcc cttttgaagag agtgacctac agtctgggtc   256560
tcagccaggg tctcaggaaa ccaggttccc accttggctc acggaggtgg ttaggggcat   256620
cagctttagc accagagttc agatcttgcc tcgtcctata taagctttgt cacctcccca   256680
tcattaaaag gagccatcct cccccctccac ctcagcagag ccctggtaaa cagcaaatgg   256740
actaacgtgc atctagaggg ttgaggatga agcctggcct ggcatgggca ctcaataaat   256800
gctaggggcc aggcacggtg gctgacacct gtaatcgcag cactttggga ggctgaggca   256860
ggtggatcgc ttgagcccag gagtctgaga ccaacctgga caacatagtg agattctgtc   256920
tctacaaaaa gtacaaaatt agcctggtgt ggtggcgtgc acctgcagtc ccatctactt   256980
aggaggctga ggtgagagga tggattcagc ccaggatgtc agggctgcag tgagtcgtga   257040
ttgagccgct gcaccccacc ctgggtgaca gagcaagacc ctgtatcaaa ataaataaat   257100
aaatgctagg aaagggatcc tactaatgga cctttttcct ccaaaacagt ggctttcatt   257160
tggtggagat gctacttatt agaagcactt gaggccaggt gtggtggctc atgcctgtag   257220
tcccagcact ttgggacttc tgccaaggca gaagaattgc ttgaacccag gcgtttcaga   257280
ccagcctggg caacatagca agacctcatc tctagaaaac attgaaaaat tagccagcat   257340
agtggcacat gactgttgtc ctaactactt aggcgaaggc aggaggatta cttgagctca   257400
ggagttcaag gctgcagtga gctgcgatca catcactgcc ctccagcctg agcaacaaca   257460
caagacccgg actctaaaaa tcaaaaaaga agcacttagg gaaatttctt aaaattaaat   257520
gataccctga gcaaacccct agatgttctg attcatttgg tttggtgagg tgggagggaa   257580
tcactgaatc tgtaatttat tattattttt ttttttttga gatggattct cactctgttg   257640
cccaggctgg agtgcagtgg tgcaatcttg gctcactgca acctctgctt cccgggttca   257700
agcaattgtc ctgcctcagc ctcccgacta gttgggatta caggcgccca ccatcacgcc   257760
cggctaattt ttgtattttt agcagagacg gggattcacc acgtcagcca ggttggtctc   257820
caactcctga cctcaggtga tccgcctgcc tcggcctccc aaagtgctgg gattataggc   257880
atgagccacc gtacctagcc tgcagttatt ttattctgag ttgatcttct gctggtgaag   257940
tgagtcttcc actggggcct ggagctgcat ctccctcacc ctgccaatcc tgcaagagcc   258000
agcactgagc ttcccctctg ctttctcttt tttttttttt tttttttttt tgagatggga   258060
tcttactctg ttgcccagcc tgttcttgaa ctcgtggcct caagcagttc tccctccttg   258120
gcctcccaaa gtgctggaat tataggcatg agccaccacg cctggtctcc cctttcagtt   258180
ttaaatgaag ccacaagttc cctgtataac atttgggaga tagaggggag ctctctagcc   258240
taggggttga ggtctgtgac caaacgccta taaagttgtc tttgtttgga ctcccccaga   258300
```

```
agcagagcct gagacaagga ttgagtgcaa ggaatttatc tgggatgcag ggcagtaagg   258360
gagagaggaa gtgacacagg gacagaaagg caaccaggaa agagtgtatt attaagccag   258420
ttcctgctgt gaacaaatgg ggctcagttt cagtggatac ctccaggagg caacagagag   258480
cacataccac agagtcatcc cacctcacag ggagggaatt ggagtattta tcctccagtg   258540
cccatcagac ataatcacag gccactccca ggggagctat taattcccta acacttgtgc   258600
agccacagag agaccctggg caaagtagtg tacctcaggt gtgtagttga gctatgggca   258660 gggcccagc aacacctgcc aaaatgccaa aagtgccagt gggacctgaa ttcctttta   258720 tttatttatt tatttattta tttatttta tttatttatt tttgacggag tctcgctctg   258780
tggcccaggc tggagtgcag tggtgcaatc tctgctcact gcaagctctg cctcccaggt   258840
tcacgccatt ctcctgcctc agcctccgga gtagctggga ctacaggcgc gcaccaccac   258900
gcctgcctga ttttgtgtg cgtgtatttt tagtagagat ggggattcac catgttatcc   258960
aggatggtct tgatctcctg acctcgtgat ccgcccacat cggcctccca aagtgctggg   259020
attgcaggcg tgagccaccg cgcccggccc cctgaattcc ttttttaggc agttgtgaaa   259080
caacaacatc ccatctgttg ggcacctact gtatattcca tgctcagcga cgcacattca   259140
ttgtctgatt gctgtgttac cactgccttc cagagaaggg cgcagaggcc ccaggcactt   259200
cgcctaggag ggaagcacag ctctaaggtc aggctccttc tctgtaaggt agaggggcta   259260
cttcagggtc acactgaccg ccccaacccc tgacctggcc tctgcttctg cgaagatgct   259320
gagaaggccc tgtgttttgt gttttgggtc ccactgaccc cagaggggag ggccatctct   259380
ttgacccaga ctcttggatc caaactgggg tgccacccat caccatgtca gtacccggtt   259440
gaggggagtc agagatagca ggagaccttg tgggacttga ggctgtgact gttctccaaa   259500
caatgtggag tatttccata ttttaacaaa agagaggcca ggcgtggtgg ctcacgcctg   259560
taatcccagc actttgggag gccgaggcgg atggatcaca acgtcaggag atcaagatca   259620
tcctggctaa catggtgaaa ccccgtctct actaaaaaat acaaaaaatt agccaggcgt   259680
ggtggtgggc gcctgtagtc ccagctactc aggagactga agcaggagaa tggtgtgaac   259740
ccgggaggca gagcttgtag tgagccgaga acgtgccact gcactccagc ctgggcgaca   259800
gagtgagact ctgtctcaaa aaaaaaaaac aaacagagag ttatgcttg tgtttcccct   259860 tgagccagca cccagcccag gaatgcagca gtcaggatag atcaagtgaa gctgcagtaa   259920
caaacagccc ccacatctca gtgacttaaa ttgatgggaa gggtttttta cattcagcag   259980
ggaagctgtt tgcctcatag ttacccaggg acccaggctc acagagtagc tgccattcaa   260040
aatgttactg gtcgccaagc ccagggttga gaggctagag agtccaacac tgaccagaaa   260100
gtgaccacac tgcttccaca cacagcacat cactgcacct agacacacat ggccccatct   260160
aaacacaagg ggaccaggaa gtgcgtgtgc ctgaaaggcc ccaaagcccc gtccagtgcc   260220
tgttctgcac cctgttactg tccgcctcca gatcaggaaa tggaggccca gagaggtaa   260280 gccacttgcc catagccaca cagctgtggt agcagagctg ggatttgaac ccagagtctc   260340
ctttctttgc gagtatgctg ccaacctagt ggggacctga acacagactg tgggctctct   260400
gaggcctggg ttcaaatcct ggctttacat ctctgtgctg ctagcctcag gcagatgagt   260460
ggcttggtta cctcctagaa aatgggtata cctgggagtg gtggctcacg cctataatcc   260520
caacactttg gaaggccaaa gtgagcagat cacttgaggt cagaagttcg agaccagcct   260580
gaccaacatg gtgaaacccc gtctctacta aaaatacaaa aattagctgg gtgtggtggc   260640
```

-continued

```
atgcacctgt ggtcctacct acttgggagg ctgaggcagg agaatcgctt gaacccagga 260700
ggcagaggtt acagtgagcc gagatcgtgc cactgcactc cagcctggat gactgagcga 260760
gactccatct caaaaaaaaa aaaaaaaaag agaaagaaag aaaagaaaa tgggtgataa 260820
cccttccctc caggatcttc atgaggagct cagtgatgtc atttataaag cccctggggt 260880
ctcgggagcc ctcaaaaatg ctggagagac aggccacagc tctgaagagc agcccagcc 260940
ctgtggagct gaagcagggt ctggaggccc cctctgggc caggccaatc atgggaaggc 261000
ccccaggagt tcccagggag ggagactcag cacagatgat gtcgaacagc ctttaccgca 261060
gcccttcgaa caaccataac tgtcccgggc actccgctga tgggcaactg tgcctctaac 261120
atgcacccgg ccagcctagg gggccgggaa ccaagccctc tgttggcatc tctgtcttgt 261180
gggtccccat tctagaatta tttccgcgat gcctggaaca tcttcgactt tgtgactgtt 261240
ctgggcagca tcaccgatat cctcgtgact gagtttgggg taagtctccc tccagcttct 261300
ctctgggtga ctctgggctg gacgaggcag gcggcagggg gcgggggagc ggtcccagag 261360
gcagtgtgtc ccggaagcca tagctgcttg agccagcact tggccatgac cagagaggga 261420
gaactgggc cccggggaca agggcagccc ctcaggaggg cattgtgggg agatgggggt 261480
aaccaaagct tggctgtagg gccagcactg aggggtgggc tttcctgcat cctggcctag 261540
gaattaataa tgcagatgag tacactgagg gaactgagac actcaaaagc tctgaaagct 261600
gagccggctc ccaaacacca ccctatgtca ggagcccaga agaatgggt ttcaagtcaa 261660
ttctgtttga accaaccctc tcctagttag tgggcaggag agagccacag ccctcaggcc 261720
agtgtgggga caccactccc agggccatag aggggtcccc agggtgtctt ccctcctcta 261780
gccccgggcc tgggagactc tcaacatggg agtctctgga cctctctgtg gtggcccac 261840
aggccacatt gcccttctcc ttttctggaa gactcagggc cccagaggtc ctgtcctaga 261900
ccctctcctt ggccatctgc caatgagccc aggcttgggg tccctcagga gattgggggg 261960
agggtagaag atccttgcag ggggaagcaa tggtcaaaaa agggtgtcaa agccaagggt 262020
caagggtgat accaatgtca tcttactaac aataaaaata acaatagctc acgagaatcg 262080
cagccttgct gtgtgccagg gaactgtgcc aagtggttta cgtggattgg ctcagggtag 262140
aggtcttggt ctcagctcgt aagagaattc cctcggaggg ttcaactgaa ggcacccaaa 262200
tgcagacctc actggtggag gggaagggaa gggtacccac aagggtgca aggtgtccag 262260
cgaccaccca ccgtggggag ctgtcacctg cccaggtgct gaagtgggga gggaacctga 262320
gccggaggcc aggagaagcc accaagtggg agctgtcctg tcaatgtgga gagacagaga 262380
ccagggccca agcaggcaga gagcaatagg ggagaaacac cccaacctt ctctcccctc 262440
atcccttatc tcctgccaga gcctcccatg gcccaaagta aaccggaagc aagctgaata 262500
tgatgctcag agcaggcagg gaagtcagga gaatagatct gggtgtggtc gggcctgagg 262560
aagagggtgt tgcctcattt cacagatggg aaaactgacc tcagctgggc acggtggctc 262620
atgcctgtaa tcccagcact tgggaggcc gaagccggcg gatcacctga ggccaggagt 262680
tcaagaccag cctggccaac atggtgaaac cccatctcta ctgacaatac aaaaaaatta 262740
gccaggtgtg gtggtgcatg cctgtaatcc cagctactcg ggaggctgag gcaggaaaat 262800
tgcttgaacc cggaaggcgg aggttgcagt gagcgacggt cataccattg cactccagcc 262860
tgggtgacaa gagcgaaaac tccatctcaa aaaaaaaaag aaagaaagaa aactgatctt 262920
caatgcctgg ggaagtgaga gacactccca aggtcacaaa gccaggcctg ggtgactcct 262980
gagagtacac tgacagctcc tggggtgtcc cagtcagatc cccctacaga aaaggatctg 263040
```

```
tttgcctgct cttccgtcct agaaggccag gaggggctgg ggaactacac aaaagagggg   263100
gccattcttt gatatgtcct acggcacccg cacccaagtg atacacactt atttgccttc   263160
agctccagtg agccagaatt ttccccttcc cctcaccctra tccctgaaac cttcctctag   263220 aggggttcttg cccacatggg ggctctctcc actggggtgc ccccacctgg tcattctccc   263280
ctgtcctgag tttctagaga gggctggagc tccagctggc aatcaaaata tcttgccatc   263340
cggctacata caagacagcc ttgaaccaat gtcccctttgg gtcaagaggt tagaaggatg   263400
gtccagctcc ccagaagggc aggtggggtg gaggaagtta gctgaaacct tcaatcacca   263460
gtaagagagc tgtagggaca gactccaaca gcctgttctc ctggctggca ggaagatggg   263520
gcatggggtg ttcatgggac atcaggaccc ttgcagtagc caaacagccc ccagccctcc   263580
ctaccagctg tttgatcttg gacaacttgc gctatctctt ctcatgtaga gtgggctaa    263640 ccattgcaac caacctcaga cacttgcaag actcacagtg atgcatgcac tcaaaagaca   263700
ttcattgagc cctactgtg tgcctggtgt gattataagt gctggagaca gaacgagaag     263760 gagggggtgcc aaacaaaaca gaccaagaat acagagtgtc tgctcccata gagctgacat   263820
tctaaggaga gagacgggaa ctttttacaa gtaaaagcat caacaggccg ggcatggtgg   263880
ctcacgcctg taatctcagc actttgggag accaaggcag gtggatcact tgaggtcagg   263940
agttcgagac cagcctggcc aacatggtga aactctgtcc ctactaaaaa tacaaaaatt   264000
agccgggcac ggtggcaggt gcctgtaatc ccagctactc aggaggctga ggcaagagaa   264060
tcacttgatt ctcaggaggc gagaggttgt agtaagccaa gattgtgcca ctgccctcca   264120
gcctgggcga cagagtgaaa ctctgtctca aaagaaaag gaagaaaaag aaagaaagaa    264180
acgtgaagtg cttggcacag aacctgccag gaaaccagga gtttgaaaat ggtggttgtt   264240
aactattact gctgttgtta ttgttattgt gaatgggtgt gtagttttgt tagccagccc   264300
tgagttacag tcaatttgag ggaaagatag ggggtgggtg tttgggtcct tctgggacaa   264360
ttaactccca acctggagta gggagaggca tgtcctggca ggcaaggagg tctcagttgc   264420 cccttttctgc ctcccaggta agcccactag ttctgaggcc agggcttggc caggctgaga   264480
caggaaatgc cagatgcttg ggcgggcagg tccctggggt ttaggggggca gagggcatgc   264540 ggcagtacta accagtgctg tctcagctgc tgccccaag tggctggggt gatgtgggtt    264600
tgccctgtgt gcaatggata atgactgtgt ttcttgtctt gtctcttttc atgcctgctc   264660
ttaaaactgt atattggcgc aacgccgtct gaaaaactca tccaatcaaa atgcactatg   264720
aaattcattt gttcatccat gacatggtct gtgtgttcat acaccaatga cttatctccc   264780
aacccaccgc caccaccacc cccactcccc gcccgggaac cgaaacccat tggttttttg   264840
gcactggtta caaatcaacc taaaaaatgc tgaacacgcc tccccaactg cccccgcccc   264900
cccgctcccc ctcatcttca acatctgcat ctagaatccg gttggtctta cttctttctg   264960
aagtctaaat gccttacatt aactgtgaac gcatctcctc gcgtcggcat tgcatgccac   265020
accctgcctc tccaacgtgg gatgcctgac gctctcctca accctccgct ctcctctgtc   265080
tgtctgtcct cccgccccca gcccctgtgc ctcccacttc ctgtagactc tgtctctctg   265140 ttttatcgg gttctgaatg ggggttttct gtttggggtg gtttgcgtct tttgcagaga    265200
aagggatggg ttttcccagc gcagcacctc tctcttgccc catcccgcac acacatcccc   265260
tacactcaga gacaatagag gcaaatccac tcccagccac ctctcaccac tcctgtcccc   265320
cattcagctc catggacccc aggccccagg aaagctgcca actgtctcct cgcccctcca   265380
```

```
gctctctcca tcctgctgtc cccaatcctc catctcaagc ccacaagatc tttggccttg   265440
accagcagag acttgactct ccaagtctga taaaggagac ctgaaggcca ggcagtgtgc   265500
cggcaaagac tctcaggcag aggaactcag aagtgccaga cttggatctg gtagcttcat   265560
gtggggctgg cccactgagg ccctctcctg gagccttgaa ctgtacgtgc acacgcagtc   265620
acacagtcac tgcacacaga cactgcacac acagtcactg tgcacacact cagtcactgc   265680
gcacacactg tgcacacagt cactgcacac agacgctgca cgcagtcact gcagtcactg   265740
cacacagtca ctatgcacac acagtcactg cacacagaca ctgcacacac agtcactatc   265800
cacacacaca gtcactgcgc agacactgca cacactgc acacacaa tcactgcgca   265860 cacacagtca ctgcacgcag aaactggaca cacagtcact atgcacacac tgcacacacc   265920
actatgcaca cacactgtgc acagtcacta tgtacacaca ctggcactgc atgtagtcac   265980
tatggacaca cactgcacag tcactgtgca cacatacact gcacacactg tcactatgca   266040
aacacagtca ctgcacacag tcactatgca cacacactgc acacagtc actgcacaca   266100 gagccactat gcatgcacac acagtctgca ttcacacatt gaacacacag tcgctataca   266160
cacacagtca ctgcacacac agtctatgca cccacacact gaacacacag tcactgcatg   266220
tacagacact gcacatagtc atgacctctt ctctttttct cactcattct ccaattctct   266280
ctctctctcg ctcttttttt ttttttttt tagacagagt ctcgctctgt cacccaggct   266340
ggcgtgcagt ggcacaatgt cagctaactg caacctctgc ctcccgttt caagcaatta   266400 tgatgcctca gcctcctgag tacctgggat tacaagcatg taccaccacg ccaggccact   266460
tcttgtattt ttagtagaga cagggtttca ccatgttggc caggctggtc tcgaactcct   266520
gacctcaagt gatgcacccg cctcagcctc ccaaagtgtt gggattacag gtgtgagcca   266580
ctacacctgg cctctaatcc tcattcactg ttcctgtctc tgtgtctctc acatacagtc   266640
atgcatgcat gcacgcatgc acacacacac acactggccc tctctgctac atctacccac   266700
cctgtacccc cactccagta catactgcac acatctctct ccctccccca cttctcagcc   266760
ccttgcacac cccttgttct gttaaatctc aactgcctct gcccctctcc tacccaccaa   266820
tgaggccctt agagggacgc cccaatggca tctttgccct ggaatcatcc cttccctgct   266880
ggcaatacac atgcattcac ccaccaaaca tttaatgagc ccctatttgg tgccacagat   266940
ggaattatgg gcagaagcag acaccattac tgtcccctct taccacatac agtcaggtgg   267000
gggaggcagg catcggtcaa ataacccctt gactccactt aaaattatac ctgcactgcg   267060
agctgaagga tgagcagcat taacaaggca gagagagatg cacagagcat tccaggccca   267120
ggacagcaca tgcaaaggcc ctgtggtggg acggaacctg tgagggggtca ggatctgcaa   267180 gcgagggaat gtggctgatg caaagacagc cgagaaaggc tggcctggag acagccgaag   267240
aaggcagaag gggacaggac ccggggctgg ggagggcggg gctatattgt ggaatatggg   267300
ctttctccta agcaccagga aggggcctggg aggataggaa gcaggggagg cgcgactggt   267360
catgtgacta gacaagctcg ctctggttgc agggcaggga acagcttgac aggaggctgg   267420
gctggaggtg ggcaccagga atcgcagcaa gagatgacag tggaggagag agaacagtgg   267480
gagggttgtc ctctgcagga cccagggaaa gatcaggtct gaactgagat gaggtgcctg   267540
ggagcagtcg ggtctggctt aaaactggga gataggctga gcacggtgac tcaagcctct   267600
aatcccagca ctttgggagg ctgaggcagg aagatcacct gaggtcagga gttcgagacc   267660
agcctgacca acatggtgaa accccatctc tccaaaaaaa tacaaaaatt agccaggcgt   267720
ggtggcaggt gcctgtaatc ccagatcctc aggaggccga gacaggagaa tcacttaaac   267780
```

```
ctgggaggtg gaggttgcag tgagccgagg tcgtgccatt gcactccagc ctgggcaaca   267840
gagtgagact ctcttaaaaa aaaaatactg ggtgatagag gtgagcgagt gcaaggaaag   267900
gaccaggttg ggggaagaga ataggtgtgg gcatagcaag tttgaggtgc ctttaggaca   267960
tcccgaaata agtcagatag gcaggtgttg tgggggctgc agcttggagc tgaggtctac   268020
aagtagtagg acttttctgg agcccttagg tgggtggtct ccatatcctt ctgagcactt   268080
gaggaacatc tgagcacagc actggaaaag aaaagaccac aaggacgctg tcctcatgtc   268140
ttccaggggc tgtgtcccac ccccatcaca ttctagccag gaagttcagg ggaggtgttg   268200
aagagaggaa gctgcacctc ccaagccatg gattgaaatg tggaaggcag gaagagggaa   268260
cttgtcagaa gttctggggg cagtggaaag aattggtact gatgcaggaa gagatggagg   268320
gtggatgagg gcagactagt acccttcccc cactgcccca aacccttccc gtctccaccc   268380
ctacctgcct catgtgtctc ctcccccact tggctccaag aagggaagca tgttttctgc   268440
acgcatctcc ctgccagatc cctggctttt ttgcatggtt gcaagcttcc cctgctctcc   268500
tccaaacccc cctcctgagg ctgcttccag ggtccgcctg ccttcgcatg cctggccgag   268560
tccacatgtt atgatccgcc ccatgaaagg gatggcttgt actctgggggt tgaacggag   268620 ggggctgggg atacctgagc catcggcccc atccccaggt ggagctgggt ggccaggcag   268680
ggatgggggt cagggcagca gggcacagag agtgactctg ttagccaagc tgggtttggg   268740
gcttgttcga ggcactggag acattctcac agcacttgag cccagtgtgg tcagggtagg   268800
atcccccagc ccccttcccc atcctagagg cctaaggacg cactgatgtg tcccagagag   268860
catcctagac attgccatca aacccagagg cctcagaaat tccttgaact ccagtccttg   268920
cctctcagct cccaggccaa agccagcaca agacacagat ctggcagcca gaaagccctc   268980
tggaagccac caagtaggat gcccatgtca cccaaactag gacactttg aaacaggagg   269040 gaggctgtga ctgtatggtc accctgtgcc atttgggggg tgaaggttag accaagttaa   269100
atcttgctac gtggcctgta gcaaatccta caaatcccat agaacaagtc tgattaagcc   269160
ccttccctta gtgtggagag accctctact cctcctgcct tcaccctgct gggtactggc   269220
cagcgaagga gggtttccat gtctgcctga ggctgggtc tcaaactcaa atgcctctgg   269280
gggccaggca gacaccagtc aaccaggaaa gcaagtgcca tttctaaaac gtgaggaccc   269340
tggaaaactg gagatcatgt ggcctgcttc cagggagcaa tcgcagcagg cctgggttg   269400 ccagaaagcc agattggtgg gcaaaatctc ttgattttta aacaatggca ataattttta   269460
attaaaaaca aggacaaatg aaaaaacact gctcgggccc aacaaaacag ttttattagc   269520
tagatttggc ccactcgtga cttcgagagt cccaccccc ccaccaaggt cccttgaagc   269580
cccacaatgg ccacttaact ctagctggtc tcctccctga ctctccaact ctctggcccc   269640
ctggttcttc tagcttgggt gggaggaggc agaggcagtg actagacagg gggttttga   269700 gcagaggcag tggccaccca gggaggtcct ggggcaggg atgccccac ctcccggccc   269760 ccagcacccg ccccttggtg ggcccgggct gatttctgag ctcacccacc catgggagct   269820
gagtgcttcc tgcttcctgc aggcctggtc ccgtgctact ccaccagcc ccagaagctg   269880 agaagccatc cctgagaggg gggaaaaggg ccccaaatgc atcttctccg actcagcggg   269940
cagcgaggac tcaccctgca gccgaacagt cccagctccc tcccgtcctc cccattcccg   270000
ctcgccaagg gggtaagaaa agatgctctt ccgcttctcc caattggctc gagccgctgc   270060
tcctcttggc cgtgggggtga ggtcaggggcg ggcaggagcg ggtgggcagc tcggcagggc   270120
```

```
agggcagggc agggtgcccg gtgagtccog tgacagatgc atttctggcc cggagcgtaa  270180
catgccctcg gaacccgcac atgtccacca ggcctgactg tgctggcgac ctccaccccc  270240
accccgccc  tggtgtttgt gcatcgtaca cgtatgatag attccgcaac ttgaccggct  270300
tgtgtccttt cgtctcagtg catttggttg ttgggagaaa caaaaaccat ctcgattttt  270360
ttcctgattg gatgattcgg atatattttc tttttcttgt tcttttgtta tttcttcccc  270420
atccccgttc cttttttcctc cttttctttt ccccattgtg ggtgggggctg  270480
gcagggaggg cttatgcttt tgagttgatg ccttttcctc cctcccaccc tctctctccc  270540
aacattattc cttttcgag ttttcctct gcatcattgc attaatagtg ctttctctct  270600
ccctccttat ttggggtctg gcttgctttt ttcctgttgg ttggcttcat gtaggggcct  270660
ctgtgagtgg tgacagctct gagcctttg gggtgggtgg atggtcaccc ctcttcctcc  270720
atctccccag aataacttca tcaacctgag ctttctccgc ctcttccgag ctgcccggct  270780
catcaaactt ctccgtcagg gttacaccat ccgcattctt ctctggacct tgtgcagtc  270840
cttcaaggtg agtcctcgtc cctgctgctg gcccagggc gagaagacag gtgaccctca  270900
tgctctggct gaatgtagaa gtcagattgg aagtgcctct gtgatgtagt cgtgcagaga  270960
atctgttatc tccaaggctg ttgtcaaact tcctgtccct ggtgtgtctt cagagctgta  271020
agggcctcat cctagagccc ccagagatgc ccaccagccc tggaaggact ctggcacgtg  271080
gcatatggcc acccaaccca gtggggcaga gcactgggac aagggaggaa gacagtgcgg  271140
ctgagggacc cccagcactc ttcttcattg cctttttcc caccaggccc tgccttatgt  271200
ctgtctgctg atcgccatgc tcttcttcat ctatgccatc attgggatgc aggtgagtgt  271260
cgtgtcccta aggttcccag agcctcccaa ggagggcagc caccettaga aagggtggg   271320
tcagaggagc ctggttcaca gaagcagcca tggaggttga gctgggtttc ccagaagcca  271380
ctggaggaat ggcagcccct ggtcgtcacc ctccaattcc acaggtgttt ggtaacattg  271440
gcatcgacgt ggaggacgag gacagtgatg aagatgagtt ccaaatcact gagcacaata  271500
acttccggac cttcttccag gccctcatgc ttctcttccg gtgagaaggg acctgctct   271560
gataattctg tttccgtggg gtgggggtgcc tgccttcatc cttctgttcc catagaggat  271620
gtaccctcct cttccaatgc aagacgtgcc ctcctccttc tcttctggca ggggcgcgcc  271680
ctcaccettc ttttccggta gggggcgtgc ccttctcttc cggtagggga cgtgccggcc  271740
ttctcttccg atagggggcg tgccctcctc ctccttttct ggtgtggggg tggccagatg  271800
tgctcttatc cttctttcc cgtgaggctg gaaatgggtg tcgtgggggg cccaggaatc  271860
ctagcagggc agaagcagag ggccctggga catagtcatc aaggtcattt tccaggcatt  271920
atctctgaat cttcctgacc accctgtgag gaagggattc ttggcagccc tatccgacaa  271980
ataagaaaac aggcttacag accgtgaggc ttgattcttt ggttcatcat cttggctgca  272040
cacaaaagtt ccttcactcg ttcagtgtag gtttttggg ggggcttttt tttttttttt  272100
tttttttttt ggagatggag tctcgctctg ttccccaggc tggagtacag tggcgcgatc  272160
tcggctcact gcaagctccg cctcccgggt tcacgccatt ctcctgcctc agcctcccga  272220
gtagctggga ctacaggcgc ccgccaccac gcccagataa ttttttttgta tttttagtag  272280
agtcggggtt tcaccatgtt agccaggatg gtctcgatct cctgacctcg tgatccgccc  272340
gcctcggcct cccaaagtgc tgggattaca ggcgtgagcc accgtgccca gccctttttt  272400
tttttttttt ttagatggag tctctctctg ttcccaggc tggagtgcag tggcgccatc  272460
tcggctcact gcaagctcct cttgtggagg tgtattgagc acctacagca tgccaggcag  272520
```

```
ggctgaaaaa cgaggatgca ccaggaaata gagaaaagag acattttaag cactttggaa   272580
gctaacatcc ccatggggaa gacgaataat caggaaacaa attatagagg atgctggaaa   272640
aagataaaat tcaagaataa aggggaatag ggccaggtgc agtgactcgt gcctgtaatc   272700
ctagcatttt gggaggccga ggtgggagga tcgctttagc ccaggagttt gagaccagcc   272760
tgggcaacat agtgagaccc cgtctctaca aaaaaattgt ttttaattaa ctgggcatag   272820
tgccacacac ctgtagtccc agctacttgg gaggctgagg caggaggatt gctcgagccc   272880
aggagttcca ggctacagta agctatgatt gtgccactgc actccagcct cggcaacaga   272940
gcgagactct gtctctaaaa agaaaaatat attttttaa tttttaaaaa aagttacaga   273000
ggtagatagt ggtgatagtt gcataataat gtgagcttac ttaatgctac tgaattgtac   273060
acttcaaaat ggttaaattg ataaacttca tgctgtgtgt attttgccac agtaaaaaat   273120
aataatgttt ttaatctaac aacaaaaaaa gaatagaggg ccggcaggtt atgcctctct   273180
gaaagtgtga catttgagag aaattggcaa gggagggagt cagtgggtat atggggaagg   273240
gcaggccaag ccgaggggac tgcctgtgta aaggccctga ggcaggagta tggctggcat   273300
gtttgaggac tgtgaggagc ccagcatacc tagaacagag tgatctaggg agaatatagt   273360
atgagatgac tgtcaccttc atggagggga gcttttttt tttttttaatc tgagacagag   273420 tttcggtctt gttgcccagg ctggagtgca gtggtgcgat ctcggctcgg cgcaacttct   273480
gcctcccagg ttcaagcagt tctcctgcct cagcctcccg agtagctgag attataggtg   273540
cccgtcacca cgcccagcta atttttgtat ttttagtaga gacggggttt tgccatgttg   273600
gtcaggccgt tctcaaactc ctgacctcag gtgatccacc cgcctcagcc acccaaagtg   273660 ctggattac aggcatgagc cactgcaccc ggcctgaagg gagctttttt tttttttgc    273720 ttttttttga cagaatct ccctctttgt cacccaggct ggagtgcagt ggcgcgatct    273780
cagctcactg caacctccgc ctcctgggtt caagcgattt tcctgcctca gcctcccaag   273840
tagctgagac tacaggtgag cgccaccaca ccgagcaaat ttttggtatt tttagtagag   273900
atagggtttc accatgttag ccaggatggt ctcaatctcc tgacctcgtg atccacccac   273960
ctcagcctcc caaagtgctg ggattacagg tgtgagccac cgcgcccagc caagagggga   274020
gcttttaaag cataacagtg accagcctga gcaatgcagt gaaacccat ctctacaaaa    274080 aaaaatagtt taaaaattag ccaggagtgg tggcgtgtgc ctgtagtccc cagctactca   274140
ggaggccgag gcgggaggat cacctgagcc tgggaagttg aggctgcagt gagcagtgat   274200
tgtgccacta cactccaacc tgggtaacag agcaagaccc tgtcaaaaaa aaaaagaga   274260 gagagagaga aagaaagga aaagaaagag agagagaagg aaaagaaaag aaaaaaacat   274320
atcagtgtcc tcaaatccca ccctagacca actgaatcca agtctgctgg ggtgggcac    274380 gggcattggt attttttcaa agctctctgt ggacttcagt gcacagccaa gaatgtgaat   274440
tcccttctct cagctcccag taaaaggagg tggtccacct ggggcttgcc tggccagctc   274500
cagagcccaa gtgctcaacg tgtgtgctcc acctcctggg gaggcgttgg tacccagtca   274560
gggctgggtg tccgagtctc tgatttctcc ctgtcctcag gagtgccacc ggggaagctt   274620
ggcacaacat catgctttcc tgcctcagcg ggaaaccgtg tgataagaac tctggcatcc   274680
tgactcgaga gtgtggcaat gaatttgctt attttttactt tgtttccttc atcttcctct   274740
gctcgtttct ggtgagtctg tggacactgt gagggccgtc tgggctccct aagcctggct   274800
tcctttcagg ggagtgggtt tctgtggaat gtggctgtgt cgaaggcttg ttccctccaa   274860
```

```
ggcttctctg aaccagcctg ggatcaggtg accctgagcg tctcaaactc agcactgttg 274920
acatttgggg gtggctgatt ctttggggtg gggccatcat gtgcactgca gtgtatggca 274980
gcatccctgt cctcccccca ccagatgctg gcagcacacg ccaccgttc ctcctgttgt 275040 gacaaccaaa aatgtctccg gacattgcca ggtgccccca gggggtgggg gtggggttgg 275100
gagtgggggc cagaattccc ccatttgaga ctcaatgaaa tatttcagct gggcgtagtg 275160
gccgatgcct gtaatcccaa cacttcggga ggctgaggtg ggagggtcac ttgagcccag 275220
gaatacaaga ccagcctgga cagcatggtg tgaaacccat ctcttaaaa aaaaaaaaa 275280 aaattgaatt agctgcacac gtggtgctgt gcacctgcag tcccagctac tcaggaggct 275340
gaggtgggag gatcacttga gccttggagg tcgaggctgc agtgagccat gatcacacca 275400 ctgcaccccca gccagggcga cagaatgaga tcctgtctca aaacaaaca aaacaaaca 275460 aaaaaaaaa aaacattgcg agggaagaaa tacctcactt tggccttgtt ggggcagat 275520 gtgggaggat ttggggtcac agtggttctc ttggtgttgg tccctgtttc agaagcctcc 275580
cctccctctc actgactctg tttctttcca tcattcttgg tctttgtctc tctctctctt 275640
tttttttttt ctttgaaatg gagtctcact ctgttgccca ggctaaagtg cagtggcgag 275700
acctcagctc actgcagcct ccacctccca ggttcaaccg attcttcagc ttcaacctcc 275760
caagtagctg ggattacagg tgcacatgcc accacaccca gctaattttt gtattttag 275820 tagagacagt gtttcaccat gttgaccagg ctggtctcaa actcctgacc tcaagtgatc 275880
tgtccacctc ggcctcccaa agtgctggga ttacaggcgt gatccaccgt gcccggccag 275940
tctttgtctc tttgtatctc tctctctcca tctctctctg tttctctctt cctcttcccc 276000
atctctccac ttgatctctc tctcactgga cctccttgtg tgagtgagca tcacctctcc 276060
attccccagt ctctttctgt ctctgtctca tttccttttcc ccatcttctc tctatccctc 276120
tctccatctg ggcctctgtg tacatgtctt tgggtctgtc tgtccgtctg tctgtctgta 276180
tccttctcac tcactcattc attccctcgg tctctgcccc cattctctct tggtccccgg 276240
ggtccccaca gatgctgaat ctctttgtcg ccgtcatcat ggacaacttt gagtacctca 276300
cccgagactc ctccatcctg ggccccccacc acctggatga gtacgtgcgt gtctgggccg 276360
agtatgaccc cgcagcttgg taagaagtca ccccgaatcc tccagccaca atactcacct 276420
ctccctggaa ctgaacacg ggctaggtca ggccccagac tctggagcac tgaactcctg 276480
gggtcctagc agggtctca caggttcagt caggagagaa gatataagaa tcatcaccct 276540 tgcataccc agattaaaca cgtagggtgc caaccctgcc caaaccctgg actttctggg 276600
aaatgaggga gggcgtcaac catgagatgt cctgaagagc cctctcctcc tacgagtctc 276660
tcctgtctct cactgtgaag tctccagatg gtgaggatgc attagccagg ctccaggag 276720 aaaaccaaca gcatcccagc ctcagttctc ttgagagtgt ggggaggagg gctggcctac 276780
ccttggcaga caggattggc agcaacatca gagtagcaga actcagctcc cactgggacc 276840
cgtgaacctg ggagtgagag gacatacagg ccagggggagg acgcagagcc tcagggccc 276900 atgcatcttt gtggccacaa agggagtggg cgctcccatc tgggtagaca ccagaggggt 276960
ccctctccac tgacgggcaa tggtttcaga gggtgggttc caccttgtgc acgtgtattg 277020
agtgcccacc caacaccaag ccttgaagga cactcagagg ctttatctga atacctggaa 277080
cccaccagcc actaactgag gatttagttc aggctggtct tggggcctga gaagcatta 277140 ctgggggggc ctcagcagcc taagcccca cttcctctgg cctcagcacc agagaggagg 277200
ccgtcacgag gaaggtgggc aggaggtggt cttggctatt cccatagcct caaacaagta 277260
```

```
ctccatgaga ccgagaggct ggggagagcc gtgggtctgg ggctgggctt tggctggttc  277320
ctaactcttc ctcttttgat tttaggtcac agcaattgga tgctgtcccc aaggcctcta  277380
ttccacaagc ccccccccac ccctgtagcc catgtagact gtggaggagg cagatgcaga  277440
gagagcccca ggggaggtgc cctgcagtcc cgaactcgac tgacatccta caccectggg  277500 tctccccagt gtctgggaat gtactgggga ccttcacttg tccccagtct ctcccactcc  277560
ttcaagccag ggacacccca gcctcgggca tcatgacctc gctgtgtgcc cagggagccc  277620
gtgtgaaccc attgcctgca ctaacccect ttcttctcct ttcagcggtc ggattcatta  277680
taaggatatg tacagtttat tacgagtaat atctcccct ctcggcttag gcaagaaatg  277740
tcctcatagg gttgcttgca aggtttgact tccactaaaa cctgctagca tccatggaat  277800
gagtgtggct tggggttctt caatatatat atttcatata tatatatata tatctctc    277860 tctctctcta aaaaacaga gccatctctc tttcttgcat taaactagaa aactctctta  277920
gccaacagaa tgcagtcatg tagactcgat aaagcatgga acatatttcc tccttcccett  277980 cagccttcag ccatctttgc ttgctcttag ctgaagctgc ccatcctggg gtctccacgg  278040
caccccaaat cagatacatc ccctgggga ttgtaacttt gcatttctcc cccaaccatc  278100
acctccactc tctcccccte cacccctcac ctcccaaagc cctagccct cctcccctcc  278160 ctggcactgg cccctgctcc ccacctaggc cccctcagag accagcctca gccaaaccag  278220
agaacgtgac ccaactgtag aaataacagt gatggccggg cgcagtggct catgcctgta  278280
atcccagcac tttgggaggc caaagcagga ggatcgcttg agcccaggag tttgagacca  278340
gcctgggcaa catagcaaga accccttct ctataaaaaa ttagccaggc attgtggcgc  278400
atgcctgtag tcccagctac ttgggaggct gaggcagaag gattgcttga gcccaggagg  278460
tggaggctgc agtgagctat gatcacacca ctgcactcca acccaggcga cagagagaga  278520
ccctgtctct ttaaaaaaa aaaaaaaaa aaaaaaggc aatgaacaaa agcatggctc  278580
tacgtcttcc aaagtgagaa ttctccctcc cctccgcatc cctccagaac tgtagctcag  278640
agcccacgct gaatctgact tttctctttt ctctctctct ccctgctccc gagcagtgaa  278700
gtaatctttt tttactgacc ttttcttcca ttttttttcc tcctcttttc cattgatttg  278760
aaatatctat tttatcattc tctgcatctt tctctctcta ttttttcggc tcgtgtggat  278820
ttcttttttc tttcttctgt ttctccccac ctctcttcct ttggttctct gttcccattc  278880
ccgttttgtt tttttgtttt tgttttgtt ttttcattt tcggtgctgc caggggccgc  278940
atgccttacc tggacatgta tcagatgctg agacacatgt ctccgcccct gggtctgggg  279000
aagaagtgtc cggccagagt ggcttacaag gtagactacc cttgccgacc accgacgtcc  279060
aggcactggg ttttttttc ttcttcttct tcttttttt tagtgctgac cagaaacacc  279120
cggccgactc tctttttcca acgtttctct tctttttgt ttttgattct ttttttctt  279180 ttctcgagtc aactgatcat gaccatccct tgattctaag cagcacactg tgtccgtcct  279240
ttctgatgag tgtcttcgtg ttttgagact ccattatggc cgacatgccg gggggagggg  279300
gaggggagcg cccaggtccc cttgcacctg gtctcccagg taccaaattg gaaacaaaca  279360
cgcttcttca gggagtcaaa acccatgctt cccacttctg cccacccaga gcggccccca  279420
tgcccaggct ggggcaggcg ccttgcagag agggcttta gccccgaaa gcaggcgagg  279480 tcccgggtcc ccgcccctgc cacgcacacc tgaagctgat ctctgaccta gggccttggg  279540
gattcgagac cttccaagga gcaccaagaa cctctcttcc cctcccttcc ttcccctgga  279600
```

```
gtttcgtccc cagcccccgt ccctaatccc cccaagacac cccaacatgc ctctccattg 279660
ttccagagtg ggcaggcggc cgcagctgga cccctggacg gtggcacact gatgcaggcc 279720
atgcacgctg ccttggcggg gcctggggcg ggcaggcacc atggccgacg ggggtggtg 279780 catgctggct gagagagcga gcgtcctgcc gccaagcggc tggcccgggc cacccctcca 279840
gatccctgtc ctggaatctc ccttggtgcc caaggacaga tgctctgttc cctccattca 279900
tccacaagaa gttcagggat gacctttaaa gattctcccc acccaaaaag tattacccca 279960
tcatcctatt ctcccatcca ccttgatctt ccctgcgtcc ctatccatca atgctatttg 280020
tacctgcccc gtgttgccac ctcattcctt tccttcctct gtgcacccct cctcacctaa 280080
cctatatgtc tccctccttt ctcaatcaaa gccggggaca aggttgtccc accagcatct 280140
cagacaatga gcctctcctg gcacctgtcg ctctgtgccc ctccctgccg ccccccccc 280200 cccccccggt tttcctcaag tcgcttctct cagtctctgc ttagatgaat gtgtgcgcat 280260
gtgcaagaga gggagggcga gcccttcctc tcctggtctt tgtgcaggac caccatgggt 280320
ccataagaca actttgtgca aatttgaaaa aggcacccct tccacagaac atgcctgttg 280380
gaaaattgtt gcaatctacc aatgtggtga gaacaagaca cttttttct atcacctggg 280440 aagctgttat atttaatata caaatcgggg gctgggcgtg gtggctcatg cctgtaatcc 280500
tagtgctttg ggaggctgag acggaggat cacttgagcc cagttcgaga ctagcctggg 280560
caacatagcg agacccatc tctacaaaaa gaaaaaatat tttaattaat aaataagtac 280620
ataaatctat catttccaag atgggagccc tttgtgcggt gtacaacctg cacaactgtg 280680
cacagtggcc cagtctatgt gtgtttctct atttcccacc tccttcccca ccctacccc 280740 agtgtcccct ccagtgtcct gctctggatt taccataccc ctccccatct tcaactctgt 280800
gtttcctgcc cacttgtgtc tgaatcccca cccaagttgc cctcacccc cttctctgtg 280860 ccacttcagc ctgggctggt gcacaccagc ccagcatcct ctcccatgcc accaagcatg 280920
gtggacagag cccctgcctg ggacatgggg aatctttct tccctgggct ggaagggagt 280980
gcccctcacc ccttcccct gccattgcac agagagccaa gatctggaca tgcccctgag 281040
atacacttcc cacggagcta tgaatgagtc tcgagattcc gtctgcatgc gcccctgtct 281100
gtgctgttct gtgtcacagc ctcgctgcat gcctgcgagg ggcctgcccc gtcagtgggg 281160
ggctgcctgc ctgctgcttc tcagaggaat gatgtggtct gtgcccatct gctctgtcct 281220
ggtctgggcc aagccaggga ttgggtgtgg ggagccagtg gcaccccca ccagcggctg 281280 tggtcctggc cccctcagcc ttggctgttg catgcactgc tcaaatccag cttgtgctct 281340
ttttctttgg ggtcagactg aaacggggcc atccagaaga actctggggc agggcggggg 281400
tggggcaagg gttgaggcaa accctggaaa tgccagctct caggtcaagc aggtggggga 281460 aaaaggaga gggcagggga ccagaagtac aagagagcct tttgtgccct ccctgcgggc 281520
caccaagaga aactgagtac tgggacaggt aacctaagta agagacacct cagccgccac 281580
agctttcaga gttcttcctg ggactccctg ggtaggggcg ggcgcggctc acggagacc 281640 caggagggat gcctgggaat gactgcgctt gccttgggtt ttctgtagcg gcttctgcgg 281700
atggacctgc ccgtcgcaga tgacaacacc gtccacttca attccaccct catggctctg 281760
atccgcacag ccctggacat caagattgcc aagggtaagg aagggacagg ggcgggcaca 281820
gacaggcgtg acagggtgga accgggggatc tccctcccta ccccaaacta gaggatctgc 281880
tgtcaccacc cggatcttca ttcactcttc cattcattcg ttccacaggg ttttttgggg 281940
tttggggttt tggtgttttt tttttttttt ttttgagaca gagtcttgct ctgttgccca 282000
```

```
ggcagcagtg cggtgacatg atcgcaagtc actgcagcct tgacctccca ggctcaagtg   282060
atccttccac ctcagcctcc ccagtagctg ggactacagg cacacaccac catactcggc   282120
taatttttt tttttttggtg tgacaatttc cctctgtcac ccaggctgaa gtgcagtggt   282180
gtgatcttgg ctcattgcta cctccgcctc ccggggttcaa gcgattctcc tgcctcagcc   282240
tcccaagtag ctgggattat aggtacccac cagcacaccc ggctaatttt ttatattttg   282300
ggtagagatg gggtttcacc atgttggcca ggctggtctc gaactcctga cctctggtct   282360
caaactcctg acctcaagtg atccacctgc ctcgacctct caaagtgctg gattacaggc   282420
gtgagccacc atgcccaacc taattttta tatttttat agagatgggg tttcatcagg   282480
ttgcccaggc tggtctcaaa ctcctgggct caagcagtcc tcccaccttg gtctcccaaa   282540
atgctggtat tacaggcatg agccaccaca cccggcccat ttggcagata tttagtgcac   282600
tccttcaatg tgccagagac ccgtccaagc aggggaggac ccagcagctt acactttaga   282660
tggatgggga ggccgccact gaggaggtaa ggcagtgtct catggatccc tgggggaag   282720
gtgctccagg cagaaggact ggcaaaggcc ctgacagagg ggtgaacaca ggacacccgg   282780
ggcattgagc tgactcacct tctgagtgag ggcacgccac gcaggttcag agcagaggag   282840
gaacctgacc caactcacat ttgaacaggt tccctccggc cactgagggg atgggagacc   282900
gaaaggaggc cagtgtgggg gctgctgata tcatctgggt ggagacaggg cggcagctta   282960
gatctagggg taggctcgac gtggtggctc acgcctgtaa tctcagcact ttgggaggcc   283020
aaggtgggtg gattacttga ggtcaggatg accagcctgg ccaatgtggt gaaaccccg   283080
tctctactaa aaatacaaaa tttagccaga cgtggtggtg ggtactgtag tcccagctac   283140
tagggaggat gaggcagaag aatcgcttga acctgggagg cggaggttgc agtgagccga   283200
gatcacgcca ctgcactaca gcctgggtga cagagcaaga ctctgtctca aaaattaaat   283260
taaattaaat taactggaca tggtggcata tgcctgtggt cccagctact caggaggcag   283320
agatgagagt attgcttgaa gccaggagtt tgaggctgca gtgagtcatg atcgcaccac   283380
tgcactccag cctgggcgac agaacgagat cctagctcaa aacaacagaa agaaaaagaa   283440
aaaaacattt tttttaaagc tgagaagggg ctgggcgcag tggcttacgc ctgtaatccc   283500
agcactttgg gaggccaagg tgggtggatc acgaggtcag gagttcaaga ccagcctggc   283560
caacatggtg aaaccccatc tctaccaaaa atacaaaaag tagccgggtg tcatggtggg   283620
cgcctgtaac cccagctact ccggaggctg aggcaggaga atcacttgaa cctgggagac   283680
agaggttgca gtgagccaag atcgcgccac tgaactccag cctggatgac agagcaagac   283740
gctgtctcaa aaaaaaaaa agctgaggcc gggcacgctg gctcacgcct gtaatagcag   283800
cactttggga ggccgaggcg ggcagatcat gaggtcaaga atcgagacc atcctgggta   283860
acacggtgaa accccttctc tactaaaaat acaaaaaatt agctgggtgt ggtggcacgc   283920
acctgtagtc cctgctactc agaaggctga ggcaggagaa ttgcttgaac ccgagaggca   283980
gaggttgcag cgagccgagc ttgtgccact gcactccagc ctgggtgaca gagtgagact   284040
tcatctgaaa aaaaaaaaa aaaaaagccg agaaggctgg acatggtggc tcacacctgt   284100
aatctcagca ttttgttgag gccaggcaca gtggttcacg cctgtaatct gagcacgctg   284160
ggaggccgag gtgggtggat catttgaggt caggagttcg agatcagcct ggccaacgtg   284220
gcaaaaccct gtctctacta aaaatacaaa aattagccgg gtgtcgtggc gtgtgcctgt   284280
aatcccagca ctttgggagg ctgaagcggg tggatcactt gaggtcagga gttcaagacc   284340
```

-continued

```
agcctggtca acatggcaaa accctgtctc tactaaaaat acaaaaatta gccaggtgtg   284400
gtggcgggta cctgtaatcc cagttactag ggaggctgag gcagaagaat cacttgaacc   284460
cgggaggcag agattgcagt gagccgagat cacatcactg cactttagcc tgggcgacag   284520
agcaagactc catctcaaaa ataaaaataa aaataaaaaa taccgagaaa ttcccccaaa   284580
gacctagctc agggctcact ctccatcatt aggggggaaag aagaagagga ggccagggag   284640
gcgggcagag accagggcag tgtgggctcc tggaggcagc ttctatgttt aaaagggcgg   284700
cttcaggagg aaggggacca accgtgtcag gcactgccca gagaccaagg atgacaagga   284760
tcacaagtga ctggtcatca tggtcacttt gaccagtgca gctttggcgg aggggtcagg   284820
ggtcccctgt ctggagtgca tttcggaggc ccgaaagggg atgtgatgtg atttggcagc   284880
tgattaagga cagcagggca gagagacagg cgcacaattg ccagaagaaa cggggacctg   284940
aggctcacgc ctgtaatccc agcactttgg gaggctgagg aaggtggatc acttgaggcc   285000
aggaatttga gaccagcctg gccaacatgg cgaaacccca tctccactaa aaatacaaaa   285060
attagccagg catggtggtg cacacctata atcccaacaa cttgggaagc tgagcacaag   285120
aattacttga acctgggagg cagaggttgc agtgagccga gatcaaacca ttgcactcca   285180
gcctggggga cacagcaaga ctctgtctca aaaaaaaaa aaaaagaaa gaagaaaga   285240 aaagaaaaaa caaatgggac cagaaaaaag gagtgggtgg gagaggagca ggtggatagt   285300
cccacacatg gaaggtgct gagcccagct gaaaccacta gtaagtcagg aggagggaag    285360
actgagcctc gagacatatg tgccttccag ggtcttgagg gaaagaaggg aggaagagcc   285420
aaggccacgt ggcaagactc aaggaggaag tggcagggaa ggtgggggac tggaggggtg   285480
gaggacagat attgttaatg ccaggaacaa agtgaaggta aagagagcac aaggaagttg   285540
ggagcagtgc ctcacacctg taatcccagc actttgggaa gccaaggcag gaggatcact   285600
tgaggccagg agttcaagat cagcctggcc aacacagaga gaccccatct ctacagaaaa   285660
ttttaaaatt agccaggtgt ggtgatgtgc acctgtagtc ccaactactt gggaggctgg   285720
agtgggagga tcactgggga ctgggatgtc aaggctgcag tgagctatat gatgaccaca   285780
gacatagcag cttaagacac acctatttgt cagctcacag tcctgtaggt cagaagtcca   285840
aaaagctgga ctgggctgtc tgctgagggt ctcacgaggc tgaaatcaag gtgtcagcca   285900
agctgggctc ctctctggag gatctggggg agaatctact tccaggttca ttcaggtgtt   285960
ggcagaattg aagtccttgt ggctgtagga ctgaggtctt gttttatcac tggcttttta   286020 gcttttttgct cctggaagtg catgtaatcc tccatgtgct ctcattctct ctgacttccc   286080
catctgccac ccagcagaga caatactgtg cttttcaagg gctcacctga ttggggcagg   286140
cctaccctga tcatctctgt attttgaggt cagctgactt gatatttttt tttttcttg    286200 agacagaatt tcactcttgt tgccaaggct ggagtataat agtgtgatct cagttcactg   286260
caatctccgc ctcccaggtt caagcaattc tcctgcctca gcctcctgag tagctgagat   286320
tacaggtgcc caccaccacg cccagctaaa tttttttgta ttttagtag atgggggtt     286380 tcacaaggtt ggccaggctg gttttgaact cctgacctca ggtgatccac ccgcctcagc   286440
ctcccaaagt gctgggatta caggagtgag ccaccatgcc cagcattttc tttcttttt    286500 tttttttttt tgaaacggag tcttgttctg tcacccaggc tggagtgcag tggcgcaatc   286560
tcggctcact gcaacctcca tctcccgggt tcaagtgatt ctgcctcagc ctcccaagta   286620
ggtgggacta cagatgcgtg ccaccacgcc cggataattt tttgtatttt tagtagaaac   286680
ggggtttcac catgatagca ggatggtctc gatctcccaa cctcgtgatc tgcccacctc   286740
```

```
ggcctcccaa agtgctggga ttacaggcgt gagccaccgc accgggcctc cggtattttta 286800 attatatctg caaagtccct tcatagcctg ggcaatggtc cctagattag tgtttgaata 286860
aacagaatct tggcagaagg gcagcttttg aattctgcct accacagttc cttcgtttgt 286920
acaacgggtc taacaacacc cccactcttt gtatgtaatg ccatcgtaac tcagcttctg 286980
tggcactctg agaatctgtg ttcaggggtc ccaaaaccac ccacaggttc agtgattccc 287040
tggaagaact cagaactgag aaaagttttt atactcacag tttattacag tgaaagaata 287100
tagattaaaa tctgcaaagg gccgggcacg gtggctcacg cctgtaatcc cagcactttg 287160
ggagggcgag gtaggcagat cacttgaggt cacgagttca agaccagcct gaccaacatg 287220
gtgaaaccct gtctctacta aaatacaaaa attagccag gcgtggtggc tggcgccagt 287280
aatcccagct acttggaagg ctaaggtagg agaatcactt gagcccagga ggcagaggtt 287340
gcagtgagcc gagatcccgc cacttcactc caggctggac agagtgagac tctattagaa 287400
aaaaaaaaaa aaaaaaaatc tgcaaagggc ctggcatggt ggcttacgcc tgtaatcctg 287460
gcactttggg agggcaaggc gggcagatca cttgaggtca caagtttgag accagcctgg 287520
ccaacatggc gaaaccccgt ctctaccaaa aatacaaaaa ttaggcatgg tgccagaccc 287580
ctgtaatccc aactactcag gaggctgagg caggagaatc gcttgaccct gggaggcaga 287640
ggttgcagtg agctgagact gtgccattgc actccagcct gtgtgacaag atcaaaactc 287700
tgtccaaaaa gaaaattagc caggtgtggt ggcatacacc tgtagtccca gctactccag 287760
aggctgaggc acaagaatcc tttcaaccca ggagatagag ctacattaag ccaagatcac 287820
gccactgcac tccagcctgg gcaacagagc aagactctgt ctcaaacaaa caaacaaatt 287880
ccaaaaacat aaaatgcgca aaggaagggc atctggggaa gggtccagga gacaccaggt 287940
gcgagcttcc agttgtctgc ctccagtgga gttgcacaga caacgcttaa ttctccctgc 288000
agtgtgtgac aacacgcacc gtgtactgcc aaccagggaa gctcacctga gccttggtgc 288060
cccagggttt ttattgaggg tttgtcatat aggcagggct gacgtagtta ctcagtctcc 288120
agtccctcca gaggtcaaac tgataccacg tggcccaaga ccccaacgat aaatcgcatt 288180
gttagaatga actgtatgga aaattatcca ggcgtggcgg cgggcggctg taatcccagc 288240
tactggggaa gctgaggcag gagaatcact tgaaactagg aggccgaggt tgcagtgagc 288300
caagatcgca ccattgcact ccagcctggg caatagagca aaaacaccat ctcaaaataa 288360
ataaataaat agaatgaact gtattggccg ggtacagtga ctcatgccta taatcccagc 288420
actttgggag gctgaggctg gaggatcgtt tgaggccagg agttcgagac cagcctaggc 288480
aacatagtga gaccctatct ctttttttta aaaaaaaaa aaaaaaaaa aaagaatgaa 288540 ctatacagtg tggcccaagg ccccctgcta ataaagaca ctcttcaggc aggacatttc 288600
aaaggcttag agatcaccctc ccaggagcaa gtcaatgggc cagtcctttc atcggaatgt 288660
gcagggtttg gacaacacta gcctactgag ctagtcctta ctgcttagca ccccagcttc 288720
tatgacacct actggattcc cttcctgagg gttttcaaaga ctcctggaga tgtctctgaa 288780
tttggctgtc acagttgtta cttgtacccc agatgccact cagttccctg aagacaatga 288840
tcccccagat ttctcagcca ggagcccctc cacctcttgt cctcagtggg tgccaggcct 288900
catcctggag ttccacagct gagccaggct ctcggggtta cggaaggtca agagggtgtg 288960
gggacaacaa tggaagagtg ataacagtgg cagcccttg agcagatgcg ggtctcagga 289020
gaacataacg cgctttcttt tcatagttca gctcactttc taagcacact gagcttcctt 289080
```

```
tccagcaggc taaggggctg caaaggggt  acagattaac ctcattcttc agattctcaa  289140
aaatggtgtc accattcatt gctggagact gggagaaagg gggcaagtcc atctcattct  289200
ctctgtctct gtctctctct ctctcttccc tgtccatctg tttctctctc ccacccaccc  289260
ctctgttctc tctgcccaga agaatctcta ttttggtttt ggttttgttt gttttgtatt  289320
gttttgagac ggagtctcgt tctgtcgccc aggctggagt gcagtggcgc agtctcaact  289380
caccactgca gcctccacct cccaggttca agcgattctc atgcctcagc ctcccgagta  289440
gttgggatta caggcgcacg ccaccacgcc cagctaattt ttgcattttt actagagact  289500
ggtttcacca tgttgaccag gctggaccct atcctctttc aagcccccca ccccaggcat  289560
tgagggcaga gccaactacc tgcctgaacc aattagcata ttaaacgtaa acccagttag  289620
catatccaaa tagcagccca cagtgacatt ctgactgtca gaatgtggat tgcttgagcc  289680
caggagctca aggcttcggt gaacaaagat tgtgccacag cctgggcaac agagtaagtc  289740
cctgtcgatc gatagataga tgatagatag atagatagat agatagatag atagatagat  289800
agatagatag ataaattttt aaaaaaaata ataggccagg cacagtggct catgcctgta  289860
atcccagcac tttgggaggc cgaggcaggc agatcacctg aggtcaggag ttcgagacca  289920
gcctggccaa catggtgaaa ccctgtctct acaaaaatat aaaaatagcc aggcagtgt   289980
ctgtaatccc agctactcag gaggctgagg taggagaatc gcttgaactc tgaaggtgga  290040
ggttgcagtg agccgagatc atgccattgc actccagcct gagtgacaga gcgagactcc  290100
atctcaaaaa taataacaat aataaaaata ataataaatg ctctggcccc aaagtggcac  290160
attacatggt gcacacccca ttagcaagga ctcatcacat ggccctgcca accacaggag  290220
gaaccccccc atgtactcag gtaggagggc caggaaacac cgtcagagag ctttaatgac  290280
tcaccccatg actggggtga gggacgaggg actggctgca ggccaaggc  atgtccgtgg  290340
cagtggagac ttgggaaagg ggaaaagacc tcctctgagc cacgcacagt ggctttcatc  290400
tgtaattcca gcactttggg aggctgaggt gggaggatct tgagcccagg aggtcgagac  290460
tgcagtgagc tatgtttgtg ccacggcact ctagcctggg cgacagagca aaccctgtc   290520
tcaaaaatca aaataaaacc aaaaccaaaa cttcctctgt tggggatgct ccagggcgtc  290580
ccagccttga acagatgggt cactgcagta ataatcctat ggcagacact gtcccaaggc  290640
tgcacgcacg ttactttgat catcaaacaa ccaggtgata gccaggcatg gtggtgcgtg  290700
cctgtagtcc cagctactca ggaagctgaa gcgggagaat ctcttgaacc tgggaggcgg  290760
aggtaacagt gagtcgagat cacatgactg cacttcagcc tgggaacaga gagagactct  290820
gtcaaaaaaa aaaaaaaaac aggccagacg cggtggctca cgcatgtaat cgccagcact  290880
ttgggaggct gaggagggtg gatcacctga ggtcaggagt ttgagaccag cctggccaac  290940
atggtgaaac cccgtctcta ctaaaaatac aaaattagtt gggcgtggtg gtgcacacct  291000
gtaatcccag ctactcggga ggctgaggca ggagaatcgc ttgaacccag gaggcagagg  291060
ttgcagtgag ctgagattgc accattgcac tccagcctgg caacaagag  tgaaactcca  291120
tctcaaaaaa aaaacaaaaa aaaacaacc agccaggcgc ggtggcttac gcctgtaatc  291180
ccagcacttt ggaggccga  ggcgtgtgga tcacccgagg ttaggagttc gagaccagct  291240
tgaccaacat ggtgaaactc cgtctctact aaaaatacaa aaattagcc  aggcatggtg  291300
gtgcatgtct gtaatcccag ctactcggga agctgagaca ggagaattgc ttgaacccag  291360
gagtcggagg ttgcagtgag ccaagctcgt gccactgcac tccagcctgg gcaacagagc  291420
aagactctgt ctaaaaaaaa aaaaaaaaca cacacacaca cacacaacaa ccaggtgagg  291480
```

```
caagtactct tgctatcatc tccatttcac agatggagaa actgagttac taagtggtag  291540
agtaacctaa gtcatgcagc cgataactgg gagacaagat tgggacccag gtcgcccagc  291600
tgttctccat gccgggctgt ctcctgcaca gctgctccat ggtcctggcc ccaccgaaaa  291660
ccagagccca caaggtcatt ccagcagcac tgcccagggc ctcctctggg ccaggccgtt  291720
ggggaactgg agaccccatg gggaccagaa agattggggt ctcgttctcg ggagcctatg  291780
gctttgcagc tgacccagag tccagctgac acccaggcag gcagtcaggg tctgtctaca  291840
cccccattgc aggaggagcc gacaaacagc agatggacgc tgagctgcgg aaggagatga  291900
tggcgatttg gcccaatctg tcccagaaga cgctagacct gctggtcaca cctcacaagt  291960
gtaagagctg agcccagccc tgggatccaa tccaccagga cagatggagg gggagggaaa  292020
ggggaggcct ggggagagtg ttggcctggg ctggtataca cagggaccca ggacaagggc  292080
cccaaagagg cctgcccttg gtgagctcac cgtgtgtgtg cccccagcca cggacctcac  292140
cgtggggaag atctacgcag ccatgatgat catggagtac taccggcaga gcaaggccaa  292200
gaagctgcag gccatgcgcg aggagcaggt gcgctgttcg ccgctctggg gacatctggg  292260
ctggggacag tggcttgcat gtcaccacgg gaaccaactg gaatatgagg gtggctgagc  292320
cccagggcag gtccctgaaa gtaggggct gtgcacagca gctcacacct gcaatctcag  292380
tgctttgaga ggccagggca gagggatcgt ttgagaccag gatgagacca ccctgggcaa  292440
cacagtgaga ctccatctct acaaaataaa acattagcca ggcatggtgg tgcacacctg  292500
tagtcccagc tatttaggag gccaagatgg gaggatcact tgaggccagg agtgggagac  292560
cagtctgggc aacatagaaa gacccatatc tctacaaaaa aaaaataaaa ttagctgcat  292620
gtggcgccat gcacctgtgg tcccagctac ttgggaggct gaggcaggag aatcacttga  292680
acctgggagg tggaggttgc agcaagccaa gatcaagcca ctgcactcca gcccgggtga  292740
taagagcagg actctatctc aaaaaaaaa aaaaaaaaaa aaaaaaagt tcttgccaag  292800 gacacatcat gtggattcat tcttcattca gctgctccac caacacttat tgagtattac  292860
tgtgtgcagg gcgctgttct cagtcctcgg ggatgcaccc atggggaaaa taggccagaa  292920
tccctgccct cagggagcag acattccaag tggggaaatg ccaatggtag caaatgactg  292980
aatcgtgcaa catccagcaa agagaaagaa agtgtcgtgg gggaaagtgg agaagaatcc  293040
agaagatagg agtatccagg ggaggagggg atgcggtggg aaatgggtag ttggggagcc  293100
tccctgagaa agtgacatgt gagcaaaggc ttgaaggaaa aggggagagg gagtgagcta  293160
agcaatacct ggaagggtgt tccaggcaga ggaaacagcc agtgcaaagg ctctgaggct  293220
ggaccgtgcc tgggttgttt gggtaacagc aaagaggcca gtgtggtgga aaagagcagg  293280
gaggagacaa gggcaaggag gtgacagggc agatccttca gggccatggg agctgcagga  293340
aggactctgg ctttttcccc aagcaagtgg gagccatgga gggttctaag caaaggaggg  293400
ataggacctg actcaagtgc tcatgggcgc cctctggtgg ctcttgtgga acagtggggt  293460
tgaaggtagg agcgggagac ctgggagaag gtgcctgcag tgagagatga ggacgtggga  293520
ccaggctggg gctatgactt gggtggagga gtgagaagtg gtccagttct gcgtggaatt  293580
ggaagggtct agatggatga gacctgagag agtgtgtgtg tgtgtgtgtg tgtatactgg  293640
ggatgtcgca atgccttctg ggtaccaccg tcccaccacc ccaccttgt ccacacactg  293700 ctctctgccc cattcccag gaccggacac ccctcatgtt ccagcgcatg gagccccgt  293760 ccccaacgca ggaaggggga cctggccaga acgccctccc ctcccaccag ctggacccag  293820
```

```
gaggagccct gtgagtgtca cccctgccag ggaggtggag tgtgggggtg ccgtggtccc 293880
cacgttctgg aagctgccca agcgcccact gctaccccgg cctctgtccc ccatgcagga 293940
tggctcacga aagcggcctc aaggagagcc cgtcctgggt gacccagcgt gcccaggaga 294000
tgttccagaa gacgggcaca tggagtccgg aacaaggccc ccctaccgac atgcccaaca 294060
gccagcctaa ctctcaggtg cctctgtccc ccaactcccc aatggctccc agggcccggg 294120
tggttcaggt ggaagggatc tgggcccccc acacacacac acctgcagct ccctccctct 294180
gcagacacca gggatctgga ggtcaggccc cagagctcat ctggctttgc catctgctcc 294240
gcagtccgtg gagatgcgag agatgggcag agatggctac tccgacagcg agcactacct 294300
ccccatggaa ggccagggcc gggctgcctc catgccccgc ctccctgcag agaaccaggt 294360
gagggctttc accactgccc tggggctgga cccctcactc tgcactgggt agggccaggc 294420 cccccacaa gcagcccagt gcatcccctc cctgccggac tcaggcctgg gtagggactc 294480
cttcagtctc tgaagcagtc tgcaggcccc acccaccacc tggtcacacc tggagcacct 294540
gcagaccctc ctccctcaca gaggacagag aggaaagtgc tcccccctggg gcagagggca 294600 gtggccactg caaaatggtc tctggctgcc ctggttggag gctgcagaca ggggaggttg 294660
tggaagattt gtgggtgcag cagggttcaa cagggccagc tgagacctgc cacgaagatc 294720 accccctacac aaacacacac acacatgctc aacatacatg cacacacatg tgcagctgtg 294780
cgcctactca gatgcttgca tacacacacg tgtgtgcacg tgggcatata cacactgcac 294840
atgtactcac acatgcacac atgtacgtgc acacgtgtct gcatatggga acttggcagg 294900
tcctaggata cagtagcaga gtctgggtgg gtctggggg cagctgggct cgtatttcttct 294960 gtctggtctc tgtgggagtc attgggggc acaggggtgt gtgcttgatg tgtgtctgtg 295020
tgtggccgct tcacccagct gccaggccca cctgcaggtg atcccgttgc cttggactca 295080
tgggacagag ggcccagagg catagctggc tgcccacccg gcctgaacag cggggcccca 295140
tgcacgcagc ccgcctctgg aggagaacag ggcatggctg tgagagcctg gcccgggtgc 295200
gtggcatgtg tggctgtggc gagctttccg tgtgccgtgt gtggcgtctg cacggggcag 295260
gaggctgtgc tgtgcctggc tggaccaggg tcacctgagg gcctggcctc tggctgctgg 295320
gaacgtgggt tggggagcac ccagcgtgca tgctgctgct ccctcaggac cgagctgctg 295380
ggccccagga gagggttggg acaagcccag ctgacggcca ccacatggaa gctttgagca 295440
tcggccggag ccaggggttg gggtgtgcat cgcatgaggc agagcccagg gccaggggct 295500
cgaggctgcg ccgtcctgtc tttcggtccc atgcctctgc catttgtctg tctgcatctc 295560
ctgtctgtct cctctgtacc catgggaata gaggacgccc agccccgggg gctgggaca 295620 cccacccgcc aggactttaa cttttctttt cctcccttgcc ttctccctcc gatttctctt 295680
gatgccagtg ccactcccct ccttggcttc ttctccatgc accacctcct cactctccct 295740 cttgccttt atatttattt tcttcttttct gttttttctg tgtgcaccat cccatggggc 295800
tgtgacagag gagaaggggc cggccacgtg gaataacct cagtgtatgt accgcgcctg 295860
cccagcgccc agcagggctc cggcccccctc ttcctcccca ccccccctcc agggagtccc 295920
gtcatctctc accgtcccccg gaccccaccc tttcttggc aatcgcaccc tctccctcc 295980 atggagccca atccttgtgt gtggtgtcct gtgtgtgccc ctcacccata agccctggtg 296040
ggcggggcca tccccatcct caccccctacc ccctttcttcc cagggcccccc cacgccggag 296100 gacactggct ctccaagagc ctggcccact ctgcacctct ttctgggggg cttcttctcc 296160
tgacaccacc accaacccct ggtcctgcag ctcctacctg gagcagggcc accagcgctc 296220
```

```
agctgggctg accctggga ggcgggcgtc tgccccatct ccctccttcc ctcctctgcc 296280
tgctgcagag aaacctgtgt gtcagggctt gacccaggga tgaagcacca gggaaaagag 296340
tgggccccca gagcctccag tgcctgggta tccccacccc ccacccagag ctccctagct 296400
tgggcctcac cagaaggact cagacttgtg ggggcagcga gcacagcccc gttagccggg 296460
aggacccaaa gctgccatgc cgggcacctg tcctgagcc cataggtcag ccagccacag 296520
tcggaggctt ctcaccctcc caggagagca agctggggca gggatgagtg cggcagtcca 296580
gggctcccag gtttgcaccc tggatgtgga gagggcttcc ctctggccag cctgagcctg 296640
cccaactgtg gctgggcccc caggactgga gagtgaggat cagatctttc tggtcagaac 296700
ccaggatggg ctcaaaagga gcagtcctgt tctgaggga cagaggaatc ctcaggctcc 296760
accctcagag gcctggccac acccagagcc ctgattgatc aggggagcc aaggcccat 296820 ggcatcccct ggccctgcc ccaggatggt cacaccgcag tcaccgaagg ccaccaccag 296880
gctgccacaa tggggcagga aggacccgga ccacttggtg ctagctgctg accccagccc 296940
accggcctgt cccctccccc agaccatctc agacaccagc cccatgaagc gttcagcctc 297000
cgtgctgggc cccaaggccc gacgcctgga cgattactcg ctggagcggg tcccgcccga 297060
ggagaaccag cggcaccacc agcggcgccg cgaccgcagc caccgcgcct ctgagcgctc 297120
cctgggccgc tacaccgatg tggacacagg tgggcagccc tgtggtgctc agggacaagc 297180
agaacagagg agaggagagg gaggagaag gcagggcgga ggagacacta aggaagaaga 297240
aagggagagg cctccatgga gaggggacag agggggccag gcagcagctg caggaacctg 297300
ggtactaccc cctccccca acccactgac ctgcctcggt tcagggatc tctagggccc 297360 ccacaccttc caggtggcct cctgtgtgtg catctgcccc acctctccct cacgaccacc 297420
tgtgtgtctg tctgaccctc acccggccca ggcttgggga cagacctgag catgaccacc 297480
caatccgggg acctgccgtc gaaggagcgg gaccaggagc ggggccggcc caaggatcgg 297540
aagcatcgac agcaccacca ccaccaccac caccaccacc atccccgcc ccccgacaag 297600 gaccgctatg cccaggaacg gccggaccac ggccgggcac gggctcggga ccagcgctgg 297660
tcccgctcgc ccagcgaggg ccgagagcac atggcgcacc ggcaggtggg tgcggctgca 297720 agtgaccca ggctgggctc ggccgggagg cggggaggag agaagggat accccatcca 297780 acagccactc taggcaaagg tccccggatc ccggctgtga ccacctccca tcctgccccc 297840
aagccaccgg ggtgcccggc ggccggagcg gacacggatc cccaccacac cagctgccta 297900
tgctgtcccc ccagccccct tgcccacccg ccgcccctc cccgccgccc gcagctgctt 297960
gctcctcggt tgtggatcat atttgagttc tgggccgtgc cgcccgacct ttcactttcc 298020
tttaacccgg cttctgtttt tgtttcaatt atgatttctg tcctctggac gcctgtgagt 298080 aattttgaa acttctgcta ttttaaccc cgaaacttac aaaactccat ttctcatttc 298140
tcttttcact ttgttgtgtt ggttttcgac tcctcccctc cctgtctcac tccccctcct 298200
cccctccctc ctccctgtgg ctgttgcttt tttccattca atgtcctgtg tcccccctct 298260
cctcctcctc ctcctcctcc ccctcccct cctccctctc ctcccggccc ctctcccttc 298320
gctcccctct cttcctccca atcccgtgtc tcctttgatt tgttgtatc ttttttttg 298380 atttcctttg tttcaatttt cgtgtagggc agtagttccg taagtggaag cccagccccc 298440
tcaacatctg gtaccagcac tccgcggcgg ggccgccgcc agctccccca gaccccctcc 298500
accccccggc cacacgtgtc ctattcccct gtgatccgta aggccggcgg ctcggggccc 298560
```

| | | | | |
|---|---|---|---|---|
| ccgcagcagc | agcagcagca | gcagcagcag | cagcagcagc | aggcggtggc caggccgggc 298620 |
| cgggcggcca | ccagcggccc | tcggaggtac | ccaggcccca | cggccgagcc tctggccgga 298680 |
| gatcggccgc | ccacgggggg | ccacagcagc | ggccgctcgc | ccaggatgga gaggcgggtc 298740 |
| ccaggcccgg | cccggagcga | gtccccagg | gcctgtcgac | acggcgggc ccggtggccg 298800 |
| gcatctggcc | cgcacgtgtc | cgaggggccc | ccgggtcccc | ggcaccatgg ctactaccgg 298860 |
| ggctccgact | acgacgaggc | cgatggcccg | ggcagcgggg | gcggcgagga ggccatggcc 298920 |
| ggggcctacg | acgcgccacc | ccccgtacga | cacgcgtcct | cgggcgccac cgggcgctcg 298980 |
| cccaggactc | cccgggcctc | gggcccggcc | tgcgcctcgc | cttctcggca cggccggcga 299040 |
| ctccccaacg | gctactaccc | ggcgcacgga | ctggccaggc | cccgcgggcc gggctccagg 299100 |
| aagggcctgc | acgaacccta | cagcgagagt | gacgatgatt | ggtgctaagc ccgggcgagg 299160 |
| tggcgcccgc | ccggccccc | acgcacccca | cgcacacacc | ccacccgagg agccgcgcag 299220 |
| aggccgcggg | ggcccagcac | agagggcccg | ggagagggcc | agccgggaga ccccagactc 299280 |
| tggagaggcc | agggctgggc | cacaagggtg | tcccgcagag | accctcggcc aaaagagacc 299340 |
| ctcctgggca | gccacggcgc | cccccaacca | gccccgatcc | ccccacccac gacagggct 299400 |
| ctcgggtggg | aggcagggag | cagacaaacc | acacagccaa | gggatttgaa ttaactcagc 299460 |
| cattttgga | gaactttggg | gaacatgaaa | aaaaaaaaa | aaaaaaaaaa aaaaacatt 299520 |
| tttaaagaa | aaacgggga | gaaaaaaata | gcttctattg | atgagtttta tcatctcaat 299580 |
| tgaatctttc | ctttccctga | tgaagacagc | tggtggccga | gtgcggcaaa gaagccagaa 299640 |
| ggaaccagaa | tccagtgcc | ctacacccac | caccagacac | actcacaccc acacgttc 299700 |
| tcagacacac | acaagagtgc | ttgccggtta | taccaaaccc | tactattact gcctgcagaa 299760 |
| atcaattaa | aaaataata | ataacaataa | acaattttaa | aaaggacaaa aaattaatg 299820 |
| attgagaaaa | gaggcatttt | tttctgacat | ttggtcctgc | ttgaaacaac aaaagaagaa 299880 |
| gaaaaaccca | ccatcaccac | cgattccttt | gcttcttttt | tccttttttc ctaccttgtt 299940 |
| tgaaaaccgt | gggcttggga | ctgtgaatta | ttgcatgaca | ttcaaaaaga aaaaaaaaat 300000 |
| aaaaaaagt | tgaatcaaa | | | 300019 |

<210> SEQ ID NO 44
<211> LENGTH: 1000
<212> TYPE: DNA
<213> ORGANISM: Artificial Sequence
<220> FEATURE:
<223> OTHER INFORMATION: Construct

<400> SEQUENCE: 44

| | | | | |
|---|---|---|---|---|
| atttcattta | tcaggtgttc | agtgaatgct | tactatgtaa | cagcacagtt atcagcactg 60 |
| gggaaataga | tgagtaagat | aagatttgca | ctttcattag | cttacatgcc ataagagggg 120 |
| aaataaagag | aacaccagat | gatgataagt | ttatgctgag | aattaaaatg aagtgatgaa 180 |
| ataatgggaa | tgtcaggtgg | ctacttttgg | tgggatggtc | aggaaaggca tctctgggga 240 |
| gataaatttt | aagctcagac | ctgagtgaaa | agaatgagcc | agccatggaa acattatgtt 300 |
| aactcacatg | gtagtttgaa | atgctttatc | tgatcaaagg | tacttatttt tggtgacttt 360 |
| caacaatatt | aagggtctat | aaaccaacac | tcatttgcat | aagaataact accagtgaat 420 |
| cttttttgtat | gataggtttt | ttgtttgttg | ttttttgag | acagagtctc gctctgtcgc 480 |
| ccaggctgga | gtgcagtggc | gcgatcttgg | ctcactgcaa | cctctacctc cccggttcaa 540 |
| gtgattctcc | tgcctcagcc | tcccaaagta | gctgggatta | caggtgcctg ccaccacgcc 600 |

```
tggctaattt ttgtattttt agtagagatg gggtttcacc gtgttgtcca ggctcgtgtc      660
aaacttctga cctcaagcca tccacccgcc tcggcctccc aaagtgctgg gattacaggt      720
gtgagccacc actcctggcc atgataggtt attttgtgat gaaataccct acctcttaat      780
ttgtctgata aatttaaatt ttatgtctag atttcctaag atcagcactt ccatatttta      840
aagtaatctg tatcagacta actgctcttg cattctttta ataccagtga ctactttgat      900
tcgtgaaaca atgtattttc cttatgaata gttttctca tggtgtattt attcttttaa      960
gttttgtttt ttaaatatac ttcactttg aatgtttcag                            1000
```

<210> SEQ ID NO 45
<211> LENGTH: 214
<212> TYPE: DNA
<213> ORGANISM: Artificial Sequence
<220> FEATURE:
<223> OTHER INFORMATION: Construct

<400> SEQUENCE: 45

```
acagcagcaa aagcagcaac agcagcagca gcagcagcag caggggggacc tatcaggaca      60 gagttcacat ccatgtgaaa ggccagccac cagttcagga gcacttggga gtgatctagg     120
tgatgctatg agtgaagaag acatgcttca ggcagctgtg accatgtctt tagaaactgt     180
cagaaatgat ttgaaaacag aaggaaaaaa ataa                                 214
```

<210> SEQ ID NO 46
<211> LENGTH: 135
<212> TYPE: DNA
<213> ORGANISM: Artificial Sequence
<220> FEATURE:
<223> OTHER INFORMATION: Construct

<400> SEQUENCE: 46

```
aacttgttta ttgcagctta taatggttac aaataaagca atagcatcac aaatttcaca      60
aataaagcat ttttttcact gcattctagt tgtggtttgt ccaaactcat caatgtatct     120
tatcatgtct ggatc                                                      135
```

<210> SEQ ID NO 47
<211> LENGTH: 208
<212> TYPE: DNA
<213> ORGANISM: Artificial Sequence
<220> FEATURE:
<223> OTHER INFORMATION: Construct

<400> SEQUENCE: 47

```
tccccagcat gcctgctatt ctcttcccaa tcctccccct tgctgtcctg ccccacccca      60 cccccagaa tagaatgaca cctactcaga caatgcgatg caatttcctc attttattag     120
gaaaggacag tgggagtggc accttccagg gtcaaggaag gcacgggga ggggcaaaca     180 acagatggct ggcaactaga aggcacag                                        208
```

<210> SEQ ID NO 48
<211> LENGTH: 214
<212> TYPE: DNA
<213> ORGANISM: Artificial Sequence
<220> FEATURE:
<223> OTHER INFORMATION: Construct

<400> SEQUENCE: 48

```
ctacttcttg ccctcggtct tcaggtcgtt gcgcacggtc tccaggctca tggtcacggc       60
```

```
ggcctgcagc atgtcctcct cgctcatggc gtcgcccagg tcgctgccca gggcgccgct    120
gctggtggcg gggcgctcgc aggggtggct gctctggccg ctcaggtcgc cctgctgctg    180
ctgctgctgc tgctgctgct gcttctgctg ctgt                                214

<210> SEQ ID NO 49
<211> LENGTH: 110
<212> TYPE: DNA
<213> ORGANISM: Artificial Sequence
<220> FEATURE:
<223> OTHER INFORMATION: Construct

<400> SEQUENCE: 49
ctgtaaatga atgagaaaac cggtttagaa agtgcacagc tgtcagggaa gtcaacactt     60
cagtgagcat gtgaccatgt ggagtcagct tcctgtttcg tgctgcaatc                110

<210> SEQ ID NO 50
<211> LENGTH: 374
<212> TYPE: DNA
<213> ORGANISM: Artificial Sequence
<220> FEATURE:
<223> OTHER INFORMATION: Construct

<400> SEQUENCE: 50
gtaaggcctg ctcaccattc atcatgttcg ctaccttcac actttatctg acatacgagc     60
tccatgtgat ttttgcttta cattattctt cattccctct ttaatcatat taagaatctt    120
aagtaaattt gtaatctact aaatttccct ggattaagga gcagttacca aaagaaaaaa    180
aaaaaaaaaa gctagatgtg gtggctcaca tctgtaatcc cagcactttg ggaaaccaag    240
gcaggagagg attgctagaa catttaatga atactttaac ataataattt aaacttcaca    300
gtaatttgta cagtctccaa aaattcctta gacatcatgg atattttttct tttttttgaga    360 tggagtcttg ctct                                                      374

<210> SEQ ID NO 51
<211> LENGTH: 136
<212> TYPE: DNA
<213> ORGANISM: Artificial Sequence
<220> FEATURE:
<223> OTHER INFORMATION: Target site

<400> SEQUENCE: 51
tttaagctca gacctgagtg aaaagaattt gagacagagt ctcgctctgt cgcctttcct     60
aagatcagca cttccatatt tggtgacttt caacaatatt aagggtctat aaaccaacac    120
tcatttgcat aagaat                                                    136
```